(12) United States Patent
Chokhawala

(10) Patent No.: US 12,104,160 B2
(45) Date of Patent: Oct. 1, 2024

(54) PRODUCTION OF 4,6-DIHYDROXY-2-OXO-HEXANOIC ACID

(71) Applicant: ZYMOCHEM, INC., Alameda, CA (US)

(72) Inventor: Harshal Chokhawala, Castro Valley, CA (US)

(73) Assignee: ZYMOCHEM, INC., San Leandro, CA (US)

( * ) Notice: Subject to any disclaimer, the term of this patent is extended or adjusted under 35 U.S.C. 154(b) by 226 days.

(21) Appl. No.: 17/307,850

(22) Filed: May 4, 2021

(65) Prior Publication Data

US 2022/0389433 A1 Dec. 8, 2022

Related U.S. Application Data

(63) Continuation of application No. 16/595,252, filed on Oct. 7, 2019, now abandoned, which is a continuation
(Continued)

(51) Int. Cl.
*C12P 7/42* (2006.01)
*C12N 9/00* (2006.01)
(Continued)

(52) U.S. Cl.
CPC .............. *C12N 15/52* (2013.01); *C12N 9/00* (2013.01); *C12N 9/0006* (2013.01);
(Continued)

(58) Field of Classification Search
CPC ........ C12N 15/52; C12N 9/00; C12N 9/0006; C12N 9/0008; C12N 9/001; C12N 9/0016; C12N 9/1029; C12N 9/1096; C12N 9/1205; C12N 9/13; C12N 9/16; C12N 9/2402; C12N 9/88; C12N 9/93; C12P 7/04; C12P 7/18; C12P 7/24; C12P 7/40; C12P 7/42; C12P 7/44; C12P 7/6409; C12P 13/001; C12P 13/005; C12P 17/08; C12P 17/10; C12Y 101/01001; C12Y 101/01002; C12Y 101/01035; C12Y 101/01078; C12Y 101/01268; C12Y 101/01269; C12Y 102/01003; C12Y 102/01005; C12Y 102/01022; C12Y 102/01024; C12Y 102/01026; C12Y 102/01048; C12Y 102/01063; C12Y 102/07005; C12Y 102/99006; C12Y 103/01044; C12Y 103/01045; C12Y 103/01086; C12Y 104/01; C12Y 203/01001; C12Y 203/01032; C12Y 203/01035; C12Y 203/01057; C12Y 206/01008; C12Y 206/01009; C12Y 206/01036; C12Y 206/01043; C12Y 206/01048; C12Y 206/01076; C12Y 206/01082; C12Y 207/01031; C12Y 207/01165; C12Y 208/03; C12Y 301/03; C12Y 301/03002; C12Y 301/03008; C12Y 301/03019; C12Y 301/0302; C12Y 302/01; C12Y 401/01001; C12Y 401/02; C12Y 401/02014; C12Y 401/0202; C12Y 401/02021; C12Y 401/03016; C12Y 401/03017; C12Y 402/01002; C12Y 402/01003;
(Continued)

(56) References Cited

U.S. PATENT DOCUMENTS 11,692,208 B2 7/2023 Chokhawala et al.
2006/0252135 A1 11/2006 Brazeau et al.
(Continued)

FOREIGN PATENT DOCUMENTS

CN 102066551 A 5/2011
WO WO-2009/151728 A2 12/2009
(Continued)

OTHER PUBLICATIONS

Singh et al., Current Protein and Peptide Science 19(1):5-15, 2018.*
GenBank accession No. WP_00431706.1, May 15, 2013.*
GenBank accession No. WP_000992954.1, May 16, 2013.*
GenBank accession No. WP_003450974.1, May 7, 2013.*
Baker, P. and Seah, S.Y.K., Rational design of stereoselectivity in the Class II Pyruvate Aldolase Bphl, Journal of the American Chemical Society, 134(1):507-513, (2012).
Baker, P., et al., Probing the molecular basis of substrate specificity, stereospecificity, and catalysis in the class II pyruvate aldolase, Bphl, Biochemistr including biophysical chemistry and molecular biology,50(17):3559-3569, (2011).
(Continued)

*Primary Examiner* — Delia M Ramirez
(74) *Attorney, Agent, or Firm* — Choate, Hall & Stewart LLP; Xiaodong Li; Alisha A. Contractor

(57) ABSTRACT

Provided herein are methods, compositions, and non-naturally occurring microbial organism for preparing compounds such as 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid comprising: a) converting a $C_N$ aldehyde and pyruvate to a $C_{N+3}$ β-hydroxyketone intermediate through an aldol addition; and b) converting the $C_{N+3}$ β-hydroxyketone intermediate to the compounds through enzymatic steps, or a combination of enzymatic and chemical steps.

25 Claims, 7 Drawing Sheets

Figure 1:
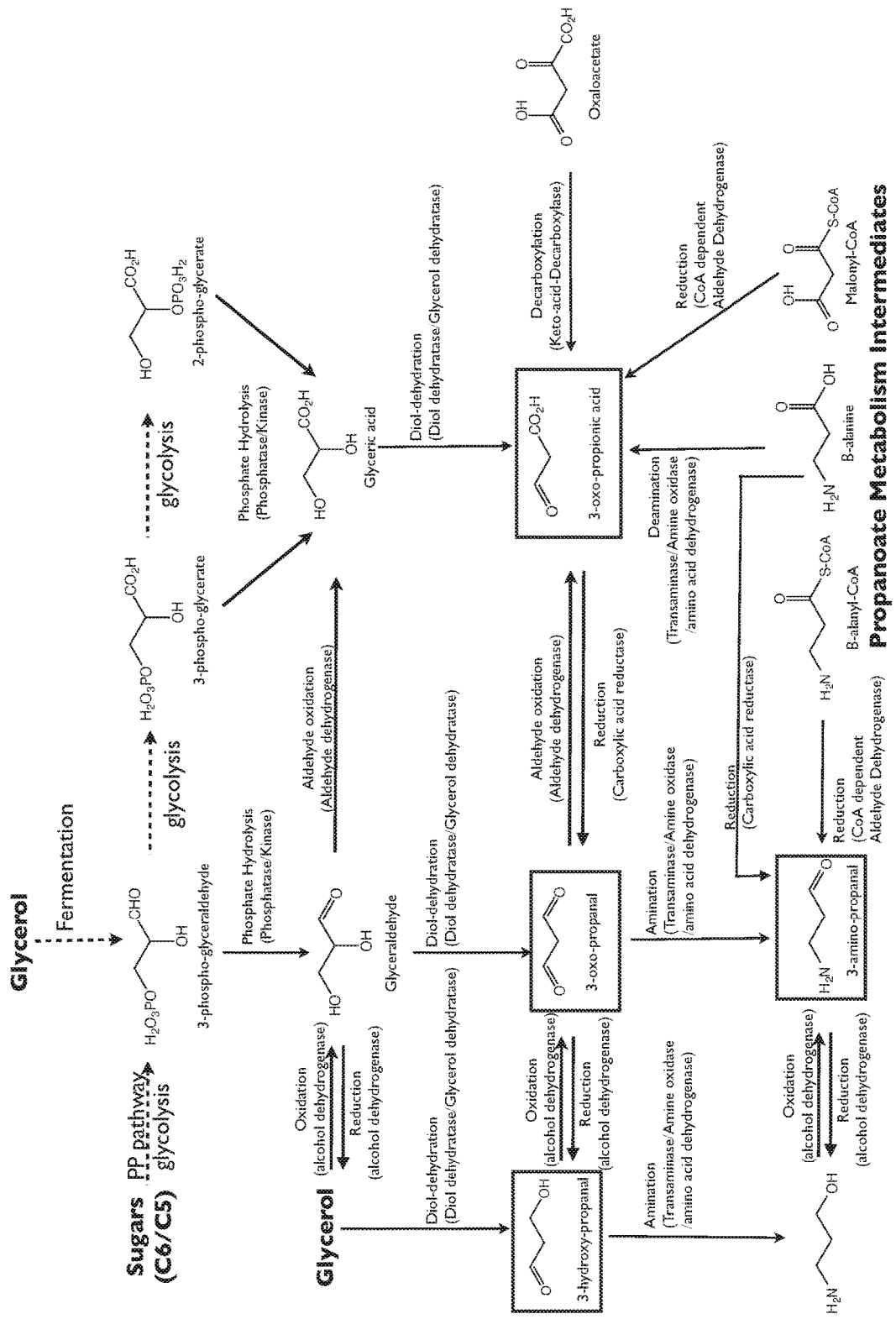

Specification includes a Sequence Listing.

Related U.S. Application Data of application No. 15/072,140, filed on Mar. 16, 2016, now abandoned, which is a continuation of application No. PCT/US2014/056175, filed on Sep. 17, 2014.

(60) Provisional application No. 61/945,715, filed on Sep. 17, 2013, provisional application No. 61/878,996, filed on Sep. 17, 2013.

(51) Int. Cl.
    C12N 9/02     (2006.01)
    C12N 9/04     (2006.01)
    C12N 9/06     (2006.01)
    C12N 9/10     (2006.01)
    C12N 9/12     (2006.01)
    C12N 9/16     (2006.01)
    C12N 9/24     (2006.01)
    C12N 9/88     (2006.01)
    C12N 15/52    (2006.01)
    C12P 7/04     (2006.01)
    C12P 7/18     (2006.01)
    C12P 7/24     (2006.01)
    C12P 7/40     (2006.01)
    C12P 7/44     (2006.01)
    C12P 7/6409   (2022.01)
    C12P 13/00    (2006.01)
    C12P 17/08    (2006.01)
    C12P 17/10    (2006.01)

(52) U.S. Cl.
    CPC .......... *C12N 9/0008* (2013.01); *C12N 9/001* (2013.01); *C12N 9/0016* (2013.01); *C12N 9/1029* (2013.01); *C12N 9/1096* (2013.01); *C12N 9/1205* (2013.01); *C12N 9/13* (2013.01); *C12N 9/16* (2013.01); *C12N 9/2402* (2013.01); *C12N 9/88* (2013.01); *C12N 9/93* (2013.01); *C12P 7/04* (2013.01); *C12P 7/18* (2013.01); *C12P 7/24* (2013.01); *C12P 7/40* (2013.01); *C12P 7/42* (2013.01); *C12P 7/44* (2013.01); *C12P 7/6409* (2013.01); *C12P 13/001* (2013.01); *C12P 13/005* (2013.01); *C12P 17/08* (2013.01); *C12P 17/10* (2013.01); *C12Y 101/01001* (2013.01); *C12Y 101/01002* (2013.01); *C12Y 101/01035* (2013.01); *C12Y 101/01078* (2013.01); *C12Y 101/01268* (2013.01); *C12Y 101/01269* (2013.01); *C12Y 102/01003* (2013.01); *C12Y 102/01005* (2013.01); *C12Y 102/01022* (2013.01); *C12Y 102/01024* (2013.01); *C12Y 102/01026* (2013.01); *C12Y 102/01048* (2013.01); *C12Y 102/01063* (2013.01); *C12Y 102/07005* (2013.01); *C12Y 102/99006* (2013.01); *C12Y 103/01044* (2013.01); *C12Y 103/01045* (2013.01); *C12Y 103/01086* (2013.01); *C12Y 104/01* (2013.01); *C12Y 203/01001* (2013.01); *C12Y 203/01032* (2013.01); *C12Y 203/01035* (2013.01); *C12Y 203/01057* (2013.01); *C12Y 206/01008* (2013.01); *C12Y 206/01009* (2013.01); *C12Y 206/01036* (2013.01); *C12Y 206/01043* (2013.01); *C12Y 206/01048* (2013.01); *C12Y 206/01076* (2013.01); *C12Y 206/01082* (2013.01); *C12Y 207/01031* (2013.01); *C12Y 207/01165* (2013.01); *C12Y 208/03* (2013.01); *C12Y 301/03* (2013.01); *C12Y 301/03002* (2013.01); *C12Y 301/03008* (2013.01); *C12Y 301/03019* (2013.01); *C12Y 301/0302* (2013.01); *C12Y 302/01* (2013.01); *C12Y 401/01001* (2013.01); *C12Y 401/02* (2013.01); *C12Y 401/02014* (2013.01); *C12Y 401/0202* (2013.01); *C12Y 401/02021* (2013.01); *C12Y 401/03016* (2013.01); *C12Y 401/03017* (2013.01); *C12Y 402/01002* (2013.01); *C12Y 402/01003* (2013.01); *C12Y 402/01028* (2013.01); *C12Y 402/0103* (2013.01); *C12Y 402/01079* (2013.01); *C12Y 402/0112* (2013.01); *C12Y 602/01* (2013.01); *Y02E 50/30* (2013.01)

(58) Field of Classification Search
    CPC ...... C12Y 402/01028; C12Y 402/0103; C12Y 402/01079; C12Y 402/0112; C12Y 602/01; Y02E 50/30
    See application file for complete search history.

(56) References Cited

U.S. PATENT DOCUMENTS

| | | |
|---|---|---|
| 2011/0177571 A1 | 7/2011 | Lee |
| 2011/0195466 A1 | 8/2011 | Burgard et al. |
| 2011/0236938 A1 | 9/2011 | Yoshikuni et al. |
| 2012/0282661 A1 | 11/2012 | Burk et al. |
| 2017/0044551 A1 | 2/2017 | Chokhawala |
| 2020/0255840 A1 | 8/2020 | Chokhawala |

FOREIGN PATENT DOCUMENTS

| | | |
|---|---|---|
| WO | WO-2013/090837 A2 | 6/2013 |
| WO | WO-2015/042201 A2 | 3/2015 |

OTHER PUBLICATIONS

Branden et al., Introduction to Protein Structure, Garland Publishing Inc., 247 (1991).

Cheng, G., 1,6-Hexanediol Process Study, Thesis, 84 pages (Mar. 1, 2006). English Abstract on p. 3.

Cheriyan et al., Directed evolution of a pyruvate aldolase to recognize a long chain acyl substrate, Bioorganic & Medicinal Chemistry, 19:6447-6453, (2011).

Ehrlich, K.C. et al., An Acid Phosphatase from *Aspergillus ficuum* Has Homology to *Penicillium chrysogenum* PhoA, Biochem. Biophys. Res. Commun., 204(1):63-68, (1994).

Hara et al., Characterization of the 4-Carboxy-4-Hydroxy-2-Oxoadipate Aldolase Gene and Operon Structure of the Proctocatechuate 4,5-Cleavage Pathway Genes in *Sphingomonas paucimobilis* SYK-6, Journal of Bacteriology, 41-50, (2003).

International Search Report for PCT/US2014/056175, 4 pages, (mailed Mar. 24, 2015).

Locus AAA62393.1, Aspergillus niger acid phosphatase protein, Accession L20566-1, 1 page (Feb. 23, 1995).

Rea, et al., Crystal Structure and Functional Assignement of YfaU, a metal Ion Dependent class II Aldolase from *Escherichia coli* K12, American Chemical Society, 47(38):9955-9965, (2008).

Sadowski., M.I., and Jones, J.T., The sequence-structure relationship and protein function prediction, Current Opinion in Structural Biology, 19:357-362, (2009).

Seffernick et al., Melamine Deaminase and Atrazine Chlorohydrolase: 98 Percent Identical but Functionally Different, J. Bacteriol. 183(8):2405-2410, (2001).

Sousa, S.,et. al., The ARO4 gene of *Candida albicans* encodes a tyrosine-sensitive DAHP synthase: evolution, functional conservation and phenotype of Aro3p-, Aro4p-deficient mutants, Microbiology148(Pt5):1291-1303, (2002).

Wang, W. et al., Comparison of two metal-dependant pyruvate alsolases related by convergent evolution:Substrate specificity, Kinetic mechanism, and substrate channeling, Biochemistry including biophysical chemistry abd molecular biology, 49(17):3774-3782, (2010).

(56) References Cited

OTHER PUBLICATIONS

Witkowski et al., Conversion of a B-Ketoacyl Synthase to a Malonyl Decaboxylase by Replacement of the Active-Site Cysteine with Glutamine, Biochemistry, 38:11643-11650, (1999).
Wolterink-Van Loo, S. et al., "Improving low-temperature activity of Sulfolobus acidocaldarius 2-keto-3-deoxygluconate aldolase," Archaea 2, 233-239, (2009).
Written Opinion for PCT/US2014/056175, 7 pages, (mailed Mar. 24, 2015).
NCBI Reference Sequence: WP_000431706.1, Multispecies: 4-hydroxy-2-oxoheptanedioate aldolase [Enterobacteriaceae], 1 page, (2019).
NCBI Reference Sequence: WP_000992954.1, Multispecies: 2-keto-3-deoxy-L-rhamnonate aldolase [Enterobacteriaceae], 1 page, (2020).
NCBI Reference Sequence: WP_003450974.1, Multispecies: 4-hydroxy-2-oxovalerate aldolase Bphl [Pseudomonadota], 2 pages, (2023).
NCBI Reference Sequence: YP_001731183, putative aldolase [*Escherichia coli* str. K-12 substr. DH10B], 2 pages, (2014).
NCBI Reference Sequence: YP_006127221, 2,4-dihydroxyhept-2-ene-1,7-dioic acid aldolase [*Escherichia coli* W], 2 pages, (2014).
NCBI Reference Sequence: YP_556399, 4-hydroxy-2-ketovalerate aldolase [Burkholderia xenovorans LB400], 2 pages, (2014).

\* cited by examiner

SEQUENCE LISTING

<160> NUMBER OF SEQ ID NOS: 3

<210> SEQ ID NO 1
<211> LENGTH: 262
<212> TYPE: PRT
<213> ORGANISM: Escherichia coli

<400> SEQUENCE: 1

Met Glu Asn Ser Phe Lys Ala Ala Leu Lys Ala Gly Arg Pro Gln Ile
1               5                   10                  15

Gly Leu Trp Leu Gly Leu Ser Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
    50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln
                85                  90                  95

Asn Ala Asp Glu Ala Arg Glu Ala Val Arg Ala Thr Arg Tyr Pro Pro
            100                 105                 110

Ala Gly Ile Arg Gly Val Gly Ser Ala Leu Ala Arg Ala Ser Arg Trp
        115                 120                 125

Asn Arg Ile Pro Asp Tyr Leu Gln Lys Ala Asn Asp Gln Met Cys Val
    130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
            180                 185                 190

Ala Ala Ile Glu Gln Ala Ile Val Gln Ile Arg Glu Ser Gly Lys Ala
        195                 200                 205

Pro Gly Ile Leu Ile Ala Asn Glu Gln Leu Ala Lys Arg Tyr Leu Glu
    210                 215                 220

```
Leu Gly Ala Leu Phe Ala Val Gly Val Asp Thr Thr Leu Leu Ala
225                 230                 235                 240

Arg Ala Ala Glu Ala Leu Ala Ala Arg Phe Gly Ala Gln Ala Thr Ala
                245                 250                 255

Val Lys Pro Gly Val Tyr
            260

<210> SEQ ID NO 2
<211> LENGTH: 267
<212> TYPE: PRT
<213> ORGANISM: Escherichia coli

<400> SEQUENCE: 2

Met Asn Ala Leu Leu Ser Asn Pro Phe Lys Glu Arg Leu Arg Lys Gly
1               5                   10                  15

Glu Val Gln Ile Gly Leu Trp Leu Ser Ser Thr Thr Ala Tyr Met Ala
            20                  25                  30

Glu Ile Ala Ala Thr Ser Gly Tyr Asp Trp Leu Leu Ile Asp Gly Glu
        35                  40                  45

His Ala Pro Asn Thr Ile Gln Asp Leu Tyr His Gln Leu Gln Ala Val
    50                  55                  60

Ala Pro Tyr Ala Ser Gln Pro Val Ile Arg Pro Val Glu Gly Ser Lys
65                  70                  75                  80

Pro Leu Ile Lys Gln Val Leu Asp Ile Gly Ala Gln Thr Leu Leu Ile
                85                  90                  95

Pro Met Val Asp Thr Ala Glu Gln Ala Arg Gln Val Val Ser Ala Thr
            100                 105                 110

Arg Tyr Pro Pro Tyr Gly Glu Arg Gly Val Gly Ala Ser Val Ala Arg
        115                 120                 125

Ala Ala Arg Trp Gly Arg Ile Glu Asn Tyr Met Ala Gln Val Asn Asp
    130                 135                 140

Ser Leu Cys Leu Leu Val Gln Val Glu Ser Lys Thr Ala Leu Asp Asn
145                 150                 155                 160

Leu Asp Glu Ile Leu Asp Val Glu Gly Ile Asp Gly Val Phe Ile Gly
                165                 170                 175

Pro Ala Asp Leu Ser Ala Ser Leu Gly Tyr Pro Asp Asn Ala Gly His
            180                 185                 190

Pro Glu Val Gln Arg Ile Ile Glu Thr Ser Ile Arg Arg Ile Arg Ala
        195                 200                 205

Ala Gly Lys Ala Ala Gly Phe Leu Ala Val Ala Pro Asp Met Ala Gln
    210                 215                 220

Gln Cys Leu Ala Trp Gly Ala Asn Phe Val Ala Val Gly Val Asp Thr
225                 230                 235                 240

Met Leu Tyr Ser Asp Ala Leu Asp Gln Arg Leu Ala Met Phe Lys Ser
                245                 250                 255

Gly Lys Asn Gly Pro Arg Ile Lys Gly Ser Tyr
            260                 265

<210> SEQ ID NO 3
<211> LENGTH: 346
<212> TYPE: PRT
<213> ORGANISM: Burkholderia xenovorans

<400> SEQUENCE: 3

Met Lys Leu Glu Gly Lys Lys Val Thr Val His Asp Met Thr Leu Arg
1               5                   10                  15
```

```
Asp Gly Met His Pro Lys Arg His Gln Met Thr Leu Glu Gln Met Lys
            20                  25                  30

Ser Ile Ala Cys Gly Leu Asp Ala Ala Gly Ile Pro Leu Ile Glu Val
            35                  40                  45

Thr His Gly Asp Gly Leu Gly Gly Ser Ser Val Asn Tyr Gly Phe Pro
            50                  55                  60

Ala His Ser Asp Glu Glu Tyr Leu Gly Ala Val Ile Pro Leu Met Lys
65                  70                  75                  80

Gln Ala Lys Val Ser Ala Leu Leu Leu Pro Gly Ile Gly Thr Val Glu
                85                  90                  95

His Leu Lys Met Ala Lys Asp Leu Gly Val Asn Thr Ile Arg Val Ala
                100                 105                 110

Thr His Cys Thr Glu Ala Asp Val Ser Glu Gln His Ile Thr Gln Ser
            115                 120                 125

Arg Lys Leu Gly Leu Asp Thr Val Gly Phe Leu Met Met Ala His Met
130                 135                 140

Ala Ser Pro Glu Lys Leu Val Ser Gln Ala Leu Leu Met Gln Gly Tyr
145                 150                 155                 160

Gly Ala Asn Cys Ile Tyr Val Thr Asp Ser Ala Gly Tyr Met Leu Pro
                165                 170                 175

Asp Asp Val Lys Ala Arg Leu Ser Ala Val Arg Ala Ala Leu Lys Pro
            180                 185                 190

Glu Thr Glu Leu Gly Phe His Gly His His Asn Leu Ala Met Gly Val
            195                 200                 205

Ala Asn Ser Ile Ala Ala Ile Glu Ala Gly Ala Thr Arg Ile Asp Ala
            210                 215                 220

Ala Ala Ala Gly Leu Gly Ala Gly Ala Gly Asn Thr Pro Met Glu Val
225                 230                 235                 240

Phe Ile Ala Val Cys Ala Arg Met Gly Ile Glu Thr Gly Val Asp Val
            245                 250                 255

Phe Lys Ile Gln Asp Val Ala Glu Asp Leu Val Val Pro Ile Met Asp
            260                 265                 270

His Val Ile Arg Ile Asp Arg Asp Ser Leu Thr Leu Gly Tyr Ala Gly
            275                 280                 285

Val Tyr Ser Ser Phe Leu Leu Phe Ala Lys Arg Ala Ser Ala Lys Tyr
            290                 295                 300

Gly Val Pro Ala Arg Asp Ile Leu Val Glu Leu Gly Arg Arg Gly Met
305                 310                 315                 320

Val Gly Gly Gln Glu Asp Met Ile Glu Asp Thr Ala Met Thr Met Ala
                325                 330                 335

Arg Glu Arg Gly Leu Thr Leu Thr Ala Ala
                340                 345
```

PRODUCTION OF 4,6-DIHYDROXY-2-OXO-HEXANOIC ACID

CROSS-REFERENCE TO RELATED APPLICATIONS

This application is a Continuation of Ser. No. 16/595,252, filed on Oct. 7, 2019, which is a Continuation of Ser. No. 15/072,140, filed on Mar. 16, 2016, which is a Continuation of International Application No. PCT/US2014/056175, filed on Sep. 17, 2014, which in turn claims the benefit under 35 U.S.C. § 119(e) of U.S. Provisional Application No. 61/878,996, filed on Sep. 17, 2013, and 61/945,715, filed on Feb. 27, 2014. All of the above-mentioned applications are incorporated herein by reference in their entirety.

SEQUENCE LISTING

This application contains a Sequence Listing which has been submitted electronically in TXT format and is hereby incorporated by reference in its entirety. Said TXT copy, created on May 9, 2024, is named "SequenceListing.txt" and is 8, 124 bytes in size.

TECHNICAL FIELD

This disclosure relates generally to compositions and methods of preparation of industrially useful alcohols, amines, lactones, lactams, and acids, linear fatty acids and linear fatty alcohols that are between 7-25 carbons long, linear alkanes and linear α-alkenes that are between 6-24 carbons long.

BACKGROUND

Throughout this disclosure, various publications, patents and published patent specifications are referenced by an identifying citation or by reference to an Arabic numeral. These publications, patents, and published patent specifications are hereby incorporated by reference in their entirety into the present disclosure to more fully describe the state of the art.

Adipic acid (ADA) is a widely used chemical with an estimated 2.3 million metric tons demand in 2012 (IHS Chemical, Process Economics Program Report: Bio-Based Adipic Acid (December 2012)). Along with hexamethylenediamine (HMDA) it is used in the production of nylon6,6, polyester resins, plasticizers, foods, and other materials. Thus, methods of preparing adipic acid and HMDA in high yield using renewable sources are highly desirable.

Glutaric acid is mainly used industrially for the production of 1,5-pentanediol, a major component of polyurethanes and polyesters. 1,6-Hexanediol, is a linear diol with terminal hydroxyl groups. It is used in polyesters for industrial coating applications, two-component polyurethane coatings for automotive applications. It is also used for production of macrodiols for example adipate esters and polycarbonate diols used in elastomers and polyurethane dispersions for parquet flooring and leather coatings.

1-Butanol, 1-pentanol and 1-hexanol are widely used as industrial solvents. They can also be dehydrated to make 1-butene, 1-pentene, 1-hexence which are used as co-monomers for polyethylene applications. 1-Butanol is also a good substitute for gasoline. 1-Hexanol is directly used in the perfume industry (as a fragrance), as a flavoring agent, as an industrial solvent, a pour point depressant and as an agent to break down foam. It is also a valuable intermediate in the chemical industry.

6-Amino-hexanoic acid (also referred to as 6-amino-caproic acid or ε-amino-caproic acid) can be converted to ε-Caprolactam by cyclization. ε-Caprolactam is used for the production of Nylon6, a widely used polymer in many different industries. Thus methods for more efficient production of ε-Caprolactam precursor 6-amino hexanoic acid are industrially important. 6-hydroxy hexanoic acid can be cyclized to make ε-Caprolactone which can then be aminated to make ε-Caprolactam.

Butyric acid, pentanoic acid and hexanoic acid are widely used indsutrially for the preparation of esters with applications in food, additives and plastics industry.

Linear fatty acids ($C_7$-$C_{25}$) represent a class of molecules that are only one catalytic step away from petroleum-derived diesel molecules. In addition to being incorporated into biodiesel through acid-catalyzed esterification, free fatty acids can be catalytically decarboxylated, giving rise to linear alkanes in the diesel range. Fatty acids are used commercially as surfactants, for example, in detergents and soaps.

Alkanes and α-alkenes having more than sixteen carbon atoms are important components of fuel oils and lubricating oils. Even longer alkanes, which are solid at room temperature, can be used, for example, as a paraffin wax. Longer chain alkanes (e.g., from five to sixteen carbons) are used as transportation fuels (e.g., gasoline, diesel, or aviation fuel).

Linear fatty alcohols ($C_7$-$C_{25}$) are mainly used in the production of detergents and surfactants. Due to their amphiphilic nature, fatty alcohols behave as nonionic surfactants, which are useful as detergents.

Linear fatty diacid sebacic acid can be used in plasticizers, lubricants, hydraulic fluids, cosmetics, candles, etc. Sebacic acid is also used as an intermediate for aromatics, antiseptics, and painting materials. Dodecanedioic acid is used for manufacturing of adhesives, lubricants, polyamide fibres, resins, polyester coatings and plasticizers. Thus methods for more efficient production of these chemicals are industrially important.

SUMMARY

Disclosed herein are novel methods, compositions and non-naturally occurring microbial organisms for preparing 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear cx-alkenes that are between 6-24 carbons long, sebacic acid and dodecanedioic acid in high yield using renewable sources.

In one aspect, this disclosure provides a method for preparing a compound of Formula I, II, III or IV:

(I)

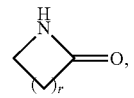
(II)

-continued

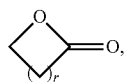
(III)

(IV)

wherein
$R^1$ is $CH_2OH$, $CH_2NH_2$ or $CO_2H$,
$R^2$ is $CH_3$, $CH_2OH$, $CH_2NH_2$ or $CO_2H$,
$R^3$ is $CH_2CH_3$ or $CH=CH_2$,
r is 4;
s is 2, 3, 4, 5, 6, 7, 8, 9, 10, 11, 12, 13, 14, 15, 16, 17, 18, 19, 20, 21, 22 or 23,
t is 3, 4, 5, 6, 7, 8, 9, 10, 11, 12, 13, 14, 15, 16, 17, 18, 19, 20 or 21,
or a salt thereof, or a solvate of the compound or the salt, which method comprises enzymatic steps or a combination of enzymatic and chemical steps.

In some aspects, the method above comprises, or alternatively consists essentially of, or yet further consists of, combining or incubating a $C_N$ aldehyde and a pyruvate in a solution under conditions that (a) convert the $C_N$ aldehyde and the pyruvate to a $C_{N+3}$ β-hydroxyketone intermediate through an aldol addition; and then (b) convert the $C_{N+3}$ β-hydroxyketone intermediate to the compound of Formula I, II, III or IV or salt thereof, or a solvate of the compound or the salt, through enzymatic steps or a combination of enzymatic and chemical steps. In some aspects, N is s-1 or N=t+1 or N=r−1, wherein N is 1-22 preferably N is 1-6, s is 2-23 preferably s is 2-7, tis 2-21, preferably t is 9-19. In certain aspects, N=s provided s=3. In some aspects, N is not equal to s.

In some aspects, this disclosure provides a method for preparing a compound selected from 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid, or a mixture thereof, or a salt thereof, or a solvate of the compound or the salt, said method comprising, or alternatively consisting essentially of, or yet further consisting of: a) converting a $C_N$ aldehyde and a pyruvate to a $C_{N+3}$ β-hydroxyketone intermediate through an aldol addition; and b) converting the $C_{N+3}$ β-hydroxyketone intermediate to the compound through enzymatic steps or a combination of enzymatic and chemical steps, wherein N is M−3, wherein M is the number of carbon in the compound being prepared and N is 1, 2, 3, 4, 5, 6, 7, 8, 9, 10, 11, 12, 13, 14, 15, 16, 17, 18, 19, 20, 21 or 22.

In one aspect of the above noted methods, a microorganism is used as a host for the preparation of a compound of Formula I, II, III or IV, or a compound selected from 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid, or a salt thereof, or a solvate of the compound or the salt. As used herein, a "host" refers to a cell or microorganism that can produce one or more enzymes capable of catalyzing a reaction either inside (by, e.g., uptaking the starting material(s) and optionally secreting the product(s)) or outside (by, e.g., secreting the enzyme) the cell or microorganism.

One aspect of the present disclosure provides a method for preparing a compound selected from 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid or a mixture thereof, or a salt thereof, or a solvate of the compound or the salt, the method comprises or alternatively consists essentially of, or yet further consists of, combining or incubating a $C_N$ aldehyde and a pyruvate in a solution under conditions that (a) convert the $C_N$ aldehyde and the pyruvate to a $C_{N+3}$ β-hydroxyketone intermediate through an aldol addition; and then (b) convert the $C_{N+3}$ β-hydroxyketone intermediate to the compound through enzymatic steps, wherein N is M−3, wherein M is the number of carbon in the compound being prepared and N is 1, 2, 3, 4, 5, 6, 7, 8, 9, 10, 11, 12, 13, 14, 15, 16, 17, 18, 19, 20, 21 or 22.

In some aspects, the method further comprises or alternatively consists essentially of, or yet further consists of, isolating the compound of Formula I, II, III or IV, or 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic or dodecanedioic acid or a salt thereof, or a solvate of the compound or the salt from the solution, culture, and/or the host cell.

In some aspects of the above methods, the conditions comprise or alternatively consist essentially of, or yet further consist of, the presence of a class I/II pyruvate dependent aldolase. In some aspects, the conditions comprise, or alternatively consist essentially of, or yet further consist of, the incubating the reactants in the presence of one or more enzymes selected from the group consisting of dehydratase, reductase, aldehyde dehydrogenase, primary alcohol dehydrogenase, secondary alcohol dehydrogenase, phosphatase, keto-acid decarboxylase, kinase, coenzyme A transferase, coenzyme A synthase, thioesterase, coenzyme A dependent oxidoreductase, carboxylic acid reductase, transaminase, amino acid dehydrogenase, amine oxidase, lactonase, lactamase, fatty acid decarboxylase, aldehyde decarbonylase, N-acetyltransferase, and peptide synthase.

In some aspects, the conditions of the above methods comprise or alternatively consist essentially of, or yet further consist of, incubating or contacting the components at a temperature from about 10 to about 200° C., or alternatively at least (all temperatures provided in degrees Celcius) 10, 15, 20, 25, 28, 29, 30, 31, 32, 33, 34, 35, 37, 37, 38, 39, 40, 45, 50, 60, 70, 80, 90, 100, 110, 120, 130, 140, 150, 160, 170, 180 or 190° C., or not higher than 190, 180, 170, 160, 150, 140, 130, 120, 110, 100, 90, 80, 70, 60, 50, 40, 39, 38, 37, 36, 35, 34, 33, 32, 31, 30, 29, 28, or 25° C. with the lower temperature limit being 10. In some aspects, the conditions or alternatively consists essentially of, or yet further consists of, the pH of the incubation solution is from about 2 to about 12. In some aspects, the pH is at least 2, or 3, 4, 5, 5.5, 6, 6.5, 7, 7.5, 8, or 9 up to about 12. In some aspects, the pH is not higher than 12, 11, 10, 9, 8, 7.5, 7, 6.5, 6, 5.5, or 4 with the lower pH limit being no lower than 2.

In some aspects, the conditions comprise or alternatively consist essentially of, or yet further consist of, a molar concentration of pyruvate and $C_N$ aldehyde are present at a concentration from about 0.1 µMolar to about 5 Molar. In some aspects, the concentration is at least about 0.1, 0.5, 1, 10, 100, 500 µM or 1 M. In some aspects, the concentration is not higher than about 4 M, 3 M, 2 M, 1 M, 500 M, 200 µM, 100 µM, or 10 µM. The concentration of pyruvate and $C_N$ can be independently the same or different and will vary with the other conditions of the incubation.

In some aspects, the conditions comprise the presence of a non-natural microorganism that produces one or more enzymes selected from the group consisting of a class I/II pyruvate dependent aldolase, dehydratase, reductase, aldehyde dehydrogenase, primary alcohol dehydrogenase, secondary alcohol dehydrogenase, phosphatase, keto-acid decarboxylase, kinase, coenzyme A transferase, coenzyme A synthase, thioesterase, coenzyme A dependent oxidoreductase, carboxylic acid reductase, transaminase, amino acid dehydrogenase, amine oxidase, lactonase, lactamase, fatty acid decarboxylase, aldehyde decarbonylase, N-acetyltransferase, and peptide synthase. Each of these enzymes will be a reaction specific enzyme.

In some aspects, the microorganism or host is genetically engineered to overexpress the enzymes or to express enzymes in an amount greater than the wild-type counterpart. Methods to determine the expression level of an enzyme or expression product are known in the art, e.g., by PCR.

In some aspects of the above methods, the C3 aldehyde is not glyceraldehyde.

In some aspects, the enzymatic or chemical steps comprise enoyl or enoate reduction, ketone reduction, primary alcohol oxidation, secondary alcohol oxidation, aldehyde oxidation, aldehyde reduction, dehydration, decarboxylation, thioester formation, thioester hydrolysis, trans thioesterification, thioester reduction, phosphate ester hydrolysis, lactonization, lactam formation, lactam hydrolysis, lactone hydrolysis, carboxylic acid reduction, amination, aldehyde decarbonylation, primary amine acylation, or combinations thereof.

In some aspects, the C3 aldehyde is selected from a group comprising or alternatively consisting essentially of, or yet further consisting of, 3-oxo-propionic acid, 3-hydroxypropanal, 3-amino-propanal, or propanal. In some aspects, C2 aldehyde is selected from the group consisting of acetaldehyde, hydroxyl acetaldehyde, or glyoxylate. In some aspects, Cx aldehyde is linear chain aldehyde where N corresponds to the carbon chain length of the aldehyde, wherein N is M–3, wherein M is the number of carbon in the compound being prepared and N is 1, 2, 3, 4, 5, 6, 7, 8, 9, 10, 11, 12, 13, 14, 15, 16, 17, 18, 19, 20, 21 or 22.

In some aspects, the method further comprises or alternatively consists essentially of, or yet further consists of, preparing the C3 aldehyde and pyruvate from glycerol, C5 sugars, C6 sugars, phospho-glycerates, other carbon sources, intermediates of the glycolysis pathway, intermediates of propanoate metabolism, or combinations thereof.

In some aspects, the C3 aldehyde is obtained through a series of enzymatic steps, wherein the enzymatic steps comprise or alternatively consist essentially of, or yet further consist of, phosphate ester hydrolysis, alcohol oxidation, diol-dehydration, aldehyde oxidation, aldehyde reduction, thioester reduction, trans thioesterification, decarboxylation, carboxylic acid reduction, amination, primary amine acylation, or combinations thereof.

In some aspects, the C5 sugar comprises or alternatively consists essentially of, or yet further consists of, one or more of xylose, xylulose, ribulose, arabinose, lyxose, and ribose.

In some aspects, the C6 sugar comprises or alternatively consists essentially of, or yet further consists of, one or more of allose, altrose, glucose, mannose, gulose, idose, talose, galactose, fructose, psicose, sorbose, and tagatose.

In some aspects, the other carbon source is a feedstock suitable as a carbon source for a microorganism, wherein the feedstock comprises or alternatively consists essentially of, or yet further consists of, amino acids, lipids, corn stover, *miscanthus*, municipal waste, energy cane, sugar cane, bagasse, starch stream, dextrose stream, methanol, formate, or combinations thereof.

In some aspects of the above methods, a microorganism is used as a host for the preparation of 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid.

In some aspects, the microorganism contains endogenous or exogenously added genes transiently or permanently encoding the enzymes necessary to catalyze the enzymatic steps of converting a $C_N$ aldehyde and pyruvate to a $C_{N+3}$ β-hydroxyketone intermediate, and/or endogenous or exogenously added genes transiently or permanently encoding the enzymes necessary to catalyze the enzymatic steps of converting the $C_{N+3}$ β-hydroxyketone intermediate to 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid wherein N is M-3, wherein M is the number of carbon in the compound being prepared and N is 1, 2, 3, 4, 5, 6, 7, 8, 9, 10, 11, 12, 13, 14, 15, 16, 17, 18, 19, 20, 21 or 22.

In some aspects, the microorganism has the ability to convert C5 sugars, C6 sugars, glycerol, other carbon sources, or a combination thereof to pyruvate.

In some aspects, the microorganism is engineered for enhanced sugar uptake, e.g., C5 sugar uptake, simultaneous C6/C5 sugar uptake, simultaneous C6 sugar/glycerol uptake, simultaneous C5 sugar/glycerol uptake, or combinations thereof.

BRIEF DESCRIPTION OF THE DRAWINGS AND TABLES

FIG. 1 shows the various pathways for the synthesis of C3 aldehydes such as 3-oxo-propionic acid, 3-hydroxy-propanal, 3-amino-propanal and propanal, from C6/C5 sugars and/or glycerol and their interconversion by enzymatic transformations. Enzymes that can catalyze the various steps in the synthesis of C3 aldehydes are shown in parenthesis. Cofactors required for catalysis of each step have been omitted to improve clarity. As used herein, PP pathway stands for pentose phosphate pathway.

Figure 2:
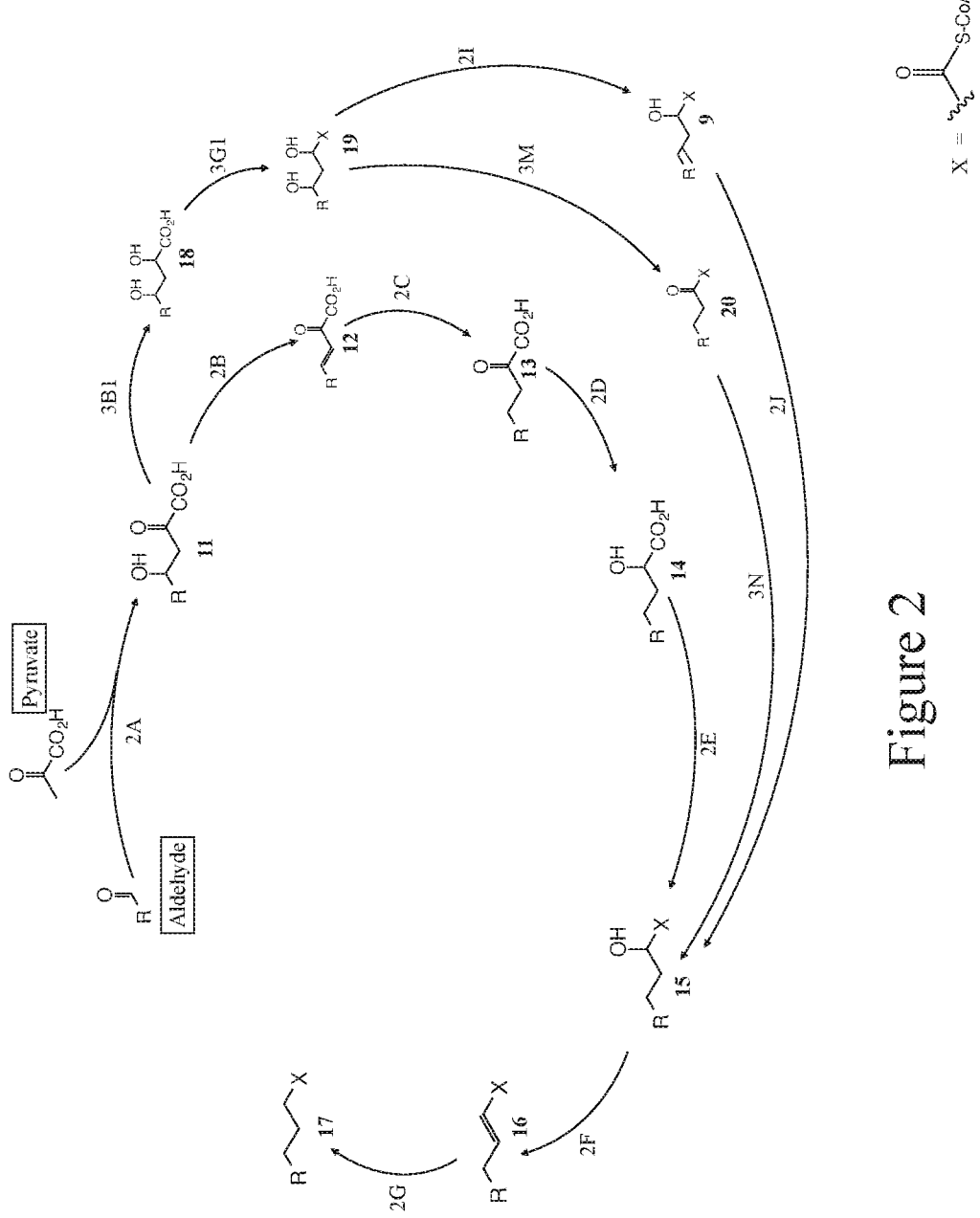

FIG. 2 shows exemplary pathways for synthesis of adipyl-CoA, 6-hydroxy-adipyl-CoA, and 6-aminoadipyl-CoA from pyruvate and C3 aldehydes 3-oxo-propionic acid (R=CH$_2$COOH), 3-hydroxypropanal (R=CH$_2$CH$_2$OH) and 3-amino-propanal (R=CH$_2$CH$_2$NH$_2$).

Figure 3:
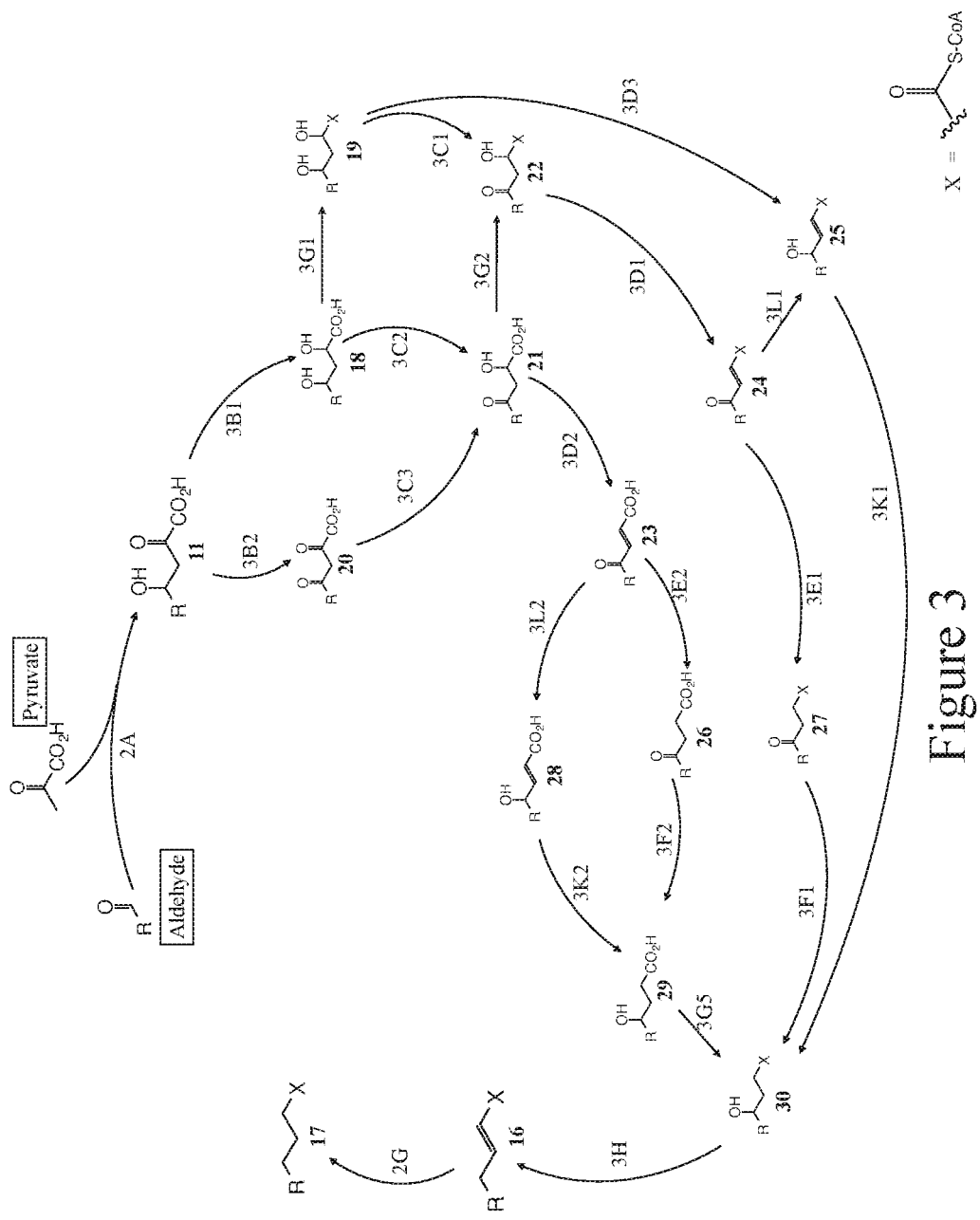

FIG. 3 shows exemplary pathways for synthesis of adipyl-CoA, 6-hydroxy-adipyl-CoA, and 6-aminoadipyl-CoA from pyruvate and C3 aldehydes 3-oxo-propionic acid (R=CH$_2$COOH), 3-hydroxypropanal (R=CH$_2$CH$_2$OH) and 3-amino-propanal (R=CH$_2$CH$_2$NH$_2$).

Figure 4:
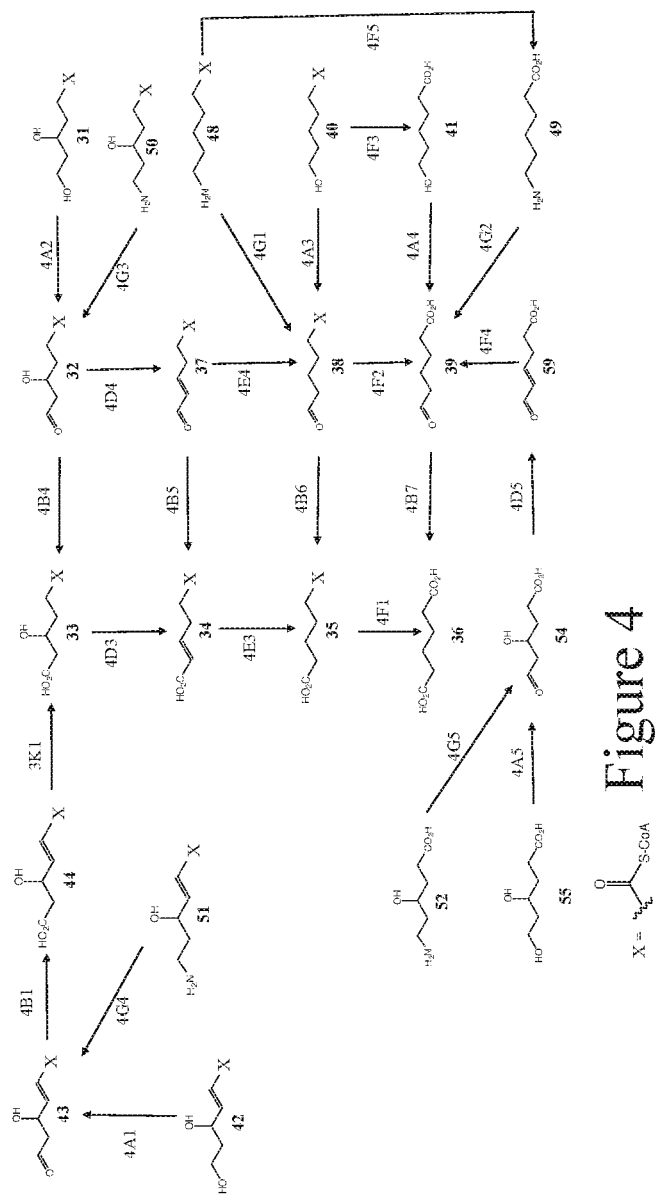

FIG. 4 shows additional pathways for synthesis of adipic acid from intermediates in FIGS. 2 and 3.

Figure 5:
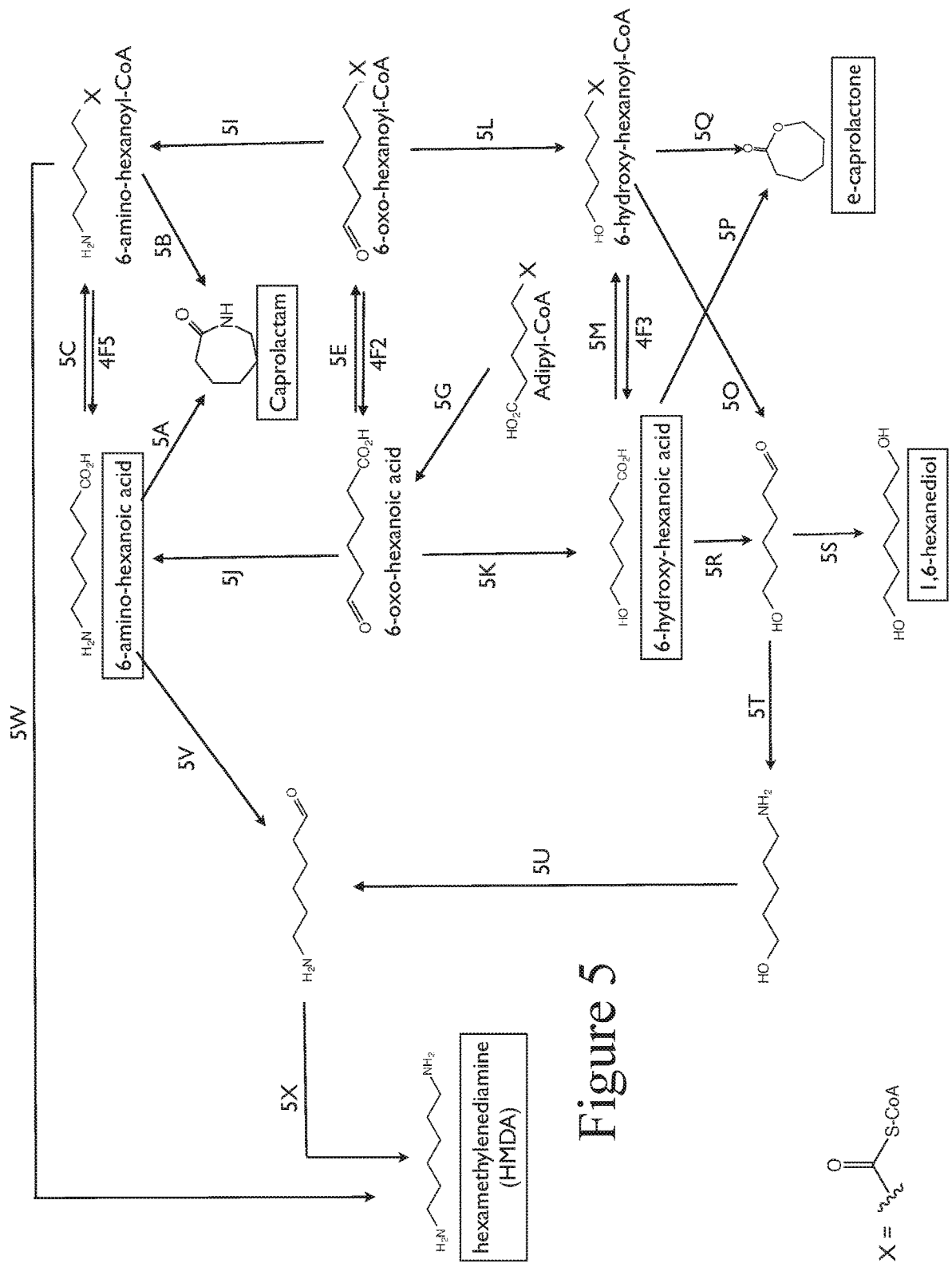

FIG. 5 shows the synthesis of 1,6-hexanediol, 6-hydroxy hexanoate, ε-Caprolactone, 6-amino-hexanoate, ε-Caprolactam, and hexamethylenediamine, from precursors 6-amino-hexanoate, 6-hydroxy hexanoate, 6-hydroxy hexanoyl-CoA, 6-amino-hexanoyl-CoA, 6-oxohexanoate and 6-oxo-hexanoyl-CoA. Synthesis of these precursors from pyruvate and C3 aldehydes (3-oxo-propionic acid, 3-hydroxy-propanal and 3-amino-propanal) is depicted in FIGS. 2-4.

Figure 6:
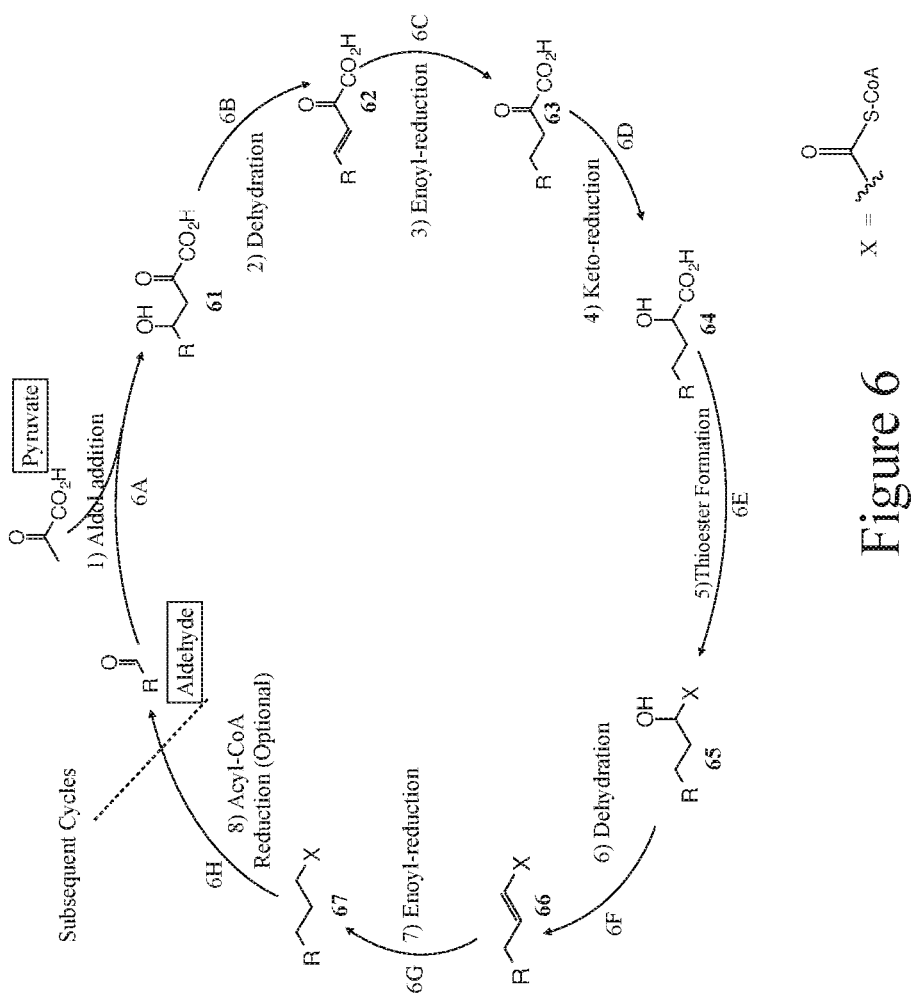

FIG. 6 shows the cyclical pathway for the synthesis of acyl-CoA from pyruvate and linear aldehydes through 2-hydroxy-acyl-CoA intermediates. The steps depicted correspond to the following transformations: Step 1: aldol addition (catalyzed by aldolase), Step 2: dehydration (catalyzed by dehydratase), Step 3: reduction (catalyzed by reductase), Step 4: reduction (catalyzed by secondary alcohol dehydrogenase), Step 5: thioester formation (catalyzed by coenzyme A transferase or ligase), Step 6: dehydration (catalyzed by dehydratase), Step 7: reduction (catalyzed by enoyl reductase), Step 8: optional reduction (catalyzed by reductase). Each elongation cycle (Steps 1-7) results in the extension of the starting linear aldehyde by 3-carbons. Starting with a $C_N$ aldehyde (N=number of carbons) will result in an acyl-CoA that is $C_{N+3x}$ carbons long (N=number of carbons in starting aldehyde and x=number of elongation cycles). Some cofactors required for catalysis have been omitted to improve clarity.

Figure 7:
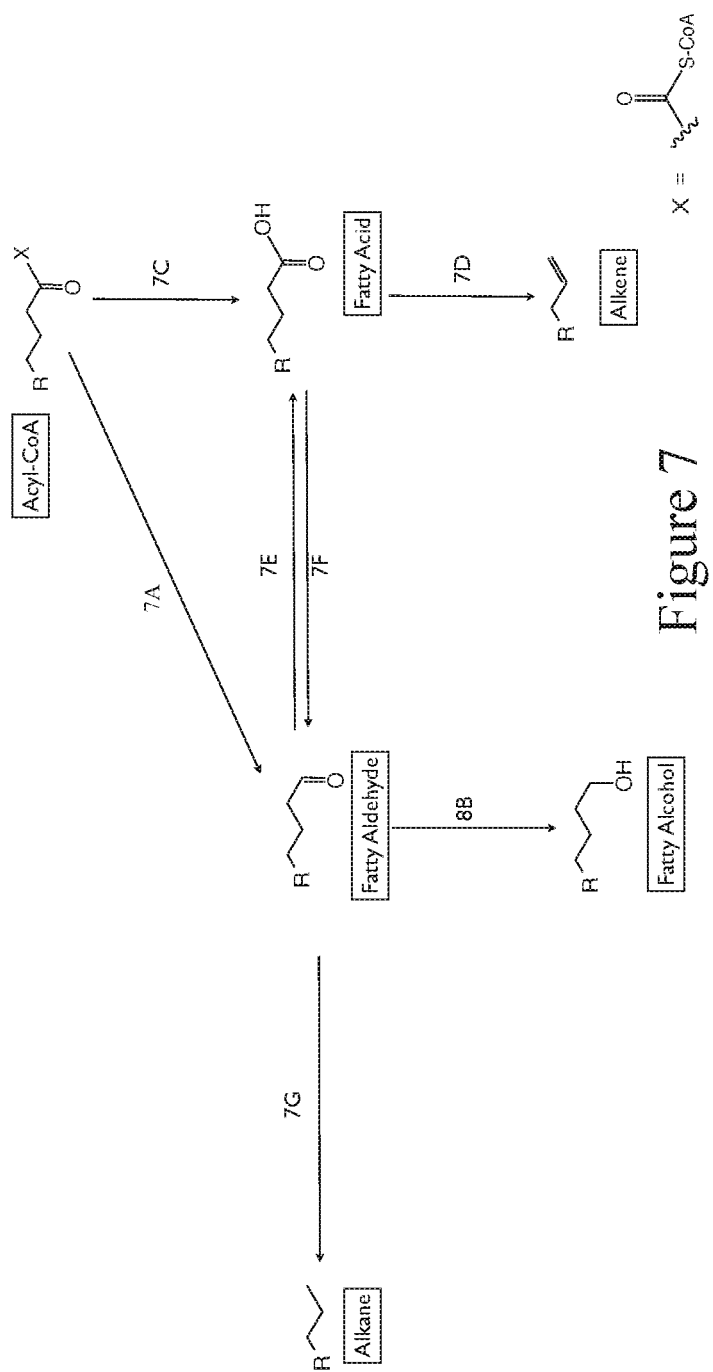

FIG. 7 shows the conversion of Acyl-CoA synthesized as shown in FIG. 6 to alcohols (fatty alcohols), acids (fatty acids), alkanes and α-alkenes. Cofactors required for catalysis of each step have been omitted to improve clarity.

DETAILED DESCRIPTION

Definitions

As used herein, certain terms may have the following defined meanings. As used herein, the singular form "a," "an" and "the" include singular and plural references unless the context clearly indicates otherwise.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Aspects defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Wild-type" defines the cell, composition, tissue or other biological material as its exists in nature.

As used herein, the term "C3 aldehyde" refers to any linear alkyl compound consisting of three carbons, wherein one terminal carbon is part of an aldehyde functional group. In all aspects of the invention, the C3 aldehyde does not include glyceraldehyde. In some aspects, the C3 aldehyde is selected from a group comprising 3-oxopropionic acid, 3-hydroxypropanal, 3-aminopropanal, or propanal.

As used herein, the term "$C_N$ aldehyde" refers to any linear alkyl compound consisting of N carbons, wherein one terminal carbon is part of an aldehyde functional group and the other terminal carbon can be unsubstituted, or be a part of a carobyxlate group, or bear a hydroxyl, amino, or acetamido group. In some aspects, N is 1, 2, 3, 4, 5, 6, 7, 8, 9, 10, 11, 12, 13, 14, 15, 16, 17, 18, 19, 20, 21, or 22 or any range between two of the numbers, end points inclusive.

In one aspect of the invention, the C3 aldehyde and pyruvate are prepared from one or more of glycerol, C5 sugars, C6 sugars, phosphor-glycerates, other carbon sources, intermediates of the glycolysis pathway, intermediates of the propanoate pathway or combinations thereof through a series of enzymatic steps, wherein the steps comprise or alternatively consist essentially of, or yet further consist of, phosphate ester hydrolysis, alcohol oxidation, diol-dehydration, aldehyde oxidation, aldehyde reduction, thioester reduction, trans thioesterification, decarboxylation, carboxylic acid reduction, amination, primary amine acylation, and combinations thereof. In another aspect, the C5 sugars comprise or alternatively consists essentially of, or yet further consists of, one or more of xylose, xylulose, ribulose, arabinose, lyxose, and ribose and the C6 sugars comprise or alternatively consist essentially of, or yet further consist of, allose, altrose, glucose, mannose, gulose, idose, talose, fructose, psicose, sorbose, and tagatose. In a further aspect, the other carbon source is a feedstock suitable as a carbon source for a microorganism wherein the feedstock comprises or alternatively consists essentially of, or yet further consists of, one or more of amino acids, lipids, corn stover, *miscanthus*, municipal waste, energy cane, sugar cane, bagasse, starch stream, dextrose stream, formate, methanol, and combinations thereof.

As used herein, the term "C5 sugar" refers to a sugar molecule containing 5 carbons.

As used herein, the term "C6 sugar" refers to a sugar molecule containing 6 carbons.

As used herein, the term "aldol addition" refers to a chemical reaction in which a pyruvate molecule forms a corresponding enol or an enolate ion or a schiff's base or an enamine that reacts with the aldehyde functional group of the $C_N$ aldehyde to produce a $C_{N+3}$ β-hydroxyketone intermediate. In some aspects, the $C_N$ aldehyde is C3 aldehyde and the $C_{N+3}$ β-hydroxyketone intermediate is C6 β-hydroxyketone intermediate.

As used herein, the term $C_{N+3}$ β-hydroxyketone intermediate" refers to a linear alkyl compound consisting of N+3 carbons that is a product of an aldol addition between a $C_N$ aldehyde and pyruvate, wherein a terminal carbon is part of a carboxylic acid functional group, the adjacent carbon is part of a ketone functional group, and the second carbon to the ketone carbon is covalently bonded to a hydroxyl functional group, such as shown in the formula below:

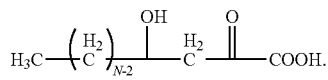

In some aspects, the $C_{N+3}$ β-hydroxyketone intermediate is a C6 β-hydroxyketone intermediate having 6 carbons.

In one aspect of the invention, the $C_{N+3}$ β-hydroxyketone intermediate is converted to one or more of: 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid through enzymatic steps or a combination of enzymatic and chemical steps. In another aspect, the enzymatic or chemical steps comprise or alternatively consists essentially of, or yet further consists of, one or more of enoyl or enoate reduction, ketone reduction, primary alcohol oxidation, secondary alcohol oxidation, aldehyde oxidation, aldehyde reduction, dehydration, decarboxylation, thioester formation, thioester hydrolysis, trans thioesterification, thioester reduction, lactonization, lactam formation, lactam hydrolysis, lactone hydrolysis, carboxylic acid reduction, amination, aldehyde deacarbonylation, primary amine acylation, primary amine deacylation, and combinations thereof.

As used herein, the following compounds have the following structures

| | |
|---|---|
| linear fatty acids that are between 7-25 carbons long | 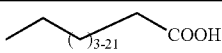 |
| linear fatty alcohols that are between 7-25 carbons long | 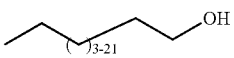 |
| linear alkanes that are between 6-24 carbons long | 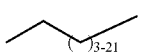 |
| linear α-alkenes that are between 6-24 carbons long | 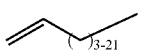 |

As used herein, the term "solution" refers to a liquid composition that contains a solvent and a solute, such as a starting material used in the methods described herein. In one aspect, the solvent is water. In another aspect, the solvent is an organic solvent.

As used herein, the term "enzymatic step" or "enzymatic reaction" refers to a molecular reaction catalyzed by an enzyme that is selected to facilitate the desired enzymatic reaction. Enzymes are large biological molecules and highly selective catalysts. Most enzymes are proteins, but some catalytic RNA molecules have been identified.

Throughout the application, enzymatic steps are denoted as "step 2A", "step 2B" and so on so forth and the enzyme specifically catalyzing these steps is denoted as "2A", "2B" and so on so forth, respectively. Such a enzyme is also referred to as a "reaction specific enzyme".

As used herein, the term "CoA" or "coenzyme A" is intended to mean an organic cofactor or prosthetic group (nonprotein portion of an enzyme) whose presence is required for the activity of many enzymes to form an active enzyme system.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "non-naturally occurring" or "non-natural" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary polypeptides include enzymes or proteins of a 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid synthesis pathway described herein.

As is used herein "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a enzymatic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is originally or naturally present in the wild-type host. Similarly, the term when used in reference to expression of an encoding nucleic acid refers to expression of an encoding nucleic acid contained within the wild-type microorganims.

The term "heterologous" refers to a molecule or activity derived from a source other than the referenced species whereas "homologous" when used in this context refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism, that the more than one exogenous nucleic acids refers to the referenced encoding nucleic acid or enzymatic activity, as discussed above. It is further understood, as disclosed herein, that more than one exogenous nucleic acids can be introduced into the host microbial organism on separate nucleic acid molecules, on polycistronic nucleic acid molecules, or a combination thereof, and still be considered as more than one exogenous nucleic acid. For example as disclosed herein, a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or enzymatic activities refers to the number of encoding nucleic acids or the number of enzymatic activities, not the number of separate nucleic acids introduced into the host organism.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

Those skilled in the art will understand that the genetic alterations, are described with reference to a suitable host organism such as *E. coli* and their corresponding metabolic reactions or a suitable source organism for desired genetic material such as genes for a desired biosynthetic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

Sources of encoding nucleic acids the pathway enzymes can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Pseudomonas knackmussii, Pseudomonas putida, Pseudomonas fluorescens, Klebsiella pneumoniae, Serratia proteamaculans, Streptomyces* sp. 2065, *Pseudomonas aeruginosa, Ralstonia eutropha, Clostridium acetobutylicum, Euglena gracilis, Treponema denticola, Clostridium kluyveri, Homo sapiens, Rattus norvegicus, Acinetobacter* sp. ADP1, *Streptomyces coelicolor, Eubacterium barkeri, Peptostreptococcus asaccharolyticus, Clostridium botulinum, Clostridium tyrobutyricum, Clostridium thermoaceticum* (*Moorella thermoaceticum*), *Acinetobacter calcoaceticus, Mus musculus, Sus scrofa, Flavobacterium* sp, *Arthrobacter aurescens, Penicillium chrysogenum, Aspergillus niger, Aspergillus nidulans, Bacillus subtilis, Saccharomyces cerevisiae, Zymomonas mobilis, Mannheimia succiniciproducens, Clostridium ljungdahlii, Clostridium carboxydivorans, Geobacillus stearothermophilus, Agrobacterium tumefaciens, Achromobacter denitrificans, Arabidopsis thaliana, Haemophilus influenzae, Acidaminococcus fermentans, Clostridium* sp. M62/1, *Fusobacterium nucleatum*, as well as other exemplary species disclosed herein or available as source organisms for corresponding genes (see Examples). However, with the complete genome sequence available for now more than 400 microorganism genomes and a variety of yeast, fungi, plant, and mammalian genomes, the identification of genes encoding the requisite pathway enzymes, for one or more genes in related or distant species, including for example, homologues, orthologs, paralogs and nonorthologous gene displacements of known genes, and the interchange of genetic alterations between organisms is routine and well known in the art.

Ortholog refers to genes in different species that evolved from a common ancestral gene by speciation. Normally, orthologs retain the same function in the course of evolution. Identification of orthologs is critical for reliable prediction of gene function in newly sequenced genomes.

Paralog refers to genes related by duplication within a genome. While orthologs generally retain the same function in the course of evolution, paralogs can evolve new functions, even if these are related to the original one.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

As used herein, the term "microorganism" or "microbial organism" or "microbes" refers to a living biological and isolated prokaryotic or eukaryotic cell that can be transformed or transfected via insertion of an exogenous or recombinant nucleic acid, such as DNA or RNA. Any suitable prokaryotic or eukaryotic microorganism may be used in the present invention so long as it remains viable after being transformed with a sequence of nucleic acids. A suitable microorganism of the present invention is one capable of expressing one or more nucleic acid constructs encoding one or more recombinant proteins that can catalyze at least one step in the methods. Microorganism can be selected from group of bacteria, yeast, fungi, mold, and archaea. These are commercially available.

As used herein, "fungal" refers to any eukaryotic organism categorized within the kingdom of Fungi. Phyla within the kingdom of Fungi include Ascomycota, Basidiomycota, Blastocladiomycota, Chytridiomycota, Glomeromycota, Microsporidia, and Neocallimastigomycota. As used herein, "yeast" refers to fungi growing in single-celled forms (for example, by budding), whereas "mold" refers to fungi growing in filaments made of multicellular hyphae or mycelia (McGinnis, M. R. and Tyring, S. K. "Introduction to Mycology." Medical Microbiology. 4$^{th}$ ed. Galveston: Univ. of TX Medical Branch at Galveston, 1996).

In some aspects, the microorganisms are yeast cells. In some aspects, the yeast cell is from a *Candida, Hansenula, Issatchenkia, Kluyveromyces, Pichia, Saccharomyces, Schizosaccharomyces*, or *Yarrowia* species.

In some aspects, the microorganisms are mold cells. In some aspects, the mold host cell is from a *Neurospora, Trichoderma, Aspergillus, Fusarium*, or *Chrysosporium* species.

In some aspects, the microorganism is an archaea. In some aspects, suitable archaea is from an *Archaeoglobus, Aeropyrum, Halobacterium, Pyrobaculum, Pyrococcus, Sulfolobus*, Methanococcus, Methanosphaera, Methanopyrus, Methanobrevibacter, Methanocaldococcus, or *Methanosarcina* species.

The term "bacteria" refers to any microorganism within the domain or kingdom of prokaryotic organisms. Phyla within the domain or kingdom of bacteria include Acidobacteria, Actinobacteria, *Actinobacillus, Agrobacterium*, Anaerobiospirrulum, Aquificae, Armatimonadetes, Bacteroidetes, *Burkholderia*, Caldiserica, Chlamydiae, Chlorobi, *Chlorella*, Chloroflexi, Chrysiogenetes, *Citrobacter, Clostridium*, Cyanobacteria, Deferribacteres, Deinococcus-*thermus*, Dictyoglomi, *Enterobacter*, Elusimicrobia, Fibrobacteres, Firmicutes, Fusobacteria, *Geobacillus, Gemmatimonadetes, Gluconobacter, Halanaerobium, Klebsiella, Kluyvera, Lactobacillus*, Lentisphaerae, *Methylobacterium*, Nitrospira, Pasteurellaceae, *Paenibacillus, Planctomycetes, Propionibacterium, Pseudomonas, Proteobacteria, Ralstonia*, Schizochytrium, Spirochaetes, *Streptomyces*, Synergistetes, Tenericutes, *Thermoanaerobacterium*, Thermodesulfobacteria, Thermotogae, Verrucomicrobia, Zobellella, and *Zymomonas*. In some aspects, the bacterial microorganisms are *E. coli* cells. In some aspects, the bacterial microorganisms are *Bacillus* sp. cells. Examples of *Bacillus* species include without limitation *Bacillus subtilis, Bacillus megaterium, Bacillus cereus, Bacillus thuringiensis, Bacillus mycoides*, and *Bacillus licheniformis*.

A carboxylic acid compound prepared by the methods of this invention can form a salt with a counter ion including, but not limited to, a metal ion, e.g., an alkali metal ion, such as sodium, potassium, an alkaline earth ion, such as calcium, magnesium, or an aluminum ion; or coordinates with an organic base such as tetraalkylammonium, ethanolamine, diethanolamine, triethanolamine, trimethylamine, N-methylglucamine, and the like. The acid can form a salt with a counter ion or organic base present in the reaction conditions or can be converted to a salt by reacting with an inorganic or organic base.

Any carboxylic acid containing compound herein is referred to as either an acid or a salt, which has been used interchangeably throughout to refer to the compound in any of its neutral or ionized forms, including any salt forms thereof. It is understood by those skilled understand that the specific form will depend on the pH.

An amino compound prepared by the methods described herein can form a salt, such as hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. The acid can form a salt with a counter ion or an acid present in the reaction conditions or can be converted to a salt by reacting with an inorganic or organic acid.

Any amino containing compound herein is referred to as either a free base or a salt, which has been used interchangeably throughout to refer to the compound in any of its neutral or ionized forms, including any salt forms thereof. It is understood by those skilled understand that the specific form will depend on the pH.

A solvate of a compound is a solid-form of the compound that crystallizes with less than one, one or more than one molecules of solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some aspects, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

For each species, any cell belonging to that species is considered a suitable microorganism of the present invention. A host cell of any species may exist as it was isolated from nature, or it may contain any number of genetic modifications (e.g., genetic mutations, deletions, or recombinant polynucleotides).

The term "recombinant nucleic acid" or "recombinant polynucleotide" as used herein refers to a polymer of nucleic acids where at least one of the following is true: (a) the sequence of nucleic acids is foreign to (i.e., not naturally found in) a given microorganism; (b) the sequence may be naturally found in a given microorganism, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid.

In some aspects, recombinant polypeptides or proteins or enzymes of the present invention may be encoded by genetic material as part of one or more expression vectors. An expression vector contains one or more polypeptide-encoding nucleic acids, and it may further contain any desired elements that control the expression of the nucleic acid(s), as well as any elements that enable the replication and maintenance of the expression vector inside a given host cell. All of the recombinant nucleic acids may be present on a single expression vector, or they may be encoded by multiple expression vectors.

An expression vector or vectors can be constructed to include one or more pathway-encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Exogenous nucleic acid sequences involved in a pathway for synthesis of desired compounds described herein can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. It is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

"Operatively linked" refers to a juxtaposition wherein the elements are in an arrangement allowing them to function.

The term "culturing" refers to the in vitro propagation of cells or organisms on or in media (culture) of various kinds. It is understood that the descendants of a cell grown in culture may not be completely identical (i.e., morphologically, genetically, or phenotypically) to the parent cell.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product. The term overexpression refers to the production of the mRNA transcribed from the gene or the protein product encoded by the gene that is more than that of a normal or control cell, for example 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher than the expression level detected in a control sample or wild-type cell.

As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller, CABIOS 4:11 17 (1988); the local homology algorithm of Smith et al., Adv. Appl. Math. 2:482 (1981); the homology alignment algorithm of Needleman and Wunsch, J. Mol. Biol. 48:443 453 (1970); the search-for-similarity-method of Pearson and Lipman, Proc. Natl. Acad. Sci. 85:2444 2448 (1988); the algorithm Karlin and Altschul Proc. Natl. Acad. Sci. USA 90:5873 5877 (1993).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch, J Mol Biol 48(3): 443-453 (1970), by the search for similarity method of Pearson and Lipman, Proc Natl Acad Sci USA 85(8):2444-2448 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al., Nucleic Acids Res 25(17):3389-3402 (1997) and Altschul et al., J. Mol Biol 215(3)-403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix (see Henikoff and Henikoff, Proc Natl Acad Sci USA 89(22): 10915-10919 (1992)) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc Natl Acad Sci USA 90(12):5873-5877 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

The phrase "functionally equivalent protein" refers to protein or polynucleotide which hybridizes to the exemplified polynucleotide under stringent conditions and which exhibit similar or enhanced biological activity in vivo, e.g., over 120%, or alternatively over 110%, or alternatively over 100%, or alternatively, over 90% or alternatively over 85% or alternatively over 80%, as compared to the standard or control biological activity. Additional embodiments within the scope of this invention are identified by having more than 80%, or alternatively, more than 85%, or alternatively, more than 90%, or alternatively, more than 95%, or alternatively more than 97%, or alternatively, more than 98 or 99% sequence homology. Percentage homology can be determined by sequence comparison programs such as BLAST run under appropriate conditions. In one aspect, the program is run under default parameters. In some aspects, reference to a certain enzyme or protein includes its functionally equivalent enzyme or protein.

When an enzyme is mentioned with reference to an enzyme class (EC), the enzyme class is a class wherein the enzyme is classified or may be on classified on the basis of the enzyme nomenclature provided by the Nomenclature Committee of the International Union of Biochemistry and Molecular Biology. Other suitable enzymes that have not yet been classified in a specific class but may be classified as such are also included.

Non-naturally Occurring Microbial Organisms

The non-naturally occurring microbial organisms provided herein are constructed using methods well known in the art as exemplified herein to exogenously express at least one nucleic acid encoding an enzyme or protein used in a biosynthetic pathway described herein in sufficient amounts to produce compounds such as 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid. It is understood that the microbial organisms are cultured under conditions sufficient to produce 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid.

Successful engineering of a microbial host capable of producing the desired product described herein involves identifying the appropriate set of enzymes with sufficient activity and specificity for catalyzing various steps in the pathway, for example those described in Table A for production of adipate and in Examples herein and in literature. The individual enzyme or protein activities from the exogenous DNA sequences can also be assayed using methods well known in the art. In addition, these enzymes can be engineered using modern protein engineering approaches (Protein Engineering Handbook; Lutz S., & Bornscheuer U. T. Wiley-VCH Verlag GmbH & Co. KGaA: 2008; Vol. 1 & 2) such as directed evolution, rational mutagenesis, computational design (Zanghellini, A et al, 2008) or a combination thereof, for achieving the desired substrate specificity, controlling the stereoselectivity to synthesize enantiopure or racemic products, stabilizing the enzyme to withstand harsh industrial process conditions by improving half-life, thermostability, inhibitor/product tolerance and improving enzyme expression and solubility in the desired microbial production host of choice. Once the desired enzymes that can catalyze each step of the pathway are characterized, the genes encoding these enzymes will be cloned in the microorganism of choice, fermentation conditions will be optimized and product formation will be monitored following fermentation. After the enzymes are identified, the genes corresponding to one or more of the enzymes are cloned into a microbial host. In some aspects, the genes encoding each enzyme of a particular pathway described herein is cloned into a microbial host.

Methods to introduce recombinant/exogenous nucleic acids/proteins into a microorganism, and vectors suitable for this purpose, are well known in the art. For example, various techniques are illustrated in Current Protocols in Molecular Biology, Ausubel et al., eds. (Wiley & Sons, New York, 1988, and quarterly updates). Methods for transferring expression vectors into microbial host cells are well known in the art. Specific methods and vectors may differ depending upon the species of the desired microbial host. For example, bacterial host cells may be transformed by heat shock, calcium chloride treatment, electroporation, liposomes, or phage infection. Yeast host cells may be transformed by lithium acetate treatment (may further include carrier DNA and PEG treatment) or electroporation. These methods are included for illustrative purposes and are in no way intended to be limiting or comprehensive. Routine experimentation through means well known in the art may be used to determine whether a particular expression vector or transformation method is suited for a given microbial host. Furthermore, reagents and vectors suitable for many different microbial hosts are commercially available and well known in the art.

Methods for construction, expression or overexpression of enzymes and testing the expression levels in non-naturally occurring microbial hosts are well known in art (Protein Expression Technologies: Current Status and Future Trends, Baneyx F. eds. Horizon Bioscience, 2004, Norfolk, UK; and Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, MD (1999)).

Methods for carrying out fermentation of microorganisms are well known in art. For example, various techniques are illustrated in Biochemical Engineering, Clark et al., eds. (CRC press, 1997, $2^{nd}$ edition). Specific methods for fermenting may differ depending upon the species of the desired microbial host. Typically microorganism is grown in appropriate media along with the carbon source in a batch or a continuous fermentation mode. The use of agents known to modulate catabolite repression or enzyme activity can be used to enhance adipic acid or glutaric acid production. Suitable pH for fermentation is between 3-10. Fermentation can be performed under aerobic, anaerobic, or anoxic conditions based on the requirements of the microorganism. Fermentations can be performed in a batch, fed-batch or continuous manner. Fermentations can also be conducted in two phases, if desired. For example, the first phase can be aerobic to allow for high growth and therefore high productivity, followed by an anaerobic phase of high caprolactone yields.

The carbon source can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of desired compound.

The reactions described herein can be monitored and the starting materials, the products or intermediates in the fermentation media can be identified by analyzing the media using high pressure liquid chromatography (HPLC) analysis, GC-MS (Gas Chromatography-Mass Spectroscopy) and LC-MS (Liquid Chromatography-Mass Spectroscopy) or other suitable analytical methods using routine procedures well known in the art.

For example, to a solution of glycerol and/or other carbon sources such as glucose is added one or more microorganisms that together produces enzymes used in a pathway described herein, such as in FIG. 1. The mixture is maintained at a temperature of from 18° C. to 70° C. for a period of 1-30 days. The reaction is stopped and the product is isolated according to methods generally known in the art, such as those described below. Alternatively, the reaction is continued while the product is continuously separated.

Any of the non-naturally occurring microbial organisms described herein can be cultured to produce and/or secrete the products of the invention.

Compounds prepared by the methods described herein can be isolated by methods generally known in the art for isolation of a organic compound prepared by biosynthesis or fermentation. For example, 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, &-Caprolactam and hexamethylenediamine, can be isolated from solution by crystallization, salt formation, pervaporation, reactive extraction, extraction (liquid-liquid and two-phase), adsorption, ion exchange, dialysis, distillation, gas stripping, and membrane based separations (Roffler et al., Trends Biotechnolgy.2: 129-136 (1984)). 1-Hexanol and 1,5-pentanediol can be isolated from solution using distillation, extraction (liquid-liquid and two-phase), pervaporation, and membrane based separations (Roffler et al., Trends Biotechnolgy.2: 129-136 (1984)). Linear fatty acids and linear fatty alcohols that are between 7-25 carbons long, linear alkanes and linear α-alkenes that are between 6-24 carbons long, sebacic acid and dodecanedioic acid will phase separate from the aqueous phase.

Following the teachings and guidance provided herein, the non-naturally occurring microbial organisms can achieve synthesis of compounds such as 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid, resulting in intracellular or extracellular concentrations between about 0.1-500 mM or more. Generally, the intracellular or extracellular concentration of 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid is between about 3-150 mM, particularly between about 5-125 mM and more particularly between about 8-100 mM, including about 10 mM, 20 mM, 50 mM, 80 mM, or more. Intracellular or extracellular concentrations between and above each of these exemplary ranges also can be achieved from the non-naturally occurring microbial organisms provided herein.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of desired product includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of products. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production in commercial quantities. Generally, and as with non-continuous culture procedures, the continuous and/or near-continuous production of adipate, 6-aminocaproic acid, caprolactam, 6-hydroxyhexanoate, caprolactone, 1,6-hexandiol, 1-hexanol, and HMDA will include culturing a non-naturally occurring adipate, 6-aminocaproic acid, caprolactam, 6-hydroxyhexanoate, caprolactone, 1,6-hexandiol, 1-hexanol, or HMDA producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose. Fermentation procedures are well known in the art. Examples of batch and continuous fermentation procedures are well known in the art.

The term "pathway enzyme expressed in a sufficient amount" implies that the enzyme is expressed in an amount that is sufficient to allow detection of the desired pathway product. The enzyme is apart of.

When referring to a compound for which several isomers exist (e.g. cis and trans isomer, and R and S isomer, or combinations thereof), the compound in principle includes all possible enantiomers, diastereomers and cis/trans isomers of that compound that may be used in the method of the invention.

In one aspect of the invention, a microorganism serves as a host for the preparation of 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid. In another aspect, the microorganism contains one or more genes encoding for the enzymes necessary to catalyze the enzymatic steps of converting a $C_{N\times3}$ β-hydroxyketone intermediate to 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid. In an additional aspect, the microorganism has the ability to convert C5 sugars, C6 sugars, glycerol, other carbon sources, or a combination thereof to pyruvate. In a further aspect, the microorganism is engineered for enhanced sugar uptakes comprising C5 sugar uptake, simultaneous C6/C5 sugar uptake, simultaneous C6 sugar/glycerol uptake, simultaneous C5 sugar/glycerol uptake, and combinations thereof.

In one aspect, the invention is directed to the design and production of microbial organisms having production capabilities for 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid. Described herein are metabolic pathways that enable to achieve the biosynthesis of these compounds in *Escherichia coli* and other cells or organisms. Biosynthetic production of these compounds can be confirmed by construction of strains having the designed metabolic pathway.

In one aspect, provided is a non-naturally occurring microbial organism comprising at least one exogenous nucleic acid encoding an adipate (ADA) pathway enzyme expressed in a sufficient amount to produce adipate, wherein said adipate pathway comprises a pathway selected from Table A:

TABLE A

| Pathway No | Pathway Steps | Aldehyde |
|---|---|---|
| ADA1 | 2A, 2B, 2C, 2D, 2E, 2F, 2G, 4F1 | 3-oxo propionate |
| ADA2 | 2A, 3B1, 3G1, 3M, 3N, 2F, 2G, 4F1 | 3-oxo propionate |
| ADA3 | 2A, 3B1, 3G1, 3D3, 3K1, 3H, 2G, 4F1 | 3-oxo propionate |
| ADA4 | 2A, 3B1, 3G1, 3D3, 3K1, 4D3, 4E3, 4F1 | 3-oxo propionate |
| ADA5 | 2A, 3B1, 3G1, 3C1, 3D1, 3E1, 3F1, 3H, 2G, 4F1 | 3-oxo propionate |
| ADA6 | 2A, 3B1, 3G1, 3C1, 3D1, 3E1, 3F1, 4D3, 4E3, 4F1 | 3-oxo propionate |
| ADA7 | 2A, 3B1, 3C2, 3D2, 3E2, 3F2, 3G5, 3H, 2G, 4F1 | 3-oxo propionate |
| ADA8 | 2A, 3B1, 3C2, 3D2, 3E2, 3F2, 3G5, 4D3, 4E3, 4F1 | 3-oxo propionate |
| ADA9 | 2A, 3B1, 3C2, 3D2, 3L2, 3K2, 3G5, 3H, 2G, 4F1 | 3-oxo propionate |
| ADA10 | 2A, 3B1, 3C2, 3D2, 3L2, 3K2, 3G5, 4D3, 4E3, 4F1 | 3-oxo propionate |
| ADA11 | 2A, 3B1, 3C2, 3G2, 3D1, 3E1, 3F1, 3H, 2G, 4F1 | 3-oxo propionate |
| ADA12 | 2A, 3B1, 3C2, 3G2, 3D1, 3E1, 3F1, 4D3, 4E3, 4F1 | 3-oxo propionate |
| ADA13 | 2A, 3B2, 3C3, 3D2, 3E2, 3F2, 3G5, 3H, 2G, 4F1 | 3-oxo propionate |
| ADA14 | 2A, 3B2, 3C3, 3D2, 3E2, 3F2, 3G5, 4D3, 4E3, 4F1 | 3-oxo propionate |
| ADA15 | 2A, 3B2, 3C3, 3D2, 3L2, 3K2, 3G5, 3H, 2G, 4F1 | 3-oxo propionate |
| ADA16 | 2A, 3B2, 3C3, 3D2, 3L2, 3K2, 3G5, 4D3, 4E3, 4F1 | 3-oxo propionate |
| ADA17 | 2A, 3B2, 3C3, 3G2, 3D1, 3E1, 3F1, 3H, 2G, 4F1 | 3-oxo propionate |
| ADA18 | 2A, 3B2, 3C3, 3G2, 3D1, 3E1, 3F1, 4D3, 4E3, 4F1 | 3-oxo propionate |
| ADA19 | 2A, 3B2, 3C3, 3G2, 3D1, 3L1, 3K1, 3H, 2G, 4F1 | 3-oxo propionate |
| ADA20 | 2A, 3B2, 3C3, 3G2, 3D1, 3L1, 3K1, 4D3, 4E3, 4F1 | 3-oxo propionate |
| ADA21 | 2A, 3B1, 3C2, 3G2, 3D1, 3L1, 3K1, 3H, 2G, 4F1 | 3-oxo propionate |
| ADA22 | 2A, 3B1, 3C2, 3G2, 3D1, 3L1, 3K1, 4D3, 4E3, 4F1 | 3-oxo propionate |
| ADA23 | 2A, 3B1, 3G1, 3C1, 3D1, 3L1, 3K1, 3H, 2G, 4F1 | 3-oxo propionate |
| ADA24 | 2A, 3B1, 3G1, 3C1, 3D1, 3L1, 3K1, 4D3, 4E3, 4F1 | 3-oxo propionate |
| ADA25 | 2A, 3B1, 3G1, 2I, 2J, 2F, 2G, 4F1 | 3-oxo propionate |
| ADA26 | 2A, 2B, 2C, 2D, 2E, 2F, 2G, 4A3, 4B6, 4F1 | 3-oxo propanol |
| ADA27 | 2A, 2B, 2C, 2D, 2E, 2F, 2G, 4A3, 4F2, 4B7 | 3-oxo propanol |
| ADA28 | 2A, 2B, 2C, 2D, 2E, 2F, 2G, 4F3, 4A4, 4B7 | 3-oxo propanol |
| ADA29 | 2A, 3B1, 3G1, 3M, 3N, 2F, 2G, 4A3, 4B6, 4F1 | 3-oxo propanol |
| ADA30 | 2A, 3B1, 3G1, 3M, 3N, 2F, 2G, 4A3, 4F2, 4B7 | 3-oxo propanol |
| ADA31 | 2A, 3B1, 3G1, 3M, 3N, 2F, 2G, 4F3, 4A4, 4B7 | 3-oxo propanol |
| ADA32 | 2A, 3B1, 3G1, 3D3, 3K1, 4A2, 4B4, 4D3, 4E3, 4F1 | 3-oxo propanol |
| ADA33 | 2A, 3B1, 3G1, 3C1, 3D1, 3E1, 3F1, 4A2, 4B4, 4D3, 4E3, 4F1 | 3-oxo propanol |
| ADA34 | 2A, 3B1, 3C2, 3D2, 3E2, 3F2, 3G5, 4A2, 4B4, 4D3, 4E3, 4F1 | 3-oxo propanol |
| ADA35 | 2A, 3B1, 3C2, 3D2, 3L2, 3K2, 3G5, 4A2, 4B4, 4D3, 4E3, 4F1 | 3-oxo propanol |
| ADA36 | 2A, 3B2, 3C3, 3D2, 3E2, 3F2, 3G5, 4A2, 4B4, 4D3, 4E3, 4F1 | 3-oxo propanol |
| ADA37 | 2A, 3B2, 3C3, 3D2, 3L2, 3K2, 3G5, 4A2, 4B4, 4D3, 4E3, 4F1 | 3-oxo propanol |
| ADA38 | 2A, 3B2, 3C3, 3G2, 3D1, 3E1, 3F1, 4A2, 4B4, 4D3, 4E3, 4F1 | 3-oxo propanol |
| ADA39 | 2A, 3B1, 3C2, 3G2, 3D1, 3E1, 3F1, 4A2, 4B4, 4D3, 4E3, 4F1 | 3-oxo propanol |
| ADA40 | 2A, 3B2, 3C3, 3G2, 3D1, 3L1, 3K1, 4A2, 4B4, 4D3, 4E3, 4F1 | 3-oxo propanol |
| ADA41 | 2A, 3B1, 3C2, 3G2, 3D1, 3L1, 3K1, 4A2, 4B4, 4D3, 4E3, 4F1 | 3-oxo propanol |
| ADA42 | 2A, 3B1, 3G1, 3C1, 3D1, 3L1, 3K1, 4A2, 4B4, 4D3, 4E3, 4F1 | 3-oxo propanol |
| ADA43 | 2A, 3B1, 3G1, 3D3, 3K1, 4A2, 4D4, 4E4, 4B6, 4F1 | 3-oxo propanol |
| ADA44 | 2A, 3B1, 3G1, 3C1, 3D1, 3E1, 3F1, 4A2, 4D4, 4E4, 4B6, 4F1 | 3-oxo propanol |
| ADA45 | 2A, 3B1, 3C2, 3D2, 3E2, 3F2, 3G5, 4A2, 4D4, 4E4, 4B6, 4F1 | 3-oxo propanol |
| ADA46 | 2A, 3B1, 3C2, 3D2, 3L2, 3K2, 3G5, 4A2, 4D4, 4E4, 4B6, 4F1 | 3-oxo propanol |
| ADA47 | 2A, 3B2, 3C3, 3D2, 3E2, 3F2, 3G5, 4A2, 4D4, 4E4, 4B6, 4F1 | 3-oxo propanol |
| ADA48 | 2A, 3B2, 3C3, 3D2, 3L2, 3K2, 3G5, 4A2, 4D4, 4E4, 4B6, 4F1 | 3-oxo propanol |
| ADA49 | 2A, 3B2, 3C3, 3G2, 3D1, 3E1, 3F1, 4A2, 4D4, 4E4, 4B6, 4F1 | 3-oxo propanol |

TABLE A-continued

| Pathway No | Pathway Steps | Aldehyde |
|---|---|---|
| ADA50 | 2A, 3B1, 3C2, 3G2, 3D1, 3E1, 3F1, 4A2, 4D4, 4E4, 4B6, 4F1 | 3-oxo propanol |
| ADA51 | 2A, 3B2, 3C3, 3G2, 3D1, 3L1, 3K1, 4A2, 4D4, 4E4, 4B6, 4F1 | 3-oxo propanol |
| ADA52 | 2A, 3B1, 3C2, 3G2, 3D1, 3L1, 3K1, 4A2, 4D4, 4E4, 4B6, 4F1 | 3-oxo propanol |
| ADA53 | 2A, 3B1, 3G1, 3C1, 3D1, 3L1, 3K1, 4A2, 4D4, 4E4, 4B6, 4F1 | 3-oxo propanol |
| ADA54 | 2A, 3B1, 3G1, 3D3, 3K1, 4A2, 4D4, 4B5, 4E3, 4F1 | 3-oxo propanol |
| ADA55 | 2A, 3B1, 3G1, 3C1, 3D1, 3E1, 3F1, 4A2, 4D4, 4B5, 4E3, 4F1 | 3-oxo propanol |
| ADA56 | 2A, 3B1, 3C2, 3D2, 3E2, 3F2, 3G5, 4A2, 4D4, 4B5, 4E3, 4F1 | 3-oxo propanol |
| ADA57 | 2A, 3B1, 3C2, 3D2, 3L2, 3K2, 3G5, 4A2, 4D4, 4B5, 4E3, 4F1 | 3-oxo propanol |
| ADA58 | 2A, 3B2, 3C3, 3D2, 3E2, 3F2, 3G5, 4A2, 4D4, 4B5, 4E3, 4F1 | 3-oxo propanol |
| ADA59 | 2A, 3B2, 3C3, 3D2, 3L2, 3K2, 3G5, 4A2, 4D4, 4B5, 4E3, 4F1 | 3-oxo propanol |
| ADA60 | 2A, 3B2, 3C3, 3G2, 3D1, 3E1, 3F1, 4A2, 4D4, 4B5, 4E3, 4F1 | 3-oxo propanol |
| ADA61 | 2A, 3B1, 3C2, 3G2, 3D1, 3E1, 3F1, 4A2, 4D4, 4B5, 4E3, 4F1 | 3-oxo propanol |
| ADA62 | 2A, 3B2, 3C3, 3G2, 3D1, 3L1, 3K1, 4A2, 4D4, 4B5, 4E3, 4F1 | 3-oxo propanol |
| ADA63 | 2A, 3B1, 3C2, 3G2, 3D1, 3L1, 3K1, 4A2, 4D4, 4B5, 4E3, 4F1 | 3-oxo propanol |
| ADA64 | 2A, 3B1, 3G1, 3C1, 3D1, 3L1, 3K1, 4A2, 4D4, 4B5, 4E3, 4F1 | 3-oxo propanol |
| ADA65 | 2A, 3B1, 3G1, 3D3, 3K1, 4A2, 4D4, 4E4, 4F2, 4B7 | 3-oxo propanol |
| ADA66 | 2A, 3B1, 3G1, 3C1, 3D1, 3E1, 3F1, 4A2, 4D4, 4E4, 4F2, 4B7 | 3-oxo propanol |
| ADA67 | 2A, 3B1, 3C2, 3D2, 3E2, 3F2, 3G5, 4A2, 4D4, 4E4, 4F2, 4B7 | 3-oxo propanol |
| ADA68 | 2A, 3B1, 3C2, 3D2, 3L2, 3K2, 3G5, 4A2, 4D4, 4E4, 4F2, 4B7 | 3-oxo propanol |
| ADA69 | 2A, 3B2, 3C3, 3D2, 3E2, 3F2, 3G5, 4A2, 4D4, 4E4, 4F2, 4B7 | 3-oxo propanol |
| ADA70 | 2A, 3B2, 3C3, 3D2, 3L2, 3K2, 3G5, 4A2, 4D4, 4E4, 4F2, 4B7 | 3-oxo propanol |
| ADA71 | 2A, 3B2, 3C3, 3G2, 3D1, 3E1, 3F1, 4A2, 4D4, 4E4, 4F2, 4B7 | 3-oxo propanol |
| ADA72 | 2A, 3B1, 3C2, 3G2, 3D1, 3E1, 3F1, 4A2, 4D4, 4E4, 4F2, 4B7 | 3-oxo propanol |
| ADA73 | 2A, 3B2, 3C3, 3G2, 3D1, 3L1, 3K1, 4A2, 4D4, 4E4, 4F2, 4B7 | 3-oxo propanol |
| ADA74 | 2A, 3B1, 3C2, 3G2, 3D1, 3L1, 3K1, 4A2, 4D4, 4E4, 4F2, 4B7 | 3-oxo propanol |
| ADA75 | 2A, 3B1, 3G1, 3C1, 3D1, 3L1, 3K1, 4A2, 4D4, 4E4, 4F2, 4B7 | 3-oxo propanol |
| ADA76 | 2A, 3B1, 3G1, 3D3, 4A1, 4B1, 3K1, 4D3, 4E3, 4F1 | 3-oxo propanol |
| ADA77 | 2A, 3B2, 3C3, 3G2, 3D1, 4A1, 4B1, 3K1, 4D3, 4E3, 4F1 | 3-oxo propanol |
| ADA78 | 2A, 3B1, 3C2, 3G2, 3D1, 4A1, 4B1, 3K1, 4D3, 4E3, 4F1 | 3-oxo propanol |
| ADA79 | 2A, 3B1, 3G1, 3C1, 3D, 4A1, 4B1, 3K1, 4D3, 4E3, 4F1 | 3-oxo propanol |
| ADA80 | 2A, 3B1, 3C2, 3D2, 3E2, 3F2, 4A5, 4D5, 4F4, 4B7 | 3-oxo propanol |
| ADA81 | 2A, 3B1, 3C2, 3D2, 3L2, 3K2, 4A5, 4D5, 4F4, 4B7 | 3-oxo propanol |
| ADA82 | 2A, 3B2, 3C3, 3D2, 3E2, 3F2, 4A5, 4D5, 4F4, 4B7 | 3-oxo propanol |
| ADA83 | 2A, 3B2, 3C3, 3D2, 3L2, 3K2, 4A5, 4D5, 4F4, 4B7 | 3-oxo propanol |
| ADA84 | 2A, 2B, 2C, 2D, 2E, 2F, 2G, 4G1, 4B6, 4F1 | 3-aminopropanal |
| ADA85 | 2A, 2B, 2C, 2D, 2E, 2F, 2G, 4G1, 4F2, 4B7 | 3-aminopropanal |
| ADA86 | 2A, 2B, 2C, 2D, 2E, 2F, 2G, 4F5, 4G2, 4B7 | 3-aminopropanal |
| ADA87 | 2A, 3B1, 3G1, 3M, 3N, 2F, 2G, 4G1, 4B6, 4F1 | 3-aminopropanal |
| ADA88 | 2A, 3B1, 3G1, 3M, 3N, 2F, 2G, 4G1, 4F2, 4B7 | 3-aminopropanal |
| ADA89 | 2A, 3B1, 3G1, 3M, 3N, 2F, 2G, 4F5, 4G2, 4B7 | 3-aminopropanal |
| ADA90 | 2A, 3B1, 3G1, 3D3, 3K1, 4G3, 4B4, 4D3, 4E3, 4F1 | 3-aminopropanal |
| ADA91 | 2A, 3B1, 3G1, 3C1, 3D1, 3E1, 3F1, 4G3, 4B4, 4D3, 4E3, 4F1 | 3-aminopropanal |
| ADA92 | 2A, 3B1, 3C2, 3D2, 3E2, 3F2, 3G5, 4G3, 4B4, 4D3, 4E3, 4F1 | 3-aminopropanal |
| ADA93 | 2A, 3B1, 3C2, 3D2, 3L2, 3K2, 3G5, 4G3, 4B4, 4D3, 4E3, 4F1 | 3-aminopropanal |
| ADA94 | 2A, 3B2, 3C3, 3D2, 3E2, 3F2, 3G5, 4G3, 4B4, 4D3, 4E3, 4F1 | 3-aminopropanal |
| ADA95 | 2A, 3B2, 3C3, 3D2, 3L2, 3K2, 3G5, 4G3, 4B4, 4D3, 4E3, 4F1 | 3-aminopropanal |
| ADA96 | 2A, 3B2, 3C3, 3G2, 3D1, 3E1, 3F1, 4G3, 4B4, 4D3, 4E3, 4F1 | 3-aminopropanal |
| ADA97 | 2A, 3B1, 3C2, 3G2, 3D1, 3E1, 3F1, 4G3, 4B4, 4D3, 4E3, 4F1 | 3-aminopropanal |
| ADA98 | 2A, 3B2, 3C3, 3G2, 3D1, 3L1, 3K1, 4G3, 4B4, 4D3, 4E3, 4F1 | 3-aminopropanal |
| ADA99 | 2A, 3B1, 3C2, 3G2, 3D1, 3L1, 3K1, 4G3, 4B4, 4D3, 4E3, 4F1 | 3-aminopropanal |
| ADA100 | 2A, 3B1, 3G1, 3C1, 3D1, 3L1, 3K1, 4G3, 4B4, 4D3, 4E3, 4F1 | 3-aminopropanal |
| ADA101 | 2A, 3B1, 3G1, 3D3, 3K1, 4G3, 4D4, 4E4, 4B6, 4F1 | 3-aminopropanal |
| ADA102 | 2A, 3B1, 3G1, 3C1, 3D1, 3E1, 3F1, 4G3, 4D4, 4E4, 4B6, 4F1 | 3-aminopropanal |
| ADA103 | 2A, 3B1, 3C2, 3D2, 3E2, 3F2, 3G5, 4G3, 4D4, 4E4, 4B6, 4F1 | 3-aminopropanal |
| ADA104 | 2A, 3B1, 3C2, 3D2, 3L2, 3K2, 3G5, 4G3, 4D4, 4E4, 4B6, 4F1 | 3-aminopropanal |
| ADA105 | 2A, 3B2, 3C3, 3D2, 3E2, 3F2, 3G5, 4G3, 4D4, 4E4, 4B6, 4F1 | 3-aminopropanal |
| ADA106 | 2A, 3B2, 3C3, 3D2, 3L2, 3K2, 3G5, 4G3, 4D4, 4E4, 4B6, 4F1 | 3-aminopropanal |
| ADA107 | 2A, 3B2, 3C3, 3G2, 3D1, 3E1, 3F1, 4G3, 4D4, 4E4, 4B6, 4F1 | 3-aminopropanal |
| ADA108 | 2A, 3B1, 3C2, 3G2, 3D1, 3E1, 3F1, 4G3, 4D4, 4E4, 4B6, 4F1 | 3-aminopropanal |
| ADA109 | 2A, 3B2, 3C3, 3G2, 3D1, 3L1, 3K1, 4G3, 4D4, 4E4, 4B6, 4F1 | 3-aminopropanal |
| ADA110 | 2A, 3B1, 3C2, 3G2, 3D1, 3L1, 3K1, 4G3, 4D4, 4E4, 4B6, 4F1 | 3-aminopropanal |
| ADA111 | 2A, 3B1, 3G1, 3C1, 3D1, 3L1, 3K1, 4G3, 4D4, 4E4, 4B6, 4F1 | 3-aminopropanal |
| ADA112 | 2A, 3B1, 3G1, 3D3, 3K1, 4G3, 4D4, 4B5, 4E3, 4F1 | 3-aminopropanal |
| ADA113 | 2A, 3B1, 3G1, 3C1, 3D1, 3E1, 3F1, 4G3, 4D4, 4B5, 4E3, 4F1 | 3-aminopropanal |
| ADA114 | 2A, 3B1, 3C2, 3D2, 3E2, 3F2, 3G5, 4G3, 4D4, 4B5, 4E3, 4F1 | 3-aminopropanal |
| ADA115 | 2A, 3B1, 3C2, 3D2, 3L2, 3K2, 3G5, 4G3, 4D4, 4B5, 4E3, 4F1 | 3-aminopropanal |
| ADA116 | 2A, 3B2, 3C3, 3D2, 3E2, 3F2, 3G5, 4G3, 4D4, 4B5, 4E3, 4F1 | 3-aminopropanal |
| ADA117 | 2A, 3B2, 3C3, 3D2, 3L2, 3K2, 3G5, 4G3, 4D4, 4B5, 4E3, 4F1 | 3-aminopropanal |
| ADA118 | 2A, 3B2, 3C3, 3G2, 3D1, 3E1, 3F1, 4G3, 4D4, 4B5, 4E3, 4F1 | 3-aminopropanal |
| ADA119 | 2A, 3B1, 3C2, 3G2, 3D1, 3E1, 3F1, 4G3, 4D4, 4B5, 4E3, 4F1 | 3-aminopropanal |
| ADA120 | 2A, 3B2, 3C3, 3G2, 3D1, 3L1, 3K1, 4G3, 4D4, 4B5, 4E3, 4F1 | 3-aminopropanal |
| ADA121 | 2A, 3B1, 3C2, 3G2, 3D1, 3L1, 3K1, 4G3, 4D4, 4B5, 4E3, 4F1 | 3-aminopropanal |
| ADA122 | 2A, 3B1, 3G1, 3C1, 3D1, 3L1, 3K1, 4G3, 4D4, 4B5, 4E3, 4F1 | 3-aminopropanal |
| ADA123 | 2A, 3B1, 3G1, 3D3, 3K1, 4G3, 4D4, 4E4, 4F2, 4B7 | 3-aminopropanal |
| ADA124 | 2A, 3B1, 3G1, 3C1, 3D1, 3E1, 3F1, 4G3, 4D4, 4E4, 4F2, 4B7 | 3-aminopropanal |
| ADA125 | 2A, 3B1, 3C2, 3D2, 3E2, 3F2, 3G5, 4G3, 4D4, 4E4, 4F2, 4B7 | 3-aminopropanal |

TABLE A-continued

| Pathway No | Pathway Steps | Aldehyde |
|---|---|---|
| ADA126 | 2A, 3B1, 3C2, 3D2, 3L2, 3K2, 3G5, 4G3, 4D4, 4E4, 4F2, 4B7 | 3-aminopropanal |
| ADA127 | 2A, 3B2, 3C3, 3D2, 3E2, 3F2, 3G5, 4G3, 4D4, 4E4, 4F2, 4B7 | 3-aminopropanal |
| ADA128 | 2A, 3B2, 3C3, 3D2, 3L2, 3K2, 3G5, 4G3, 4D4, 4E4, 4F2, 4B7 | 3-aminopropanal |
| ADA129 | 2A, 3B2, 3C3, 3G2, 3D1, 3E1, 3F1, 4G3, 4D4, 4E4, 4F2, 4B7 | 3-aminopropanal |
| ADA130 | 2A, 3B1, 3C2, 3G2, 3D1, 3E1, 3F1, 4G3, 4D4, 4E4, 4F2, 4B7 | 3-aminopropanal |
| ADA131 | 2A, 3B2, 3C3, 3G2, 3D1, 3L1, 3K1, 4G3, 4D4, 4E4, 4F2, 4B7 | 3-aminopropanal |
| ADA132 | 2A, 3B1, 3C2, 3G2, 3D1, 3L1, 3K1, 4G3, 4D4, 4E4, 4F2, 4B7 | 3-aminopropanal |
| ADA133 | 2A, 3B1, 3G1, 3C1, 3D1, 3L1, 3K1, 4G3, 4D4, 4E4, 4F2, 4B7 | 3-aminopropanal |
| ADA134 | 2A, 3B1, 3G1, 3D3, 4G4, 4B1, 3K1, 4D3, 4E3, 4F1 | 3-aminopropanal |
| ADA135 | 2A, 3B2, 3C3, 3G2, 3D1, 4G4, 4B1, 3K1, 4D3, 4E3, 4F1 | 3-aminopropanal |
| ADA136 | 2A, 3B1, 3C2, 3G2, 3D1, 4G4, 4B1, 3K1, 4D3, 4E3, 4F1 | 3-aminopropanal |
| ADA137 | 2A, 3B1, 3G1, 3C1, 3D, 4G4, 4B1, 3K1, 4D3, 4E3, 4F1 | 3-aminopropanal |
| ADA138 | 2A, 3B1, 3C2, 3D2, 3E2, 3F2, 3G5, 4D5, 4F4, 4B7 | 3-aminopropanal |
| ADA139 | 2A, 3B1, 3C2, 3D2, 3L2, 3K2, 3G5, 4D5, 4F4, 4B7 | 3-aminopropanal |
| ADA140 | 2A, 3B2, 3C3, 3D2, 3E2, 3F2, 3G5, 4D5, 4F4, 4B7 | 3-aminopropanal |
| ADA141 | 2A, 3B2, 3C3, 3D2, 3L2, 3K2, 3G5, 4D5, 4F4, 4B7 | 3-aminopropanal | wherein in 2A is a 4-hydroxy-2-oxo-adipate aldolase, a 4,6-dihydroxy-2-oxo-hexanoate aldolase or a 6-amino-4-hydroxy-2-oxo-hexanoate aldolase, 2B is a 4-hydroxy-2-oxo-adipate dehydratase, a 4,6-dihydroxy-2-oxo-hexanoate 4-dehydratase or a 6-amino-4-hydroxy-2-oxo-hexanoate dehydratase, 3B1 is a 4-hydroxy-2-oxo-adipate 2-reductase, a 4,6-dihydroxy-2-oxo-hexanoate 2-reductase or a 6-amino-4-hydroxy-2-oxo-hexanoate 2-reductase, and 3B2 is a 4-hydroxy-2-oxo-adipate 4-dehydrogenase, a 4,6-dihydroxy-2-oxo-hexanoate 4-dehydrogenase or a 6-amino-4-hydroxy-2-oxo-hexanoate 4-dehydrogenase, 2C is a 3,4-dehydro-2-oxo-adipate 3-reductase, a 6-hydroxy-3,4-dehydro-2-oxohexanoate 3-reductase or a 6-amino-3,4-dehydro-2-oxohexanoate 3-reductase, 3G1 is a 2,4-dihydroxyadipate CoA-transferase or a 2,4-dihydroxyadipate-CoA ligase, a 2,4,6-trihydroxyhexanoate CoA-transferase or a 2,4,6-trihydroxyhexanoate-CoA ligase, or a 6-amino-2,4-dihydroxyhexanoate CoA-transferase or a 6-amino-2,4-dihydroxyhexanoate-CoA ligase, 3C2 is a 2,4-dihydroxyadipate 4-dehydrogenase, a 2,4,6-trihydroxyhexanoate 4-dehydrogenase or a 6-amino-2,4-dihydroxyhexanoate 4-dehydrogenase, and 3C3 is a 2,4-dioxoadipate 2-reductase, a 6-hydroxy-2,4-dioxohexanoate 2-reductase or a 6-amino-2,4-dioxohexanoate 2-reductase, 2J is a 4,5-dehydro-2-hydroxyadipyl-CoA 4,5-reductase, 2G is a 2,3-dehydro-adipyl-CoA 2,3-reductase, a 6-hydroxy-2,3-dehydro-hexanoyl-CoA 2,3-reductase or a 6-amino-2,3-dehydro-hexanoyl-CoA 2,3-reductase,3E1 is a 2,3-dehydro-4-oxoadipyl-CoA 2,3-reductase, a 6-hydroxy-2,3-dehydro-4-oxohexanoyl-CoA 2,3-reductase or a 6-amino-2,3-dehydro-4-oxohexanoyl-CoA 2,3-reductase, 3E2 is a 2,3-dehydro-4-oxoadipate 2,3-reductase, a 6-hydroxy-2,3-dehydro-4-oxohexanoate 2,3-reductase or a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase, a 4,6-dihydroxy-2,3-dehydrohexanoate 2,3-reductase or a 6-amino-2,3-dehydro-4-hydroxyhexanoate 2,3-reductase, 3K1 is a 2,3-dehydro-4-hydroxyadipyl-CoA 2,3-reductase, a 4,6-dihydroxy-2,3-dehydrohexanoyl-CoA 2,3-reductase or a 6-amino-2,3-dehydro-4-hydroxyhexanoyl-CoA 2,3-reductase, 4F4 is a 4,5-dehydro-6-oxohexanoate 4,5-reductase, 3N is a 2-oxoadipyl-CoA 2-reductase, a 6-hydroxy-2-oxohexanoyl-CoA 2-reductase or a 6-amino-2-oxohexanoyl-CoA 2-reductase, 2D is a 2-oxoadipate 2-reductase, a 6-hydroxy-2oxohexanoate 2-reductase or a 6-amino-2-oxohexanoate 2-reductase, 3L2 is a 2,3-dehydro-4-oxoadipate 4-reductase, a 6-hydroxy-2,3-dehydro-4-oxohexanoate 4-reductase or a 6-amino-2,3-dehydro-4-oxohexanoate 4-reductase, 3L1 is a 2,3-dehydro-4-oxoadipyl-CoA 4-reductase, a 6-hydroxy-2,3-dehydro-4-oxohexanoyl-CoA 4-reductase or a 6-amino-2,3-dehydro-4-oxohexanoyl-CoA 4-reductase, 3F2 is a 4-oxoadipate 4-reductase, a 6-hydroxy-4-oxohexanoate 4-reductase or a 6-amino-4-oxohexanoate 4-reductase, 3F1 is a 4-oxoadipyl-CoA 3-reductase, a 6-hydroxy-4-oxohexanoyl-CoA 4-reductase or a 6-amino-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase, a 2,4,6-trihydroxyhexanoyl-CoA 4-dehydrogenase or a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4B6 is a 6-oxohexanoyl-CoA 6-dehydrogenase, 4B7 is a 6-oxohexanoate 6-dehydrogenase, 4F1 is an adipyl-CoA transferase, an adipyl-CoA hydrolase or an adipyl-CoA ligase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, 4F5 6-aminohexanoyl-CoA transferase, a 6-aminohexanoyl-CoA hydrolase or an 6-aminohexanoyl-CoA ligase, 2E is a 2-hydroxy-adipate CoA-transferase or a 2-hydroxyadipate-CoA ligase, 2,6-dihydroxy-hexanoate CoA-transferase or a 2,6-dihydroxy-hexanoate-CoA ligase, 6-amino-2-hydroxyhexanoate CoA-transferase or 6-amino-2-hydroxyhexanoate-CoA ligase, 3G2 is a 2-hydroxy-4oxoadipate CoA-transferase or a 2-hydroxy-4oxoadipate-CoA ligase, a 2,6-dihydroxy-4oxohexanoate CoA-transferase or a 2,6-dihydroxy-4oxohexanoate-CoA ligase, or a 6-amino-2-hydroxy-4oxohexanoate CoA-transferase or a 6-amino-2-hydroxy-4oxohexanoate-CoA ligase, 3G5 is a 4-hydroxyadipate CoA-transferase or a 4-hydroxyadipate-CoA ligase, a 4,6-dihydroxyhexanoate CoA-transferase or a 4,6-dihydroxyhexanoate-CoA ligase, or a 6-amino-4-hydroxyhexanoate CoA-transferase or a 6-amino-4-hydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), a 2,4,6-trihydroxyhexanoyl-CoA 4-dehydratase (2,3-dehydro forming), or a 6-amino-2,4-dihydroxyhexanoyl-CoA 4-dehydratase (2,3-dehydro forming), 3H is a 4-hydroxyadipyl-CoA 4-dehdyratase (2,3-dehydro forming), a 4,6-dihydroxyhexanoyl-CoA 4-dehydratase (2,3-dehydro forming) or a 6-amino-4-hydroxyhexanoyl-CoA 4-dehydratase (2,3-dehydro forming), 2F is a 2-hydroxy-adipyl-CoA 2-dehydratase, a 2,6-dihydroxy-hexanoyl-CoA 2-dehydratase or a 6-amino-2-hydroxy-hexanoyl-CoA 2-dehydratase, 3D3 is a 2,4-dihydroxyadipyl-CoA 2-dehydratase, a 2,4,6-trihydroxyhexanoyl-CoA 2-dehydratase or a 6-amino-2,4-dihydroxyhexanoyl-CoA 2-dehydratase, 3D2 is a 2-hydroxy-4oxoadipate 2-dehydratase, a 2,6-dihydroxy-4oxohexanoate 2-dehydratase or a 6-amino-2-hydroxy-4oxohexanoate 2-dehydratase, 3D1 is a 2-hydroxy-4oxoadipyl-CoA 2-dehydratase, a 2,6-dihydroxy-4oxohexanoyl-CoA 2-dehydratase or a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 4G1 is a 6-aminohexanoyl-CoA transaminase or a 6-aminohexanoyl-CoA dehydrogenase (deaminating), 4G2 is a 6-aminohexanoate transaminase or a 6-aminohexanoate dehydrogenase (deaminating), 4G3 is a 6-amino-4-hydroxyhexanoyl-CoA transaminase or a 6-amino-4-hydroxyhexanoyl-CoA dehydrogenase (deaminating), 4G4 is a 6-amino-4-hydroxy-2,3-dehdyrohexanoyl-CoA transaminase or a 6-amino-4-hydroxy-2,3-dehdyrohexanoyl-CoA dehydrogenase (deaminating), and 4G5 is a 6-amino-4-hydroxyhexanoate transaminase or a 6-amino-4-hydroxyhexanoate dehydrogenase (deaminating).

In another aspect, particularly when adipic acid synthesis pathway is selected from ADA1-ADA25, 2A is a 4-hydroxy-2-oxo-adipate aldolase, 2B is a 4-hydroxy-2-oxo-adipate dehydratase, 3B1 is a 4-hydroxy-2-oxo-adipate 2-reductase, 3B2 is a 4-hydroxy-2-oxo-adipate 4-dehydrogenase, 2C is a 3,4-dehydro-2-oxo-adipate 3-reductase, 3G1 is a 2,4-dihydroxyadipate CoA-transferase or a 2,4-dihydroxyadipate-CoA ligase, 3C2 is a 2,4-dihydroxyadipate 4-dehydrogenase, 3C3 is a 2,4-dioxoadipate 2-reductase, 2J is a 4,5-dehydro-2-hydroxy-adipyl-CoA 4,5-reductase, 2G is a 2,3-dehydro-adipyl-CoA 2,3-reductase, 3E1 is a 2,3-dehydro-4-oxoadipyl-CoA 2,3-reductase, 3E2 is a 2,3-dehydro-4-oxoadipate 2,3-reductase, 4E3 is a 4,5-dehydroadipyl-CoA 4,5-reductase, 3K2 is a 2,3-dehydro-4-hydroxyadipate 2,3-reductase, 3K1 is a 2,3-dehydro-4-hydroxyadipyl-CoA 2,3-reductase, 3N is a 2-oxoadipyl-CoA 2-reductase, 2D is a 2-oxoadipate 2-reductase, 3L2 is a 2,3-dehydro-4-oxoadipate 4-reductase, 3L1 is a 2,3-dehydro-4-oxoadipyl-CoA 4-reductase, 3F2 is a 4-oxoadipate 4-reductase, 3F1 is a 4-oxoadipyl-CoA 3-reductase, 3C1 is a 2,4-dihydroxyadipyl-CoA 4-dehydrogenase, 4F1 is an adipyl-CoA transferase, an adipyl-CoA hydrolase or an adipyl-CoA ligase, 2E is a 2-hydroxy-adipate CoA-transferase or a 2-hydroxyadipate-CoA ligase, 3G2 is a 2-hydroxy-4oxoadipate CoA-transferase or a 2-hydroxy-4oxoadipate-CoA ligase, 3G5 is a 4-hydroxyadipate CoA-transferase or a 4-hydroxyadipate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), 3H is a 4-hydroxyadipyl-CoA 4-dehdyratase (2,3-dehydro forming), 2F is a 2-hydroxy-adipyl-CoA 2-dehydratase, 3D3 is a 2,4-dihydroxyadipyl-CoA 2-dehydratase, 3D2 is a 2-hydroxy-4oxoadipate 2-dehydratase, 3D1 is a 2-hydroxy-4oxoadipyl-CoA 2-dehydratase, 4D3 is a 4-hydroxy-adipyl-CoA 4-dehydratase (4,5-dehydro forming).

In another aspect, particularly when adipic acid synthesis pathway is selected from ADA 26-ADA83, 2A is a 4,6-dihydroxy-2-oxo-hexanoate aldolase, 2B is a 4,6-dihydroxy-2-oxo-hexanoate 4-dehydratase, 3B1 is a 4,6-dihydroxy-2-oxo-hexanoate 2-reductase, 3B2 is a 4,6-dihydroxy-2-oxo-hexanoate 4-dehydrogenase, 2C is a 6-hydroxy-3,4-dehydro-2-oxohexanoate 3-reductase, 3G1 is a 2,4,6-trihydroxyhexanoate CoA-transferase or a 2,4,6-trihydroxyhexanoate-CoA ligase, 3C2 is a 2,4,6-trihydroxyhexanoate 4-dehydrogenase, 3C3 is a 6-hydroxy-2,4-dioxohexanoate 2-reductase, 2G is a 6-hydroxy-2,3-dehydro-hexanoyl-CoA 2,3-reductase, 3E1 is a 6-hydroxy-2,3-dehydro-4-oxohexanoyl-CoA 2,3-reductase, 3E2 is a 6-hydroxy-2,3-dehydro-4-oxohexanoate 2,3-reductase, 4E4 is a 4,5-dehydro-6-oxohexanoyl-CoA 4,5-reductase, 3K2 is a 4,6-dihydroxy-2,3-dehydrohexanoate 2,3-reductase, 3K1 is a 4,6-dihydroxy-2,3-dehydrohexanoyl-CoA 2,3-reductase, 4F4 is a 4,5-dehydro-6-oxohexanoate 4,5-reductase, 3N is a 6-hydroxy-2-oxohexanoyl-CoA 2-reductase, 2D is a 6-hydroxy-2oxohexanoate 2-reductase, 3L2 is a 6-hydroxy-2,3-dehydro-4-oxohexanoate 4-reductase, 3L1 is a 6-hydroxy-2,3-dehydro-4-oxohexanoyl-CoA 4-reductase, 3F2 is a 6-hydroxy-4-oxohexanoate 4-reductase, 3F1 is a 6-hydroxy-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4,6-trihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4B6 is a 6-oxohexanoyl-CoA 6-dehydrogenase, 4B7 is a 6-oxohexanoate 6-dehydrogenase, 4F1 is an adipyl-CoA transferase, an adipyl-CoA hydrolase or an adipyl-CoA ligase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, 2E is a 2,6-dihydroxy-hexanoate CoA-transferase or a 2,6-dihydroxy-hexanoate-CoA ligase, 3G2 is a 2,6-dihydroxy-4oxohexanoate CoA-transferase or a 2,6-dihydroxy-4oxohexanoate-CoA ligase, 3G5 is a 4,6-dihydroxyhexanoate CoA-transferase or a 4,6-dihydroxyhexanoate-CoA ligase, 3M is a 2,4,6-trihydroxyhexanoyl-CoA 4-dehydratase (2,3-dehydro forming), 3H is a 4,6-dihydroxyhexanoyl-CoA 4-dehydratase (2,3-dehydro forming), 2F is a 2,6-dihydroxy-hexanoyl-CoA 2-dehydratase, 3D3 is a 2,4,6-trihydroxyhexanoyl-CoA 2-dehydratase, 3D2 is a 2,6-dihydroxy-4oxohexanoate 2-dehydratase, 3D1 is an a 2,6-dihydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming) and 4E3 is a 4,5-dehydroadipyl-CoA 4,5-reductase.

In another aspect, particularly when adipic acid synthesis pathway is selected from ADA 84-ADA141, 2A is a 6-amino-4-hydroxy-2-oxo-hexanoate aldolase, 2B is a 6-amino-4-hydroxy-2-oxo-hexanoate dehydratase, 3B1 is a 6-amino-4-hydroxy-2-oxo-hexanoate 2-reductase, 3B2 is a 6-amino-4-hydroxy-2-oxo-hexanoate 4-dehydrogenase, 2C is 6-amino-3,4-dehydro-2-oxohexanoate 3-reductase, 3G1 is a 6-amino-2,4-dihydroxyhexanoate CoA-transferase or a 6-amino-2,4-dihydroxyhexanoate-CoA ligase, 3C2 is a 6-amino-2,4-dihydroxyhexanoate 4-dehydrogenase, 3C3 is a 6-amino-2,4-dioxohexanoate 2-reductase, 2G is a 6-amino-2,3-dehydro-hexanoyl-CoA 2,3-reductase, 3E1 is a 6-amino-2,3-dehydro-4-oxohexanoyl-CoA 2,3-reductase, 3E2 is a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 6-amino-2,3-dehydro-4-hydroxyhexanoate 2,3-reductase, 3K1 is a 6-amino-2,3-dehydro-4-hydroxyhexanoyl-CoA 2,3-reductase, 4F4 is a 4,5-dehydro-6-oxohexanoate 4,5-reductase, 3N is a 6-amino-2-oxohexanoyl-CoA 2-reductase, 2D is a 6-amino-2-oxohexanoate 2-reductase, 3L2 is a 6-amino-2,3-dehydro-4-oxohexanoate 4-reductase, 3L1 is a 6-amino-2,3-dehydro-4-oxohexanoyl-CoA 4-reductase, 3F2 is a 6-amino-4-oxohexanoate 4-reductase, 3F1 is a 6-amino-4-oxohexanoyl-CoA 4-reductase, 3C1 is a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4B6 is a 6-oxohexanoyl-CoA 6-dehydrogenase, 4B7 is a 6-oxohexanoate 6-dehydrogenase, 4F1 is an adipyl-CoA transferase, an adipyl-CoA hydrolase or an adipyl-CoA ligase, 4F2 is a 6-oxohexanoyl-CoA transferase, a 6-oxohexanoyl-CoA hydrolase or an 6-oxohexanoyl-CoA ligase, 4F5 6-aminohexanoyl-CoA transferase, a 6-aminohexanoyl-CoA hydrolase or an 6-aminohexanoyl-CoA ligase, 2E is a 6-amino-2-hydroxyhexanoate CoA-transferase or 6-amino-2-hydroxyhexanoate-CoA ligase, 3G2 is a 6-amino-2-hydroxy-4oxohexanoate CoA-transferase or a 6-amino-2-hydroxy-4oxohexanoate-CoA ligase, 3G5 is a 6-amino-4-hydroxyhexanoate CoA-transferase or a 6-amino-4-hydroxyhexanoate-CoA ligase, 3M is a 6-amino-2,4-dihydroxyhexanoyl-CoA 4-dehydratase (2,3-dehydro forming), 3H is a 6-amino-4-hydroxyhexanoyl-CoA 4-dehydratase (2,3-dehydro forming), 2F is a 6-amino-2-hydroxy-hexanoyl-CoA 2-dehydratase, 3D3 is a 6-amino-2,4-dihydroxyhexanoyl-CoA 2-dehydratase, 3D2 is a 6-amino-2-hydroxy-4oxohexanoate 2-dehydratase, 3D1 is a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 4G1 is a 6-aminohexanoyl-CoA transaminase or a 6-aminohexanoyl-CoA dehydrogenase (deaminating), 4G2 is a 6-aminohexanoate transaminase or a 6-aminohexanoate dehydrogenase (deaminating), 4G3 is a 6-amino-4-hydroxyhexanoyl-CoA transaminase or a 6-amino-4-hydroxyhexanoyl-CoA dehydrogenase (deaminating), 4G4 is a 6-amino-4-hydroxy-2,3-dehdyrohexanoyl-CoA transaminase or a 6-amino-4-hydroxy-2,3-dehdyrohexanoyl-CoA dehydrogenase (deaminating), and 4G5 is a 6-amino-4-hydroxyhexanoate transaminase or a 6-amino-4-hydroxyhexanoate dehydrogenase (deaminating).

In another aspect, particularly when adipic acid synthesis pathway is selected from ADA 84-ADA141, the non-naturally occurring microbial organism further comprises a N-acetyltransferase and/or a N-deacetylase.

In one aspect, provided is a non-naturally occurring microbial organism as described herein, wherein the microbial organism includes two, three, four, five, six, seven, eight, nine, ten, eleven or twelve exogenous nucleic acids each encoding an adipate pathway enzyme. For example, the microbial organism can include exogenous nucleic acids encoding each of the enzymes of at least one of the pathways selected from ADA1-ADA141 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding an 6-aminohexanoate (AHA) pathway enzyme expressed in a sufficient amount to produce 6-aminohexanoate, wherein said 6-aminohexanoate pathway comprises a pathway selected from Table B:

TABLE B

| Pathway No | Pathway Steps | Aldehyde |
|---|---|---|
| AHA1 | 2A, 2B, 2C, 2D, 2E, 2F, 2G, 4F5 | 3-aminopropanal |
| AHA2 | 2A, 3B1, 3G1, 3M, 3N, 2F, 2G, 4F5 | 3-aminopropanal |
| AHA3 | 2A, 2B, 2C, 2D, 2E, 2F, 2G, 4A3, 4F2, 5J | 3-oxo propanol |
| AHA4 | 2A, 2B, 2C, 2D, 2E, 2F, 2G, 4F3, 4A4, 5J | 3-oxo propanol |
| AHA5 | 2A, 3B1, 3G1, 3M, 3N, 2F, 2G, 4A3, 4F2, 5J | 3-oxo propanol |
| AHA6 | 2A, 3B1, 3G1, 3M, 3N, 2F, 2G, 4F3, 4A4, 5J | 3-oxo propanol |
| AHA7 | 2A, 3B1, 3G1, 3D3, 3K1, 4A2, 4D4, 4E4, 4F2, 5J | 3-oxo propanol |
| AHA8 | 2A, 3B1, 3G1, 3C1, 3D1, 3E1, 3F1, 4A2, 4D4, 4E4, 4F2, 5J | 3-oxo propanol |
| AHA9 | 2A, 3B1, 3C2, 3D2, 3E2, 3F2, 3G5, 4A2, 4D4, 4E4, 4F2, 5J | 3-oxo propanol |
| AHA10 | 2A, 3B1, 3C2, 3D2, 3L2, 3K2, 3G5, 4A2, 4D4, 4E4, 4F2, 5J | 3-oxo propanol |
| AHA11 | 2A, 3B2, 3C3, 3D2, 3E2, 3F2, 3G5, 4A2, 4D4, 4E4, 4F2, 5J | 3-oxo propanol |
| AHA12 | 2A, 3B2, 3C3, 3D2, 3L2, 3K2, 3G5, 4A2, 4D4, 4E4, 4F2, 5J | 3-oxo propanol |
| AHA13 | 2A, 3B2, 3C3, 3G2, 3D1, 3E1, 3F1, 4A2, 4D4, 4E4, 4F2, 5J | 3-oxo propanol |
| AHA14 | 2A, 3B1, 3C2, 3G2, 3D1, 3E1, 3F1, 4A2, 4D4, 4E4, 4F2, 5J | 3-oxo propanol |
| AHA15 | 2A, 3B2, 3C3, 3G2, 3D1, 3L1, 3K1, 4A2, 4D4, 4E4, 4F2, 5J | 3-oxo propanol |
| AHA16 | 2A, 3B1, 3C2, 3G2, 3D1, 3L1, 3K1, 4A2, 4D4, 4E4, 4F2, 5J | 3-oxo propanol |
| AHA17 | 2A, 3B1, 3G1, 3C1, 3D1, 3L1, 3K1, 4A2, 4D4, 4E4, 4F2, 5J | 3-oxo propanol |
| AHA18 | 2A, 3B1, 3C2, 3D2, 3E2, 3F2, 4A5, 4D5, 4F4, 5J | 3-oxo propanol |
| AHA19 | 2A, 3B1, 3C2, 3D2, 3L2, 3K2, 4A5, 4D5, 4F4, 5J | 3-oxo propanol |
| AHA20 | 2A, 3B2, 3C3, 3D2, 3E2, 3F2, 4A5, 4D5, 4F4, 5J | 3-oxo propanol |
| AHA21 | 2A, 3B2, 3C3, 3D2, 3L2, 3K2, 4A5, 4D5, 4F4, 5J | 3-oxo propanol |
| AHA22 | 2A, 2B, 2C, 2D, 2E, 2F, 2G, 4A3, 5I, 4F5 | 3-oxo propanol |
| AHA23 | 2A, 3B1, 3G1, 3M, 3N, 2F, 2G, 4A3, 5I, 4F5 | 3-oxo propanol |
| AHA24 | 2A, 3B1, 3G1, 3D3, 3K1, 4A2, 4D4, 4E4, 5I, 4F5 | 3-oxo propanol |
| AHA25 | 2A, 3B1, 3G1, 3C1, 3D1, 3E1, 3F1, 4A2, 4D4, 4E4, 5I, 4F5 | 3-oxo propanol |
| AHA26 | 2A, 3B1, 3C2, 3D2, 3E2, 3F2, 3G5, 4A2, 4D4, 4E4, 5I, 4F5 | 3-oxo propanol |
| AHA27 | 2A, 3B1, 3C2, 3D2, 3L2, 3K2, 3G5, 4A2, 4D4, 4E4, 5I, 4F5 | 3-oxo propanol |
| AHA28 | 2A, 3B2, 3C3, 3D2, 3E2, 3F2, 3G5, 4A2, 4D4, 4E4, 5I, 4F5 | 3-oxo propanol |
| AHA29 | 2A, 3B2, 3C3, 3D2, 3L2, 3K2, 3G5, 4A2, 4D4, 4E4, 5I, 4F5 | 3-oxo propanol |
| AHA30 | 2A, 3B2, 3C3, 3G2, 3D1, 3E1, 3F1, 4A2, 4D4, 4E4, 5I, 4F5 | 3-oxo propanol |
| AHA31 | 2A, 3B1, 3C2, 3G2, 3D1, 3E1, 3F1, 4A2, 4D4, 4E4, 5I, 4F5 | 3-oxo propanol |
| AHA32 | 2A, 3B2, 3C3, 3G2, 3D1, 3L1, 3K1, 4A2, 4D4, 4E4, 5I, 4F5 | 3-oxo propanol |
| AHA33 | 2A, 3B1, 3C2, 3G2, 3D1, 3L1, 3K1, 4A2, 4D4, 4E4, 5I, 4F5 | 3-oxo propanol |
| AHA34 | 2A, 3B1, 3G1, 3C1, 3D1, 3L1, 3K1, 4A2, 4D4, 4E4, 5I, 4F5 | 3-oxo propanol |
| AHA35 | 2A, 2B, 2C, 2D, 2E, 2F, 2G, 5G, 5J | 3-oxo propionate |
| AHA36 | 2A, 3B1, 3G1, 3M, 3N, 2F, 2G, 5G, 5J | 3-oxo propionate |
| AHA37 | 2A, 3B1, 3G1, 3D3, 3K1, 3H, 2G, 5G, 5J | 3-oxo propionate |

TABLE B-continued

| Pathway No | Pathway Steps | Aldehyde |
|---|---|---|
| AHA38 | 2A, 3B1, 3G1, 3D3, 3K1, 4D3, 4E3, 5G, 5J | 3-oxo propionate |
| AHA39 | 2A, 3B1, 3G1, 3C1, 3D1, 3E1, 3F1, 3H, 2G, 5G, 5J | 3-oxo propionate |
| AHA40 | 2A, 3B1, 3G1, 3C1, 3D1, 3E1, 3F1, 4D3, 4E3, 5G, 5J | 3-oxo propionate |
| AHA41 | 2A, 3B1, 3C2, 3D2, 3E2, 3F2, 3G5, 3H, 2G, 5G, 5J | 3-oxo propionate |
| AHA42 | 2A, 3B1, 3C2, 3D2, 3E2, 3F2, 3G5, 4D3, 4E3, 5G, 5J | 3-oxo propionate |
| AHA43 | 2A, 3B1, 3C2, 3D2, 3L2, 3K2, 3G5, 3H, 2G, 5G, 5J | 3-oxo propionate |
| AHA44 | 2A, 3B1, 3C2, 3D2, 3L2, 3K2, 3G5, 4D3, 4E3, 5G, 5J | 3-oxo propionate |
| AHA45 | 2A, 3B1, 3C2, 3G2, 3D1, 3E1, 3F1, 3H, 2G, 5G, 5J | 3-oxo propionate |
| AHA46 | 2A, 3B1, 3C2, 3G2, 3D1, 3E1, 3F1, 4D3, 4E3, 5G, 5J | 3-oxo propionate |
| AHA47 | 2A, 3B2, 3C3, 3D2, 3E2, 3F2, 3G5, 3H, 2G, 5G, 5J | 3-oxo propionate |
| AHA48 | 2A, 3B2, 3C3, 3D2, 3E2, 3F2, 3G5, 4D3, 4E3, 5G, 5J | 3-oxo propionate |
| AHA49 | 2A, 3B2, 3C3, 3D2, 3L2, 3K2, 3G5, 3H, 2G, 5G, 5J | 3-oxo propionate |
| AHA50 | 2A, 3B2, 3C3, 3D2, 3L2, 3K2, 3G5, 4D3, 4E3, 5G, 5I | 3-oxo propionate |
| AHA51 | 2A, 3B2, 3C3, 3G2, 3D1, 3E1, 3F1, 3H, 2G, 5G, 5J | 3-oxo propionate |
| AHA52 | 2A, 3B2, 3C3, 3G2, 3D1, 3E1, 3F1, 4D3, 4E3, 5G, 5J | 3-oxo propionate |
| AHA53 | 2A, 3B2, 3C3, 3G2, 3D1, 3L1, 3K1, 3H, 2G, 5G, 5J | 3-oxo propionate |
| AHA54 | 2A, 3B2, 3C3, 3G2, 3D1, 3L1, 3K1, 4D3, 4E3, 5G, 5J | 3-oxo propionate |
| AHA55 | 2A, 3B1, 3C2, 3G2, 3D1, 3L1, 3K1, 3H, 2G, 5G, 5J | 3-oxo propionate |
| AHA56 | 2A, 3B1, 3C2, 3G2, 3D1, 3L1, 3K1, 4D3, 4E3, 5G, 5J | 3-oxo propionate |
| AHA57 | 2A, 3B1, 3G1, 3C1, 3D1, 3L1, 3K1, 3H, 2G, 5G, 5J | 3-oxo propionate |
| AHA58 | 2A, 3B1, 3G1, 3C1, 3D1, 3L1, 3K1, 4D3, 4E3, 5G, 5J | 3-oxo propionate |
| AHA59 | 2A, 3B1, 3G1, 2I, 2J, 2F, 2G, 5G, 5J | 3-oxo propionate |

In Table B 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 4F5, 2E, 3G2, 3G5, 21, 3M, 3H, 2F, 3D3, 3D2, 3D1, 4D3, 4D4, 4D5, are same as above and 5J is a 6-oxohexanoic acid transaminase (aminating) or a 6-oxohexanoic acid dehydrogenase (aminating), 5I is a 6-oxohexanoyl-CoA transaminase (aminating), or a 6-oxohexanoyl-CoA dehydrogenase (aminating), and 5G is an adipyl-CoA 1-reductase.

In one aspect, particularly when 6-aminohexanoate synthesis pathway is selected from AHA1-AHA2, 2A, 2C, 2D, 2E, 2F, 2G, 4F5. 3B1, 3G1, 3M, and 3N are the same as when the adipate pathway selected is any one of ADA84-ADA141 and 5J, 5I and 5C are defined above In another aspect, particularly when 6-aminohexanoate synthesis pathway is selected from AHA3-AHA34, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 4F5, 2E, 3G2, 3G5, 21, 3M, 3H, 2F, 3D3, 3D2, 3D1, 4D3, 4D4, and 4D5, are the same as when the adipate pathway selected is any one of ADA26-ADA83 and 5J, 5I and 5C are defined above.

In another aspect, particularly when 6-aminohexanoate synthesis pathway is selected from AHA35-AHA59, 2A, 2B, 3B1, 3B2, 2C, 3G1, 3C2, 3C3, 2G, 2J, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 4F5, 2E, 3G2, 3G5, 21, 3M, 3H, 2F, 3D3, 3D2, 3D1, 4D3, 4D4, and 4D5, are the same as when the adipate pathway selected is any one of ADA1-ADA25 and 5J, 5I and 5C are defined above.

In another aspect, particularly when 6-aminohexanoate synthesis pathway is selected from AHA 1-AHA2, the non-naturally occurring microbial organism further comprises a N-acetyltransferase and/or a N-deacetylase.

In one aspect, provided is a non-naturally occurring microbial organism as described herein, wherein the microbial organism includes two, three, four, five, six, seven, eight, nine, ten, eleven or twelve exogenous nucleic acids each encoding a 6-aminohexanoate pathway enzyme.

For example, the microbial organism can include exogenous nucleic acids encoding each of the enzymes of at least one of the pathways selected from AHA1-AHA59 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding an caprolactam pathway enzyme expressed in a sufficient amount to produce caprolactam (CPL), wherein said caprolactam pathway comprises a pathway selected from Table C:

TABLE C

| Pathway No | Pathway Steps | Aldehyde |
|---|---|---|
| CPL1 | 2A, 2B, 2C, 2D, 2E, 2F, 2G | 3-aminopropanal |
| CPL2 | 2A, 3B1, 3G1, 3M, 3N, 2F, 2G | 3-ammopropanal |
| CPL3 | 2A, 2B, 2C, 2D, 2E, 2F, 2G, 4A3, 5I | 3-oxo propanol |
| CPL4 | 2A, 3B1, 3G1, 3M, 3N, 2F, 2G, 4A3, 5I | 3-oxo propanol |
| CPL5 | 2A, 3B1, 3G1, 3D3, 3K1, 4A2, 4D4, 4E4, 5I | 3-oxo propanol |
| CPL6 | 2A, 3B1, 3G1, 3C1, 3D1, 3E1, 3F1, 4A2, 4D4, 4E4, 5I | 3-oxo propanol |
| CPL7 | 2A, 3B1, 3C2, 3D2, 3E2, 3F2, 3G5, 4A2, 4D4, 4E4, 5I | 3-oxo propanol |
| CPL8 | 2A, 3B1, 3C2, 3D2, 3L2, 3K2, 3G5, 4A2, 4D4, 4E4, 5I | 3-oxo propanol |
| CPL9 | 2A, 3B2, 3C3, 3D2, 3E2, 3F2, 3G5, 4A2, 4D4, 4E4, 5I | 3-oxo propanol |
| CPL10 | 2A, 3B2, 3C3, 3D2, 3L2, 3K2, 3G5, 4A2, 4D4, 4E4, 5I | 3-oxo propanol |
| CPL11 | 2A, 3B2, 3C3, 3G2, 3D1, 3E1, 3F1, 4A2, 4D4, 4E4, 5I | 3-oxo propanol |
| CPL12 | 2A, 3B1, 3C2, 3G2, 3D1, 3E1, 3F1, 4A2, 4D4, 4E4, 5I | 3-oxo propanol |
| CPL13 | 2A, 3B2, 3C3, 3G2, 3D1, 3L1, 3K1, 4A2, 4D4, 4E4, 5I | 3-oxo propanol |
| CPL14 | 2A, 3B1, 3C2, 3G2, 3D1, 3L1, 3K1, 4A2, 4D4, 4E4, 5I | 3-oxo propanol |
| CPL15 | 2A, 3B1, 3G1, 3C1, 3D1, 3L1, 3K1, 4A2, 4D4, 4E4, 5I | 3-oxo propanol |
| CPL16 | 2A, 2B, 2C, 2D, 2E, 2F, 2G, 4A3, 4F2, 5A | 3-oxo propanol |
| CPL17 | 2A, 2B, 2C, 2D, 2E, 2F, 2G, 4F3, 4A4, 5A | 3-oxo propanol |
| CPL18 | 2A, 3B1, 3G1, 3M, 3N, 2F, 2G, 4A3, 4F2, 5A | 3-oxo propanol |
| CPL19 | 2A, 3B1, 3G1, 3M, 3N, 2F, 2G, 4F3, 4A4, 5A | 3-oxo propanol |
| CPL20 | 2A, 3B1, 3G1, 3D3, 3K1, 4A2, 4D4, 4E4, 4F2, 5A | 3-oxo propanol |

TABLE C-continued

| Pathway No | Pathway Steps | Aldehyde |
|---|---|---|
| CPL21 | 2A, 3B1, 3G1, 3C1, 3D1, 3E1, 3F1, 4A2, 4D4, 4E4, 4F2, 5A | 3-oxo propanol |
| CPL22 | 2A, 3B1, 3C2, 3D2, 3E2, 3F2, 3G5, 4A2, 4D4, 4E4, 4F2, 5A | 3-oxo propanol |
| CPL23 | 2A, 3B1, 3C2, 3D2, 3L2, 3K2, 3G5, 4A2, 4D4, 4E4, 4F2, 5A | 3-oxo propanol |
| CPL24 | 2A, 3B2, 3C3, 3D2, 3E2, 3F2, 3G5, 4A2, 4D4, 4E4, 4F2, 5A | 3-oxo propanol |
| CPL25 | 2A, 3B2, 3C3, 3D2, 3L2, 3K2, 3G5, 4A2, 4D4, 4E4, 4F2, 5A | 3-oxo propanol |
| CPL26 | 2A, 3B2, 3C3, 3G2, 3D1, 3E1, 3F1, 4A2, 4D4, 4E4, 4F2, 5A | 3-oxo propanol |
| CPL27 | 2A, 3B1, 3C2, 3G2, 3D1, 3E1, 3F1, 4A2, 4D4, 4E4, 4F2, 5A | 3-oxo propanol |
| CPL28 | 2A, 3B2, 3C3, 3G2, 3D1, 3L1, 3K1, 4A2, 4D4, 4E4, 4F2, 5A | 3-oxo propanol |
| CPL29 | 2A, 3B1, 3C2, 3G2, 3D1, 3L1, 3K1, 4A2, 4D4, 4E4, 4F2, 5A | 3-oxo propanol |
| CPL30 | 2A, 3B1, 3G1, 3C1, 3D1, 3L1, 3K1, 4A2, 4D4, 4E4, 4F2, 5A | 3-oxo propanol |
| CPL31 | 2A, 3B1, 3C2, 3D2, 3E2, 3F2, 4A5, 4D5, 4F4, 5A | 3-oxo propanol |
| CPL32 | 2A, 3B1, 3C2, 3D2, 3L2, 3K2, 4A5, 4D5, 4F4, 5A | 3-oxo propanol |
| CPL33 | 2A, 3B2, 3C3, 3D2, 3E2, 3F2, 4A5, 4D5, 4F4, 5A | 3-oxo propanol |
| CPL34 | 2A, 3B2, 3C3, 3D2, 3L2, 3K2, 4A5, 4D5, 4F4, 5A | 3-oxo propanol |
| CPL35 | 2A, 3B1, 3G1, 3C1, 3D1, 3E1, 3F1, 4A2, 4D4, 4E4, 5I, 4F5, 5A | 3-oxo propanol |
| CPL36 | 2A, 3B1, 3C2, 3D2, 3E2, 3F2, 3G5, 4A2, 4D4, 4E4, 5I, 4F5, 5A | 3-oxo propanol |
| CPL37 | 2A, 3B1, 3C2, 3D2, 3L2, 3K2, 3G5, 4A2, 4D4, 4E4, 5I, 4F5, 5A | 3-oxo propanol |
| CPL38 | 2A, 3B2, 3C3, 3D2, 3E2, 3F2, 3G5, 4A2, 4D4, 4E4, 5I, 4F5, 5A | 3-oxo propanol |
| CPL39 | 2A, 3B2, 3C3, 3D2, 3L2, 3K2, 3G5, 4A2, 4D4, 4E4, 5I, 4F5, 5A | 3-oxo propanol |
| CPL40 | 2A, 3B2, 3C3, 3G2, 3D1, 3E1, 3F1, 4A2, 4D4, 4E4, 5I, 4F5, 5A | 3-oxo propanol |
| CPL41 | 2A, 3B1, 3C2, 3G2, 3D1, 3E1, 3F1, 4A2, 4D4, 4E4, 5I, 4F5, 5A | 3-oxo propanol |
| CPL42 | 2A, 3B1, 3G1, 3C1, 3D1, 3L1, 3K1, 4A2, 4D4, 4E4, 5I, 4F5, 5A | 3-oxo propanol |
| CPL43 | 2A, 2B, 2C, 2D, 2E, 2F, 2G, 5G, 5A | 3-oxo propionate |
| CPL44 | 2A, 3B1, 3G1, 3M, 3N, 2F, 2G, 5G, 5A | 3-oxo propionate |
| CPL45 | 2A, 3B1, 3G1, 3D3, 3K1, 3H, 2G, 5G, 5A | 3-oxo propionate |
| CPL46 | 2A, 3B1, 3G1, 3D3, 3K1, 4D3, 4E3, 5G, 5A | 3-oxo propionate |
| CPL47 | 2A, 3B1, 3G1, 3C1, 3D1, 3E1, 3F1, 3H, 2G, 5G, 5A | 3-oxo propionate |
| CPL48 | 2A, 3B1, 3G1, 3C1, 3D1, 3E1, 3F1, 4D3, 4E3, 5G, 5A | 3-oxo propionate |
| CPL49 | 2A, 3B1, 3C2, 3D2, 3E2, 3F2, 3G5, 3H, 2G, 5G, 5A | 3-oxo propionate |
| CPL50 | 2A, 3B1, 3C2, 3D2, 3E2, 3F2, 3G5, 4D3, 4E3, 5G, 5A | 3-oxo propionate |
| CPL51 | 2A, 3B1, 3C2, 3D2, 3L2, 3K2, 3G5, 3H, 2G, 5G, 5A | 3-oxo propionate |
| CPL52 | 2A, 3B1, 3C2, 3D2, 3L2, 3K2, 3G5, 4D3, 4E3, 5G, 5A | 3-oxo propionate |
| CPL53 | 2A, 3B1, 3C2, 3G2, 3D1, 3E1, 3F1, 3H, 2G, 5G, 5A | 3-oxo propionate |
| CPL54 | 2A, 3B1, 3C2, 3G2, 3D1, 3E1, 3F1, 4D3, 4E3, 5G, 5A | 3-oxo propionate |
| CPL55 | 2A, 3B2, 3C3, 3D2, 3E2, 3F2, 3G5, 3H, 2G, 5G, 5A | 3-oxo propionate |
| CPL56 | 2A, 3B2, 3C3, 3D2, 3E2, 3F2, 3G5, 4D3, 4E3, 5G, 5A | 3-oxo propionate |
| CPL57 | 2A, 3B2, 3C3, 3D2, 3L2, 3K2, 3G5, 3H, 2G, 5G, 5A | 3-oxo propionate |
| CPL58 | 2A, 3B2, 3C3, 3D2, 3L2, 3K2, 3G5, 4D3, 4E3, 5G, 5A | 3-oxo propionate |
| CPL59 | 2A, 3B2, 3C3, 3G2, 3D1, 3EL, 3F1, 3H, 2G, 5G, 5A | 3-oxo propionate |
| CPL60 | 2A, 3B2, 3C3, 3G2, 3D1, 3E1, 3F1, 4D3, 4E3, 5G, 5A | 3-oxo propionate |
| CPL61 | 2A, 3B2, 3C3, 3G2, 3D1, 3L1, 3K1, 3H, 2G, 5G, 5A | 3-oxo propionate |
| CPL62 | 2A, 3B2, 3C3, 3G2, 3D1, 3L1, 3K1, 4D3, 4E3, 5G, 5A | 3-oxo propionate |
| CPL63 | 2A, 3B1, 3C2, 3G2, 3D1, 3L1, 3K1, 3H, 2G, 5G, 5A | 3-oxo propionate |
| CPL64 | 2A, 3B1, 3C2, 3G2, 3D1, 3L1, 3K1, 4D3, 4E3, 5G, 5A | 3-oxo propionate |
| CPL65 | 2A, 3B1, 3G1, 3C1, 3D1, 3L1, 3K1, 3H, 2G, 5G, 5A | 3-oxo propionate |
| CPL66 | 2A, 3B1, 3G1, 3C1, 3D1, 3L1, 3K1, 4D3, 4E3, 5G, 5A | 3-oxo propionate |
| CPL67 | 2A, 3B1, 3G1, 2I, 2J, 2F, 2G, 5G, 5A | 3-oxo propionate |
| CPL68 | 2A, 2B, 2C, 2D, 2E, 2F, 2G, 4A3, 4F2, 5C | 3-oxo propanol |
| CPL69 | 2A, 2B, 2C, 2D, 2E, 2F, 2G, 4F3, 4A4, 5C | 3-oxo propanol |
| CPL70 | 2A, 3B1, 3G1, 3M, 3N, 2F, 2G, 4A3, 4F2, 5C | 3-oxo propanol |
| CPL71 | 2A, 3B1, 3G1, 3M, 3N, 2F, 2G, 4F3, 4A4, 5C | 3-oxo propanol |
| CPL72 | 2A, 3B1, 3G1, 3D3, 3K1, 4A2, 4D4, 4E4, 4F2, 5C | 3-oxo propanol |
| CPL73 | 2A, 3B1, 3G1, 3C1, 3D1, 3E1, 3F1, 4A2, 4D4, 4E4, 4F2, 5C | 3-oxo propanol |
| CPL74 | 2A, 3B1, 3C2, 3D2, 3E2, 3F2, 3G5, 4A2, 4D4, 4E4, 4F2, 5C | 3-oxo propanol |
| CPL75 | 2A, 3B1, 3C2, 3D2, 3L2, 3K2, 3G5, 4A2, 4D4, 4E4, 4F2, 5C | 3-oxo propanol |
| CPL76 | 2A, 3B2, 3C3, 3D2, 3E2, 3F2, 3G5, 4A2, 4D4, 4E4, 4F2, 5C | 3-oxo propanol |
| CPL77 | 2A, 3B2, 3C3, 3D2, 3L2, 3K2, 3G5, 4A2, 4D4, 4E4, 4F2, 5C | 3-oxo propanol |
| CPL78 | 2A, 3B2, 3C3, 3G2, 3D1, 3E1, 3F1, 4A2, 4D4, 4E4, 4F2, 5C | 3-oxo propanol |
| CPL79 | 2A, 3B1, 3C2, 3G2, 3D1, 3E1, 3F1, 4A2, 4D4, 4E4, 4F2, 5C | 3-oxo propanol |
| CPL80 | 2A, 3B2, 3C3, 3G2, 3D1, 3L1, 3K1, 4A2, 4D4, 4E4, 4F2, 5C | 3-oxo propanol |
| CPL81 | 2A, 3B1, 3C2, 3G2, 3D1, 3L1, 3K1, 4A2, 4D4, 4E4, 4F2, 5C | 3-oxo propanol |
| CPL82 | 2A, 3B1, 3G1, 3C1, 3D1, 3L1, 3K1, 4A2, 4D4, 4E4, 4F2, 5C | 3-oxo propanol |
| CPL83 | 2A, 3B1, 3C2, 3D2, 3E2, 3F2, 4A5, 4D5, 4F4, 5C | 3-oxo propanol |
| CPL84 | 2A, 3B1, 3C2, 3D2, 3L2, 3K2, 4A5, 4D5, 4F4, 5C | 3-oxo propanol |
| CPL85 | 2A, 3B2, 3C3, 3D2, 3E2, 3F2, 4A5, 4D5, 4F4, 5C | 3-oxo propanol |
| CPL86 | 2A, 3B2, 3C3, 3D2, 3L2, 3K2, 4A5, 4D5, 4F4, 5C | 3-oxo propanol |
| CPL87 | 2A, 3B1, 3G1, 3C1, 3D1, 3E1, 3F1, 4A2, 4D4, 4E4, 5I, 4F5, 5C | 3-oxo propanol |
| CPL88 | 2A, 3B1, 3C2, 3D2, 3E2, 3F2, 3G5, 4A2, 4D4, 4E4, 5I, 4F5, 5C | 3-oxo propanol |
| CPL89 | 2A, 3B1, 3C2, 3D2, 3L2, 3K2, 3G5, 4A2, 4D4, 4E4, 5I, 4F5, 5C | 3-oxo propanol |
| CPL90 | 2A, 3B2, 3C3, 3D2, 3E2, 3F2, 3G5, 4A2, 4D4, 4E4, 5I, 4F5, 5C | 3-oxo propanol |
| CPL91 | 2A, 3B2, 3C3, 3D2, 3L2, 3K2, 3G5, 4A2, 4D4, 4E4, 5I, 4F5, 5C | 3-oxo propanol |
| CPL92 | 2A, 3B2, 3C3, 3G2, 3D1, 3E1, 3F1, 4A2, 4D4, 4E4, 5I, 4F5, 5C | 3-oxo propanol |
| CPL93 | 2A, 3B1, 3C2, 3G2, 3D1, 3E1, 3F1, 4A2, 4D4, 4E4, 5I, 4F5, 5C | 3-oxo propanol |
| CPL94 | 2A, 3B1, 3G1, 3C1, 3D1, 3L1, 3K1, 4A2, 4D4, 4E4, 5I, 4F5, 5C | 3-oxo propanol |
| CPL95 | 2A, 2B, 2C, 2D, 2E, 2F, 2G, 5G, 5C | 3-oxo propionate |
| CPL96 | 2A, 3B1, 3G1, 3M, 3N, 2F, 2G, 5G, 5C | 3-oxo propionate |
| CPL97 | 2A, 3B1, 3G1, 3D3, 3K1, 3H, 2G, 5G, 5C | 3-oxo propionate |
| CPL98 | 2A, 3B1, 3G1, 3D3, 3K1, 4D3, 4E3, 5G, 5C | 3-oxo propionate |

TABLE C-continued

| Pathway No | Pathway Steps | Aldehyde |
|---|---|---|
| CPL99 | 2A, 3B1, 3G1, 3C1, 3D1, 3E1, 3F1, 3H, 2G, 5G, 5C | 3-oxo propionate |
| CPL100 | 2A, 3B1, 3G1, 3C1, 3D1, 3E1, 3F1, 4D3, 4E3, 5G, 5C | 3-oxo propionate |
| CPL101 | 2A, 3B1, 3C2, 3D2, 3E2, 3F2, 3G5, 3H, 2G, 5G, 5C | 3-oxo propionate |
| CPL102 | 2A, 3B1, 3C2, 3D2, 3E2, 3F2, 3G5, 4D3, 4E3, 5G, 5C | 3-oxo propionate |
| CPL103 | 2A, 3B1, 3C2, 3D2, 3L2, 3K2, 3G5, 3H, 2G, 5G, 5C | 3-oxo propionate |
| CPL104 | 2A, 3B1, 3C2, 3D2, 3L2, 3K2, 3G5, 4D3, 4E3, 5G, 5C | 3-oxo propionate |
| CPL105 | 2A, 3B1, 3C2, 3G2, 3D1, 3E1, 3F1, 3H, 2G, 5G, 5C | 3-oxo propionate |
| CPL106 | 2A, 3B1, 3C2, 3G2, 3D1, 3E1, 3F1, 4D3, 4E3, 5G, 5C | 3-oxo propionate |
| CPL107 | 2A, 3B2, 3C3, 3D2, 3E2, 3F2, 3G5, 3H, 2G, 5G, 5C | 3-oxo propionate |
| CPL108 | 2A, 3B2, 3C3, 3D2, 3E2, 3F2, 3G5, 4D3, 4E3, 5G, 5C | 3-oxo propionate |
| CPL109 | 2A, 3B2, 3C3, 3D2, 3L2, 3K2, 3G5, 3H, 2G, 5G, 5C | 3-oxo propionate |
| CPL110 | 2A, 3B2, 3C3, 3D2, 3L2, 3K2, 3G5, 4D3, 4E3, 5G, 5C | 3-oxo propionate |
| CPL111 | 2A, 3B2, 3C3, 3G2, 3D1, 3E1, 3F1, 3H, 2G, 5G, 5C | 3-oxo propionate |
| CPL112 | 2A, 3B2, 3C3, 3G2, 3D1, 3E1, 3F1, 4D3, 4E3, 5G, 5C | 3-oxo propionate |
| CPL113 | 2A, 3B2, 3C3, 3G2, 3D1, 3L1, 3K1, 3H, 2G, 5G, 5C | 3-oxo propionate |
| CPL114 | 2A, 3B2, 3C3, 3G2, 3D1, 3L1, 3K1, 4D3, 4E3, 5G, 5C | 3-oxo propionate |
| CPL115 | 2A, 3B1, 3C2, 3G2, 3D1, 3L1, 3K1, 3H, 2G, 5G, 5C | 3-oxo propionate |
| CPL116 | 2A, 3B1, 3C2, 3G2, 3D1, 3L1, 3K1, 4D3, 4E3, 5G, 5C | 3-oxo propionate |
| CPL117 | 2A, 3B1, 3G1, 3C1, 3D1, 3L1, 3K1, 3H, 2G, 5G, 5C | 3-oxo propionate |
| CPL118 | 2A, 3B1, 3G1, 3C1, 3D1, 3L1, 3K1, 4D3, 4E3, 5G, 5C | 3-oxo propionate |
| CPL119 | 2A, 3B1, 3G1, 2I, 2J, 2F, 2G, 5G, 5C | 3-oxo propionate |

Wherein 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, and 4D5, are the same when the adipate pathway selected is any one of ADA1-ADA141, and 5J is a 6-oxohexanoic acid transaminase (aminating) or a 6-oxohexanoic acid dehydrogenase (aminating), 5I is a 6-oxohexanoyl-CoA transaminase (aminating), or a 6-oxohexanoyl-CoA dehydrogenase (aminating), 5G is an adipyl-CoA 1-reductase, 5C is a 6-aminohexanoate CoA-transferase or a 6-aminohexanoate-CoA ligase, and 5A is spontaneous cyclization or an amidohydrolase.

In one aspect, particularly when CPL synthesis pathway is selected from CPL1-2, 2A, 2C, 2D, 2E, 2F, 2G, 3B1, 3G1, 3M, and 3N are the same as when AHA pathway is selected is any one of AHA1-AHA2.

In another aspect, particularly when CPL pathway is selected from CPL3-42, 68-94, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, 4D5, are the same as when ADA pathway selected is one of ADA26-ADA83, and 5J, 5I, 5G, 5A, and 5C are defined above.

In another aspect, particularly when CPL pathway is selected from CPL43-67, 95-119, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 2E, 3G2, 3G5, 2I, 3M, 3H, 2F, 3D3, 3D2, 3D1, 4D3, 4D4, 4D5, are the same as when ADA pathway selected is one of ADA1-ADA25, and 5J, 5I, 5G, 5A, and 5C are defined above.

In another aspect, particularly when CPL pathway is selected from CPL1-2, the non-naturally occurring microbial organism further comprises a N-acetyltransferase and/or a N-deacetylase.

In one aspect, provided is a non-naturally occurring microbial organism as described herein, wherein the microbial organism includes two, three, four, five, six, seven, eight, nine, ten, eleven, twelve or thirteen exogenous nucleic acids each encoding a CPL pathway enzyme.

For example, the microbial organism can include exogenous nucleic acids encoding each of the enzymes of at least one of the pathways selected from CPL1-CPL119 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding an 6-hydroxyhexanoate (HHA) pathway enzyme expressed in a sufficient amount to produce 6-hydroxyhexanoate, wherein said 6-hydroxyhexanoate pathway comprises a pathway selected from Table D:

TABLE D

| Pathway No | Pathway Steps | Aldehyde |
|---|---|---|
| HHA1 | 2A, 2B, 2C, 2D, 2E, 2F, 2G, 4F3 | 3-oxo propanol |
| HHA2 | 2A, 3B1, 3G1, 3M, 3N, 2F, 2G, 4F3 | 3-oxo propanol |
| HHA3 | 2A, 2B, 2C, 2D, 2E, 2F, 2G, 4A3, 4F2, 5K | 3-oxo propanol |
| HHA4 | 2A, 2B, 2C, 2D, 2E, 2F, 2G, 4F3, 4A4, 5K | 3-oxo propanol |
| HHA5 | 2A, 3B1, 3G1, 3M, 3N, 2F, 2G, 4A3, 4F2, 5K | 3-oxo propanol |
| HHA6 | 2A, 3B1, 3G1, 3M, 3N, 2F, 2G, 4F3, 4A4, 5K | 3-oxo propanol |
| HHA7 | 2A, 3B1, 3G1, 3D3, 3K1, 4A2, 4D4, 4E4, 4F2, 5K | 3-oxo propanol |
| HHA8 | 2A, 3B1, 3G1, 3C1, 3D1, 3E1, 3F1, 4A2, 4D4, 4E4, 4F2, 5K | 3-oxo propanol |
| HHA9 | 2A, 3B1, 3C2, 3D2, 3E2, 3F2, 3G5, 4A2, 4D4, 4E4, 4F2, 5K | 3-oxo propanol |
| HHA10 | 2A, 3B1, 3C2, 3D2, 3L2, 3K2, 3G5, 4A2, 4D4, 4E4, 4F2, 5K | 3-oxo propanol |
| HHA11 | 2A, 3B2, 3C3, 3D2, 3E2, 3F2, 3G5, 4A2, 4D4, 4E4, 4F2, 5K | 3-oxo propanol |
| HHA12 | 2A, 3B2, 3C3, 3D2, 3L2, 3K2, 3G5, 4A2, 4D4, 4E4, 4F2, 5K | 3-oxo propanol |
| HHA13 | 2A, 3B2, 3C3, 3G2, 3D1, 3E1, 3F1, 4A2, 4D4, 4E4, 4F2, 5K | 3-oxo propanol |
| HHA14 | 2A, 3B1, 3C2, 3G2, 3D1, 3E1, 3F1, 4A2, 4D4, 4E4, 4F2, 5K | 3-oxo propanol |
| HHA15 | 2A, 3B2, 3C3, 3G2, 3D1, 3L1, 3K1, 4A2, 4D4, 4E4, 4F2, 5K | 3-oxo propanol |
| HHA16 | 2A, 3B1, 3C2, 3G2, 3D1, 3L1, 3K1, 4A2, 4D4, 4E4, 4F2, 5K | 3-oxo propanol |
| HHA17 | 2A, 3B1, SG1, 3C1, 3D1, 3L1, 3K1, 4A2, 4D4, 4E4, 4F2, 5K | 3-oxo propanol |
| HHA18 | 2A, 3B1, 3C2, 3D2, 3E2, 3F2, 4A5, 4D5, 4F4, 5K | 3-oxo propanol |
| HHA19 | 2A, 3B1, 3C2, 3D2, 3L2, 3K2, 4A5, 4D5, 4F4, 5K | 3-oxo propanol |
| HHA20 | 2A, 3B2, 3C3, 3D2, 3E2, 3F2, 4A5, 4D5, 4F4, 5K | 3-oxo propanol |

TABLE D-continued

| Pathway No | Pathway Steps | Aldehyde |
|---|---|---|
| HHA21 | 2A, 3B2, 3C3, 3D2, 3L2, 3K2, 4A5, 4D5, 4F4, 5K | 3-oxo propanol |
| HHA22 | 2A, 3B2, 3C3, 3D2, 3E2, 3F2, 3G5, 4A2, 4D4, 4E4, 4F2, 5K | 3-oxo propanol |
| HHA23 | 2A, 3B2, 3C3, 3D2, 3L2, 3K2, 3G5, 4A2, 4D4, 4E4, 4F2, 5K | 3-oxo propanol |
| HHA24 | 2A, 3B2, 3C3, 3G2, 3D1, 3E1, 3F1, 4A2, 4D4, 4E4, 4F2, 5K | 3-oxo propanol |
| HHA25 | 2A, 3B1, 3C2, 3G2, 3D1, 3E1, 3F1, 4A2, 4D4, 4E4, 4F2, 5K | 3-oxo propanol |
| HHA26 | 2A, 3B2, 3C3, 3G2, 3D1, 3L1, 3K1, 4A2, 4D4, 4E4, 4F2, 5K | 3-oxo propanol |
| HHA27 | 2A, 3B1, 3C2, 3G2, 3D1, 3L1, 3K1, 4A2, 4D4, 4E4, 4F2, 5K | 3-oxo propanol |
| HHA28 | 2A, 3B1, 3G1, 3C1, 3D1, 3L1, 3K1, 4A2, 4D4, 4E4, 4F2, 5K | 3-oxo propanol |
| HHA29 | 2A, 3B1, 3C2, 3D2, 3E2, 3F2, 4A5, 4D5, 4F4, 5K | 3-oxo propanol |
| HHA30 | 2A, 3B1, 3C2, 3D2, 3L2, 3K2, 4A5, 4D5, 4F4, 5K | 3-oxo propanol |
| HHA31 | 2A, 2B, 2C, 2D, 2E, 2F, 2G, 4A3, 5L, 4F3 | 3-oxo propanol |
| HHA32 | 2A, 3B1, 3G1, 3M, 3N, 2F, 2G, 4A3, 5L, 4F3 | 3-oxo propanol |
| HHA33 | 2A, 3B1, 3G1, 3D3, 3K1, 4A2, 4D4, 4E4, 5L, 4F3 | 3-oxo propanol |
| HHA34 | 2A, 3B1, 3G1, 3C1, 3D1, 3E1, 3F1, 4A2, 4D4, 4E4, 5L, 4F3 | 3-oxo propanol |
| HHA35 | 2A, 3B1, 3C2, 3D2, 3E2, 3F2, 3G5, 4A2, 4D4, 4E4, 5L, 4F3 | 3-oxo propanol |
| HHA36 | 2A, 3B1, 3C2, 3D2, 3L2, 3K2, 3G5, 4A2, 4D4, 4E4, 5L, 4F3 | 3-oxo propanol |
| HHA37 | 2A, 3B2, 3C3, 3D2, 3E2, 3F2, 3G5, 4A2, 4D4, 4E4, 5L, 4F3 | 3-oxo propanol |
| HHA38 | 2A, 3B2, 3C3, 3D2, 3L2, 3K2, 3G5, 4A2, 4D4, 4E4, 5L, 4F3 | 3-oxo propanol |
| HHA39 | 2A, 3B2, 3C3, 3G2, 3D1, 3E1, 3F1, 4A2, 4D4, 4E4, 5L, 4F3 | 3-oxo propanol |
| HHA40 | 2A, 3B1, 3C2, 3G2, 3D1, 3E1, 3F1, 4A2, 4D4, 4E4, 5L, 4F3 | 3-oxo propanol |
| HHA41 | 2A, 3B2, 3C3, 3G2, 3D1, 3L1, 3K1, 4A2, 4D4, 4E4, 5L, 4F3 | 3-oxo propanol |
| HHA42 | 2A, 3B1, 3C2, 3G2, 3D1, 3L1, 3K1, 4A2, 4D4, 4E4, 5L, 4F3 | 3-oxo propanol |
| HHA43 | 2A, 3B1, 3G1, 3C1, 3D1, 3L1, 3K1, 4A2, 4D4, 4E4, 5L, 4F3 | 3-oxo propanol |
| HHA44 | 2A, 2B, 2C, 2D, 2E, 2F, 2G, 5G, 5K | 3-oxo propionate |
| HHA45 | 2A, 3B1, 3G1, 3M, 3N, 2F, 2G, 5G, 5K | 3-oxo propionate |
| HHA46 | 2A, 3B1, 3G1, 3D3, 3K1, 3H, 2G, 5G, 5K | 3-oxo propionate |
| HHA47 | 2A, 3B1, 3G1, 3D3, 3K1, 4D3, 4E3, 5G, 5K | 3-oxo propionate |
| HHA48 | 2A, 3B1, 3G1, 3C1, 3D1, 3E1, 3F1, 3H, 2G, 5G, 5K | 3-oxo propionate |
| HHA49 | 2A, 3B1, 3G1, 3C1, 3D1, 3E1, 3F1, 4D3, 4E3, 5G, 5K | 3-oxo propionate |
| HHA50 | 2A, 3B1, 3C2, 3D2, 3E2, 3F2, 3G5, 3H, 2G, 5G, 5K | 3-oxo propionate |
| HHA51 | 2A, 3B1, 3C2, 3D2, 3E2, 3F2, 3G5, 4D3, 4E3, 5G, 5K | 3-oxo propionate |
| HHA52 | 2A, 3B1, 3C2, 3D2, 3L2, 3K2, 3G5, 3H, 2G, 5G, 5K | 3-oxo propionate |
| HHA53 | 2A, 3B1, 3C2, 3D2, 3L2, 3K2, 3G5, 4D3, 4E3, 5G, 5K | 3-oxo propionate |
| HHA54 | 2A, 3B2, 3C3, 3D2, 3E2, 3F2, 3G5, 3H, 2G, 5G, 5K | 3-oxo propionate |
| HHA55 | 2A, 3B2, 3C3, 3D2, 3E2, 3F2, 3G5, 4D3, 4E3, 5G, 5K | 3-oxo propionate |
| HHA56 | 2A, 3B2, 3C3, 3D2, 3L2, 3K2, 3G5, 3H, 2G, 5G, 5K | 3-oxo propionate |
| HHA57 | 2A, 3B2, 3C3, 3D2, 3L2, 3K2, 3G5, 4D3, 4E3, 5G, 5K | 3-oxo propionate |
| HHA58 | 2A, 3B2, 3C3, 3G2, 3D1, 3E1, 3F1, 3H, 2G, 5G, 5K | 3-oxo propionate |
| HHA59 | 2A, 3B2, 3C3, 3G2, 3D1, 3E1, 3F1, 4D3, 4E3, 5G, 5K | 3-oxo propionate |
| HHA60 | 2A, 3B2, 3C3, 3G2, 3D1, 3L1, 3K1, 3H, 2G, 5G, 5K | 3-oxo propionate |
| HHA61 | 2A, 3B2, 3C3, 3G2, 3D1, 3L1, 3K1, 4D3, 4E3, 5G, 5K | 3-oxo propionate |
| HHA62 | 2A, 3B1, 3C2, 3G2, 3D1, 3L1, 3K1, 3H, 2G, 5G, 5K | 3-oxo propionate |
| HHA63 | 2A, 3B1, 3C2, 3G2, 3D1, 3L1, 3K1, 4D3, 4E3, 5G, 5K | 3-oxo propionate |
| HHA64 | 2A, 3B1, 3G1, 3C1, 3D1, 3L1, 3K1, 3H, 2G, 5G, 5K | 3-oxo propionate |
| HHA65 | 2A, 3B1, 3G1, 3C1, 3D1, 3L1, 3K1, 4D3, 4E3, 5G, 5K | 3-oxo propionate |
| HHA66 | 2A, 3B1, 3G1, 2I, 2J, 2F, 2G, 5G, 5K | 3-oxo propionate |

Wherein 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, and 4D5, are the same when the adipate pathway selected is any one of ADA1-ADA83, and 5L is an 6-oxohexanoyl-CoA 6-reductase, 5G is an adipyl-CoA 1-reductase, and 5K is an 6-oxohexanoate 6-reductase.

In one aspect, particularly when 6-hydroxyhexanoate synthesis pathway is selected from HHA1-43, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4F2, 4F3, 2E, 3G2, 3G5, 3M, 3H, 2F, 3D3, 3D2, 3D1, 4D3, 4D4, and 4D5, are the same as when ADA pathway selected is one of ADA26-ADA83, and 5L, 5G and 5K are defined as above.

In another aspect, particularly when 6-hydroxyhexanoate synthesis pathway is selected from HHA44-66, 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, and 4D5, re the same as when ADA pathway selected is one of ADA1-ADA25, and 5L, 5G and 5K are defined as above.

In another aspect, particularly when 6-hydroxyhexanoate synthesis pathway is selected from HHA 1-66, the non-naturally occurring microbial organism further comprises a lactonase.

In one aspect, provided is a non-naturally occurring microbial organism as described herein, wherein the microbial organism includes two, three, four, five, six, seven, eight, nine, ten, eleven or twelve exogenous nucleic acids each encoding a 6-hydroxyhexanoate pathway enzyme.

For example, the microbial organism can include exogenous nucleic acids encoding each of the enzymes of at least one of the pathways selected from HHA1-HHA66 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding a caprolactone (CLO) pathway enzyme expressed in a sufficient amount to produce caprolactone, wherein said carpolactone pathway comprises a pathway selected from Table F:

TABLE F

| Pathway No | Pathway Steps | Aldehyde |
|---|---|---|
| CLO1 | 2A, 2B, 2C, 2D, 2E, 2F, 2G, 4A3, 4F2, 5K, 5P | 3-oxo propanol |
| CLO2 | 2A, 2B, 2C, 2D, 2E, 2F, 2G, 4F3, 4A4, 5K, 5P | 3-oxo propanol |
| CLO3 | 2A, 3B1, 3G1, 3M, 3N, 2F, 2G, 4A3, 4F2, 5K, 5P | 3-oxo propanol |
| CLO4 | 2A, 3B1, 3G1, 3M, 3N, 2F, 2G, 4F3, 4A4, 5K, 5P | 3-oxo propanol |
| CLO5 | 2A, 3B1, 3G1, 3D3, 3K1, 4A2, 4D4, 4E4, 4F2, 5K, 5P | 3-oxo propanol |
| CLO6 | 2A, 3B1, 3G1, 3C1, 3D1, 3E1, 3F1, 4A2, 4D4, 4E4, 4F2, 5K, 5P | 3-oxo propanol |
| CLO7 | 2A, 3B1, 3C2, 3D2, 3E2, 3F2, 3G5, 4A2, 4D4, 4E4, 4F2, 5K, 5P | 3-oxo propanol |
| CLO8 | 2A, 3B1, 3C2, 3D2, 3L2, 3K2, 3G5, 4A2, 4D4, 4E4, 4F2, 5K, 5P | 3-oxo propanol |
| CLO9 | 2A, 3B2, 3C3, 3D2, 3E2, 3F2, 3G5, 4A2, 4D4, 4E4, 4F2, 5K, 5P | 3-oxo propanol |
| CLO10 | 2A, 3B2, 3C3, 3D2, 3L2, 3K2, 3G5, 4A2, 4D4, 4E4, 4F2, 5K, 5P | 3-oxo propanol |
| CLO11 | 2A, 3B2, 3C3, 3G2, 3D1, 3E1, 3F1, 4A2, 4D4, 4E4, 4F2, 5K, 5P | 3-oxo propanol |
| CLO12 | 2A, 3B1, 3C2, 3G2, 3D1, 3E1, 3F1, 4A2, 4D4, 4E4, 4F2, 5K, 5P | 3-oxo propanol |
| CLO13 | 2A, 3B2, 3C3, 3G2, 3D1, 3L1, 3K1, 4A2, 4D4, 4E4, 4F2, 5K, 5P | 3-oxo propanol |
| CLO14 | 2A, 3B1, 3C2, 3G2, 3D1, 3L1, 3K1, 4A2, 4D4, 4E4, 4F2, 5K, 5P | 3-oxo propanol |
| CLO15 | 2A, 3B1, 3G1, 3C1, 3D1, 3L1, 3K1, 4A2, 4D4, 4E4, 4F2, 5K, 5P | 3-oxo propanol |
| CLO16 | 2A, 3B1, 3C2, 3D2, 3E2, 3F2, 4A5, 4D5, 4F4, 5K, 5P | 3-oxo propanol |
| CLO17 | 2A, 3B1, 3C2, 3D2, 3L2, 3K2, 4A5, 4D5, 4F4, 5K, 5P | 3-oxo propanol |
| CLO18 | 2A, 3B2, 3C3, 3D2, 3E2, 3F2, 4A5, 4D5, 4F4, 5K, 5P | 3-oxo propanol |
| CLO19 | 2A, 3B2, 3C3, 3D2, 3L2, 3K2, 4A5, 4D5, 4F4, 5K, 5P | 3-oxo propanol |
| CLO20 | 2A, 3B2, 3C3, 3D2, 3E2, 3F2, 3G5, 4A2, 4D4, 4E4, 4F2, 5K, 5P | 3-oxo propanol |
| CLO21 | 2A, 3B2, 3C3, 3D2, 3L2, 3K2, 3G5, 4A2, 4D4, 4E4, 4F2, 5K, 5P | 3-oxo propanol |
| CLO22 | 2A, 3B2, 3C3, 3G2, 3D1, 3E1, 3F1, 4A2, 4D4, 4E4, 4F2, 5K, 5P | 3-oxo propanol |
| CLO23 | 2A, 3B1, 3C2, 3G2, 3D1, 3E1, 3F1, 4A2, 4D4, 4E4, 4F2, 5K, 5P | 3-oxo propanol |
| CLO24 | 2A, 3B2, 3C3, 3G2, 3D1, 3L1, 3K1, 4A2, 4D4, 4E4, 4F2, 5K, 5P | 3-oxo propanol |
| CLO25 | 2A, 3B1, 3C2, 3G2, 3D1, 3L1, 3K1, 4A2, 4D4, 4E4, 4F2, 5K, 5P | 3-oxo propanol |
| CLO26 | 2A, 3B1, 3C1, 3D1, 3L1, 3K1, 4A2, 4D4, 4E4, 4F2, 5K, 5P | 3-oxo propanol |
| CLO27 | 2A, 3B1, 3C2, 3D2, 3E2, 3F2, 4A5, 4D5, 4F4, 5K, 5P | 3-oxo propanol |
| CLO28 | 2A, 3B1, 3C2, 3D2, 3L2, 3K2, 4A5, 4D5, 4F4, 5K, 5P | 3-oxo propanol |
| CLO29 | 2A, 2B, 2C, 2D, 2E, 2F, 2G, 4A3, 4F2, 5K, 5M, 5Q | 3-oxo propanol |
| CLO30 | 2A, 2B, 2C, 2D, 2E, 2F, 2G, 4F3, 4A4, 5K, 5M, 5Q | 3-oxo propanol |
| CLO31 | 2A, 3B1, 3G1, 3M, 3N, 2F, 2G, 4A3, 4F2, 5K, 5M, 5Q | 3-oxo propanol |
| CLO32 | 2A, 3B1, 3G1, 3M, 3N, 2F, 2G, 4F3, 4A4, 5K, 5M, 5Q | 3-oxo propanol |
| CLO33 | 2A, 3B1, 3G1, 3D3, 3K1, 4A2, 4D4, 4E4, 4F2, 5K, 5M, 5Q | 3-oxo propanol |
| CLO34 | 2A, 3B1, 3G1, 3C1, 3D1, 3E1, 3F1, 4A2, 4D4, 4E4, 4F2, 5K, 5M, 5Q | 3-oxo propanol |
| CLO35 | 2A, 3B1, 3C2, 3D2, 3E2, 3F2, 3G5, 4A2, 4D4, 4E4, 4F2, 5K, 5M, 5Q | 3-oxo propanol |
| CLO36 | 2A, 3B1, 3C2, 3D2, 3L2, 3K2, 3G5, 4A2, 4D4, 4E4, 4F2, 5K, 5M, 5Q | 3-oxo propanol |
| CLO37 | 2A, 3B2, 3C3, 3D2, 3E2, 3F2, 3G5, 4A2, 4D4, 4E4, 4F2, 5K, 5M, 5Q | 3-oxo propanol |
| CLO38 | 2A, 3B2, 3C3, 3D2, 3L2, 3K2, 3G5, 4A2, 4D4, 4E4, 4F2, 5K, 5M, 5Q | 3-oxo propanol |
| CLO39 | 2A, 3B2, 3C3, 3G2, 3D1, 3E1, 3F1, 4A2, 4D4, 4E4, 4F2, 5K, 5M, 5Q | 3-oxo propanol |
| CLO40 | 2A, 3B1, 3C2, 3G2, 3D1, 3E1, 3F1, 4A2, 4D4, 4E4, 4F2, 5K, 5M, 5Q | 3-oxo propanol |
| CLO41 | 2A, 3B2, 3C3, 3G2, 3D1, 3L1, 3K1, 4A2, 4D4, 4E4, 4F2, 5K, 5M, 5Q | 3-oxo propanol |
| CLO42 | 2A, 3B1, 3C2, 3G2, 3D1, 3L1, 3K1, 4A2, 4D4, 4E4, 4F2, 5K, 5M, 5Q | 3-oxo propanol |
| CLO43 | 2A, 3B1, 3G1, 3C1, 3D1, 3L1, 3K1, 4A2, 4D4, 4E4, 4F2, 5K, 5M, 5Q | 3-oxo propanol |
| CLO44 | 2A, 3B1, 3C2, 3D2, 3E2, 3F2, 4A5, 4D5, 4F4, 5K, 5M, 5Q | 3-oxo propanol |
| CLO45 | 2A, 3B1, 3C2, 3D2, 3L2, 3K2, 4A5, 4D5, 4F4, 5K, 5M, 5Q | 3-oxo propanol |
| CLO46 | 2A, 3B2, 3C3, 3D2, 3E2, 3F2, 4A5, 4D5, 4F4, 5K, 5M, 5Q | 3-oxo propanol |
| CLO47 | 2A, 3B2, 3C3, 3D2, 3L2, 3K2, 4A5, 4D5, 4F4, 5K, 5M, 5Q | 3-oxo propanol |
| CLO48 | 2A, 3B2, 3C3, 3D2, 3E2, 3F2, 3G5, 4A2, 4D4, 4E4, 4F2, 5K, 5M, 5Q | 3-oxo propanol |
| CLO49 | 2A, 3B2, 3C3, 3D2, 3L2, 3K2, 3G5, 4A2, 4D4, 4E4, 4F2, 5K, 5M, 5Q | 3-oxo propanol |
| CLO50 | 2A, 3B2, 3C3, 3G2, 3D1, 3E1, 3F1, 4A2, 4D4, 4E4, 4F2, 5K, 5M, 5Q | 3-oxo propanol |
| CLO51 | 2A, 3B1, 3C2, 3G2, 3D1, 3E1, 3F1, 4A2, 4D4, 4E4, 4F2, 5K, 5M, 5Q | 3-oxo propanol |
| CLO52 | 2A, 3B2, 3C3, 3G2, 3D1, 3L1, 3K1, 4A2, 4D4, 4E4, 4F2, 5K, 5M, 5Q | 3-oxo propanol |
| CLO53 | 2A, 3B1, 3C2, 3G2, 3D1, 3L1, 3K1, 4A2, 4D4, 4E4, 4F2, 5K, 5M, 5Q | 3-oxo propanol |
| CLO54 | 2A, 3B1, 3G1, 3C1, 3D1, 3L1, 3K1, 4A2, 4D4, 4E4, 4F2, 5K, 5M, 5Q | 3-oxo propanol |
| CLO55 | 2A, 3B1, 3C2, 3D2, 3E2, 3F2, 4A5, 4D5, 4F4, 5K, 5M, 5Q | 3-oxo propanol |
| CLO56 | 2A, 3B1, 3C2, 3D2, 3L2, 3K2, 4A5, 4D5, 4F4, 5K, 5M, 5Q | 3-oxo propanol |
| CLO57 | 2A, 2B, 2C, 2D, 2E, 2F, 2G, 4A3, 5L, 5Q | 3-oxo propanol |
| CLO58 | 2A, 3B1, 3G1, 3M, 3N, 2F, 2G, 4A3, 5L, 5Q | 3-oxo propanol |
| CLO59 | 2A, 3B1, 3G1, 3D3, 3K1, 4A2, 4D4, 4E4, 5L, 5Q | 3-oxo propanol |
| CLO60 | 2A, 3B1, 3G1, 3C1, 3D1, 3E1, 3F1, 4A2, 4D4, 4E4, 5L, 5Q | 3-oxo propanol |
| CLO61 | 2A, 3B1, 3C2, 3D2, 3E2, 3F2, 3G5, 4A2, 4D4, 4E4, 5L, 5Q | 3-oxo propanol |
| CLO62 | 2A, 3B1, 3C2, 3D2, 3L2, 3K2, 3G5, 4A2, 4D4, 4E4, 5L, 5Q | 3-oxo propanol |
| CLO63 | 2A, 3B2, 3C3, 3D2, 3E2, 3F2, 3G5, 4A2, 4D4, 4E4, 5L, 5Q | 3-oxo propanol |
| CLO64 | 2A, 3B2, 3C3, 3D2, 3L2, 3K2, 3G5, 4A2, 4D4, 4E4, 5L, 5Q | 3-oxo propanol |
| CLO65 | 2A, 3B2, 3C3, 3G2, 3D1, 3E1, 3F1, 4A2, 4D4, 4E4, 5L, 5Q | 3-oxo propanol |
| CLO66 | 2A, 3B1, 3C2, 3G2, 3D1, 3E1, 3F1, 4A2, 4D4, 4E4, 5L, 5Q | 3-oxo propanol |
| CLO67 | 2A, 3B2, 3C3, 3G2, 3D1, 3L1, 3K1, 4A2, 4D4, 4E4, 5L, 5Q | 3-oxo propanol |
| CLO68 | 2A, 3B1, 3C2, 3G2, 3D1, 3L1, 3K1, 4A2, 4D4, 4E4, 5L, 5Q | 3-oxo propanol |
| CLO69 | 2A, 3B1, 3G1, 3C1, 3D1, 3L1, 3K1, 4A2, 4D4, 4E4, 5L, 5Q | 3-oxo propanol | wherein 2A, 2B, 3B1, 3B2, 2C, 3G1, 3C2, 3C3, 2G, 3E1, 3E2, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 3M, 3H, 2F, 3D3, 3D2, 3D1, 4D4, and 4D5, are the same as when ADA pathway selected is one of ADA26-ADA83, and 5L, 5K, are same as above and 5M is an 6-hydroxyhexanoate CoA-transferase or a 6-hydroxyhexanoate-CoA ligase, 5P is spontaneous cyclization or a 6-hydroxyhexanoate cyclase, and 5Q is spontaneous cyclization or a 6-hydroxyhexanoyl-CoA cyclase.

In one aspect, provided is a non-naturally occurring microbial organism as described herein, wherein the microbial organism includes two, three, four, five, six, seven, eight, nine, ten, eleven, twelve, thirteen, or fourteen enzymes exogenous nucleic acids each encoding a caprolactone pathway enzyme.

For example, the microbial organism can include exogenous nucleic acids encoding each of the enzymes of at least one of the pathways selected from CPO1-CPO69 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding an 1,6-hexanediol (HDO) pathway enzyme expressed in a sufficient amount to produce 1,6-hexanediol, wherein said 1,6-hexanediol pathway comprises a pathway selected from Table E:

TABLE E

| Pathway No | Pathway Steps | Aldehyde |
|---|---|---|
| HDO1 | 2A, 2B, 2C, 2D, 2E, 2F, 2G, 4A3, 4F2, 5K, 5R, 5S | 3-oxo propanol |
| HDO2 | 2A, 2B, 2C, 2D, 2E, 2F, 2G, 4F3, 4A4, 5K, 5R, 5S | 3-oxo propanol |
| HDO3 | 2A, 3B1, 3G1, 3M, 3N, 2F, 2G, 4A3, 4F2, 5K, 5R, 5S | 3-oxo propanol |
| HDO4 | 2A, 3B1, 3G1, 3M, 3N, 2F, 2G, 4F3, 4A4, 5K, 5R, 5S | 3-oxo propanol |
| HDO5 | 2A, 3B1, 3G1, 3D3, 3K1, 4A2, 4D4, 4E4, 4F2, 5K, 5R, 5S | 3-oxo propanol |
| HDO6 | 2A, 3B1, 3G1, 3C1, 3D1, 3E1, 3F1, 4A2, 4D4, 4E4, 4F2, 5K, 5R, 5S | 3-oxo propanol |
| HDO7 | 2A, 3B1, 3C2, 3D2, 3E2, 3F2, 3G5, 4A2, 4D4, 4E4, 4F2, 5K, 5R, 5S | 3-oxo propanol |
| HDO8 | 2A, 3B1, 3C2, 3D2, 3L2, 3K2, 3G5, 4A2, 4D4, 4E4, 4F2, 5K, 5R, 5S | 3-oxo propanol |
| HDO9 | 2A, 3B2, 3C3, 3D2, 3E2, 3F2, 3G5, 4A2, 4D4, 4E4, 4F2, 5K, 5R, 5S | 3-oxo propanol |
| HDO10 | 2A, 3B2, 3C3, 3D2, 3L2, 3K2, 3G5, 4A2, 4D4, 4E4, 4F2, 5K, 5R, 5S | 3-oxo propanol |
| HDO11 | 2A, 3B2, 3C3, 3G2, 3D1, 3E1, 3F1, 4A2, 4D4, 4E4, 4F2, 5K, 5R, 5S | 3-oxo propanol |
| HDO12 | 2A, 3B1, 3C2, 3G2, 3D1, 3E1, 3F1, 4A2, 4D4, 4E4, 4F2, 5K, 5R, 5S | 3-oxo propanol |
| HDO13 | 2A, 3B2, 3C3, 3G2, 3D1, 3L1, 3K1, 4A2, 4D4, 4E4, 4F2, 5K, 5R, 5S | 3-oxo propanol |
| HDO14 | 2A, 3B1, 3C2, 3G2, 3D1, 3L1, 3K1, 4A2, 4D4, 4E4, 4F2, 5K, 5R, 5S | 3-oxo propanol |
| HDO15 | 2A, 3B1, 3G1, 3C1,, 3D1, 3L1, 3K1, 4A2, 4D4, 4E4, 4F2, 5K, 5R, 5S | 3-oxo propanol |
| HDO16 | 2A, 3B1, 3C2, 3D2, 3E2, 3F2, 4A5, 4D5, 4F4, 5K, 5R, 5S | 3-oxo propanol |
| HDO17 | 2A, 3B1, 3C2, 3D2, 3L2, 3K2, 4A5, 4D5, 4F4, 5K, 5R, 5S | 3-oxo propanol |
| HDO18 | 2A, 3B2, 3C3, 3D2, 3E2, 3F2, 4A5, 4D5, 4F4, 5K, 5R, 5S | 3-oxo propanol |
| HDO19 | 2A, 3B2, 3C3, 3D2, 3L2, 3K2, 4A5, 4D5, 4F4, 5K, 5R, 5S | 3-oxo propanol |
| HDO20 | 2A, 3B2, 3C3, 3D2, 3E2, 3F2, 3G5, 4A2, 4D4, 4E4, 4F2, 5K, 5R, 5S | 3-oxo propanol |
| HDO21 | 2A, 3B2, 3C3, 3D2, 3L2, 3K2, 3G5, 4A2, 4D4, 4E4, 4F2, 5K, 5R, 5S | 3-oxo propanol |
| HDO22 | 2A, 3B2, 3C3, 3G2, 3D1, 3E1, 3F1, 4A2, 4D4, 4E4, 4F2, 5K, 5R, 5S | 3-oxo propanol |
| HDO23 | 2A, 3B1, 3C2, 3G2, 3D1, 3E1, 3F1, 4A2, 4D4, 4E4, 4F2, 5K, 5R, 5S | 3-oxo propanol |
| HDO24 | 2A, 3B2, 3C3, 3G2, 3D1, 3L1, 3K1, 4A2, 4D4, 4E4, 4F2, 5K, 5R, 5S | 3-oxo propanol |
| HDO25 | 2A, 3B1, 3C2, 3G2, 3D1, 3L1, 3K1, 4A2, 4D4, 4E4, 4F2, 5K, 5R, 5S | 3-oxo propanol |
| HDO26 | 2A, 3B1, 3G1, 3C1,, 3D1, 3L1, 3K1, 4A2, 4D4, 4E4, 4F2, 5K, 5R, 5S | 3-oxo propanol |
| HDO27 | 2A, 3B1, 3C2, 3D2, 3E2, 3F2, 4A5, 4D5, 4F4, 5K, 5R, 5S | 3-oxo propanol |
| HDO28 | 2A, 3B1, 3C2, 3D2, 3L2, 3K2, 4A5, 4D5, 4F4, 5K, 5R, 5S | 3-oxo propanol |
| HDO29 | 2A, 2B, 2C, 2D, 2E, 2F, 2G, 4A3, 4F2, 5K, 5M, 5O, 5S | 3-oxo propanol |
| HDO30 | 2A, 2B, 2C, 2D, 2E, 2F, 2G, 4F3, 4A4, 5K, 5M, 5O, 5S | 3-oxo propanol |
| HDO31 | 2A, 3B1, 3G1, 3M, 3N, 2F, 2G, 4A3, 4F2, 5K, 5M, 5O, 5S | 3-oxopropionate |
| HDO32 | 2A, 3B1, 3G1, 3M, 3N, 2F, 2G, 4F3, 4A4, 5K, 5M, 5O, 5S | 3-oxopropionate |
| HDO33 | 2A, 3B1, 3G1, 3D3, 3K1, 4A2, 4D4, 4E4, 4F2, 5K, 5M, 5O, 5S | 3-oxopropionate |
| HDO34 | 2A, 3B1, 3G1, 3C1, 3D1, 3E1, 3F1, 4A2, 4D4, 4E4, 4F2, 5K, 5M, 5O, 5S | 3-oxopropionate |
| HDO35 | 2A, 3B1, 3C2, 3D2, 3E2, 3F2, 3G5, 4A2, 4D4, 4E4, 4F2, 5K, 5M, 5O, 5S | 3-oxopropionate |
| HDO36 | 2A, 3B1, 3C2, 3D2, 3L2, 3K2, 3G5, 4A2, 4D4, 4E4, 4F2, 5K, 5M, 5O, 5S | 3-oxopropionate |
| HDO37 | 2A, 3B2, 3C3, 3D2, 3E2, 3F2, 3G5, 4A2, 4D4, 4E4, 4F2, 5K, 5M, 5O, 5S | 3-oxopropionate |
| HDO38 | 2A, 3B2, 3C3, 3D2, 3L2, 3K2, 3G5, 4A2, 4D4, 4E4, 4F2, 5K, 5M, 5O, 5S | 3-oxopropionate |
| HDO39 | 2A, 3B2, 3C3, 3G2, 3D1, 3E1, 3F1, 4A2, 4D4, 4E4, 4F2, 5K, 5M, 5O, 5S | 3-oxopropionate |
| HDO40 | 2A, 3B1, 3C2, 3G2, 3D1, 3E1, 3F1, 4A2, 4D4, 4E4, 4F2, 5K, 5M, 5O, 5S | 3-oxopropionate |
| HDO41 | 2A, 3B2, 3C3, 3G2, 3D1, 3L1, 3K1, 4A2, 4D4, 4E4, 4F2, 5K, 5M, 5O, 5S | 3-oxopropionate |
| HDO42 | 2A, 3B1, 3C2, 3G2, 3D1, 3L1, 3K1, 4A2, 4D4, 4E4, 4F2, 5K, 5M, 5O, 5S | 3-oxopropionate |
| HDO43 | 2A, 3B1, 3G1, 3C1,, 3D1, 3L1, 3K1, 4A2, 4D4, 4E4, 4F2, 5K, 5M, 5O, 5S | 3-oxopropionate |
| HDO44 | 2A, 3B1, 3C2, 3D2, 3E2, 3F2, 4A5, 4D5, 4F4, 5K, 5M, 5O, 5S | 3-oxopropionate |
| HDO45 | 2A, 3B1, 3C2, 3D2, 3L2, 3K2, 4A5, 4D5, 4F4, 5K, 5M, 5O, 5S | 3-oxopropionate |
| HDO46 | 2A, 3B2, 3C3, 3D2, 3E2, 3F2, 4A5, 4D5, 4F4, 5K, 5M, 5O, 5S | 3-oxopropionate |
| HDO47 | 2A, 3B2, 3C3, 3D2, 3L2, 3K2, 4A5, 4D5, 4F4, 5K, 5M, 5O, 5S | 3-oxopropionate |
| HDO48 | 2A, 3B2, 3C3, 3D2, 3E2, 3F2, 3G5, 4A2, 4D4, 4E4, 4F2, 5K, 5M, 5O, 5S | 3-oxopropionate |
| HDO49 | 2A, 3B2, 3C3, 3D2, 3L2, 3K2, 3G5, 4A2, 4D4, 4E4, 4F2, 5K, 5M, 5O, 5S | 3-oxopropionate |
| HDO50 | 2A, 3B2, 3C3, 3G2, 3D1, 3E1, 3F1, 4A2, 4D4, 4E4, 4F2, 5K, 5M, 5O, 5S | 3-oxopropionate |
| HDO51 | 2A, 3B1, 3C2, 3G2, 3D1, 3E1, 3F1, 4A2, 4D4, 4E4, 4F2, 5K, 5M, 5O, 5S | 3-oxopropionate |
| HDO52 | 2A, 3B2, 3C3, 3G2, 3D1, 3L1, 3K1, 4A2, 4D4, 4E4, 4F2, 5K, 5M, 5O, 5S | 3-oxopropionate |
| HDO53 | 2A, 3B1, 3C2, 3G2, 3D1, 3L1, 3K1, 4A2, 4D4, 4E4, 4F2, 5K, 5M, 5O, 5S | 3-oxo propanol |
| HDO54 | 2A, 3B1, 3G1, 3C1,, 3D1, 3L1, 3K1, 4A2, 4D4, 4E4, 4F2, 5K, 5M, 5O, 5S | 3-oxo propanol |

TABLE E-continued

| Pathway No | Pathway Steps | Aldehyde |
|---|---|---|
| HDO55 | 2A, 3B1, 3C2, 3D2, 3E2, 3F2, 4A5, 4D5, 4F4, 5K, 5M, 5O, 5S | 3-oxo propanol |
| HDO56 | 2A, 3B1, 3C2, 3D2, 3L2, 3K2, 4A5, 4D5, 4F4, 5K, 5M, 5O, 5S | 3-oxo propanol |
| HDO57 | 2A, 2B, 2C, 2D, 2E, 2F, 2G, 4A3, 5L, 5O, 5S | 3-oxo propanol |
| HDO58 | 2A, 3B1, 3G1, 3M, 3N, 2F, 2G, 4A3, 5L, 5O, 5S | 3-oxo propanol |
| HDO59 | 2A, 3B1, 3G1, 3D3, 3K1, 4A2, 4D4, 4E4, 5L, 5O, 5S | 3-oxo propanol |
| HDO60 | 2A, 3B1, 3G1, 3C1, 3D1, 3E1, 3F1, 4A2, 4D4, 4E4, 5L, 5O, 5S | 3-oxo propanol |
| HDO61 | 2A, 3B1, 3C2, 3D2, 3E2, 3F2, 3G5, 4A2, 4D4, 4E4, 5L, 5O, 5S | 3-oxo propanol |
| HDO62 | 2A, 3B1, 3C2, 3D2, 3L2, 3K2, 3G5, 4A2, 4D4, 4E4, 5L, 5O, 5S | 3-oxo propanol |
| HDO63 | 2A, 3B2, 3C3, 3D2, 3E2, 3F2, 3G5, 4A2, 4D4, 4E4, 5L, 5O, 5S | 3-oxo propanol |
| HDO64 | 2A, 3B2, 3C3, 3D2, 3L2, 3K2, 3G5, 4A2, 4D4, 4E4, 5L, 5O, 5S | 3-oxo propanol |
| HDO65 | 2A, 3B2, 3C3, 3G2, 3D1, 3E1, 3F1, 4A2, 4D4, 4E4, 5L, 5O, 5S | 3-oxo propanol |
| HDO66 | 2A, 3B1, 3C2, 3G2, 3D1, 3E1, 3F1, 4A2, 4D4, 4E4, 5L, 5O, 5S | 3-oxo propanol |
| HDO67 | 2A, 3B2, 3C3, 3G2, 3D1, 3L1, 3K1, 4A2, 4D4, 4E4, 5L, 5O, 5S | 3-oxo propanol |
| HDO68 | 2A, 3B1, 3C2, 3G2, 3D1, 3L1, 3K1, 4A2, 4D4, 4E4, 5L, 5O, 5S | 3-oxo propanol |
| HDO69 | 2A, 3B1, 3G1, 3C1,, 3D1, 3L1, 3K1, 4A2, 4D4, 4E4, 5L, 5O, 5S | 3-oxo propanol | wherein 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 2I, 3M, 3H, 2F, 3D3, 3D2, 3D1, 4D3, 4D4, and 4D5, are the same as when ADA pathway selected is one of ADA1-ADA83, and 5M, 5L, 5G, and 5K are defined as above and 5O is a 6-hydroxyhexanoyl-CoA 1-reductase, 5R is a 6-hydroxyhexanoate 1-reductase, and 5S is a 6-hydroxyhexanal 1-reductase.

In one aspect, particularly when 1,6-hexanediol synthesis pathway is selected from HDO31-52, 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 21, 3M, 3H, 2F, 3D3, 3D2, 3D1, 4D3, 4D4, and 4D5, are the same as when ADA pathway selected is one of ADA1-ADA25, and 5M, 5L, 5G, 5K, 5O, 5R, and 5S are defined as above.

In another aspect, particularly when 1,6-hexanediol synthesis pathway is selected from HDO1-31, 53-69, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 3M, 3H, 2F, 3D3, 3D2, 3D1, 4D3, 4D4, and 4D5, are the same as when ADA pathway selected is one of ADA26-ADA83, and 5M, 5L, 5G, 5K, 5O, 5R, and 5S are defined as above.

In one aspect, provided is a non-naturally occurring microbial organism as described herein, wherein the microbial organism includes two, three, four, five, six, seven, eight, nine, ten, eleven, twelve, thirteen, fourteen or fifteen exogenous nucleic acids each encoding a 1,6-hexanediol pathway enzyme.

For example, the microbial organism can include exogenous nucleic acids encoding each of the enzymes of at least one of the pathways selected from HDO1-HDO169 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In one aspect, provided is a non-naturally occurring microbial organism comprising at least one exogenous nucleic acid encoding an HMDA pathway enzyme expressed in a sufficient amount to produce HMDA, wherein said HMDA pathway comprises a pathway selected from Table G:

TABLE G

| Pathway No | Pathway Steps | Aldehyde |
|---|---|---|
| HMDA1 | 2A, 2B, 2C, 2D, 2E, 2F, 2G, 4F5, 5V, 5X | 3-aminopropanal |
| HMDA2 | 2A, 3B1, 3G1, 3M, 3N, 2F, 2G, 4F5, 5V, 5X | 3-aminopropanal |
| HMDA3 | 2A, 2B, 2C, 2D, 2E, 2F, 2G, 4A3, 4F2, 5J, 5V, 5X | 3-oxo propanol |
| HMDA4 | 2A, 2B, 2C, 2D, 2E, 2F, 2G, 4F3, 4A4, 5J, 5V, 5X | 3-oxo propanol |
| HMDA5 | 2A, 3B1, 3G1, 3M, 3N, 2F, 2G, 4A3, 4F2, 5J, 5V, 5X | 3-oxo propanol |
| HMDA6 | 2A, 3B1, 3G1, 3M, 3N, 2F, 2G, 4F3, 4A4, 5J, 5V, 5X | 3-oxo propanol |
| HMDA7 | 2A, 3B1, 3G1, 3D3, 3K1, 4A2, 4D4, 4E4, 4F2, 5J, 5V, 5X | 3-oxo propanol |
| HMDA8 | 2A, 3B1, 3G1, 3C1, 3D1, 3E1, 3F1, 4A2, 4D4, 4E4, 4F2, 5J, 5V, 5X | 3-oxo propanol |
| HMDA9 | 2A, 3B1, 3C2, 3D2, 3E2, 3F2, 3G5, 4A2, 4D4, 4E4, 4F2, 5J, 5V, 5X | 3-oxo propanol |
| HMDA10 | 2A, 3B1, 3C2, 3D2, 3L2, 3K2, 3G5, 4A2, 4D4, 4E4, 4F2, 5J, 5V, 5X | 3-oxo propanol |
| HMDA11 | 2A, 3B2, 3C3, 3D2, 3E2, 3F2, 3G5, 4A2, 4D4, 4E4, 4F2, 5J, 5V, 5X | 3-oxo propanol |
| HMDA12 | 2A, 3B2, 3C3, 3D2, 3L2, 3K2, 3G5, 4A2, 4D4, 4E4, 4F2, 5J, 5V, 5X | 3-oxo propanol |
| HMDA13 | 2A, 3B2, 3C3, 3G2, 3D1, 3E1, 3F1, 4A2, 4D4, 4E4, 4F2, 5J, 5V, 5X | 3-oxo propanol |
| HMDA14 | 2A, 3B1, 3C2, 3G2, 3D1, 3E1, 3F1, 4A2, 4D4, 4E4, 4F2, 5J, 5V, 5X | 3-oxo propanol |
| HMDA15 | 2A, 3B2, 3C3, 3G2, 3D1, 3L1, 3K1, 4A2, 4D4, 4E4, 4F2, 5J, 5V, 5X | 3-oxo propanol |
| HMDA16 | 2A, 3B1, 3C2, 3G2, 3D1, 3L1, 3K1, 4A2, 4D4, 4E4, 4F2, 5J, 5V, 5X | 3-oxo propanol |
| HMDA17 | 2A, 3B1, 3G1, 3C1, 3D1, 3L1, 3K1, 4A2, 4D4, 4E4, 4F2, 5J, 5V, 5X | 3-oxo propanol |
| HMDA18 | 2A, 3B1, 3C2, 3D2, 3E2, 3F2, 4A5, 4D5, 4F4, 5J, 5V, 5X | 3-oxo propanol |
| HMDA19 | 2A, 3B1, 3C2, 3D2, 3L2, 3K2, 4A5, 4D5, 4F4, 5J, 5V, 5X | 3-oxo propanol |
| HMDA20 | 2A, 3B2, 3C3, 3D2, 3E2, 3F2, 4A5, 4D5, 4F4, 5J, 5V, 5X | 3-oxo propanol |
| HMDA21 | 2A, 3B2, 3C3, 3D2, 3L2, 3K2, 4A5, 4D5, 4F4, 5J, 5V, 5X | 3-oxo propanol |
| HMDA22 | 2A, 2B, 2C, 2D, 2E, 2F, 2G, 5G, 5J, 5V, 5X, 5V, 5X | 3-oxo propionate |
| HMDA23 | 2A, 3B1, 3G1, 3M, 3N, 2F, 2G, 5G, 5J, 5V, 5X, 5V, 5X | 3-oxo propionate |
| HMDA24 | 2A, 3B1, 3G1, 3D3, 3K1, 3H, 2G, 5G, 5J, 5V, 5X, 5V, 5X | 3-oxo propionate |
| HMDA25 | 2A, 3B1, 3G1, 3D3, 3K1, 4D3, 4E3, 5G, 5J, 5V, 5X, 5V, 5X | 3-oxo propionate |
| HMDA26 | 2A, 3B1, 3G1, 3C1, 3D1, 3E1, 3F1, 3H, 2G, 5G, 5J, 5V, 5X, 5V, 5X | 3-oxo propionate |

TABLE G-continued

| Pathway No | Pathway Steps | Aldehyde |
|---|---|---|
| HMDA27 | 2A, 3B1, 3G1, 3C1, 3D1, 3E1, 3F1, 4D3, 4E3, 5G, 5J, 5V, 5X, 5V, 5X | 3-oxo propionate |
| HMDA28 | 2A, 3B1, 3C2, 3D2, 3E2, 3F2, 3G5, 3H, 2G, 5G, 5J, 5V, 5X, 5V, 5X | 3-oxo propionate |
| HMDA29 | 2A, 3B1, 3C2, 3D2, 3E2, 3F2, 3G5, 4D3, 4E3, 5G, 5J, 5V, 5X, 5V, 5X | 3-oxo propionate |
| HMDA30 | 2A, 3B1, 3C2, 3D2, 3L2, 3K2, 3G5, 3H, 2G, 5G, 5J, 5V, 5X, 5V, 5X | 3-oxo propionate |
| HMDA31 | 2A, 3B1, 3C2, 3D2, 3L2, 3K2, 3G5, 4D3, 4E3, 5G, 5J, 5V, 5X, 5V, 5X | 3-oxo propionate |
| HMDA32 | 2A, 3B1, 3C2, 3G2, 3D1, 3E1, 3F1, 3H, 2G, 5G, 5J, 5V, 5X, 5V, 5X | 3-oxo propionate |
| HMDA33 | 2A, 3B1, 3C2, 3G2, 3D1, 3E1, 3F1, 4D3, 4E3, 5G, 5J, 5V, 5X, 5V, 5X | 3-oxo propionate |
| HMDA34 | 2A, 3B2, 3C3, 3D2, 3E2, 3F2, 3G5, 3H, 2G, 5G, 5J, 5V, 5X, 5V, 5X | 3-oxo propionate |
| HMDA35 | 2A, 3B2, 3C3, 3D2, 3E2, 3F2, 3G5, 4D3, 4E3, 5G, 5J, 5V, 5X, 5V, 5X | 3-oxo propionate |
| HMDA36 | 2A, 3B2, 3C3, 3D2, 3L2, 3K2, 3G5, 3H, 2G, 5G, 5J, 5V, 5X, 5V, 5X | 3-oxo propionate |
| HMDA37 | 2A, 3B2, 3C3, 3D2, 3L2, 3K2, 3G5, 4D3, 4E3, 5G, 5J, 5V, 5X, 5V, 5X | 3-oxo propionate |
| HMDA38 | 2A, 3B2, 3C3, 3G2, 3D1, 3E1, 3F1, 3H, 2G, 5G, 5J, 5V, 5X, 5V, 5X | 3-oxo propionate |
| HMDA39 | 2A, 3B2, 3C3, 3G2, 3D1, 3E1, 3F1, 4D3, 4E3, 5G, 5J, 5V, 5X, 5V, 5X | 3-oxo propionate |
| HMDA40 | 2A, 3B2, 3C3, 3G2, 3D1, 3L1, 3K1, 3H, 2G, 5G, 5J, 5V, 5X, 5V, 5X | 3-oxo propionate |
| HMDA41 | 2A, 3B2, 3C3, 3G2, 3D1, 3L1, 3K1, 4D3, 4E3, 5G, 5J, 5V, 5X, 5V, 5X | 3-oxo propionate |
| HMDA42 | 2A, 3B1, 3C2, 3G2, 3D1, 3L1, 3K1, 3H, 2G, 5G, 5J, 5V, 5X, 5V, 5X | 3-oxo propionate |
| HMDA43 | 2A, 3B1, 3C2, 3G2, 3D1, 3L1, 3K1, 4D3, 4E3, 5G, 5J, 5V, 5X, 5V, 5X | 3-oxo propionate |
| HMDA44 | 2A, 3B1, 3G1, 3C1, 3D1, 3L1, 3K1, 3H, 2G, 5G, 5J, 5V, 5X, 5V, 5X | 3-oxo propionate |
| HMDA45 | 2A, 3B1, 3G1, 3C1, 3D1, 3L1, 3K1, 4D3, 4E3, 5G, 5J, 5V, 5X, 5V, 5X | 3-oxo propionate |
| HMDA46 | 2A, 3B1, 3G1, 2I, 2J, 2F, 2G, 5G, 5J, 5V, 5X, 5V, 5X | 3-oxo propionate |
| HMDA47 | 2A, 2B, 2C, 2D, 2E, 2F, 2G, 4A3, 4F2, 5K, 5R, 5T, 5U, 5X | 3-oxo propanol |
| HMDA48 | 2A, 2B, 2C, 2D, 2E, 2F, 2G, 4F3, 4A4, 5K, 5R, 5T, 5U, 5X | 3-oxo propanol |
| HMDA49 | 2A, 3B1, 3G1, 3M, 3N, 2F, 2G, 4A3, 4F2, 5K, 5R, 5T, 5U, 5X | 3-oxo propanol |
| HMDA50 | 2A, 3B1, 3G1, 3M, 3N, 2F, 2G, 4F3, 4A4, 5K, 5R, 5T, 5U, 5X | 3-oxo propanol |
| HMDA51 | 2A, 3B1, 3G1, 3D3, 3K1, 4A2, 4D4, 4E4, 4F2, 5K, 5R, 5T, 5U, 5X | 3-oxo propanol |
| HMDA52 | 2A, 3B1, 3G1, 3C1, 3D1, 3E1, 3F1, 4A2, 4D4, 4E4, 4F2, 5K, 5R, 5T, 5U, 5X | 3-oxo propanol |
| HMDA53 | 2A, 3B1, 3C2, 3D2, 3E2, 3F2, 3G5, 4A2, 4D4, 4E4, 4F2, 5K, 5R, 5T, 5U, 5X | 3-oxo propanol |
| HMDA54 | 2A, 3B1, 3C2, 3D2, 3L2, 3K2, 3G5, 4A2, 4D4, 4E4, 4F2, 5K, 5R, 5T, 5U, 5X | 3-oxo propanol |
| HMDA55 | 2A, 3B2, 3C3, 3D2, 3E2, 3F2, 3G5, 4A2, 4D4, 4E4, 4F2, 5K, 5R, 5T, 5U, 5X | 3-oxo propanol |
| HMDA56 | 2A, 3B2, 3C3, 3D2, 3L2, 3K2, 3G5, 4A2, 4D4, 4E4, 4F2, 5K, 5R, 5T, 5U, 5X | 3-oxo propanol |
| HMDA57 | 2A, 3B2, 3C3, 3G2, 3D1, 3E1, 3F1, 4A2, 4D4, 4E4, 4F2, 5K, 5R, 5T, 5U, 5X | 3-oxo propanol |
| HMDA58 | 2A, 3B1, 3C2, 3G2, 3D1, 3E1, 3F1, 4A2, 4D4, 4E4, 4F2, 5K, 5R, 5T, 5U, 5X | 3-oxo propanol |
| HMDA59 | 2A, 3B2, 3C3, 3G2, 3D1, 3L1, 3K1, 4A2, 4D4, 4E4, 4F2, 5K, 5R, 5T, 5U, 5X | 3-oxo propanol |
| HMDA60 | 2A, 3B1, 3C2, 3G2, 3D1, 3L1, 3K1, 4A2, 4D4, 4E4, 4F2, 5K, 5R, 5T, 5U, 5X | 3-oxo propanol |
| HMDA61 | 2A, 3B1, 3G1, 3C1, 3D1, 3L1, 3K1, 4A2, 4D4, 4E4, 4F2, 5K, 5R, 5T, 5U, 5X | 3-oxo propanol |
| HMDA62 | 2A, 3B1, 3C2, 3D2, 3E2, 3F2, 4A5, 4D5, 4F4, 5K, 5R, 5T, 5U, 5X | 3-oxo propanol |
| HMDA63 | 2A, 3B1, 3C2, 3D2, 3L2, 3K2, 4A5, 4D5, 4F4, 5K, 5R, 5T, 5U, 5X | 3-oxo propanol |
| HMDA64 | 2A, 3B2, 3C3, 3D2, 3E2, 3F2, 4A5, 4D5, 4F4, 5K, 5R, 5T, 5U, 5X | 3-oxo propanol |
| HMDA65 | 2A, 3B2, 3C3, 3D2, 3L2, 3K2, 4A5, 4D5, 4F4, 5K, 5R, 5T, 5U, 5X | 3-oxo propanol |
| HMDA66 | 2A, 3B2, 3C3, 3D2, 3E2, 3F2, 3G5, 4A2, 4D4, 4E4, 4F2, 5K, 5R, 5T, 5U, 5X | 3-oxo propanol |
| HMDA67 | 2A, 3B2, 3C3, 3D2, 3L2, 3K2, 3G5, 4A2, 4D4, 4E4, 4F2, 5K, 5R, 5T, 5U, 5X | 3-oxo propanol |
| HMDA68 | 2A, 3B2, 3C3, 3G2, 3D1, 3E1, 3F1, 4A2, 4D4, 4E4, 4F2, 5K, 5R, 5T, 5U, 5X | 3-oxo propanol |
| HMDA69 | 2A, 3B1, 3C2, 3G2, 3D1, 3E1, 3F1, 4A2, 4D4, 4E4, 4F2, 5K, 5R, 5T, 5U, 5X | 3-oxo propanol |
| HMDA70 | 2A, 3B2, 3C3, 3G2, 3D1, 3L1, 3K1, 4A2, 4D4, 4E4, 4F2, 5K, 5R, 5T, 5U, 5X | 3-oxo propanol |
| HMDA71 | 2A, 3B1, 3C2, 3G2, 3D1, 3L1, 3K1, 4A2, 4D4, 4E4, 4F2, 5K, 5R, 5T, 5U, 5X | 3-oxo propanol |
| HMDA72 | 2A, 3B1, 3G1, 3C1, 3D1, 3L1, 3K1, 4A2, 4D4, 4E4, 4F2, 5K, 5R, 5T, 5U, 5X | 3-oxo propanol |
| HMDA73 | 2A, 3B1, 3C2, 3D2, 3E2, 3F2, 4A5, 4D5, 4F4, 5K, 5R, 5T, 5U, 5X | 3-oxo propanol |
| HMDA74 | 2A, 3B1, 3C2, 3D2, 3L2, 3K2, 4A5, 4D5, 4F4, 5K, 5R, 5T, 5U, 5X | 3-oxo propanol |
| HMDA75 | 2A, 2B, 2C, 2D, 2E, 2F, 2G, 4A3, 4F2, 5K, 5M, 5O, 5T, 5U, 5X | 3-oxo propanol |
| HMDA76 | 2A, 2B, 2C, 2D, 2E, 2F, 2G, 4F3, 4A4, 5K, 5M, 5O, 5T, 5U, 5X | 3-oxo propanol |
| HMDA77 | 2A, 3B1, 3G1, 3M, 3N, 2F, 2G, 4A3, 4F2, 5K, 5M, 5O, 5T, 5U, 5X | 3-oxopropionate |
| HMDA78 | 2A, 3B1, 3G1, 3M, 3N, 2F, 2G, 4F3, 4A4, 5K, 5M, 5O, 5T, 5U, 5X | 3-oxopropionate |
| HMDA79 | 2A, 3B1, 3G1, 3D3, 3K1, 4A2, 4D4, 4E4, 4F2, 5K, 5M, 5O, 5T, 5U, 5X | 3-oxopropionate |

TABLE G-continued

| Pathway No | Pathway Steps | Aldehyde |
|---|---|---|
| HMDA80 | 2A, 3B1, 3G1, 3C1, 3D1, 3E1, 3F1, 4A2, 4D4, 4E4, 4F2, 5K, 5M, 5O, 5T, 5U, 5X | 3-oxopropionate |
| HMDA81 | 2A, 3B1, 3C2, 3D2, 3E2, 3F2, 3G5, 4A2, 4D4, 4E4, 4F2, 5K, 5M, 5O, 5T, 5U, 5X | 3-oxopropionate |
| HMDA82 | 2A, 3B1, 3C2, 3D2, 3L2, 3K2, 3G5, 4A2, 4D4, 4E4, 4F2, 5K, 5M, 5O, 5T, 5U, 5X | 3-oxopropionate |
| HMDA83 | 2A, 3B2, 3C3, 3D2, 3E2, 3F2, 3G5, 4A2, 4D4, 4E4, 4F2, 5K, 5M, 5O, 5T, 5U, 5X | 3-oxopropionate |
| HMDA84 | 2A, 3B2, 3C3, 3D2, 3L2, 3K2, 3G5, 4A2, 4D4, 4E4, 4F2, 5K, 5M, 5O, 5T, 5U, 5X | 3-oxopropionate |
| HMDA85 | 2A, 3B2, 3C3, 3G2, 3D1, 3E1, 3F1, 4A2, 4D4, 4E4, 4F2, 5K, 5M, 5O, 5T, 5U, 5X | 3-oxopropionate |
| HMDA86 | 2A, 3B1, 3C2, 3G2, 3D1, 3E1, 3F1, 4A2, 4D4, 4E4, 4F2, 5K, 5M, 5O, 5T, 5U, 5X | 3-oxopropionate |
| HMDA87 | 2A, 3B2, 3C3, 3G2, 3D1, 3L1, 3K1, 4A2, 4D4, 4E4, 4F2, 5K, 5M, 5O, 5T, 5U, 5X | 3-oxopropionate |
| HMDA88 | 2A, 3B1, 3C2, 3G2, 3D1, 3L1, 3K1, 4A2, 4D4, 4E4, 4F2, 5K, 5M, 5O, 5T, 5U, 5X | 3-oxopropionate |
| HMDA89 | 2A, 3B1, 3G1, 3C1, 3D1, 3L1, 3K1, 4A2, 4D4, 4E4, 4F2, 5K, 5M, 5O, 5T, 5U, 5X | 3-oxopropionate |
| HMDA90 | 2A, 3B1, 3C2, 3D2, 3E2, 3F2, 4A5, 4D5, 4F4, 5K, 5M, 5O, 5T, 5U, 5X | 3-oxopropionate |
| HMDA91 | 2A, 3B1, 3C2, 3D2, 3L2, 3K2, 4A5, 4D5, 4F4, 5K, 5M, 5O, 5T, 5U, 5X | 3-oxopropionate |
| HMDA92 | 2A, 3B2, 3C3, 3D2, 3E2, 3F2, 4A5, 4D5, 4F4, 5K, 5M, 5O, 5T, 5U, 5X | 3-oxopropionate |
| HMDA93 | 2A, 3B2, 3C3, 3D2, 3L2, 3K2, 4A5, 4D5, 4F4, 5K, 5M, 5O, 5T, 5U, 5X | 3-oxopropionate |
| HMDA94 | 2A, 3B2, 3C3, 3D2, 3E2, 3F2, 3G5, 4A2, 4D4, 4E4, 4F2, 5K, 5M, 5O, 5T, 5U, 5X | 3-oxopropionate |
| HMDA95 | 2A, 3B2, 3C3, 3D2, 3L2, 3K2, 3G5, 4A2, 4D4, 4E4, 4F2, 5K, 5M, 5O, 5T, 5U, 5X | 3-oxopropionate |
| HMDA96 | 2A, 3B2, 3C3, 3G2, 3D1, 3E1, 3F1, 4A2, 4D4, 4E4, 4F2, 5K, 5M, 5O, 5T, 5U, 5X | 3-oxopropionate |
| HMDA97 | 2A, 3B1, 3C2, 3G2, 3D1, 3E1, 3F1, 4A2, 4D4, 4E4, 4F2, 5K, 5M, 5O, 5T, 5U, 5X | 3-oxopropionate |
| HMDA98 | 2A, 3B2, 3C3, 3G2, 3D1, 3L1, 3K1, 4A2, 4D4, 4E4, 4F2, 5K, 5M, 5O, 5T, 5U, 5X | 3-oxopropionate |
| HMDA99 | 2A, 3B1, 3C2, 3G2, 3D1, 3L1, 3K1, 4A2, 4D4, 4E4, 4F2, 5K, 5M, 5O, 5T, 5U, 5X | 3-oxo propanol |
| HMDA100 | 2A, 3B1, 3G1, 3C1, 3D1, 3L1, 3K1, 4A2, 4D4, 4E4, 4F2, 5K, 5M, 5O, 5T, 5U, 5X | 3-oxo propanol |
| HMDA101 | 2A, 3B1, 3C2, 3D2, 3E2, 3F2, 4A5, 4D5, 4F4, 5K, 5M, 5O, 5T, 5U, 5X | 3-oxo propanol |
| HMDA102 | 2A, 3B1, 3C2, 3D2, 3L2, 3K2, 4A5, 4D5, 4F4, 5K, 5M, 5O, 5T, 5U, 5X | 3-oxo propanol |
| HMDA103 | 2A, 2B, 2C, 2D, 2E, 2F, 2G, 4A3, 5L, 5O, 5T, 5U, 5X | 3-oxo propanol |
| HMDA104 | 2A, 3B1, 3G1, 3M, 3N, 2F, 2G, 4A3, 5L, 5O, 5T, 5U, 5X | 3-oxo propanol |
| HMDA105 | 2A, 3B1, 3G1, 3D3, 3K1, 4A2, 4D4, 4E4, 5L, 5O, 5T, 5U, 5X | 3-oxo propanol |
| HMDA106 | 2A, 3B1, 3G1, 3C1, 3D1, 3E1, 3F1, 4A2, 4D4, 4E4, 5L, 5O, 5T, 5U, 5X | 3-oxo propanol |
| HMDA107 | 2A, 3B1, 3C2, 3D2, 3E2, 3F2, 3G5, 4A2, 4D4, 4E4, 5L, 5O, 5T, 5U, 5X | 3-oxo propanol |
| HMDA108 | 2A, 3B1, 3C2, 3D2, 3L2, 3K2, 3G5, 4A2, 4D4, 4E4, 5L, 5O, 5T, 5U, 5X | 3-oxo propanol |
| HMDA109 | 2A, 3B2, 3C3, 3D2, 3E2, 3F2, 3G5, 4A2, 4D4, 4E4, 5L, 5O, 5T, 5U, 5X | 3-oxo propanol |
| HMDA110 | 2A, 3B2, 3C3, 3D2, 3L2, 3K2, 3G5, 4A2, 4D4, 4E4, 5L, 5O, 5T, 5U, 5X | 3-oxo propanol |
| HMDA111 | 2A, 3B2, 3C3, 3G2, 3D1, 3E1, 3F1, 4A2, 4D4, 4E4, 5L, 5O, 5T, 5U, 5X | 3-oxo propanol |
| HMDA112 | 2A, 3B1, 3C2, 3G2, 3D1, 3E1, 3F1, 4A2, 4D4, 4E4, 5L, 5O, 5T, 5U, 5X | 3-oxo propanol |
| HMDA113 | 2A, 3B2, 3C3, 3G2, 3D1, 3L1, 3K1, 4A2, 4D4, 4E4, 5L, 5O, 5T, 5U, 5X | 3-oxo propanol |
| HMDA114 | 2A, 3B1, 3C2, 3G2, 3D1, 3L1, 3K1, 4A2, 4D4, 4E4, 5L, 5O, 5T, 5U, 5X | 3-oxo propanol |
| HMDA115 | 2A, 3B1, 3G1, 3C1, 3D1, 3L1, 3K1, 4A2, 4D4, 4E4, 5L, 5O, 5T, 5U, 5X | 3-oxo propanol |
| HMDA116 | 2A, 2B, 2C, 2D, 2E, 2F, 2G, 4A3, 4F2, 5C, 5W, 5X | 3-oxo propanol |
| HMDA117 | 2A, 2B, 2C, 2D, 2E, 2F, 2G, 4F3, 4A4, 5C, 5W, 5X | 3-oxo propanol |
| HMDA118 | 2A, 3B1, 3G1, 3M, 3N, 2F, 2G, 4A3, 4F2, 5C, 5W, 5X | 3-oxo propanol |
| HMDA119 | 2A, 3B1, 3G1, 3M, 3N, 2F, 2G, 4F3, 4A4, 5C, 5W, 5X | 3-oxo propanol |
| HMDA120 | 2A, 3B1, 3G1, 3D3, 3K1, 4A2, 4D4, 4E4, 4F2, 5C, 5W, 5X | 3-oxo propanol |
| HMDA121 | 2A, 3B1, 3G1, 3C1, 3D1, 3E1, 3F1, 4A2, 4D4, 4E4, 4F2, 5C, 5W, 5X | 3-oxo propanol |
| HMDA122 | 2A, 3B1, 3C2, 3D2, 3E2, 3F2, 3G5, 4A2, 4D4, 4E4, 4F2, 5C, 5W, 5X | 3-oxo propanol |
| HMDA123 | 2A, 3B1, 3C2, 3D2, 3L2, 3K2, 3G5, 4A2, 4D4, 4E4, 4F2, 5C, 5W, 5X | 3-oxo propanol |
| HMDA124 | 2A, 3B2, 3C3, 3D2, 3E2, 3F2, 3G5, 4A2, 4D4, 4E4, 4F2, 5C, 5W, 5X | 3-oxo propanol |
| HMDA125 | 2A, 3B2, 3C3, 3D2, 3L2, 3K2, 3G5, 4A2, 4D4, 4E4, 4F2, 5C, 5W, 5X | 3-oxo propanol |
| HMDA126 | 2A, 3B2, 3C3, 3G2, 3D1, 3E1, 3F1, 4A2, 4D4, 4E4, 4F2, 5C, 5W, 5X | 3-oxo propanol |
| HMDA127 | 2A, 3B1, 3C2, 3G2, 3D1, 3E1, 3F1, 4A2, 4D4, 4E4, 4F2, 5C, 5W, 5X | 3-oxo propanol |
| HMDA128 | 2A, 3B2, 3C3, 3G2, 3D1, 3L1, 3K1, 4A2, 4D4, 4E4, 4F2, 5C, 5W, 5X | 3-oxo propanol |
| HMDA129 | 2A, 3B1, 3C2, 3G2, 3D1, 3L1, 3K1, 4A2, 4D4, 4E4, 4F2, 5C, 5W, 5X | 3-oxo propanol |
| HMDA130 | 2A, 3B1, 3G1, 3C1, 3D1, 3L1, 3K1, 4A2, 4D4, 4E4, 4F2, 5C, 5W, 5X | 3-oxo propanol |
| HMDA131 | 2A, 3B1, 3C2, 3D2, 3E2, 3F2, 4A5, 4D5, 4F4, 5C, 5W, 5X | 3-oxo propanol |
| HMDA132 | 2A, 3B1, 3C2, 3D2, 3L2, 3K2, 4A5, 4D5, 4F4, 5C, 5W, 5X | 3-oxo propanol |
| HMDA133 | 2A, 3B2, 3C3, 3D2, 3E2, 3F2, 4A5, 4D5, 4F4, 5C, 5W, 5X | 3-oxo propanol |

TABLE G-continued

| Pathway No | Pathway Steps | Aldehyde |
|---|---|---|
| HMDA134 | 2A, 3B2, 3C3, 3D2, 3L2, 3K2, 4A5, 4D5, 4F4, 5C, 5W, 5X | 3-oxo propanol |
| HMDA135 | 2A, 3B1, 3G1, 3C1, 3D1, 3E1, 3F1, 4A2, 4D4, 4E4, 5I, 4F5, 5C, 5W, 5X | 3-oxo propanol |
| HMDA136 | 2A, 3B1, 3C2, 3D2, 3E2, 3F2, 3G5, 4A2, 4D4, 4E4, 5I, 4F5, 5C, 5W, 5X | 3-oxo propanol |
| HMDA137 | 2A, 3B1, 3C2, 3D2, 3L2, 3K2, 3G5, 4A2, 4D4, 4E4, 5I, 4F5, 5C, 5W, 5X | 3-oxo propanol |
| HMDA138 | 2A, 3B2, 3C3, 3D2, 3E2, 3F2, 3G5, 4A2, 4D4, 4E4, 5I, 4F5, 5C, 5W, 5X | 3-oxo propanol |
| HMDA139 | 2A, 3B2, 3C3, 3D2, 3L2, 3K2, 3G5, 4A2, 4D4, 4E4, 5I, 4F5, 5C, 5W, 5X | 3-oxo propanol |
| HMDA140 | 2A, 3B2, 3C3, 3G2, 3D1, 3E1, 3F1, 4A2, 4D4, 4E4, 5I, 4F5, 5C, 5W, 5X | 3-oxo propanol |
| HMDA141 | 2A, 3B1, 3C2, 3G2, 3D1, 3E1, 3F1, 4A2, 4D4, 4E4, 5I, 4F5, 5C, 5W, 5X | 3-oxo propanol |
| HMDA142 | 2A, 3B1, 3G1, 3C1, 3D1, 3L1, 3K1, 4A2, 4D4, 4E4, 5I, 4F5, 5C, 5W, 5X | 3-oxo propanol |
| HMDA143 | 2A, 2B, 2C, 2D, 2E, 2F, 2G, 5G, 5C, 5W, 5X | 3-oxo propionate |
| HMDA144 | 2A, 3B1, 3G1, 3M, 3N, 2F, 2G, 5G, 5C, 5W, 5X | 3-oxo propionate |
| HMDA145 | 2A, 3B1, 3G1, 3D3, 3K1, 3H, 2G, 5G, 5C, 5W, 5X | 3-oxo propionate |
| HMDA146 | 2A, 3B1, 3G1, 3D3, 3K1, 4D3, 4E3, 5G, 5C, 5W, 5X | 3-oxo propionate |
| HMDA147 | 2A, 3B1, 3G1, 3C1, 3D1, 3E1, 3F1, 3H, 2G, 5G, 5C, 5W, 5X | 3-oxo propionate |
| HMDA148 | 2A, 3B1, 3G1, 3C1, 3D1, 3E1, 3F1, 4D3, 4E3, 5G, 5C, 5W, 5X | 3-oxo propionate |
| HMDA149 | 2A, 3B1, 3C2, 3D2, 3E2, 3F2, 3G5, 3H, 2G, 5G, 5C, 5W, 5X | 3-oxo propionate |
| HMDA150 | 2A, 3B1, 3C2, 3D2, 3E2, 3F2, 3G5, 4D3, 4E3, 5G, 5C, 5W, 5X | 3-oxo propionate |
| HMDA151 | 2A, 3B1, 3C2, 3D2, 3L2, 3K2, 3G5, 3H, 2G, 5G, 5C, 5W, 5X | 3-oxo propionate |
| HMDA152 | 2A, 3B1, 3C2, 3D2, 3L2, 3K2, 3G5, 4D3, 4E3, 5G, 5C, 5W, 5X | 3-oxo propionate |
| HMDA153 | 2A, 3B1, 3C2, 3G2, 3D1, 3E1, 3F1, 3H, 2G, 5G, 5C, 5W, 5X | 3-oxo propionate |
| HMDA154 | 2A, 3B1, 3C2, 3G2, 3D1, 3E1, 3F1, 4D3, 4E3, 5G, 5C, 5W, 5X | 3-oxo propionate |
| HMDA155 | 2A, 3B2, 3C3, 3D2, 3E2, 3F2, 3G5, 3H, 2G, 5G, 5C, 5W, 5X | 3-oxo propionate |
| HMDA156 | 2A, 3B2, 3C3, 3D2, 3E2, 3F2, 3G5, 4D3, 4E3, 5G, 5C, 5W, 5X | 3-oxo propionate |
| HMDA157 | 2A, 3B2, 3C3, 3D2, 3L2, 3K2, 3G5, 3H, 2G, 5G, 5C, 5W, 5X | 3-oxo propionate |
| HMDA158 | 2A, 3B2, 3C3, 3D2, 3L2, 3K2, 3G5, 4D3, 4E3, 5G, 5C, 5W, 5X | 3-oxo propionate |
| HMDA159 | 2A, 3B2, 3C3, 3G2, 3D1, 3E1, 3F1, 3H, 2G, 5G, 5C, 5W, 5X | 3-oxo propionate |
| HMDA160 | 2A, 3B2, 3C3, 3G2, 3D1, 3E1, 3F1, 4D3, 4E3, 5G, 5C, 5W, 5X | 3-oxo propionate |
| HMDA161 | 2A, 3B2, 3C3, 3G2, 3D1, 3L1, 3K1, 3H, 2G, 5G, 5C, 5W, 5X | 3-oxo propionate |
| HMDA162 | 2A, 3B2, 3C3, 3G2, 3D1, 3L1, 3K1, 4D3, 4E3, 5G, 5C, 5W, 5X | 3-oxo propionate |
| HMDA163 | 2A, 3B1, 3C2, 3G2, 3D1, 3L1, 3K1, 3H, 2G, 5G, 5C, 5W, 5X | 3-oxo propionate |
| HMDA164 | 2A, 3B1, 3C2, 3G2, 3D1, 3LL, 3K1, 4D3, 4E3, 5G, 5C, 5W, 5X | 3-oxo propionate |
| HMDA165 | 2A, 3B1, 3G1, 3C1, 3D1, 3L1, 3K1, 3H, 2G, 5G, 5C, 5W, 5X | 3-oxo propionate |
| HMDA166 | 2A, 3B1, 3G1, 3C1, 3D1, 3L1, 3K1, 4D3, 4E3, 5G, 5C, 5W, 5X | 3-oxo propionate |
| HMDA167 | 2A, 3B1, 3G1, 21, 2J, 2F, 2G, 5G, 5C, 5W, 5X | 3-oxo propionate |

Wherein 2A, 2B, 3B1, 3B2, 2C, 3G1, 3C2, 3C3, 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4B6, 4B7, 4F1, 4F2, 4F3, 4F5, 2E, 3G2, 3G5, 21, 3M, 3H, 2F, 3D3, 3D2, 3D1, 4D3, 4D4, 4D5, 4G1, 4G2, 4G3, 4G4, and 4G5, are the same as when ADA pathway selected is one of ADA1-ADA141, 5J, 5I, 5G, 5H, 5K, 5L, 5M, 5O, and 5R, are same as above, and 5T is a 6-hydroxyhexanal amino transferase or a 6-hydroxyhexanal dehydrogenase (aminating), 5U is a 6-hydroxyhexylamine 1-dehydrogenase, 5V is a 6-aminohexanoate 1-reductase, 5W 6-aminohexanoyl-CoA 1-reductase, and 5X is a 6-aminohexanal transaminase or a 6-aminohexanal 1-dehydedrogenase (aminating).

In one aspect, particularly when HMDA synthesis pathway is selected from HMDA1-2, 2A, 2B, 2C, 2D, 2E, 2F, 2G, 3B1, 3G1, 3M, 3N, 2F, 2G, and 4F5, are same as when ADA pathway selected is one of ADA 84-141 and 5V, 5X are same as above In another aspect, particularly when HMDA synthesis pathway is selected from HMDA3-21, 47-76, 99-142, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4B6, 4B7, 4F1, 4F2, 4F3, 4F5, 2E, 3G2, 3G5, 3M, 3H, 2F, 3D3, 3D2, 3D1, 4D3, 4D4, 4D5, 4G1, 4G2, 4G3, 4G4, and 4G5, are the same as when ADA pathway selected is one of ADA26-ADA83, and 5J, 5I, 5G, 5H, 5K, 5L, 5M, 5O, 5R, 5T, 5U, 5V, and 5X are the same as above.

In another aspect, particularly when HMDA synthesis pathway is selected from HMDA22-46, 77-98, 143-167, 2A, 2B, 3B1, 3B2, 2C, 3G1, 3C2, 3C3, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4B6, 4B7, 4F1, 4F2, 4F3, 4F5, 2E, 3G2, 3G5, 3M, 3H, 2F, 3D3, 3D2, 3D1, 2J, 21, 4D3, 4D4, 4D5, 4G1, 4G2, 4G3, 4G4, and 4G5, are the same as when ADA pathway selected is one of ADA1-ADA25, and 5J, 5I, 5G, 5H, 5K, 5L, 5M, 5O, 5R, 5T, 5U, 5V, and 5X are the same as above.

In another aspect, particularly when HMDA synthesis pathway is selected from HMDA 1-167, the non-naturally occurring microbial organism further comprsises a N-acetyltransferase and/or a N-deacetylase.

In one aspect, provided is a non-naturally occurring microbial organism as described herein, wherein the microbial organism includes two, three, four, five, six, seven, eight, nine, ten, eleven, tweleve, thirteen, fourteen, fifteem, sixteen, or seventeen enzymes exogenous nucleic acids each encoding a HMDA pathway enzyme.

For example, the microbial organism can include exogenous nucleic acids encoding each of the enzymes of at least one of the pathways selected from HMDA1-HMDA167 as described above.

In one aspect, at least one exogenous nucleic acid included within the microbial organism is a heterologous nucleic acid. In another aspect, the non-naturally occurring microbial organism as disclosed herein is in a substantially anaerobic culture medium.

In another aspect, the non-naturally occurring microbial organism further includes a C3 aldehyde pathway comprising at least one exogenous nucleic acid encoding a 3-oxo-propionate pathway enzyme, wherein the 3-oxo-propionate pathway is selected from i) malonyl-CoA reductase ii) glycerate dehyratase, and a ⅔-phosphoglycerate phosphatase, iii) oxaloacetate decarboxylase iv) 3-amino propionate oxidoreductase or transaminase (deaminating) and/or v) 3-phosphoglyceraldehyde phosphatase, glyceraldehyde dehydrogenase, and a glycerol dehyratase.

In another aspect, the non-naturally occurring microbial organism further includes a C3 aldehyde pathway comprising at least one exogenous nucleic acid encoding a 3-hydroxypropanal pathway enzyme, wherein the 3-hydroxypropanal pathway is selected from
a. A glycerol dehydratase
b. 3-phosphoglyceraldehyde phosphatase, glyceraldehyde 1-reductase, and a glycerol dehydratase In another aspect, the non-naturally occurring microbial organism further includes a C3 aldehyde pathway comprising at least one exogenous nucleic acid encoding a 3-amino-propanal pathway enzyme, wherein the 3-amino-propanal pathway comprises a 3-amino propionyl-CoA reductase.

In one aspect, provided is a non-naturally occurring microbial organism comprising at least one exogenous nucleic acid encoding an 1-hexanol pathway enzyme expressed in a sufficient amount to produce 1-hexanol, wherein said 1-hexanol pathway comprises a 2-oxo-4-hydroxy-hexanoate aldolase, 2-oxo-4-hydroxy-hexanoate dehydratase, 2-oxo-3-hexenoate 3-reductase, 2oxohexanoate-2-reductase, a 2-hydroxyhexanoate-CoA Transferase or a 2-hydroxyhexanoate-CoA ligase, 2-hdyroxyhexanoyl-CoA 2,3-dehdyratase, hexenoyl-CoA 2-reductase, hexanoyl-CoA 1-reductase and a hexanol dehydrogenase.

In one aspect, provided is a non-naturally occurring microbial organism as described herein, wherein the microbial organism includes two, three, four, five, six, seven, eight, or nine, exogenous nucleic acids each encoding a 1-hexanol pathway enzyme.

For example, the microbial organism can include exogenous nucleic acids encoding each of the enzymes of at least one of the pathways selected from 1-hexanol as described above.

In one aspect, at least one exogenous nucleic acid included within the microbial organism is a heterologous nucleic acid. In another aspect, the non-naturally occurring microbial organism as disclosed herein is in a substantially anaerobic culture medium.

While generally described herein as a microbial organism that contains an adipate pathway, it is understood that the invention additionally provides a non-naturally occurring microbial organism comprising at least one exogenous nucleic acid encoding an adipate pathway enzyme expressed in a sufficient amount to produce an intermediate of an adipate pathway. For example, as disclosed herein, an adipate pathway is exemplified in FIG. 2-4 and listed in Table A. Therefore, in addition to a microbial organism containing an adipate pathway that produces adipate, the invention additionally provides a non-naturally occurring microbial organism comprising at least one exogenous nucleic acid encoding an adipate pathway enzyme, where the microbial organism produces an adipate pathway intermediate, for example, 6-hydroxyhexanoate (Example VII), 6-hydroxy-hexanoyl-CoA, 6-aminohexanoyl-CoA, 6-aminohexanoate (Example V), ε-caprolactam (Example VI), ε-carpolactone (Example VIII), 6-oxohexnoate, and 6-oxohexanoyl-CoA. It is understood that any of the pathways disclosed herein, as described in the examples and exemplified in the figures, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces an adipate pathway intermediate can be utilized to produce the intermediate as a desired product.

The invention is described herein with general reference to the reaction, reactant or product thereof, or with specific reference to one or more nucleic acids or genes encoding an enzyme associated with or catalyzing, or a protein associated with, the referenced reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these also references the gene or genes encoding the enzymes that catalyze, or proteins involved in, the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction.

The organisms and methods are described herein with general reference to the reaction, reactant or product thereof, or with specific reference to one or more nucleic acids or genes encoding an enzyme associated with or catalyzing, or a protein associated with, the referenced reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these also references the gene or genes encoding the enzymes that catalyze, or proteins involved in, the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction. Viceversa, reference to a reaction specific enzyme also constitutes a reference to the corresponding reaction it catalyzes, as well as the reactants and products of the reaction.

A host microbial organism can be selected such that it produces the precursor of a synthesis pathway described herein, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism for synthesis of the final product, such as 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid described herein.

In some aspects, provided is the following:
Aspect 1. A non-naturally occurring microbial organism comprising at least one exogenous nucleic acid encoding an enzyme from the group of: adipate pathway enzyme, 6-aminohexanoate pathway enzyme, ¿-caprolactam pathway enzyme, 6-hydroxyhexanoate pathway enzyme, caprolactone pathway enzyme, 1,6-hexanediol pathway enzyme, HMDA pathway enzyme, 1-hexanol pathway enzyme, or 3-oxo-propionate pathway enzyme.

Aspect 2. The microbial organism comprising at least enzyme selected from 2A wherein in 2A is a 4-hydroxy-2-oxo-adipate aldolase, a 4,6-dihydroxy-2-oxo-hexanoate aldolase or a 6-amino-4-hydroxy-2-oxo-hexanoate aldolase.

Aspect 3. A non-naturally occurring microbial organism, comprising at least one exogenous nucleic acid encoding an adipate pathway enzyme selected from 2A, and one or more of 2B, 3B1, 3B2, wherein 2A is a 4-hydroxy-2-oxo-adipate aldolase, a 4,6-dihydroxy-2-oxo-hexanoate aldolase or a 6-amino-4-hydroxy-2-oxo-hexanoate aldolase, 2B is a 4-hydroxy-2-oxo-adipate dehydratase, a 4,6-dihydroxy-2-oxo-hexanoate 4-dehydratase or a 6-amino-4-hydroxy-2-oxo-hexanoate dehydratase, 3B1 is a 4-hydroxy-2-oxo-adipate 2-reductase, a 4,6-dihydroxy-2-oxo-hexanoate 2-reductase or a 6-amino-4-hydroxy-2-oxo-hexanoate 2-reductase, and 3B2 is a 4-hydroxy-2-oxo-adipate 4-dehydrogenase, a 4,6-dihydroxy-2-oxo-hexanoate 4-dehydrogenase or a 6-amino-4-hydroxy-2-oxo-hexanoate 4-dehydrogenase.

Aspect 4. The organism of any one of Aspects 1-3, further comprising an adipate pathway enzyme selected from one or more of 2C, 3G1, 3C2, 3C3 wherein 2C is a 3,4-dehydro-2-oxo-adipate 3-reductase, a 6-hydroxy-3,4-dehydro-2-oxohexanoate 3-reductase or a 6-amino-3,4-dehydro-2-oxohexanoate 3-reductase, 3G1 is a 2,4-dihydroxyadipate CoA-transferase or a 2,4-dihydroxyadipate-CoA ligase, a 2,4,6-trihydroxyhexanoate CoA-transferase or a 2,4,6-trihydroxyhexanoate-CoA ligase, or a 6-amino-2,4-dihydroxyhexanoate CoA-transferase or a 6-amino-2,4-dihydroxyhexanoate-CoA ligase, 3C2 is a 2,4-dihydroxyadipate 4-dehydrogenase, a 2,4,6-trihydroxyhexanoate 4-dehydrogenase or a 6-amino-2,4-dihydroxyhexanoate 4-dehydrogenase, and 3C3 is a 2,4-dioxoadipate 2-reductase, a 6-hydroxy-2,4-dioxohexanoate 2-reductase or a 6-amino-2,4-dioxohexanoate 2-reductase.

Aspect 5. The organism of Aspects 3 or 4, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4B6, 4B7, 4F1, 4F2, 4F3, 4F5, 2E, 3G2, 3G5, 21, 3M, 3H, 2F, 3D3, 3D2, 3D1, 4D3, 4D4, 4D5, 4G1, 4G2, 4G3, 4G4 and 4G5 wherein 2J is a 4,5-dehydro-2-hydroxy-adipyl-CoA 4,5-reductase, 2G is a 2,3-dehydro-adipyl-CoA 2,3-reductase, a 6-hydroxy-2,3-dehydro-hexanoyl-CoA 2,3-reductase or a 6-amino-2,3-dehydro-hexanoyl-CoA 2,3-reductase, 3E1 is a 2,3-dehydro-4-oxoadipyl-CoA 2,3-reductase, a 6-hydroxy-2,3-dehydro-4-oxohexanoyl-CoA 2,3-reductase or a 6-amino-2,3-dehydro-4-oxohexanoyl-CoA 2,3-reductase, 3E2 is a 2,3-dehydro-4-oxoadipate 2,3-reductase, a 6-hydroxy-2,3-dehydro-4-oxohexanoate 2,3-reductase or a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase, a 4,6-dihydroxy-2,3-dehydrohexanoate 2,3-reductase or a 6-amino-2,3-dehydro-4-hydroxyhexanoate 2,3-reductase, 3K1 is a 2,3-dehydro-4-hydroxyadipyl-CoA 2,3-reductase, a 4,6-dihydroxy-2,3-dehydrohexanoyl-CoA 2,3-reductase or a 6-amino-2,3-dehydro-4-hydroxyhexanoyl-CoA 2,3-reductase, 4F4 is a 4,5-dehydro-6-oxohexanoate 4,5-reductase, 3N is a 2-oxoadipyl-CoA 2-reductase, a 6-hydroxy-2-oxohexanoyl-CoA 2-reductase or a 6-amino-2-oxohexanoyl-CoA 2-reductase, 2D is a 2-oxoadipate 2-reductase, a 6-hydroxy-2oxohexanoate 2-reductase or a 6-amino-2-oxohexanoate 2-reductase, 3L2 is a 2,3-dehydro-4-oxoadipate 4-reductase, a 6-hydroxy-2,3-dehydro-4-oxohexanoate 4-reductase or a 6-amino-2,3-dehydro-4-oxohexanoate 4-reductase, 3L1 is a 2,3-dehydro-4-oxoadipyl-CoA 4-reductase, a 6-hydroxy-2,3-dehydro-4-oxohexanoyl-CoA 4-reductase or a 6-amino-2,3-dehydro-4-oxohexanoyl-CoA 4-reductase, 3F2 is a 4-oxoadipate 4-reductase, a 6-hydroxy-4-oxohexanoate 4-reductase or a 6-amino-4-oxohexanoate 4-reductase, 3F1 is a 4-oxoadipyl-CoA 3-reductase, a 6-hydroxy-4-oxohexanoyl-CoA 4-reductase or a 6-amino-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase, a 2,4,6-trihydroxyhexanoyl-CoA 4-dehydrogenase or a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4B6 is a 6-oxohexanoyl-CoA 6-dehydrogenase, 4B7 is a 6-oxohexanoate 6-dehydrogenase, 4F1 is an adipyl-CoA transferase, an adipyl-CoA hydrolase or an adipyl-CoA ligase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, 4F5 6-aminohexanoyl-CoA transferase, a 6-aminohexanoyl-CoA hydrolase or an 6-aminohexanoyl-CoA ligase, 2E is a 2-hydroxy-adipate CoA-transferase or a 2-hydroxyadipate-CoA ligase, 2,6-dihydroxy-hexanoate CoA-transferase or a 2,6-dihydroxy-hexanoate-CoA ligase, 6-amino-2-hydroxyhexanoate CoA-transferase or 6-amino-2-hydroxyhexanoate-CoA ligase, 3G2 is a 2-hydroxy-4oxoadipate CoA-transferase or a 2-hydroxy-4oxoadipate-CoA ligase, a 2,6-dihydroxy-4oxohexanoate CoA-transferase or a 2,6-dihydroxy-4oxohexanoate-CoA ligase, or a 6-amino-2-hydroxy-4oxohexanoate CoA-transferase or a 6-amino-2-hydroxy-4oxohexanoate-CoA ligase, 3G5 is a 4-hydroxyadipate CoA-transferase or a 4-hydroxyadipate-CoA ligase, a 4,6-dihydroxyhexanoate CoA-transferase or a 4,6-dihydroxyhexanoate-CoA ligase, or a 6-amino-4-hydroxyhexanoate CoA-transferase or a 6-amino-4-hydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), a 2,4,6-trihydroxyhexanoyl-CoA 4-dehydratase (2,3-dehydro forming), or a 6-amino-2,4-dihydroxyhexanoyl-CoA 4-dehydratase (2,3-dehydro forming), 3H is a 4-hydroxyadipyl-CoA 4-dehdyratase (2,3-dehydro forming), a 4,6-dihydroxyhexanoyl-CoA 4-dehydratase (2,3-dehydro forming) or a 6-amino-4-hydroxyhexanoyl-CoA 4-dehydratase (2,3-dehydro forming), 2F is a 2-hydroxyadipyl-CoA 2-dehydratase, a 2,6-dihydroxy-hexanoyl-CoA 2-dehydratase or a 6-amino-2-hydroxy-hexanoyl-CoA 2-dehydratase, 3D3 is a 2,4-dihydroxyadipyl-CoA 2-dehydratase, a 2,4,6-trihydroxyhexanoyl-CoA 2-dehydratase or a 6-amino-2,4-dihydroxyhexanoyl-CoA 2-dehydratase, 3D2 is a 2-hydroxy-4oxoadipate 2-dehydratase, a 2,6-dihydroxy-4oxohexanoate 2-dehydratase or a 6-amino-2-hydroxy-4oxohexanoate 2-dehydratase, 3D1 is a 2-hydroxy-4oxoadipyl-CoA 2-dehydratase, a 2,6-dihydroxy-4oxohexanoyl-CoA 2-dehydratase or a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 4G1 is a 6-amino-hexanoyl-CoA transaminase or a 6-aminohexanoyl-CoA dehydrogenase (deaminating), 4G2 is a 6-aminohexanoate transaminase or a 6-aminohexanoate dehydrogenase (deaminating), 4G3 is a 6-amino-4-hydroxyhexanoyl-CoA transaminase or a 6-amino-4-hydroxyhexanoyl-CoA dehydrogenase (deaminating), 4G4 is a 6-amino-4-hydroxy-2,3-dehdyrohexanoyl-CoA transaminase or a 6-amino-4-hydroxy-2,3-dehdyrohexanoyl-CoA dehydrogenase (deaminating), and 4G5 is a 6-amino-4-hydroxyhexanoate transaminase or a 6-amino-4-hydroxyhexanoate dehydrogenase (deaminating).

Aspect 6. A non-naturally occurring microbial organism comprising one or more exogenous nucleic acids encoding two, three, four, five, six, seven, eight, nine, ten, eleven or twelve enzymes in an adipate pathway.

Aspect 7. A method for producing adipate, comprising culturing the non-naturally occurring microbial organism of any one of Aspects 3-6 in a culture comprising glycerol or a C5 or C6 sugar, or a combination thereof, and optionally, separating the adipate produced by the organism from the organism or a culture comprising the organism.

Aspect 8. A non-naturally occurring microbial organism, comprising at least one exogenous nucleic acid encoding an 6-aminohexanoate pathway enzyme selected from 2A and one or more of 2B, 3B1, 3B2, wherein 2A is a 4-hydroxy-2-oxo-adipate aldolase, a 4,6-dihydroxy-2-oxo-hexanoate aldolase or a 6-amino-4-hydroxy-2-oxo-hexanoate aldolase, 2B is a 4-hydroxy-2-oxo-adipate dehydratase, a 4,6-dihydroxy-2-oxo-hexanoate 4-dehydratase or a 6-amino-4-hydroxy-2-oxo-hexanoate dehydratase, 3B1 is a 4-hydroxy-2-oxo-adipate 2-reductase, a 4,6-dihydroxy-2-oxo-hexanoate 2-reductase or a 6-amino-4-hydroxy-2-oxo-hexanoate 2-reductase, and 3B2 is a 4-hydroxy-2-oxo-adipate 4-dehydrogenase, a 4,6-dihydroxy-2-oxo-hexanoate 4-dehydrogenase or a 6-amino-4-hydroxy-2-oxo-hexanoate 4-dehydrogenase.

Aspect 9. The organism of Aspect 8, further comprising one or more of 2C, 3G1, 3C2, 3C3 wherein 2C is a 3,4-dehydro-2-oxo-adipate 3-reductase, a 6-hydroxy-3,4-dehydro-2-oxohexanoate 3-reductase or a 6-amino-3,4-dehydro-2-oxohexanoate 3-reductase, 3G1 is a 2,4-dihydroxyadipate CoA-transferase or a 2,4-dihydroxyadipate-CoA ligase, a 2,4,6-trihydroxyhexanoate CoA-transferase or a 2,4,6-trihydroxyhexanoate-CoA ligase, or a 6-amino-2,4-dihydroxyhexanoate CoA-transferase or a 6-amino-2,4-dihydroxyhexanoate-CoA ligase, 3C2 is a 2,4-dihydroxyadipate 4-dehydrogenase, a 2,4,6-trihydroxyhexanoate 4-dehydrogenase or a 6-amino-2,4-dihydroxyhexanoate 4-dehydrogenase, and 3C3 is a 2,4-dioxoadipate 2-reductase, a 6-hydroxy-2,4-dioxohexanoate 2-reductase or a 6-amino-2,4-dioxohexanoate 2-reductase.

Aspect 10. The organism of Aspect 8 or 9, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more, or alternatively ten or more, or alternatively eleven or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 4F5, 2E, 3G2, 3G5, 21, 3M, 3H, 2F, 3D3, 3D2, 3D1, 4D3, 4D4, 4D5, 5J, 5I, and 5G, wherein 2J is a 4,5-dehydro-2-hydroxy-adipyl-CoA 4,5-reductase, 2G is a 2,3-dehydro-adipyl-CoA 2,3-reductase, a 6-hydroxy-2,3-dehydro-hexanoyl-CoA 2,3-reductase or a 6-amino-2,3-dehydro-hexanoyl-CoA 2,3-reductase, 3E1 is a 2,3-dehydro-4-oxoadipyl-CoA 2,3-reductase, a 6-hydroxy-2,3-dehydro-4-oxohexanoyl-CoA 2,3-reductase or a 6-amino-2,3-dehydro-4-oxohexanoyl-CoA 2,3-reductase, 3E2 is a 2,3-dehydro-4-oxoadipate 2,3-reductase, a 6-hydroxy-2,3-dehydro-4-oxohexanoate 2,3-reductase or a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase, a 4,6-dihydroxy-2,3-dehydrohexanoate 2,3-reductase or a 6-amino-2,3-dehydro-4-hydroxyhexanoate 2,3-reductase, 3K1 is a 2,3-dehydro-4-hydroxyadipyl-CoA 2,3-reductase, a 4,6-dihydroxy-2,3-dehydrohexanoyl-CoA 2,3-reductase or a 6-amino-2,3-dehydro-4-hydroxyhexanoyl-CoA 2,3-reductase, 4F4 is a 4,5-dehydro-6-oxohexanoate 4,5-reductase, 3N is a 2-oxoadipyl-CoA 2-reductase, a 6-hydroxy-2-oxohexanoyl-CoA 2-reductase or a 6-amino-2-oxohexanoyl-CoA 2-reductase, 2D is a 2-oxoadipate 2-reductase, a 6-hydroxy-2oxohexanoate 2-reductase or a 6-amino-2-oxohexanoate 2-reductase, 3L2 is a 2,3-dehydro-4-oxoadipate 4-reductase, a 6-hydroxy-2,3-dehydro-4-oxohexanoate 4-reductase or a 6-amino-2,3-dehydro-4-oxohexanoate 4-reductase, 3L1 is a 2,3-dehydro-4-oxoadipyl-CoA 4-reductase, a 6-hydroxy-2,3-dehydro-4-oxohexanoyl-CoA 4-reductase or a 6-amino-2,3-dehydro-4-oxohexanoyl-CoA 4-reductase, 3F2 is a 4-oxoadipate 4-reductase, a 6-hydroxy-4-oxohexanoate 4-reductase or a 6-amino-4-oxohexanoate 4-reductase, 3F1 is a 4-oxoadipyl-CoA 3-reductase, a 6-hydroxy-4-oxohexanoyl-CoA 4-reductase or a 6-amino-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase, a 2,4,6-trihydroxyhexanoyl-CoA 4-dehydrogenase or a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, 4F5 is a 6-aminohexanoyl-CoA transferase, a 6-aminohexanoyl-CoA hydrolase or an 6-aminohexanoyl-CoA ligase, 2E is a 2-hydroxyadipate CoA-transferase or a 2-hydroxyadipate-CoA ligase, 2,6-dihydroxy-hexanoate CoA-transferase or a 2,6-dihydroxy-hexanoate-CoA ligase, 6-amino-2-hydroxyhexanoate CoA-transferase or 6-amino-2-hydroxyhexanoate-CoA ligase, 3G2 is a 2-hydroxy-4oxoadipate CoA-transferase or a 2-hydroxy-4oxoadipate-CoA ligase, a 2,6-dihydroxy-4oxohexanoate CoA-transferase or a 2,6-dihydroxy-4oxohexanoate-CoA ligase, or a 6-amino-2-hydroxy-4oxohexanoate CoA-transferase or a 6-amino-2-hydroxy-4oxohexanoate-CoA ligase, 3G5 is a 4-hydroxyadipate CoA-transferase or a 4-hydroxyadipate-CoA ligase, a 4,6-dihydroxyhexanoate CoA-transferase or a 4,6-dihydroxyhexanoate-CoA ligase, or a 6-amino-4-hydroxyhexanoate CoA-transferase or a 6-amino-4-hydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), a 2,4,6-trihydroxyhexanoyl-CoA 4-dehydratase (2,3-dehydro forming), or a 6-amino-2,4-dihydroxyhexanoyl-CoA 4-dehydratase (2,3-dehydro forming), 3H is a 4-hydroxyadipyl-CoA 4-dehdyratase (2,3-dehydro forming), a 4,6-dihydroxyhexanoyl-CoA 4-dehydratase (2,3-dehydro forming) or a 6-amino-4-hydroxyhexanoyl-CoA 4-dehydratase (2,3-dehydro forming), 2F is a 2-hydroxyadipyl-CoA 2-dehydratase, a 2,6-dihydroxy-hexanoyl-CoA 2-dehydratase or a 6-amino-2-hydroxy-hexanoyl-CoA 2-dehydratase, 3D3 is a 2,4-dihydroxyadipyl-CoA 2-dehydratase, a 2,4,6-trihydroxyhexanoyl-CoA 2-dehydratase or a 6-amino-2,4-dihydroxyhexanoyl-CoA 2-dehydratase, 3D2 is a 2-hydroxy-4oxoadipate 2-dehydratase, a 2,6-dihydroxy-4oxohexanoate 2-dehydratase or a 6-amino-2-hydroxy-4oxohexanoate 2-dehydratase, 3D1 is a 2-hydroxy-4oxoadipyl-CoA 2-dehydratase, a 2,6-dihydroxy-4oxohexanoyl-CoA 2-dehydratase or a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 5J is a 6-oxohexanoic acid transaminase (aminating) or a 6-oxohexanoic acid dehydrogenase (aminating), 5I is a 6-oxohexanoyl-CoA transaminase (aminating), or a 6-oxohexanoyl-CoA dehydrogenase (aminating), and 5G is an adipyl-CoA 1-reductase Aspect 11. A non-naturally occurring microbial organism comprising one or more exogenous nucleic acids encoding two, three, four, five, six, seven, eight, nine, ten, eleven or twelve enzymes in a 6-aminohexanoate pathway.

Aspect 12. A method for producing 6-aminohexanoate, comprising culturing the non-naturally occurring microbial organism of any one of Aspects 8-11 in a culture comprising glycerol or a C5 or C6 sugar, or a combination thereof, and optionally, separating the 6-aminohexanoate produced by the organism from the organism or a culture comprising the organism.

Aspect 13. A non-naturally occurring microbial organism, comprising at least one exogenous nucleic acid encoding a caprolactam pathway enzyme selected from 2A and one or more of 2B, 3B1, 3B2, wherein 2A is a 4-hydroxy-2-oxo-adipate aldolase, a 4,6-dihydroxy-2-oxo-hexanoate aldolase or a 6-amino-4-hydroxy-2-oxo-hexanoate aldolase, 2B is a 4-hydroxy-2-oxo-adipate dehydratase, a 4,6-dihydroxy-2-oxo-hexanoate 4-dehydratase or a 6-amino-4-hydroxy-2-oxo-hexanoate dehydratase, 3B1 is a 4-hydroxy-2-oxo-adipate 2-reductase, a 4,6-dihydroxy-2-oxo-hexanoate 2-reductase or a 6-amino-4-hydroxy-2-oxo-hexanoate 2-reductase, and 3B2 is a 4-hydroxy-2-oxo-adipate 4-dehydrogenase, a 4,6-dihydroxy-2-oxo-hexanoate 4-dehydrogenase or a 6-amino-4-hydroxy-2-oxo-hexanoate 4-dehydrogenase.

Aspect 14. The organism of Aspect 13, further comprising an ε-caprolactam pathway enzyme selected from one or more of 2C, 3G1, 3C2, 3C3 wherein 2C is a 3,4-dehydro-2-oxo-adipate 3-reductase, a 6-hydroxy-3,4-dehydro-2-oxohexanoate 3-reductase or a 6-amino-3,4-dehydro-2-oxohexanoate 3-reductase, 3G1 is a 2,4-dihydroxyadipate CoA-transferase or a 2,4-dihydroxyadipate-CoA ligase, a 2,4,6-trihydroxyhexanoate CoA-transferase or a 2,4,6-trihydroxyhexanoate-CoA ligase, or a 6-amino-2,4-dihydroxyhexanoate CoA-transferase or a 6-amino-2,4-dihydroxyhexanoate-CoA ligase, 3C2 is a 2,4-dihydroxyadipate 4-dehydrogenase, a 2,4,6-trihydroxyhexanoate 4-dehydrogenase or a 6-amino-2,4-dihydroxyhexanoate 4-dehydrogenase, and 3C3 is a 2,4-dioxoadipate 2-reductase, a 6-hydroxy-2,4-dioxohexanoate 2-reductase or a 6-amino-2,4-dioxohexanoate 2-reductase.

Aspect 15. The organism of Aspect 13 or 14, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more, or alternatively ten or more, or alternatively eleven or more, or alternatively twelve or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, 4D5, 5J, 5I, 5G, 5A, 5C wherein 2J is a 4,5-dehydro-2-hydroxyadipyl-CoA 4,5-reductase, 2G is a 2,3-dehydro-adipyl-CoA 2,3-reductase, a 6-hydroxy-2,3-dehydrohexanoyl-CoA 2,3-reductase or a 6-amino-2,3-dehydro-hexanoyl-CoA 2,3-reductase,3E1 is a 2,3-dehydro-4-oxoadipyl-CoA 2,3-reductase, a 6-hydroxy-2,3-dehydro-4-oxohexanoyl-CoA 2,3-reductase or a 6-amino-2,3-dehydro-4-oxohexanoyl-CoA 2,3-reductase, 3E2 is a 2,3-dehydro-4-oxoadipate 2,3-reductase, a 6-hydroxy-2,3-dehydro-4-oxohexanoate 2,3-reductase or a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase, a 4,6-dihydroxy-2,3-dehydrohexanoate 2,3-reductase or a 6-amino-2,3-dehydro-4-hydroxyhexanoate 2,3-reductase, 3K1 is a 2,3-dehydro-4-hydroxyadipyl-CoA 2,3-reductase, a 4,6-dihydroxy-2,3-dehydrohexanoyl-CoA 2,3-reductase or a 6-amino-2,3-dehydro-4-hydroxyhexanoyl-CoA 2,3-reductase, 4F4 is a 4,5-dehydro-6-oxohexanoate 4,5-reductase, 3N is a 2-oxoadipyl-CoA 2-reductase, a 6-hydroxy-2-oxo-hexanoyl-CoA 2-reductase or a 6-amino-2-oxo-hexanoyl-CoA 2-reductase, 2D is a 2-oxoadipate 2-reductase, a 6-hydroxy-2oxohexanoate 2-reductase or a 6-amino-2-oxohexanoate 2-reductase, 3L2 is a 2,3-dehydro-4-oxoadipate 4-reductase, a 6-hydroxy-2,3-dehydro-4-oxohexanoate 4-reductase or a 6-amino-2,3-dehydro-4-oxohexanoate 4-reductase, 3L 1 is a 2,3-dehydro-4-oxoadipyl-CoA 4-reductase, a 6-hydroxy-2,3-dehydro-4-oxohexanoyl-CoA 4-reductase or a 6-amino-2,3-dehydro-4-oxohexanoyl-CoA 4-reductase, 3F2 is a 4-oxoadipate 4-reductase, a 6-hydroxy-4-oxohexanoate 4-reductase or a 6-amino-4-oxohexanoate 4-reductase, 3F1 is a 4-oxoadipyl-CoA 3-reductase, a 6-hydroxy-4-oxohexanoyl-CoA 4-reductase or a 6-amino-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase, a 2,4,6-trihydroxyhexanoyl-CoA 4-dehydrogenase or a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, a 6-aminohexanoyl-CoA hydrolase or an 6-aminohexanoyl-CoA ligase, 2E is a 2-hydroxy-adipate CoA-transferase or a 2-hydroxyadipate-CoA ligase, 2,6-dihydroxy-hexanoate CoA-transferase or a 2,6-dihydroxy-hexanoate-CoA ligase, 6-amino-2-hydroxyhexanoate CoA-transferase or 6-amino-2-hydroxyhexanoate-CoA ligase, 3G2 is a 2-hydroxy-4oxoadipate CoA-transferase or a 2-hydroxy-4oxoadipate-CoA ligase, a 2,6-dihydroxy-4oxo-hexanoate CoA-transferase or a 2,6-dihydroxy-4oxo-hexanoate-CoA ligase, or a 6-amino-2-hydroxy-4oxohexanoate CoA-transferase or a 6-amino-2-hydroxy-4oxohexanoate-CoA ligase, 3G5 is a 4-hydroxyadipate CoA-transferase or a 4-hydroxyadipate-CoA ligase, a 4,6-dihydroxyhexanoate CoA-transferase or a 4,6-dihydroxyhexanoate-CoA ligase, or a 6-amino-4-hydroxyhexanoate CoA-transferase or a 6-amino-4-hydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), a 2,4,6-trihydroxyhexanoyl-CoA 4-dehydratase (2,3-dehydro forming), or a 6-amino-2,4-dihydroxyhexanoyl-CoA 4-dehydratase (2,3-dehydro forming), 3H is a 4-hydroxyadipyl-CoA 4-dehdyratase (2,3-dehydro forming), a 4,6-dihydroxyhexanoyl-CoA 4-dehydratase (2,3-dehydro forming) or a 6-amino-4-hydroxyhexanoyl-CoA 4-dehydratase (2,3-dehydro forming), 2F is a 2-hydroxy-adipyl-CoA 2-dehydratase, a 2,6-dihydroxy-hexanoyl-CoA 2-dehydratase or a 6-amino-2-hydroxy-hexanoyl-CoA 2-dehydratase, 3D3 is a 2,4-dihydroxyadipyl-CoA 2-dehydratase, a 2,4,6-trihydroxyhexanoyl-CoA 2-dehydratase or a 6-amino-2,4-dihydroxyhexanoyl-CoA 2-dehydratase, 3D2 is a 2-hydroxy-4oxoadipate 2-dehydratase, a 2,6-dihydroxy-4oxohexanoate 2-dehydratase or a 6-amino-2-hydroxy-4oxohexanoate 2-dehydratase, 3D1 is a 2-hydroxy-4oxoadipyl-CoA 2-dehydratase, a 2,6-dihydroxy-4oxohexanoyl-CoA 2-dehydratase or a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 5J is a 6-oxohexanoic acid transaminase (aminating) or a 6-oxohexanoic acid dehydrogenase (aminating), 5I is a 6-oxohexanoyl-CoA transaminase (aminating), or a 6-oxohexanoyl-CoA dehydrogenase (aminating), 5G is an adipyl-CoA 1-reductase, 5C is a 6-aminohexanoate CoA-transferase or a 6-aminohexanoate-CoA ligase, and 5A is spontaneous cyclization or an amidohydrolase.

Aspect 16. The non-naturally occurring microbial organism comprising two, three, four, five, six, seven, eight, nine, ten, eleven, twelve, or thirteen exogenous nucleic acids each encoding a caprolactam pathway enzyme.

Aspect 17. A method for producing caprolactam, comprising culturing the non-naturally occurring microbial organism of any one of Aspects 13-16 in a culture comprising glycerol or a C5 or C6 sugar, or a combination there of, and optionally, separating the caprolactam produced by the organism from the organism or a culture comprising the organism.

Aspect 18. A non-naturally occurring microbial organism, comprising at least one exogenous nucleic acid encoding a 6-hydroxyhexanoate pathway enzyme selected from 2A and one or more of 2B, 3B1, 3B2, wherein 2A is a 4-hydroxy-2-oxo-adipate aldolase or a 4,6-dihydroxy-2-oxo-hexanoate aldolase, 2B is a 4-hydroxy-2-oxo-adipate dehydratase or a 4,6-dihydroxy-2-oxo-hexanoate 4-dehydratase, 3B1 is a 4-hydroxy-2-oxo-adipate 2-reductase or a 4,6-dihydroxy-2-oxo-hexanoate 2-reductase, and 3B2 is a 4-hydroxy-2-oxo-adipate 4-dehydrogenase or a 4,6-dihydroxy-2-oxo-hexanoate 4-dehydrogenase.

Aspect 19. The organism of Aspect 18, further comprising a 6-hydroxyhexanoate pathway enzyme selected from one or more of 2C, 3G1, 3C2, 3C3 wherein 2C is a 3,4-dehydro-2-oxo-adipate 3-reductase or a 6-hydroxy-3,4-dehydro-2-oxohexanoate 3-reductase, 3G1 is a 2,4-dihydroxyadipate CoA-transferase or a 2,4-dihydroxyadipate-CoA ligase, or a 2,4,6-trihydroxyhexanoate CoA-transferase or a 2,4,6-trihydroxyhexanoate-CoA ligase, 3C2 is a 2,4-dihydroxyadipate 4-dehydrogenase or a 2,4,6-trihydroxyhexanoate 4-dehydrogenase, and 3C3 is a 2,4-dioxoadipate 2-reductase or a 6-hydroxy-2,4-dioxohexanoate 2-reductase.

Aspect 20. The organism of Aspect 18 or 19, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more, or alternatively ten or more, or alternatively, eleven or more, or alternatively twelve or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4F2, 4F3, 2E, 3G2, 3G5, 21, 3M, 3H, 2F, 3D3, 3D2, 3D1, 4D3, 4D4, 4D5, 5G, 5L, and 5K, wherein 2J is a 4,5-dehydro-2-hydroxy-adipyl-CoA 4,5-reductase, 2G is a 2,3-dehydro-adipyl-CoA 2,3-reductase or a 6-hydroxy-2,3-dehydro-hexanoyl-CoA 2,3-reductase,3E1 is a 2,3-dehydro-4-oxoadipyl-CoA 2,3-reductase or a 6-hydroxy-2,3-dehydro-4-oxohexanoyl-CoA 2,3-reductase, 3E2 is a 2,3-dehydro-4-oxoadipate 2,3-reductase or a 6-hydroxy-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase or a 4,6-dihydroxy-2,3-dehydrohexanoate 2,3-reductase, 3K1 is a 2,3-dehydro-4-hydroxyadipyl-CoA 2,3-reductase or a 4,6-dihydroxy-2,3-dehydrohexanoyl-CoA 2,3-reductase, 4F4 is a 4,5-dehydro-6-oxohexanoate 4,5-reductase, 3N is a 2-oxoadipyl-CoA 2-reductase or a 6-hydroxy-2-oxohexanoyl-CoA 2-reductase, 2D is a 2-oxoadipate 2-reductase or a 6-hydroxy-2oxohexanoate 2-reductase, 3L2 is a 2,3-dehydro-4-oxoadipate 4-reductase or a 6-hydroxy-2,3-dehydro-4-oxohexanoate 4-reductase, 3L1 is a 2,3-dehydro-4-oxoadipyl-CoA 4-reductase or a 6-hydroxy-2,3-dehydro-4-oxohexanoyl-CoA 4-reductase, 3F2 is a 4-oxoadipate 4-reductase or a 6-hydroxy-4-oxohexanoate 4-reductase, 3F1 is a 4-oxoadipyl-CoA 3-reductase or a 6-hydroxy-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase or a 2,4,6-trihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, 2E is a 2-hydroxy-adipate CoA-transferase or a 2-hydroxyadipate-CoA ligase, or a 2,6-dihydroxy-hexanoate CoA-transferase or a 2,6-dihydroxy-hexanoate-CoA ligase, 3G2 is a 2-hydroxy-4oxoadipate CoA-transferase or a 2-hydroxy-4oxoadipate-CoA ligase, or a 2,6-dihydroxy-4oxohexanoate CoA-transferase or a 2,6-dihydroxy-4oxohexanoate-CoA ligase, 3G5 is a 4-hydroxyadipate CoA-transferase or a 4-hydroxyadipate-CoA ligase, or a 4,6-dihydroxyhexanoate CoA-transferase or a 4,6-dihydroxyhexanoate-CoA ligase, 2I is a 2,4-dihydroxyadipyl-CoA 4-dehydratase (4,5-dehydro forming), 3M is a 2,4-dihydroxyadipyl-CoA 4-dehydratase (2,3-dehydro forming), or a 2,4,6-trihydroxyhexanoyl-CoA 4-dehydratase (2,3-dehydro forming), 3H is a 4-hydroxyadipyl-CoA 4-dehdyratase (2,3-dehydro forming) or a 4,6-dihydroxyhexanoyl-CoA 4-dehydratase (2,3-dehydro forming), 2F is a 2-hydroxy-adipyl-CoA 2-dehydratase or a 2,6-dihydroxy-hexanoyl-CoA 2-dehydratase, 3D3 is a 2,4-dihydroxyadipyl-CoA 2-dehydratase or a 2,4,6-trihydroxyhexanoyl-CoA 2-dehydratase, 3D2 is a 2-hydroxy-4oxoadipate 2-dehydratase or a 2,6-dihydroxy-4oxohexanoate 2-dehydratase, 3D1 is a 2-hydroxy-4oxoadipyl-CoA 2-dehydratase or a 2,6-dihydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 5G is a adipyl-CoA 1-reductase, 5L is an 6-oxohexanoyl-CoA 6-reductase, and 5K is an 6-oxohexanoate 6-reductase.

Aspect 21. A non-naturally occurring microbial organism comprising one or more exogenous nucleic acids encoding two, three, four, five, six, seven, eight, nine, ten, eleven or twelve enzymes in a 6-hydroxyhexanoate pathway.

Aspect 22. A method for producing 6-hydroxyhexanoate, comprising culturing the non-naturally occurring microbial organism of any one of Aspects 18-21 in a culture comprising glycerol or a C5 or C6 sugar, or a combination thereof, and optionally, separating the 6-hydroxyhexanoate produced by the organism from the organism or a culture comprising the organism.

Aspect 23. A non-naturally occurring microbial organism, comprising at least one exogenous nucleic acid encoding a caprolactone pathway enzyme selected from 2A and one or more of 2B, 3B1, 3B2, wherein 2A is an 4,6-dihydroxy-2-oxo-hexanoate aldolase, 2B is an 4,6-dihydroxy-2-oxo-hexanoate 4-dehydratase, 3B1 is an 4,6-dihydroxy-2-oxo-hexanoate 2-reductase, and 3B2 is an 4,6-dihydroxy-2-oxo-hexanoate 4-dehydrogenase.

Aspect 24. The organism of Aspect 23, further comprising an caprolactone pathway enzyme selected from one or more of 2C, 3G1, 3C2, 3C3 wherein 2C is an 6-hydroxy-3,4-dehydro-2-oxohexanoate 3-reductase, 3G1 is a 2,4,6-trihydroxyhexanoate CoA-transferase or a 2,4,6-trihydroxyhexanoate-CoA ligase, 3C2 is an 2,4,6-trihydroxyhexanoate 4-dehydrogenase, and 3C3 is an 6-hydroxy-2,4-dioxohexanoate 2-reductase.

Aspect 25. The organism of Aspect 23 or 24, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more of 2G, 3E1, 3E2, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 3M, 3H, 2F, 3D3, 3D2, 3D1, 4D4, 4D5, 5L, 5K, 5M, 5P, and 5Q, wherein 2G is an 6-hydroxy-2,3-dehydro-hexanoyl-CoA 2,3-reductase,3E1 is an 6-hydroxy-2,3-dehydro-4-oxohexanoyl-CoA 2,3-reductase, 3E2 is an 6-hydroxy-2,3-dehydro-4-oxohexanoate 2,3-reductase, 4E4 is an 4,5-dehydro-6-oxohexanoyl-CoA 4,5-reductase, 3K2 is an 4,6-dihydroxy-2,3-dehydrohexanoate 2,3-reductase, 3K1 is an 4,6-dihydroxy-2,3-dehydrohexanoyl-CoA 2,3-reductase, 4F4 is a 4,5-dehydro-6-oxohexanoate 4,5-reductase, 3N is an 6-hydroxy-2-oxohexanoyl-CoA 2-reductase, 2D is an 6-hydroxy-2oxohexanoate 2-reductase, 3L2 is an 6-hydroxy-2,3-dehydro-4-oxohexanoate 4-reductase, 3L1 is an 6-hydroxy-2,3-dehydro-4-oxohexanoyl-CoA 4-reductase, 3F2 is an 6-hydroxy-4-oxohexanoate 4-reductase, 3F1 is an 6-hydroxy-4-oxohexanoyl-CoA 4-reductase, 4A1 is an 4,6-dihydroxy-2,3-dehydrohexanoyl-CoA 6-dehydrogenase, 4A2 is an 4,6-dihydroxyhexanoyl-CoA 6-dehydrogenase, 4A4 is an 6-hydroxyhexanoate 6-dehydrogenase, 4A5 is an 4,6-dihydroxyhexanoate 6-dehydrogenase, 3C1 is an 2,4,6-trihydroxyhexanoyl-CoA 4-dehydrogenase, 4B1 is an 4-hydroxy-2,3-dehydro-6-oxohexanoyl-CoA 6-dehydrogenase, 4B4 is an 4-hydroxy-6-oxohexanoyl-CoA 6-dehydrogenase, 4B5 is an 4,5-dehydro-6-oxo-hexanoyl-CoA 6-dehydrogenase, 4F2 is a 6-oxo-hexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxy-hexanoyl-CoA hydrolase or a 6-hydroxyhexanoyl-CoA ligase, 2E is an 2,6-dihydroxy-hexanoate CoA-transferase or a 2,6-dihydroxy-hexanoate-CoA ligase, 3G2 is a 2,6-dihydroxy-4oxohexanoate CoA-transferase or a 2,6-dihydroxy-4oxohexanoate-CoA ligase, 3G5 is a 4,6-dihydroxyhexanoate CoA-transferase or a 4,6-di-hydroxyhexanoate-CoA ligase, 3M is an 2,4,6-trihy-droxyhexanoyl-CoA 4-dehydratase (2,3-dehydro forming), 3H is an 4,6-dihydroxyhexanoyl-CoA 4-dehydratase (2,3-dehydro forming), 2F is an 2,6-dihydroxy-hexanoyl-CoA 2-dehydratase, 3D3 is an 2,4,6-trihydroxyhexanoyl-CoA 2-dehydratase, 3D2 is an 2,6-dihydroxy-4oxohexanoate 2-dehydratase, 3D1 is an 2,6-dihydroxy-4oxohexanoyl-CoA 2-dehydratase, 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 5L is an 6-oxo-hexanoyl-CoA 6-reductase, 5K is an 6-oxohexanoate 6-reductase, 5M is an 6-hydroxyhexanoate CoA-trans-ferase or a 6-hydroxyhexanoate-CoA ligase, 5P is spontaneous cyclization or a 6-hydroxyhexanoate cyclase, and 5Q is spontaneous cyclization or a 6-hydroxy-hexanoyl-CoA cyclase.

Aspect 26. A non-naturally occurring microbial organism comprising one or more exogenous nucleic acids encoding two, three, four, five, six, seven, eight, nine, ten, eleven, twelve, thirteen, or fourteen enzymes in a caprolactone pathway.

Aspect 27. A method for producing caprolactone, comprising culturing the non-naturally occurring microbial organism of any one of Aspects 23-26 in a culture comprising glycerol or a C5 or C6 sugar, or a combination there of, and optionally, separating the caprolactone produced by the organism from the organism or a culture comprising the organism Aspect 28. A non-naturally occurring microbial organism, comprising at least one exogenous nucleic acid encoding a 1,6-hexanediol pathway enzyme selected from 2A and one or more of 2B, 3B1, 3B2, wherein 2A is a 4-hydroxy-2-oxo-adipate aldolase or a 4,6-dihydroxy-2-oxo-hexanoate aldolase, 2B is a 4-hydroxy-2-oxo-adipate dehydratase or a 4,6-dihydroxy-2-oxo-hexanoate 4-dehydratase, 3B1 is a 4-hydroxy-2-oxo-adipate 2-reductase or a 4,6-dihydroxy-2-oxo-hexanoate 2-reductase, and 3B2 is a 4-hydroxy-2-oxo-adipate 4-dehydrogenase or a 4,6-dihydroxy-2-oxo-hexanoate 4-dehydrogenase.

Aspect 29. The organism of Aspect 28, further comprising a 1,6-hexanediol pathway enzyme selected from one or more of 2C, 3G1, 3C2, 3C3 wherein 2C is a 3,4-dehydro-2-oxo-adipate 3-reductase or a 6-hydroxy-3,4-dehydro-2-oxohexanoate 3-reductase, 3G1 is a 2,4-dihydroxyadipate CoA-transferase or a 2,4-dihydroxyadipate-CoA ligase, or a 2,4,6-trihydroxyhexanoate CoA-transferase or a 2,4,6-trihydroxyhexanoate-CoA ligase, 3C2 is a 2,4-dihydroxyadipate 4-dehydrogenase or a 2,4,6-trihydroxyhexanoate 4-dehydrogenase, and 3C3 is a 2,4-dioxoadipate 2-reductase or a 6-hydroxy-2,4-di-oxohexanoate 2-reductase.

Aspect 30. The organism of Aspect 28 or 29, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A5, 3C1, 4B1, 4B4, 4B5, 4B6, 4F2, 2E, 3G2, 3G5, 21, 3M, 3H, 2F, 3D3, 3D2, 3D1, 4D3, 4D4, 4D5, 5L, 5K, 5M, 5R, 5S, and 50 wherein wherein 2J is a 4,5-dehydro-2-hydroxy-adipyl-CoA 4,5-reductase, 2G is a 2,3-dehydro-adipyl-CoA 2,3-reductase or a 6-hydroxy-2,3-dehydro-hexanoyl-CoA 2,3-reductase,3E1 is a 2,3-dehydro-4-oxoadipyl-CoA 2,3-reductase or a 6-hy-droxy-2,3-dehydro-4-oxohexanoyl-CoA 2,3-reductase, 3E2 is a 2,3-dehydro-4-oxoadipate 2,3-reductase or a 6-hydroxy-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase or a 4,6-dihydroxy-2,3-dehydrohexanoate 2,3-reductase, 3K1 is a 2,3-dehydro-4-hydroxyadipyl-CoA 2,3-reductase or a 4,6-dihydroxy-2,3-dehydrohexanoyl-CoA 2,3-reductase, 4F4 is a 4,5-dehydro-6-oxohexanoate 4,5-reductase, 3N is a 2-oxoadipyl-CoA 2-reductase or a 6-hydroxy-2-oxohexanoyl-CoA 2-reductase, 2D is a 2-oxoadipate 2-reductase or a 6-hydroxy-2oxohexano-ate 2-reductase, 3L2 is a 2,3-dehydro-4-oxoadipate 4-reductase or a 6-hydroxy-2,3-dehydro-4-oxohexano-ate 4-reductase, 3L1 is a 2,3-dehydro-4-oxoadipyl-CoA 4-reductase or a 6-hydroxy-2,3-dehydro-4-oxo-hexanoyl-CoA 4-reductase, 3F2 is a 4-oxoadipate 4-reductase or a 6-hydroxy-4-oxohexanoate 4-reductase, 3F1 is a 4-oxoadipyl-CoA 3-reductase or a 6-hydroxy-4-oxohexanoyl-CoA 4-reductase, 4A1 is a 4,6-dihy-droxy-2,3-dehydrohexanoyl-CoA 6-dehydrogenase, 4A2 is a 4,6-dihydroxyhexanoyl-CoA 6-dehydroge-nase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase or a 2,4,6-trihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxo-hexanoyl-CoA 6-dehydrogenase, 4B6 is a 6-oxo-hexanoyl-CoA 6-dehydrogenase, 4F2 is a 6-oxohexanoyl-CoA transferase, a 6-oxohexanoyl-CoA hydrolase or an 6-oxohexanoyl-CoA ligase, 2E is a 2-hydroxy-adipate CoA-transferase or a 2-hydroxyadipate-CoA ligase, 2,6-dihydroxy-hexanoate CoA-transferase or a 2,6-dihydroxy-hexanoate-CoA ligase, 3G2 is a 2-hydroxy-4oxoadipate CoA-transferase or a 2-hydroxy-4oxoadipate-CoA ligase, or a 2,6-dihy-droxy-4oxohexanoate CoA-transferase or a 2,6-dihy-droxy-4oxohexanoate-CoA ligase, 3G5 is a 4-hy-droxyadipate CoA-transferase or a 4-hydroxyadipate-CoA ligase, or a 4,6-dihydroxyhexanoate CoA-transferase or a 4,6-dihydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming) or a 2,4,6-trihy-droxyhexanoyl-CoA 4-dehydratase (2,3-dehydro forming), 3H is a 4-hydroxyadipyl-CoA 4-dehdyratase (2,3-dehydro forming) or a 4,6-dihydroxyhexanoyl-CoA 4-dehydratase (2,3-dehydro forming), 2F is a 2-hy-droxy-adipyl-CoA 2-dehydratase or a 2,6-dihydroxyhexanoyl-CoA 2-dehydratase, 3D3 is a 2,4-dihydroxyadipyl-CoA 2-dehydratase or a 2,4,6-trihydroxyhexanoyl-CoA 2-dehydratase, 3D2 is a 2-hydroxy-4oxoadipate 2-dehydratase or a 2,6-dihydroxy-4oxohexanoate 2-dehydratase, 3D1 is a 2-hydroxy-4oxoadipyl-CoA 2-dehydratase or a 2,6-dihydroxy-4oxohexanoyl-CoA 2-dehydratase, 4D3 is an 4-hydroxy-adipyl-CoA 4-dehydratase (4,5-dehydro forming), 4D4 is an 4-hydroxy-6oxohexanoyl-CoA 4-dehydratase (4,5-dehydro forming), 4D5 is an 4-hydroxy-6oxohexanoate 4-dehydratase (4,5-dehydro forming), 5L is an 6-oxohexanoyl-CoA 6-reductase, 5K is an 6-oxohexanoate 6-reductase, 5M is a 6-hydroxyhexanoate CoA-transferase or a 6-hydroxyhexanoate-CoA ligase, 5L is an 6-oxohexanoyl-CoA 6-reductase, 5K is an 6-oxohexanoate 6-reductase, 5M is a 6-hydroxyhexanoate CoA-transferase or a 6-hydroxyhexanoate-CoA ligase, 50 is an 6-hydroxyhexanoyl-CoA 1-reductase, 5R is an 6-hydroxyhexanoate 1-reductase, and 5S is an 6-hydroxyhexanal 1-reductase.

Aspect 31. A non-naturally occurring microbial organism comprising one or more exogenous nucleic acids encoding two, three, four, five, six, seven, eight, nine, ten, eleven, twelve, thirteen, fourteen or fifteen enzymes in a 1,6-hexanediol pathway.

Aspect 32. A method for producing 1,6-hexanediol, comprising culturing the non-naturally occurring microbial organism of any one of Aspects 28-31 in a culture comprising glycerol or a C5 or C6 sugar, or a combination there of, and optionally, separating the 1,6-hexanediol produced by the organism from the organism or a culture comprising the organism.

33. A non-naturally occurring microbial organism, comprising at least one exogenous nucleic acid encoding an HMDA pathway enzyme selected from 2A and one or more of 2B, 3B1, 3B2, wherein 2A is a 4-hydroxy-2-oxo-adipate aldolase, a 4,6-dihydroxy-2-oxo-hexanoate aldolase or a 6-amino-4-hydroxy-2-oxo-hexanoate aldolase, 2B is a 4-hydroxy-2-oxo-adipate dehydratase, a 4,6-dihydroxy-2-oxo-hexanoate 4-dehydratase or a 6-amino-4-hydroxy-2-oxo-hexanoate dehydratase, 3B1 is a 4-hydroxy-2-oxo-adipate 2-reductase, a 4,6-dihydroxy-2-oxo-hexanoate 2-reductase or a 6-amino-4-hydroxy-2-oxo-hexanoate 2-reductase, and 3B2 is a 4-hydroxy-2-oxo-adipate 4-dehydrogenase, a 4,6-dihydroxy-2-oxo-hexanoate 4-dehydrogenase or a 6-amino-4-hydroxy-2-oxo-hexanoate 4-dehydrogenase.

Aspect 34. The organism of Aspect 33, further comprising an HMDA pathway enzyme selected from one or more of 2C, 3G1, 3C2, 3C3 wherein 2C is a 3,4-dehydro-2-oxo-adipate 3-reductase, a 6-hydroxy-3,4-dehydro-2-oxohexanoate 3-reductase or a 6-amino-3,4-dehydro-2-oxohexanoate 3-reductase, 3G1 is a 2,4-dihydroxyadipate CoA-transferase or a 2,4-dihydroxyadipate-CoA ligase, a 2,4,6-trihydroxyhexanoate CoA-transferase or a 2,4,6-trihydroxyhexanoate-CoA ligase, or a 6-amino-2,4-dihydroxyhexanoate CoA-transferase or a 6-amino-2,4-dihydroxyhexanoate-CoA ligase, 3C2 is a 2,4-dihydroxyadipate 4-dehydrogenase, a 2,4,6-trihydroxyhexanoate 4-dehydrogenase or a 6-amino-2,4-dihydroxyhexanoate 4-dehydrogenase, and 3C3 is a 2,4-dioxoadipate 2-reductase, a 6-hydroxy-2,4-dioxohexanoate 2-reductase or a 6-amino-2,4-dioxohexanoate 2-reductase.

Aspect 35. The organism of Aspects 33 or 34, further comprising one or more of, or alternatively two or more of, or alternatively three or more of, or alternatively four or more of, or alternatively five or more of, or alternatively six or more of, or alternatively seven or more of, or alternatively eight or more of, or alternatively nine or more, or alternatively ten or more, or alternatively eleven or more, or alternatively twelve or more of 2J, 2G, 3E1, 3E2, 4E3, 4E4, 3K2, 3K1, 4F4, 3N, 2D, 3L2, 3L1, 3F2, 3F1, 4A1, 4A2, 4A3, 4A4, 4A5, 3C1, 4B1, 4B4, 4B5, 4B6, 4B7, 4F1, 4F2, 4F3, 4F5, 2E, 3G2, 3G5, 21, 3M, 3H, 2F, 3D3, 3D2, 3D1, 4D3, 4D4, 4D5, 4G1, 4G2, 4G3, 4G4, 4G5, 5J, 5I, 5G, 5H, 5K, 5L, 5M, 50, 5R, 5T, 5U, 5V, 5W, and 5X wherein 2J is a 4,5-dehydro-2-hydroxy-adipyl-CoA 4,5-reductase, 2G is a 2,3-dehydro-adipyl-CoA 2,3-reductase, a 6-hydroxy-2,3-dehydro-hexanoyl-CoA 2,3-reductase or a 6-amino-2,3-dehydro-hexanoyl-CoA 2,3-reductase,3E1 is a 2,3-dehydro-4-oxoadipyl-CoA 2,3-reductase, a 6-hydroxy-2,3-dehydro-4-oxohexanoyl-CoA 2,3-reductase or a 6-amino-2,3-dehydro-4-oxohexanoyl-CoA 2,3-reductase, 3E2 is a 2,3-dehydro-4-oxoadipate 2,3-reductase, a 6-hydroxy-2,3-dehydro-4-oxohexanoate 2,3-reductase or a 6-amino-2,3-dehydro-4-oxohexanoate 2,3-reductase, 4E3 is a 4,5-dehydroadipyl-CoA 4,5-reductase, 4E4 is a 4,5-dehydro-6-oxohexanoyl-CoA 4,5-reductase, 3K2 is a 2,3-dehydro-4-hydroxyadipate 2,3-reductase, a 4,6-dihydroxy-2,3-dehydrohexanoate 2,3-reductase or a 6-amino-2,3-dehydro-4-hydroxyhexanoate 2,3-reductase, 3K1 is a 2,3-dehydro-4-hydroxyadipyl-CoA 2,3-reductase, a 4,6-dihydroxy-2,3-dehydrohexanoyl-CoA 2,3-reductase or a 6-amino-2,3-dehydro-4-hydroxyhexanoyl-CoA 2,3-reductase, 4F4 is a 4,5-dehydro-6-oxohexanoate 4,5-reductase, 3N is a 2-oxoadipyl-CoA 2-reductase, a 6-hydroxy-2-oxohexanoyl-CoA 2-reductase or a 6-amino-2-oxohexanoyl-CoA 2-reductase, 2D is a 2-oxoadipate 2-reductase, a 6-hydroxy-2oxohexanoate 2-reductase or a 6-amino-2-oxohexanoate 2-reductase, 3L2 is a 2,3-dehydro-4-oxoadipate 4-reductase, a 6-hydroxy-2,3-dehydro-4-oxohexanoate 4-reductase or a 6-amino-2, 3-dehydro-4-oxohexanoate 4-reductase, 3L1 is a 2,3-dehydro-4-oxoadipyl-CoA 4-reductase, a 6-hydroxy-2, 3-dehydro-4-oxohexanoyl-CoA 4-reductase or a 6-amino-2,3-dehydro-4-oxohexanoyl-CoA 4-reductase, 3F2 is a 4-oxoadipate 4-reductase, a 6-hydroxy-4-oxohexanoate 4-reductase or a 6-amino-4-oxohexanoate 4-reductase, 3F1 is a 4-oxoadipyl-CoA 3-reductase, a 6-hydroxy-4-oxohexanoyl-CoA 4-reductase or a 6-amino-4-oxohexanoyl-CoA 4-reductase, 4A1 is a 4,6-dihydroxy-2,3-dehydrohexanoyl-CoA 6-dehydrogenase, 4A2 is a 4,6-dihydroxyhexanoyl-CoA 6-dehydrogenase, 4A3 is a 6-hydroxyhexanoyl-CoA 6-dehydrogenase, 4A4 is a 6-hydroxyhexanoate 6-dehydrogenase, 4A5 is a 4,6-dihydroxyhexanoate 6-dehydrogenase, 3C1 is a 2,4-dihydroxyadipyl-CoA 4-dehydrogenase, a 2,4,6-trihydroxyhexanoyl-CoA 4-dehydrogenase or a 6-amino-2,4-dihydroxyhexanoyl-CoA 4-dehydrogenase, 4B1 is a 4-hydroxy-2,3-dehydro-6-oxohexanoyl-CoA 6-dehydrogenase, 4B4 is a 4-hydroxy-6-oxohexanoyl-CoA 6-dehydrogenase, 4B5 is a 4,5-dehydro-6-oxohexanoyl-CoA 6-dehydrogenase, 4F2 is a 6-oxohexanoyl-CoA transferase, a 6-oxohexanoyl-CoA hydrolase or an 6-oxohexanoyl-CoA ligase, 4F3 is a 6-hydroxyhexanoyl-CoA transferase, a 6-hydroxyhexanoyl-CoA hydrolase or an 6-hydroxyhexanoyl-CoA ligase, a 6-aminohexanoyl-CoA hydrolase or an 6-aminohexanoyl-CoA ligase, 2E is a 2-hydroxy-adipate CoA-transferase or a 2-hydroxyadipate-CoA ligase, 2,6-dihydroxy-hexanoate CoA-transferase or a 2,6-dihydroxy-hexanoate-CoA ligase, 6-amino-2-hydroxyhexanoate CoA-transferase or 6-amino-2-hydroxyhexanoate-CoA ligase, 3G2 is a 2-hydroxy-4oxoadipate CoA-transferase or a 2-hydroxy-4oxoadipate-CoA ligase, a 2,6-dihydroxy-4oxohexanoate CoA-transferase or a 2,6-dihydroxy-4oxohexanoate-CoA ligase, or a 6-amino-2-hydroxy-4oxohexanoate CoA-transferase or a 6-amino-2-hydroxy-4oxohexanoate-CoA ligase, 3G5 is a 4-hydroxyadipate CoA-transferase or a 4-hydroxyadipate-CoA ligase, a 4,6-dihydroxyhexanoate CoA-transferase or a 4,6-dihydroxyhexanoate-CoA ligase, or a 6-amino-4-hydroxyhexanoate CoA-transferase or a 6-amino-4-hydroxyhexanoate-CoA ligase, 21 is a 2,4-dihydroxyadipyl-CoA 4-dehydratase (4,5-dehydro forming), 3M is a 2,4-dihydroxyadipyl-CoA 4-dehydratase (2,3-dehydro forming), a 2,4,6-trihydroxyhexanoyl-CoA 4-dehydratase (2,3-dehydro forming), or a 6-amino-2,4-dihydroxyhexanoyl-CoA 4-dehydratase (2,3-dehydro forming), 3H is a 4-hydroxyadipyl-CoA 4-dehdyratase (2,3-dehydro forming), a 4,6-dihydroxyhexanoyl-CoA 4-dehydratase (2,3-dehydro forming) or a 6-amino-4-hydroxyhexanoyl-CoA 4-dehydratase (2,3-dehydro forming), 2F is a 2-hydroxyadipyl-CoA 2-dehydratase, a 2,6-dihydroxy-hexanoyl-CoA 2-dehydratase or a 6-amino-2-hydroxy-hexanoyl-CoA 2-dehydratase, 3D3 is a 2,4-dihydroxyadipyl-CoA 2-dehydratase, a 2,4,6-trihydroxyhexanoyl-CoA 2-dehydratase or a 6-amino-2,4-dihydroxyhexanoyl-CoA 2-dehydratase, 3D2 is a 2-hydroxy-4oxoadipate 2-dehydratase, a 2,6-dihydroxy-4oxohexanoate 2-dehydratase or a 6-amino-2-hydroxy-4oxohexanoate 2-dehydratase, 3D1 is a 2-hydroxy-4oxoadipyl-CoA 2-dehydratase, a 2,6-dihydroxy-4oxohexanoyl-CoA 2-dehydratase or a 6-amino-2-hydroxy-4oxohexanoyl-CoA 2-dehydratase, 4D3 is a 4-hydroxy-adipyl-CoA 4-dehydratase (4,5-dehydro forming), 4D4 is a 4-hydroxy-6oxohexanoyl-CoA 4-dehydratase (4,5-dehydro forming), 4D5 4-hydroxy-6oxohexanoate 4-dehydratase (4,5-dehydro forming), 5J is a 6-oxohexanoic acid transaminase (aminating) or a 6-oxohexanoic acid dehydrogenase (aminating), 5I is a 6-oxohexanoyl-CoA transaminase (aminating), or a 6-oxohexanoyl-CoA dehydrogenase (aminating), 5G is an adipyl-CoA 1-reductase, 5K is 6-oxohexanoate 6-reductase, 5M is 6-hydroxyhexanoate CoA-transferase or a 6-hydroxyhexanoate-CoA ligase, 5O is a 6-hydroxyhexanoyl-CoA 1-reductase, 5R is a 6-hydroxyhexanoate 1-reductase, 5T is a 6-hydroxyhexanal amino transferase or a 6-hydroxyhexanal dehydrogenase (aminating), 5U is a 6-hydroxyhexylamine 1-dehydrogenase, 5V is a 6-aminohexanoate 1-reductase, 5W 6-aminohexanoyl-CoA 1-reductase, and 5X is a 6-aminohexanal transaminase or a 6-aminohexanal 1-dehydedrogenase (aminating).

Aspect 36. A non-naturally occurring microbial organism comprising one or more exogenous nucleic acids encoding two, three, four, five, six, seven, eight, nine, ten, eleven, twelve, thirteen, fourteen, fifteem, sixteen, or seventeen enzymes in a HMDA pathway.

Aspect 37. A method for producing HMDA, comprising culturing the non-naturally occurring microbial organism of Aspects 33-36 under conditions and for a sufficient period of time to produce HMDA, and optionally, separating the HMDA produced by the organism from the organism or a culture comprising the organism.

Aspect 38. A non-naturally occurring microbial organism, comprising at least one exogenous nucleic acid encoding an 1-hexanol pathway enzyme selected from 2-oxo-4-hydroxy-hexanoate aldolase, 2-oxo-4-hydroxy-hexanoate dehydratase, 2-oxo-3-hexenoate 3-reductase, 2oxohexanoate-2-reductase, a 2-hydroxy-hexanoate-CoA Transferase or a 2-hydroxyhexanoate-CoA ligase, 2-hdyroxyhexanoyl-CoA 2,3-dehdyratase, hexenoyl-CoA 2-reductase, hexanoyl-CoA 1-reductase and a hexanol dehydrogenase.

Aspect 39. A non-naturally occurring microbial organism comprising one or more exogenous nucleic acids encoding two, three, four, five, six, seven, eight, or nine enzymes in a 1-hexanol pathway.

Aspect 40. A method for producing 1-hexanol, comprising culturing the non-naturally occurring microbial organism of Aspects 38 or 39 in a culture comprising glycerol or a C5 or C6 sugar, or a combination there of, and optionally, separating the 1-hexanol produced by the organism from the organism or a culture comprising the organism.

Aspect 41. The organism of any one of the Aspects 1-6, 8-11, 13-16, 18-21, 28-31 and 33-36, above further comprising at least one exogenous nucleic acid encoding a 3-oxo-propionate pathway enzyme, wherein the 3-oxo-propionate pathway is selected from
a) Malonyl-CoA reductase
b) Glycerate dehyratase, and a ⅔-phosphoglycerate phosphatase
c) Oxaloacetate decarboxylase
d) 3-amino propionate oxidoreductase or transaminase (deaminating)
e) 3-phosphoglyceraldehyde phosphatase, glyceraldehyde dehydrogenase, and a glycerol dehydratase Aspect 42. The organism of any one of Aspects 1-6, 8-11, 13-16, 18-21, 23-26, 28-31 and 33-36, further comprising at least one exogenous nucleic acid encoding a 3-hydroxypropanal pathway enzyme, wherein the 3-hydroxypropanal pathway is selected from a. A glycerol dehydratase b. 3-phosphoglyceraldehyde phosphatase, glyceraldehyde 1-reductase, and a glycerol dehydratase Aspect 43. The organism of any one of Aspects 1-6, 8-11, 13-16, and 33-36, further comprising at least one exogenous nucleic acid encoding a 3-amino-propanal pathway enzyme, wherein the 3-amino-propanal pathway comprises 3-amino propionyl-CoA reductase.

Throughout this application various publications have been referenced. The disclosures of these publications in their entireties, including GenBank accession number in these publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention General Synthetic Methods One embodiment of the invention provides a method for preparing a compound of Formula I, II, III or IV as described herein, or 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid, the method comprising or alternatively consisting essentially of, or yet further consisting of: a) converting a $C_N$ aldehyde and a pyruvate to a $C_{N+3}$ β-hydroxyketone intermediate through an aldol addition; and b) converting the $C_{N\times 3}$ β-hydroxyketone intermediate to a compound of Formula I, II, III or IV as described herein, or 1-butanol, butyric acid, succinic acid, 1,4-butanediol, 1-pentanol, pentanoic acid, glutaric acid, 1,5-pentanediol, 1-hexanol, hexanoic acid, adipic acid, 1,6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid and dodecanedioic acid through enzymatic steps, or a combination of enzymatic and chemical steps, wherein N is M–3, wherein M is the number of carbon in the compound being prepared and N is 1, 2, 3, 4, 5, 6, 7, 8, 9, 10, 11, 12, 13, 14, 15,16, 17, 18, 19, 20, 21 or 22. In all aspects of the invention, the C3 aldehyde is not glyceraldehyde.

One aspect of the invention provides that the enzymatic or a combination of enzymatic and chemical steps for converting the $C_{N+3}$ β-hydroxyketone intermediate to a compound of Formula I, II, III or IV as described herein, or 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear cx-alkenes that are between 6-24 carbons long, sebacic acid or dodecanedioic acid comprise enoyl or enoate reduction, ketone reduction, primary alcohol oxidation, secondary alcohol oxidation, aldehyde oxidation, aldehyde reduction, dehydration, decarboxylation, thioester formation, thioester hydrolysis, trans thioesterification, thioester reduction, lactonization, lactam formation, lactam hydrolysis, lactone hydrolysis, carboxylic acid reduction, amination, aldehyde decarbonylation, primary amine acylation, primary amine deacylation, or combinations thereof, wherein N is M–3, wherein M is the number of carbon in the compound being prepared and N is 1, 2, 3, 4, 5, 6, 7, 8, 9, 10, 11, 12, 13, 14, 15,16, 17, 18, 19, 20, 21 or 22.

In another aspect, the $C_N$ aldehyde is C3 aldehyde. In some aspects, the C3 aldehyde is selected from a group comprising 3-oxo-propionic acid, 3-hydroxypropanal, 3-aminopropanal, or propanal. In an additional aspect, the C3 aldehyde and pyruvate are obtained from glycerol, C5 sugars, C6 sugars, phosphor-glycerates, other carbon sources, intermediates of the glycolysis pathway, intermediates of the propanol pathway, or combinations thereof. In a further aspect, C5 sugars comprise xylose, xylulose, ribulose, arabinose, lyxose, and ribose and C6 sugars comprise allose, altrose, glucose, mannose, gulose, idose, talose, galactose, fructose, psicose, sorbose, and/or tagatose. In another aspect, the other carbon course is a feedstock suitable as a carbon source for a microorganism, wherein the feedstock comprises amino acids, lipids, corn stover, miscanthus, municipal waste, energy cane, sugar cane, bagasse, starch stream, dextrose stream, formate, methanol, or a combination thereof.

In another aspect, the $C_N$ aldehyde or C3 aldehyde is obtained through a series of enzymatic steps, wherein the enzymatic steps comprise phosphate ester hydrolysis, alcohol oxidation, diol-dehydration, aldehyde oxidation, aldehyde reduction, thioester reduction, trans thioesterification, decarboxylation, carboxylic acid reduction, amination, primary amine acylation, or a combination thereof.

In another aspect, a microorganism is used as a host for the preparation of a compound of Formula I, II, III or IV as described herein. In an additional aspect, the microorganism contains genes encoding for 1, 2, 3, 4, 5, 6, 7, 8, or all the enzymes necessary to catalyze the enzymatic conversion of a $C_{N+3}$ β-hydroxyketone intermediate to a compound of Formula I, II, III or IV as described herein.

In another aspect, a microorganism is used as a host for the preparation of a compound selected from 1-butanol, butyric acid, succinic acid, 1,4-butanediol, 1-pentanol, pentanoic acid, glutaric acid, 1,5-pentanediol, 1-hexanol, hexanoic acid, adipic acid, 1, 6-hexanediol, 6-hydroxy hexanoic acid, ε-Caprolactone, 6-amino-hexanoic acid, ε-Caprolactam, hexamethylenediamine, linear fatty acids and linear fatty alcohols that are between 7-25 carbons long, linear alkanes and linear α-alkenes that are between 6-24 carbons long, sebacic acid or dodecanedioic acid. In an additional aspect, the microorganism contains genes encoding for 1, 2, 3, 4, 5, 6, 7, 8, or all the enzymes necessary to catalyze the enzymatic of converting a $C_{N\times 3}$ β-hydroxyketone intermediate to the compound.

In a further aspect, the microorganism has the ability to convert C5 sugars, C6 sugars, glycerol, other carbon sources, or a combination thereof to pyruvate. In a further additional aspect, the microorganism is engineered for enhanced sugar uptakes comprising C5 sugar uptake, simultaneous C6/C5 sugar uptake, simultaneous C6 sugar/glycerol uptake, simultaneous C5 sugar/glycerol uptake, and combinations thereof.

In some aspects, the synthesis of compounds of Formula I, II, III or IV as described herein precede through pathways in schemes depicted in FIGS. 1-4 or from intermediates within these schemes.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the subject matter described herein which are apparent to one skilled in the art. Throughout the examples, sequences of enzymes or proteins are identified by their Genbank Accession Numbers (referred to as Genbank ID or Genbank Accession No).

1. Synthesis of C3 Aldehydes

Synthesis of 3-oxopropionate can be accomplished by a number of different pathways as depicted FIG. 1. Each pathway starts from metabolic precursors well known in the art or from Glycerol (also a metabolic product or a carbon source for growth of microbial organisms) Synthesis of 3-oxo-propionic acid from phosphor-glycerates One exemplary pathway for 3-oxo-propionic acid synthesis involves synthesis of glyceric acid by hydrolysis of 3-phospho-glycerate and 2-phospho-glycerate, intermediates of the pay-off phase of the glycolysis pathway (FIG. 1) followed by diol dehydration of glycerate to give 3-oxo-propionic acid. Phosphatase enzymes that can carry out this transformation belong to E.C. 3.1.3. In particular, shown below are a few examples of phosphatase enzymes that are known catalyze the phosphate hydrolysis reaction with 3-phospho-glycerate and/or 2-phospho-glycerate substrates. Other phosphatase enzymes (Table 1) belonging to the E.C. below, or homologous enzymes of these sequences can also be used to carry out this step. In addition, kinase enzymes that catalyze the phosphorylation of glycerate can also be used for dephosphorylation (in the reverse direction). In particular, glycerate kinase enzymes (Table 2) that belong to E.C. 2.7.1.31 and E.C. 2.7.1.165 are known to use glycerate and a variety of phosphate donors to form 3-phospho-glycerate and 2-phospho-glycerate products. Shown in below are a few examples of glycerate kinase enzymes that can be used for dephosphorylation of 3-phospho-glycerate and 2-phospho-glycerate to give glyceric acid. Other glycerate kinase enzymes belonging to the E.C. groups listed below or homologous enzymes of these sequences can also be used to carry out this step.

TABLE 1

| Genebank Accession | EC | Name | Organism |
| --- | --- | --- | --- |
| AAA62393.1 | 3.1.3.20 | acid phosphatase | Aspergillus niger |
| AAB96872.1 | 3.1.3.3 | phytase | Aspergillus fumigatus |
| NP_187369.1 | 3.1.3.3 | purple acid phosphatase 15 | [Arabidcpsis thaliana |
| BAD05166.1 | 3.1.3.2 | acid phosphatase | Phaseolus vulgaris |
| ACT28217.1 | 3.1.3.19 | inositol monophosphatase | Escherichia coli 'BL21-Gold(DE3)pLysS AG' |

TABLE 2

| Genebank Accession | EC | Name | Organism |
| --- | --- | --- | --- |
| AAC76158.2. | 2.7.1.165 | Glycerate 2-kinase | Escherichia coli (strain K12) |
| BAA29583.1. | 2.7.1.165 | Glycerate 2-kinase | Pyrococcus horikoshii |
| AAA66317.1. | 2.7.1.31 | Glycerate 3-kinase | Saccharomyces cerevisiae |
| AEE36393.1. | 2.7.1.31 | Glycerate 3-kinase | Arabidopsis thaliana |

The diol dehydration of glycerate to give 3-oxo-propionic acid can be catalyzed by diol-dehydratases and glycerol dehydratases belonging to E.C. 4.2.1.28 and E.C. 4.2.1.30 respectively. Glycerol and diol-dehydratases can catalyze the dehydration in a coenzyme B12-dependent or coenzyme B12-independent manner in the presence of a reactivator protein. Coenzyme B12-dependent dehydratase is composed of three subunits: the large or "α" subunit, the medium or "β" subunit, and the small or "γ" subunit. These subunits assemble in an α2β2γ2 structure to form the apoenzyme. Coenzyme B12 (the active cofactor species) binds to the apoenzyme to form the catalytically active holoenzyme. Coenzyme B12 is required for catalytic activity as it is involved in the radical mechanism by which catalysis occurs. Biochemically, both coenzyme B12-dependent glycerol and coenzyme B12-dependent diol dehydratases are known to be subject to mechanism-based suicide inactivation by glycerol and other substrates (Daniel et al., FEMS Microbiology Reviews 22:553-566 (1999); Seifert, et al., Eur. J. Biochem. 268:2369-2378 (2001)). Inactivation can be overcome by relying on dehydratase reactivation factors to restore dehydratase activity (Toraya and Mori (J. Biol. Chem. 274:3372 (1999); and Tobimatsu et al. (J. Bacteria 181:4110 (1999)). Both the dehydratase reactivation and the coenzyme B12 regeneration processes require ATP. Shown below are a few examples of glycerol dehydratases, diol dehydratases and reactivating factors. One skilled in the art will recognize that glycerol dehydratases of Citrobacter freundii, Clostridium pasteurianum, Clostridium butyricum, K. pneumoniae or their strains; diol dehydratase of Salmonella typhimurium, Klebsiella oxytoca or K. pneumoniae; and other dehydratase enzymes belonging to E.C. groups listed below or homologous enzymes of these sequences can also be used to carry out this step. Mutants of these enzymes (U.S. patent publication 8445659 B2 & 7410754) can also be used herein to increase the efficiency of the process. In particular, coenzyme B12-independent-dehydratases (Raynaud, C., et al., Proc. Natl. Acad. Sci. U.S.A. 100, 5010-5015 (2003)) are favored for the industrial process due to the high cost of vitamin-B12.

TABLE 3

| Genebank Accession | EC | Name | Organism |
| --- | --- | --- | --- |
| BAA08099.1. | 4.2.1.28 | Diol dehydrase alpha subunit | Klebsiella oxytoca |
| BAA08100.1. | 4 2.1.28 | Diol dehydrase beta subunit | Klebsiella oxytoca |
| BAA08101.1. | 4.2.1.28 | Diol dehydrase gamma subunit | Klebsiella oxytoca |
| ABR24274.1 | 4.2.1.30 | Glycerol dehydratase large subunit | Klebsiella pneumoniae |
| ABR24275.1 | 4.2.1.30 | Glycerol dehydratase medium subunit | Klebsiella pneumoniae |
| ABR24276.1 | 4.2.1.30 | Glycerol dehydratase small subunit | Klebsiella pneumoniae |
| AAM54728.1 | 4.2.1.30 | Glycerol dehydratase | Clostridium butyricum |
| AAM54729.1 | — | glycerol dehydratase activator | Clostridium butyricum |
| ACI39932.1 | 4.2.1.30 | B12-independent glycerol dehydratase | Clostridium diolis |
| ACI39933.1 | — | glycerol dehydratase activator | Clostridium diolis |

Synthesis of 3-oxo-propionic acid from 3-phospho-glyceraldehyde

Step A: Glyceraldehyde can be synthesized by phosphatase-catalyzed hydrolysis of 3-phospho-glyceraldehyde (FIG. 1) an intermediate of the glycolysis and pentose phosphate pathway and also an intermediate in the fermentation of glycerol (Clomburg et al., Trends Biotechnol. 31(1):20-28 (2013)). Phosphatase enzymes that can carry out this transformation belong to E.C. 3.1.3. In particular, shown in Table 1 above a few examples of phosphatase enzymes that can be used to catalyze the phosphate hydrolysis reaction with 3-phospho-glyceraldehyde substrate either in their wild-type forms or after engineering them using modern protein engineering approaches (Wyss et al., Appl. Environ. Microbiol. 68:1907-1913 (2002); Mullaney et al., Biochem. Biophys. Res. Commun. 312:179-184 (2003)). Other phosphatase enzymes belonging to the E.C. groups listed in Table 1 or homologous enzymes of these sequences can also be used to carry out this step. In addition, kinase enzymes that can catalyze the phosphorylation of glyceraldehyde can also be used for dephosphorylation (in the reverse direction). Shown in Table 2 are few examples of these enzymes can be used to dephosphorylate 3-phospho-glyceraldehyde either in their wild-type forms or after engineering them using modern protein engineering approaches. Other kinase enzymes belonging to the E.C. groups listed in Table 2 or homologous enzymes of these sequences can also be used to carry out this step.

Step B: Glyceraldehyde can be oxidized to glyceric acid using aldehyde dehydrogenases. This oxidation step can be carried out enzymatically by using any aldehyde dehydrogenases or aldehyde oxidoreductase belonging to E.C 1.2.1.3, E.C. 1.2.1.4, E.C. 1.2.1.5, E.C. 1.2.1.8, E.C 1.2.1.10, E.C. 1.2.1.24, E.C. 1.2.1.36, E.C. 1.2.3.1, E.C. 1.2.7.5, E.C. 1.2.99.3, E.C 1.2.99.6, & E.C 1.2.99.7 (Hempel et al., Protein Science 2(11): 1890-1900 (1993); Sophos et al., Chemico-Biological Interactions 143:5-22 (2003); McIntire W S, Faseb Journal 8(8):513-521 (1994); Garattini et al., Cellular and Molecular Life Sciences 65(7-8):1019-1048 (2008)). Typically a quinone, ferricytochrome, NAD(P), FMN, FAD-dependent dehydrogenase will be used to oxidize glyceraldehyde to glycerate.

Step C: The third step involves the conversion of glyceric acid to 3-oxo-propionic acid which is discussed above.

Synthesis of 3-oxo-propionic acid from oxaloacetate

Oxaloacetate an intermediate of TCA (tricarboxylic acid) cycle can be decarboxylated to give 3-oxo-propionic acid. Oxaloacetate decarboxylases belonging to the E.C. group 4.1.1.2 or homologous enzymes of these sequences can also be used to carry out this step.

Synthesis of 3-oxo-propionic acid from β-alanine

As a part of the propanoate metabolism, β-alanine (3-amino-propionic acid) is converted to 3-oxo-propionic acid using transaminases belonging to E.C. 2.6.1.19 (4-aminobutyrate-2-oxoglutarate transaminase) or E.C. 2.6.1.18 (β-alanine-pyruvate transferase). Exemplary proteins of this class are discussed further Example IV.

Synthesis of 3-oxo-propionic acid from malonyl-CoA

As a part of the propanoate metabolism, malonyl-CoA is converted to 3-oxo-propionic acid using a oxidoreductases belonging to E.C. 1.2.1.18 (malonyl semialdehyde dehydrogenase). Such a protein has been found in variety of archeae, and has been biochemically characterized[1-4].

Synthesis of 3-hydroxy-propanal from 3-phospho-glyceraldehyde (pathway 1)

Step A: Glyceraldehyde can be synthesized by phosphatase-catalyzed hydrolysis of 3-phospho-glyceraldehyde (FIG. 1) as described above.

Step B: Glyceraldehyde can be converted to glycerol by alcohol dehydrogenases. Primary alcohol dehydrogenases described previously that can catalyze the oxidation (reversible) of glycerol to glyceraldehyde can also catalyze the reduction of glyceraldehyde to glycerol using reduced cofactors such as quinones (QH2), NAD(P)H, FADH2 FMNH2 & reduced ferricytochrome.

Step C: 3-hydroxy-propanal can be synthesized from glycerol using diol-dehydratases or glycerol dehydratases as described above.

Synthesis of 3-hydroxy-propanal from glycerol 3-hydroxy-propanal can be synthesized from glycerol using diol-dehydratases or glycerol dehydratases (FIG. 1) as described above.

Synthesis of propanal from propanoyl-CoA

As a part of the propanoate metabolism, propanoyl-CoA is formed from multiple pathways starting from pyruvate. Propanoyl-CoA can be converted to propanal by Coenzyme-A depdendent aldehyde dehydrogenases. Many such CoA-dependent aldehyde dehydrogenases are known including pduP[5] from *salmonella* as well as BphJ.

Synthesis of 3-amino-propanal from 3-amino-propanoyl-CoA 3-amino-propanoyl-CoA (or β-alanyl-CoA) is a part of the propionate metabolism and is used in the biosynthesis of Coenzyme A and pantothenate. 3-amino-propanoyl-CoA can be converted to 3-amino-propanal using coenzyme A dependent aldehyde dehydrogenases or oxidoreductases. Due to the propensity of spontaneous cyclic lactam formation of 3-amino-propanoyl-CoA, the amino group can be masked as an amide (acetamido) to avoid this cylicization prior to carrying out its reduction as mentioned above if necessary. Protecting the primary amine of its precursor 3-amino-propanoyl-CoA by using an acetyl or succinyl functional group can prevent such cyclization. The protecting group can be removed after the synthesis of end products using the C3 aldehyde 3-amino propanal is completed This results in addition of two additional steps that would involve addition and removal of such a protecting group in any of the pathways using 3-amino propanal as the C3 aldehyde using acetylases and deacetlyases respectively. Please refer to Example IV for exemplary proteins that carry out these transformations.

2. Synthesis of Formaldehyde and C2 Aldehydes

Synthesis of formaldehyde from formyl-CoA (pathway 1 & 2)

Formaldehyde can be synthesized from formyl-CoA, using coenzyme A dependent aldehyde dehydrogenases or oxidoreductases. Formyl-CoA can be synthesized by the decarboxylation of oxalyl-CoA (a intermediate of the glyoxylate and dicarboxylate metabolsims).

Synthesis of formaldehyde from methanol (pathway 3)

Formaldehyde can also be synthesized by the oxidation of methanol by using primary alcohol dehydrogenases.

Synthesis of formaldehyde by formate reduction (pathway 4)

Formaldehyde can also be synthesized by the reduction of formate using carboxylic acid reductases. Carboxylic acid reductases belonging to E.C. 1.2.99.6 can be used to carry out the reduction. Other carboxylic acid reductases belonging to the E.C. group listed in Table 17 or homologous enzymes of these sequences can also be used to carry out this step.

Synthesis of acetaldehyde from acetyl-CoA (pathway 1)

Acetaldehyde is synthesized from acetyl-CoA a ubiquitous molecule of the central metabolism, using coenzyme A dependent aldehyde dehydrogenases or oxidoreductases.

Synthesis of acetaldehyde from pyruvate (pathway 2)

Acetaldehyde can also be synthesized from pyruvate using pyruvate decarboxylases. Decarboxylase enzymes belonging to E.C. 4.1.1.1 are used to carry out this reaction.

Synthesis of glyoxylate (pathway 1)

Glyoxylate is a product of the glyoxylate shunt of the TCA cycle ubiquitous in nature. The glyoxylate cycle is a sequence of anaplerotic reactions (reactions that form metabolic intermediates for biosynthesis) that enables an organism to use substrates that enter central carbon metabolism at the level of acetyl-CoA as the sole carbon source. Such substrates include fatty acids, alcohols, and esters (often the products of fermentation), as well as waxes, alkenes, and methylated compounds. The pathway does not occur in vertebrates, but it is found in plants and certain bacteria, fungi, and invertebrates. The two additional enzymes that permit the glyoxylate shunt are isocitrate lyase and malate synthase, which convert isocitrate to succinate or to malate via glyoxylate.

Synthesis of glycoaldehyde or hydroxyacetaldehyde

Glycolaldehyde forms from many precursors, including the amino acid glycine. It can form by action of ketolase on fructose 1,6-bisphosphate in an alternate glycolysis pathway. It is also formed as a part of the purine catabolismitamin B6 metabolsim, folate biosynthesis, L-arabinose degradation, D-arabinose degradation and xylose degradation (from biocyc.org).

3. Synthesis of Pyruvate

Conversion of Sugars to Pyruvate
Conversion of sugars to pyruvate through glycolysis is very well known. In glycolysis, each mole of glucose gives 2 moles of ATP, 2 moles of reducing equivalents in the form of NAD(P)H and 2 moles of pyruvate.

Conversion of Glycerol to Pyruvate
Glycerol can be converted to glycolysis intermediates both anaerobically and micro-aerobically. Anaerobically, glycerol is dehydrogenated to dihydroxyacetone which, after phosphorylation (using phosphoenol pyruvate or ATP), is converted to dihydroxyacetone phosphate a glycolytic pathway intermediate (Dharmadi, et al., Biotechnol. Bioeng. 94:821-829 (2006)). The respiratory pathway for glycerol conversion involves phosphorylation (by ATP) of glycerol followed by oxidation (quinone as electron acceptors) to give dihydroxyacetone phosphate that can be converted to pyruvate via glycolysis (Booth IR. Glycerol and methylglyoxal metabolism. Neidhardt F C. et al., editors. In: *Escherichia coli* and *Salmonella*: Cellular and molecular biology (web edition). 2005. Washington, DC. ASM Press: Durnin et al., Biotechnol Bioeng. 103(1): 148-161 (2009)).

4. Synthesis of adipic acid (ADA) From Pyruvate and C-3 Aldehydes (3-oxopropionate, 3-hydroxypropanal and 3-aminopropanal)

Shown in FIGS. 2 and 3 are several exemplary pathways for the synthesis of C6 Acyl-CoA molecules such as adipyl-CoA, 6-hydroxy-hexanoyl-CoA, and 6-amino-hexanoyl-CoA from pyruvate and C3 aldehydes 3-oxo-propionic acid (R=$CH_2CO_2H$), 3-hydroxy-propanal (R=$CH_2CH_2OH$) and 3-amino-propanal (R=$CH_2NH_2$) respectively. These acyl-CoA compounds and intermediates of FIG. 3 (general formula compound 25, 28-30), specifically: 4-hydroxy-adipyl-CoA 33 and 4-hydroxy-2,3-dehydro-adipyl-CoA 44, when 3-oxo-propionic acid is the aldehyde; 4-hydroxy-6-amino-hexanoyl-CoA 50, 4-hydroxy-2,3-dehydro-6-amino-hexanoyl-CoA 51, and 4-hydroxy-6-amino-hexanoate 52, when the aldehyde is 3-amino-propanal; 4,6-dihydroxy-hexanoyl-CoA 31, 4,6-dihydroxy-2,3-dehydro-hexanoyl-CoA 42, and 4,6-dihydroxy-hexanoate 55, when the aldehyde is 3-hydroxy-propanol are converted to adipic acid through various steps depicted in FIG. 4.

Due to the propensity of spontaneous cyclic imine formation of 3-amino-propanal, the amino group can be masked as an amide (acetamido) to avoid this cyclization, prior to its conversion to adipate. Alternatively, the acetylation can also be carried out on 3-amino propionyl-CoA the precursor for the synthesis of 3-amino-propanal. Additionally, C6 derivatives described below and shown in FIGS. 2-4, that contain an amino group at the C6 position and a thioester (Eg. CoA) at the C1 position can also undergo spontaneous cyclization to form the corresponding &-lactam or imines for C6 derivatives with 2-oxo group and C6-amine functionality. Protecting the primary amine by using an acetyl or succinyl functional group can prevent such cyclization. The protecting group can be removed after the synthesis is over. This results in addition of two additional steps that would involve addition and removal of such a protecting group in any of the pathways involving 3-aminopropanal as the C3 aldehyde using acetylases and deacetlyases respectively. Preferably, the acetylation will be carried out on the C3-aldehyde 3-amino propanal to give 3-amido-propanal, which will be used as the C3 aldehyde, and deacetylation will be carried out on C6 intermediate prior to any transamination/deamination steps mentioned herein. Although, the C3 aldehyde is mentioned as 3-amino propanal, it is a given that 3-amido propanal is also be used as the C3 aldehyde.

Additionally some C6 ADA pathway intermediates can undergo lactonization to form the corresponding 1,4-lactone, in particular 4-hydroxy acids (e.g. FIGS. 2, 11), and 4-hydroxyacyl-CoA esters (e.g. FIG. 3, 29, 30). Acidic and neutral pH favors the formation of the lactone. The 1,4-lactones can be converted to their corresponding linear hydroxy-acids by hydrolysis of cyclic esters (reversible reaction) using lactonases for any of the ADA pathways mentioned herein. Lactonases known to catalyze the lactone hydrolysis reaction can be used for carrying out this reaction. Esterases, lipases (PCT/US2010/055524) and peptidases (WO/2009/142489) have also been known to carry out lactonization.

Synthesis of ADA from pyruvate and 3-oxo-propionic acid

Described below are various methods and pathways for the synthesis of adipic acid starting from pyruvate and 3-oxo-propionic acid (R=$CH_2CO_2H$ in FIG. 2 and FIG. 3).

ADA Method 1. In this method, ADA is prepared from pyruvate and 3-oxo-propionic acid in the presence of 4-hydroxy-2-oxo-adipate aldolase, 4-hydroxy-2-oxo adipate dehydratase, 3,4-dehydro-2-oxo-adipate reductase, 2-oxo-adipate reductase, 2-hydroxy-adipyl-CoA transferase or synthetase, 2-hydroxy-adipyl-CoA dehydratase, 2,3-dehydro-adipyl-CoA reductase, adipyl-CoA transferase, and a adipyl-CoA synthetase or a adipyl-CoA hydrolase. In some aspects, the method comprising combining pyruvate, 3-oxo-propionic acid, 4-hydroxy-2-oxo-adipate aldolase, 4-hydroxy-2-oxo adipate dehydratase, 3,4-dehydro-2-oxo-adipate reductase, 2-oxo-adipate reductase, 2-hydroxy-adipyl-CoA transferase or synthetase, 2-hydroxy-adipyl-CoA dehydratase, 2,3-dehydro-adipyl-CoA reductase, adipyl-CoA transferase, and a adipyl-CoA synthetase or a adipyl-CoA hydrolase, in an aqueous solution under conditions to prepare ADA. In some aspects, 4-hydroxy-2-oxo-adipate aldolase, 4-hydroxy-2-oxo adipate dehydratase, 3,4-dehydro-2-oxo-adipate reductase, 2-oxo-adipate reductase, 2-hydroxy-adipyl-CoA transferase or synthetase, 2-hydroxy-adipyl-CoA dehydratase, 2,3-dehydro-adipyl-CoA reductase, adipyl-CoA transferase, and a adipyl-CoA synthetase or a adipyl-CoA hydrolase are produced by one or more microorganisms that produces the enzymes in situ, such as *E. coli*, Yeast and/or Clostridia. In some aspects, the method comprises combining pyruvate and 3-oxo-propionic acid with one or more microorganisms that produces 4-hydroxy-2-oxo-adipate aldolase, 4-hydroxy-2-oxo adipate dehydratase, 3,4-dehydro-2-oxo-adipate reductase, 2-oxo-adipate reductase, 2-hydroxy-adipyl-CoA transferase or synthetase, 2-hydroxy-adipyl-CoA dehydratase, 2,3-dehydro-adipyl-CoA reductase, adipyl-CoA transferase, and a adipyl-CoA synthetase or a adipyl-CoA hydrolase in situ. In some aspects, the condition comprises a ratio of pyruvate to 3-oxo-propionic acid from 0.01 to 1000. In some aspects, the ratio of the enzymes is from 0.01 to 1000. In some aspects, the conditions comprises a temperature from 10 to 70C, preferably in the range of 20C to 30C, 30C to 40C and 40C to 50C. In some aspects, the conditions comprise anaerobic, substantially anaerobic, or aerobic conditions.

FIG. 2 shows exemplifying pathway steps 2A, 2B, 2C, 2D, 2E, 2F, 2G, 4F1 of Method 1, wherein the first step (step 2A) is the aldolase catalyzed aldol addition of pyruvate to 3-oxo-propionic acid to give 4-hydroxy-2-oxo-adipic acid which is dehydrated (Step 2B) to give 3,4-dehydro 2-oxo adipic acid that is reduced (step 2C) to give 2-oxo-adipic acid. 2-oxo-adipic acid is reduced (Step 2D) to 2-hydroxy adipic acid followed by attachment of a Coenzyme A molecule (step 2E) by a acyl-CoA synthase or ligase or transferase to give 2-hydroxy adipyl-CoA which is dehydrated (step 2F) to give 2,3-dehydro adipyl-CoA. This can be reduced by enoyl-CoA reductases (step 2G) to give adipyl-CoA which inturn can be hydrolyzed or transesterfied (4F1, FIG. 4) to adipic acid.

ADA Pathway 2 (Steps 2A, 3B1, 3G1, 3M, 3N, 2F, 2G, 4F1). Alternative pathway involves reduction of 2-keto group of 4-hydroxy-2-oxo-adipic acid (pathway 1 intermediate) to give 2,4-dihydroxy adipic acid followed by attachment of CoA molecule (Step 3G1) to give 2,4-dihydroxy adipyl-CoA. Dehydration of 2,4-dihydroxy adipyl-CoA by 4-hydroxy acyl-CoA dehydratase (step 3M) gives 2-oxo adipyl-CoA, which is reduced (step 3N) to 2-hydroxy adipyl-CoA that is converted to adipic acid as mentioned above. Alternatively, dehydration of 2,4-dihydroxy adipyl-CoA gives 5,6-dehydro 2-hydroxy adipyl-CoA(step 21), which is reduced to 2-hydroxy adipyl-CoA (step 2J) by a enoate reductase (ADA Pathway 27).

ADA Pathway 3 (Steps 2A, 3B1, 3G1, 3D3, 3K1, 3H, 2G, 4F1). Another pathway depicted in FIG. 3 involves dehydration (step 3D3) of 2,4-dihydroxy adipyl-CoA (pathway 2 intermediate) by 2-hydroxy acyl-CoA dehydratase to give 2,3-dehydro-4-hydroxy adipyl-CoA, which is reduced by enoyl-CoA reductase (step 3K1) to give 4-hydroxy adipyl-CoA. Dehydration of 4-hydroxy adipyl-CoA by 4-hydroxy acyl-CoA dehydratase (step 3H) gives 2,3-dehydro adipyl-CoA that is converted to adipic acid as mentioned before.

ADA Pathway 4 (Steps 2A, 3B1, 3G1, 3D3, 3K1, 4D3, 4E3, 4F1). Another pathway depicted in FIGS. 3 and 4, involves the conversion dehydration (step 4D3) of 4-hydroxy adipyl-CoA by dehydratase to give 5,6-dehydro adipyl-CoA, which can be reduced by enoate reductases (4E3) to give adipyl-CoA that is converted to adipic acid as mentioned before ADA Pathway 5 (Steps 2A, 3B1, 3G1, 3C1, 3D1, 3E1, 3F1, 3H, 2G, 4F1) and 6 (Steps 2A, 3B1, 3G1, 3C1, 3D1, 3E1, 3F1, 4D3, 4E3, 4F1). Another pathway as depicted in FIG. 3 involves oxidation (step 3C1) of 2,4-dihydroxy adipyl-CoA (pathway 2 intermediate) to give 2-hydroxy 4-oxo adipyl-CoA that is dehydrated (step 3D1) to give 2,3-dehydro 4-oxo-adipyl-CoA. Its reduction (step 3E1) by enoyl reductase gives 4-oxo-adipyl-CoA, which is further reduced by alcohol dehydrogenase to give 4-hydroxy adipyl-CoA that is converted to adipic acid by two routes as mentioned in pathways 3 and 4.

ADA Pathway 7 and 8 (Steps 2A, 3B1, 3C2, 3D2, 3E2, 3F2, 3G5, with 3H, 2G, 4F1 or 4D3, 4E3, 4F1) Another pathway (FIG. 3) involves oxidation (step 3C2) of 2,4-dihydroxy adipate (pathway 2 intermediate) to give 2-hydroxy 4-oxo adipate that is dehydrated (step 3D2) to give 2,3-dehydro 4-oxo-adipate. Its reduction (step 3E2) gives 4-oxo-adipate, which is further reduced by alcohol dehydrogenase (step 3F2) to give 4-hydroxy adipate that is converted to 4-hydroxy adipyl-CoA by attaching a Coenzyme A molecule (3G5). Conversion of 4-hydroxy adipyl-CoA to adipate is described before.

ADA Pathway 9-10 (Steps 2A, 3B1, 3C2, 3D2, 3L2, 3K2, 3G5, with 3H, 2G, 4F1 or 4D3, 4E3, 4F1) Another pathway (FIG. 3) involves reduction (step 3L2) by alcohol dehydrogenase of 2,3-dehydro 4-oxo-adipate (pathway 7-8 intermediate) to give 2,3-dehydro 4-hydroxy-adipate that is reduced (step 3K2) to give 4-hydroxy-adipic acid, which is converted to adipiate as described above.

ADA Pathway 11-12 (Steps 2A, 3B1, 3C2, 3G2, 3D1, 3E1, 3F1, with 3H, 2G, 4F1 or 4D3, 4E3, 4F1): Another pathway involves Coenzyme A molecule attachment (step 3G2) to 2-hydroxy-4-oxo-adipic acid (also a intermediate in pathway 7) by a acyl-CoA synthase or ligase or transferase to give 2-hydroxy-4-oxo-adipyl-CoA, which is dehyrated (step 3D1) to give 2,3-dehydro-4oxoadipyl-CoA followed by reduction (Step 3E1) to give 4-oxoadipyl-CoA which is reduced by alcohol dehydrogenases (step 3F1) to give 4-hydroxyadipyl-CoA, which can be converted to adipate by the two ways mentioned above.

ADA Pathway 13-18: Another set of pathways (FIG. 3, see list below) involve oxidation (step 3B2) by alcohol dehydrogenase of 4-hydroxy-2-oxo-adipic acid (pathway 1 intermediate) to give 2,4-dioxo adipate that is selectively reduced at 2-keto position (step 3C3) to give 2-hydroxy-4-oxo-adipic acid, which is converted to adipiate as described in pathways 7-10. Alternatively, Coenzyme A molecule attachment (step 3G2) to 2-hydroxy-4-oxo-adipic acid (also a intermediate in pathway 9) by a acyl-CoA synthase or ligase or transferase gives 2-hydroxy-4-oxo-adipyl-CoA which is converted to adipate by pathways ADA11-12.

ADA Pathway 20-24: Another set of pathways involve reduction (step 3L1, FIG. 3) of 2,3-dehydro 4-keto-adipyl-CoA (24) (pathway 5, 11, 17 intermediate) to 2,3-dehydro 4-hydroxy-adipyl-CoA (B) which is converted to adipic acid as mentioned before by two routes (ADA pathways 3 and 4) (Steps 3H, 2G, 4F1 or 4D3, 4E3, 4F1).

ADA Pathway 25: Another pathway involves the dehydration (Step 21) of 2,4-dihydroxy adipyl-CoA (19, pathway 2 intermediate) to give 4,5-dehydro-2-hydroxy adipyl-CoA, which is reduced by enoate reductases (step 2J) to give 2-hydroxy-adipyl-CoA, which can be converted to adipate as mentioned above in ADA pathway 1.

Synthesis of ADA from pyruvate and
3-hydroxypropanal (R=CH$_2$CH$_2$OH in FIG. 2 and FIG. 3)

ADA Pathway 26-28: As shown in FIG. 2, first step (step 2A) is the aldolase catalyzed aldol addition of pyruvate to 3-hydroxypropanal to give 4,6-dihydroxy-2-oxo-hexanoic acid which is dehydrated (Step 2B) to give 2,3-dehydro-6-hydroxy-2-oxo-hexanoic acid that is reduced (step 2C) to give 6-hydroxy-2-oxo-hexanoic acid. 6-hydroxy-2-oxo-hexanoic acid is reduced (Step 2D) to 2,6-dihydroxy-hexanoic acid followed by attachment of a Coenzyme A molecule (step 2E) by a acyl-CoA synthase or ligase or transferase to give 2,6-dihydroxy-hexanoyl-CoA which is dehydrated (step 2F) to give 2,3-dehydro-6-hydroxy hexanoyl-CoA. This can be reduced by enoyl-CoA reductases (step 2G) to give 6-hydroxy hexanoyl-CoA. 6-hydroxy hexanoyl-CoA is oxidized to 6-oxo hexanoyl-CoA (Step 4A3, FIG. 4), which is converted to adipic acid by two pathways. 6-oxo hexanoyl-CoA is oxidized by aldehyde dehydrogenases to give adipyl-CoA (Step 4B6, FIG. 4), which is converted to adipic acid (Step 4F1, FIG. 4) as mentioned above. Alternatively (ADA Pathway 27), 6-oxo hexanoyl-CoA is hydrolyzed or transesterfied to 6-oxo-hexanoic acid by thioesterases or CoA-transferases (Step 4F2, FIG. 4) and subsequently oxidized to adipate by aldehyde dehydrogenases (Step 4B7, FIG. 4). Alternatively (ADA Pathway 28), 6-hydroxy-hexanoyl-CoA is hydrolyzed or transesterfied to 6-hydroxy-hexanoic acid by thioesterases or CoA-transferases (Step 4F3, FIG. 4) and subsequently oxidized to adipate by alcohol/aldehyde dehydrogenases (Steps 4A4/4B7, FIG. 4).

ADA Pathway 29-31: As shown in FIG. 2, these pathways involve reduction of 2-keto group of 4,6-dihydroxy-2-oxo-hexanoic acid (pathway 26 intermediate) to give 2,4,6-trihydroxyl-hexanoic acid (Step 3B1) followed by attachment of CoA molecule (Step 3G1) and subsequent dehydration by 4-hydroxy acyl-CoA dehydratase (step 3M) to give 6-hydroxy-2-oxo-hexanoyl-CoA, which is reduced (step 3N) to 2,6-dihydroxy-hexanoyl-CoA that is converted to adipic acid as mentioned above by three routes (ADA pathway 26-28).

Due to the large number of possible pawthways for synthesis of adipic acid starting from pyruvate and 3-hydroxypropanal as depicted in FIGS. 3-4, pathways are broken down into modular pathways for synthesizing intermediates 4,6-dihydroxy-hexanoyl-CoA 31 and its conversion to adipate, 4,6-dihydroxy-2,3-dehydro-hexanoyl-CoA 42 and its conversion to adipate, and 4,6-dihydroxy-hexanoate 55 and its conversion to adipate, when the aldehyde is 3-hydroxy-propanol.

Pathways (P1-P11 in above table) for synthesis of 4,6-dihydroxy-hexanoyl-CoA (31, FIG. 4 or 30, FIG. 3): One pathway depicted in FIG. 3 involves dehydration (step 3D3) of 2,4,6-trihydroxy-hexanoyl-CoA (19) by 2-hydroxy acyl-CoA dehydratase to give 2,3-dehydro-4,6-dihydroxy-hexanoyl-CoA, which is reduced by enoyl-CoA reductase (step 3K1) to give 4,6-dihydroxy-hexanoyl-CoA (30). Another pathway involves oxidation (step 3C1) of 2,4,6-trihydroxy-hexanoyl-CoA (19) to give 2,6-hydroxy 4-oxo hexanoyl-CoA (22) that is dehydrated (step 3D1) to give 2,3-dehydro-4oxo-6-hydroxyhexanoyl-CoA (24). Its reduction (step 3E1) by enoyl reductase gives 4oxo-6-hydroxy-hexanoyl-CoA (27), which is further reduced by alcohol dehydrogenase (step 3F1) to give 4,6-dihydroxy-hexanoyl-CoA. Another pathway (P3) (FIG. 3) involves oxidation (step 3C2) of 2,4,6-trihydroxy-hexanoyl-CoA (19) to give 2,6-dihydroxy 4-oxo hexanoic acid that is dehydrated (step 3D2) to give 2,3-dehydro 4-oxo-6-hydroxy hexanoic acid (23). Its reduction (step 3E2) gives 4-oxo-6-hydroxy hexanoic acid (26), which is further reduced by alcohol dehydrogenase (step 3F2) to give 4,6-dihydroxyhexanoic acid (29) that is converted to give 4,6-dihydroxy-hexanoyl-CoA by attaching a Coenzyme A molecule (step 3G5). Another pathway (P4) (FIG. 3) involves reduction (step 3L2) by alcohol dehydrogenase of 2,3-dehydro 4-oxo-6-hydroxy hexanoic acid (23) to give 2,3-dehydro 4,6-dihydroxy hexanoic acid (28) which is reduced (step 3K2) to give 4,6-dihydroxyhexanoic acid (29) which is converted to 4,6-dihydroxy-hexanoyl-CoA (29) by attaching a Coenzyme A molecule (Step 3G5). Another set of pathways (FIG. 3, P5-P6) involve oxidation (step 3B2) by alcohol dehydrogenase of 4,6-dihydroxy-2-oxo-hexanoic acid (11) to give 6-hydroxy-2,4-dioxo-hexanoic acid (20) that is selectively reduced at 2-keto position (step 3C3) to give 2,6-dihydroxy-4-oxo-hexanoic acid (21), which is converted to 4,6-dihydroxy-hexanoyl-CoA (30) as described above (P3-P4). Alternatively (pathways P7, P8), Coenzyme A molecule attachment (step 3G2) to 2,6-hydroxy-4oxo-hexanoic acid (21) by a acyl-CoA ligase or transferase gives 2,6-hydroxy-4oxo-hexanoyl-CoA (22) which is converted to 4,6-dihydroxy-hexanoyl-CoA (30) as described above in pathways P3-P4. Another set of pathways (P9-P11) involve reduction (step 3L1) of 2,3-dehydro-4-keto-6-hydroxy-hexanoyl-CoA (24) (pathway P2, P7 and P8 intermediate) to 2,3-dehydro-4,6-dihydroxy-hexanoyl-CoA (25) which is converted to 4,6-dihydroxy-hexanoyl-CoA (30) as described above.

Pathways (P12-P15) for synthesis of adipate from 4,6-dihydroxy-hexanoyl-CoA: Oxidation of 4,6-dihydroxy-hexanoyl-CoA by alcohol dehydrogenases (step 4A2, FIG. 4) gives 4-hydroxy 6-oxo-hexanoyl-CoA which is oxidized to 4-hydroxy-adipyl-CoA (Step 4B4, FIG. 4) which is converted to adipate as described previously (steps 4D3, 4E3, and4F1, FIG. 4). Dehydration of 4-hydroxy 6-oxohexanoyl-CoA by (step 4D4) gives 4,5-dehydro 6-oxo-hexanoyl-CoA. This can be reduced by ene reductases (step 4E4) to give 6-oxo hexanoyl-CoA. that is oxidized to adipyl-CoA (Step B6) and converted to adipiate (step 4F1). Alternatively, 4,5-dehydro-6-oxo-hexanoyl-CoA is also oxidized by aldehyde dehydrogenases (step 4B5) to give 4,5-dehydro-adipyl-CoA which is converted to adipate as described previously (Steps 4E3 and 4F1). Alternatively, 6-oxo hexanoyl-CoA is converted to 6-oxohexanoate (Step 4F2), prior to oxidation to adipate (Step 4B7). Combination of pathways for synthesis of 4,6-dihydroxy-hexanoyl-CoA 31 and its conversion to adipate as described here give ADA pathways 32-75.

give 6-amino-2-hydroxy-hexanoyl-CoA which is dehydrated (step 2F) to give 2,3-dehydro-6-amino hexanoyl-CoA. This can be reduced by enoyl-CoA reductases (step 2G) to give 6-amino hexanoyl-CoA. 6-amino hexanoyl-CoA is converted to 6-oxo hexanoyl-CoA (Step 4G1, FIG. 4), which is converted to adipic acid by two pathways (Step 4B6,4F1 or 4F2, 4B7) as mentioned above. Alternatively, 6-amino-hexanoyl-CoA is hydrolyzed or transesterfied to 6-amino-hexanoic acid by thioesterases or CoA-transferases (Step 4F5, FIG. 4), which is subsequently converted to 6-oxohexanoic acid by transaminases/amino acid oxidases or dehydrogenases, that is converted to adipate by alcohol/aldehyde dehydrogenases (Step 4A4/4B7, FIG. 4).

| Pathway No | Pathway Steps | Product | Starting Substrate |
|---|---|---|---|
| P1 | 2A, 3B1, 3G1, 3D3, 3K1 | 31 or 50 | Pyruvate and 3-oxo-propanol or 3-amino-propanal |
| P2 | 2A, 3B1, 3G1, 3C1, 3D1, 3E1, 3F1 | 31 or 50 | Pyruvate and 3-oxo-propanol or 3-amino-propanal |
| P3 | 2A, 3B1, 3C2, 3D2, 3E2, 3F2, 3G5 | 31 or 50 | Pyruvate and 3-oxo-propanol or 3-amino-propanal |
| P4 | 2A, 3B1, 3C2, 3D2, 3L2, 3K2, 3G5 | 31 or 50 | Pyruvate and 3-oxo-propanol or 3-amino-propanal |
| P5 | 2A, 3B2, 3C3, 3D2, 3E2, 3F2, 3G5 | 31 or 50 | Pyruvate and 3-oxo-propanol or 3-amino-propanal |
| P6 | 2A, 3B2, 3C3, 3D2, 3L2, 3K2, 3G5 | 31 or 50 | Pyruvate and 3-oxo-propanol or 3-amino-propanal |
| P7 | 2A, 3B2, 3C3, 3G2, 3D1, 3E1, 3F1 | 31 or 50 | Pyruvate and 3-oxo-propanol or 3-amino-propanal |
| P8 | 2A, 3B1, 3C2, 3G2, 3D1, 3E1, 3F1 | 31 or 50 | Pyruvate and 3-oxo-propanol or 3-amino-propanal |
| P9 | 2A, 3B2, 3C3, 3G2, 3D1, 3L1, 3k1 | 31 or 50 | Pyruvate and 3-oxo-propanol or 3-amino-propanal |
| P10 | 2A, 3B1, 3C2, 3G2, 3D1, 3L1, 3k1 | 31 or 50 | Pyruvate and 3-oxo-propanol or 3-amino-propanal |
| P11 | 2A, 3B1, 3G1, 3C1,, 3D1, 3L1, 3k1 | 31 or 50 | Pyruvate and 3-oxo-propanol or 3-amino-propanal |
| P12 | 4A2, 4B4, 4D3, 4E3, 4F1 | Adipate | 4,6-dihydroxy-hexanoyl-CoA |
| P13 | 4A2, 4D4, 4E4, 4B6, 4F1 | Adipate | 4,6-dihydroxy-hexanoyl-CoA |
| P14 | 4A2, 4D4, 4B5, 4E3, 4F1 | Adipate | 4,6-dihydroxy-hexanoyl-CoA |
| P15 | 4A2, 4D4, 4E4, 4F2, 4B7 | Adipate | 4,6-dihydroxy-hexanoyl-CoA |
| P18 | 4G3, 4B4, 4D3, 4E3, 4F1 | Adipate | 6-amino-4-hydroxy-hexanoyl-CoA |
| P19 | 4G3, 4D4, 4E4, 4B6, 4F1 | Adipate | 6-amino-4-hydroxy-hexanoyl-CoA |
| P20 | 4G3, 4D4, 4B5, 4E3, 4F1 | Adipate | 6-amino-4-hydroxy-hexanoyl-CoA |
| P21 | 4G3, 4D4, 4E4, 4F2, 4B7 | Adipate | 6-amino-4-hydroxy-hexanoyl-CoA |

ADA Pathways (76-79) for synthesis of 4,6-dihydroxy-2,3-dehydro-hexanoyl-CoA (42, FIG. 4 or 25, FIG. 3) and its conversion to adipate: 4,6-dihydroxy-2,3-dehydro-hexanoyl-CoA is a intermediate in pathways P1, P9-P11. As depicted in FIG. 4, oxidation of 4,6-dihydroxy-2,3-dehydro-hexanoyl-CoA by primary alcohol dehydrogenase (step 4A1) gives 4-hydroxy-2,3-dehydro-6-oxo-hexanoyl-CoA that is oxidized by dehydrogenase to give 4-hydroxy-2,3-dehydro-adipyl-CoA (step 4B1) that is converted to adipate as described in ADA pathway 4.

ADA Pathways (80-83) for synthesis of 4,6-dihydroxy-hexanoic acid (29, FIG. 3 or 55, FIG. 4) and its conversion to adipate: 4,6-dihydroxy-hexanoic acid is an intermediate in pathways P3-P6. Alcohol dehydrogenase catalyzed oxidation of 4,6-dihydroxy-hexanoic acid gives 4-hydroxy-6-oxo-hexanoic acid (step 4A5) which is dehydrated to give 2,3-dehydro-6-oxo-hexanoic acid (step 4D5), which is reduced (step 4F4) to give 6-oxo-hexnoate that is oxidized to adipdate as described before (step 4B7).

Synthesis of ADA from pyruvate and 3-amino-propanal ($R=CH_2CH_2NH_2$ in FIG. 2 and FIG. 3)

ADA Pathway 84-86: As shown in FIG. 2, first step (step 2A) is the aldolase catalyzed aldol addition of pyruvate to 3-amino-propanal to give 6-amino-4-hydroxy-2-oxo-hexanoic acid, which is dehydrated (Step 2B) to give 2,3-dehydro-6-amino-2-oxo-hexanoic acid that is reduced (step 2C) to give 6-amino-2-oxo-hexanoic acid. 6-amino-2-oxo-hexanoic acid is reduced (Step 2D) to 6-amino-2-hydroxy-hexanoic acid followed by attachment of a Coenzyme A molecule (step 2E) by a acyl-CoA ligase or transferase to ADA Pathway 87-89: As depicted in FIG. 2, several pathways involve reduction (Step 3B1) of 2-keto group of 6-amino-4-hydroxy-2-oxo-hexanoic acid (product of Step 2A) to give 2,4-dihydroxyl-6-amino hexanoic acid followed by attachment of CoA molecule (Step 3G1) and subsequent dehydration by 4-hydroxy acyl-CoA dehydratase (step 3M) to give 6-amino-2-oxo-hexanoyl-CoA, which is converted to adipic acid as mentioned above by three routes (ADA pathway 84-86).

Due to the large number of possible pathways for synthesis of adipic acid starting from pyruvate and 3-amino-propanal as depicted in FIGS. 3-4, pathways are broken down into modular pathways for synthesizing intermediates 6-amino-4-hydroxy-hexanoyl-CoA 50 and its conversion to adipate, 6-amino-4-hydroxy-2,3-dehydro-hexanoyl-CoA 51 and its conversion to adipate, and 6-amino-4-hydroxy-hexanoate 52 and its conversion to adipate, as well as pathways for conversion of these intermediates to adipic acid. Pathways (P1-P11) for synthesis of 6-amino-4-hydroxy-hexanoyl-CoA 50, from pyruvate and 3-amino-propanal are identical to the pathways for the synthesis of for synthesis of 4,6-dihydroxy-hexanoyl-CoA (P1-P11), from pyruvate and 3-hydroxypropanal. The general set of transformations involved is the same, however the substrates for each transformation differ at C6 position (amino group vs aldehyde group).

Pathways (P1-P11 in above table) for synthesis of 6-amino-4-hydroxy-hexanoyl-CoA (50, FIG. 4 or 30, FIG. 3): One pathway depicted in FIG. 3 involves dehydration (step 3D3) of 6-amino-2,4-dihydroxy-hexanoyl-CoA (19) by 2-hydroxy acyl-CoA dehydratase (step 3D3) to give 6-amino-2,3-dehydro-4-hydroxy-hexanoyl-CoA (25), which is reduced by enoyl-CoA reductase (step 3K1) to give 6-amino-4-hydroxy-hexanoyl-CoA (30). Another pathway involves oxidation (step 3C1) of 6-amino-2,4-dihydroxy-hexanoyl-CoA (19) to give 6-amino-2-hydroxy 4-oxo hexanoyl-CoA (22) that is dehydrated (step 3D1) to give 6-amino-2,3-dehydro-4-oxo-hexanoyl-CoA (24). Its reduction (step 3E1) by enoyl reductase gives 6-amino-4-oxo-hexanoyl-CoA (27), which is further reduced by alcohol dehydrogenase (step 3F1) to give 6-amino-4-hydroxy-hexanoyl-CoA (30). Another pathway (P3) (FIG. 3) involves oxidation (step 3C2) of 6-amino-2,4-dihydroxy-hexanoic acid (18) to give give 6-amino-2-hydroxy 4-oxo-hexanoic acid (21) that is dehydrated (step 3D2) to give 6-amino-2,3-dehydro 4-oxo-hexanoic acid (23). Its reduction (step 3E2) gives 6-amino-4-oxo-hexanoic acid (26), which is further reduced by alcohol dehydrogenase (step 3F2) to give 6-amino-4-hydroxy hexanoic acid (29) that is converted to give 6-amino-4-hydroxy-hexanoyl-CoA (30) by attaching a Coenzyme A molecule (Step 3G5). Another pathway (P4) (FIG. 3) involves reduction (step 3L2) by alcohol dehydrogenase of 6-amino-2,3-dehydro 4-oxohexanoic acid (23) to give 6-amino-2,3-dehydro-4-hydroxy-hexanoic acid (28) which is reduced (step 3K2) to give 6-amino-4-hydroxy-hexanoic acid (29) which is converted to 6-amino-4-hydroxy-hexanoyl-CoA (30) by attaching a Coenzyme A molecule (Step 3G5). Another set of pathways (FIG. 3, P5-P6) involve oxidation (step 3B2) by alcohol dehydrogenase of 6-amino-4-hydroxy-2-oxo-hexanoic acid (11) to give 6-amino-2,4-dioxo-hexanoic acid (20) that is selectively reduced at 2-keto position (step 3C3) to give 6-amino-2-hydroxy-4-oxo-hexanoic acid (21), which is converted to 6-amino-4-hydroxy-hexanoyl-CoA (30) as described above (P3-P4). Alternatively (pathways P7, P8), Coenzyme A molecule attachment (step 3G2) to 6-amino-2-hydroxy-4oxo-hexanoic acid (21) by a acyl-CoA ligase or transferase gives 6-amino-2-hydroxy-4oxo-hexanoyl-CoA (22) which is converted to 6-amino-4-hydroxy-hexanoyl-CoA (30) as described above in pathways P3-P4. Another set of pathways (P9-P11) involve reduction (step 3L1) of 6-amino-2,3-dehydro-4-oxo-hexanoyl-CoA (24) (pathway P2, P7 and P8 intermediate) to 6-amino-2,3-dehydro-4-hydroxy-hexanoyl-CoA (25) which is converted to 6-amino-4-hydroxy-hexanoyl-CoA (30) as described above.

Pathways (P16-19) for synthesis of adipate from 6-amino-4-hydroxy-hexanoyl-CoA: Transamination of 6-amino-4-hydroxy-hexanoyl-CoA by transaminases or amino acid oxidases or dehydrogenases (step 4G3, FIG. 4) gives 4-hydroxy 6-oxo-hexanoyl-CoA (32) which is converted to adipate as described previously (P12-P15). Combination of pathways for synthesis of 6-amino-4-hydroxy-hexanoyl-CoA 50 and its conversion to adipate as described here give ADA pathways 90-133.

ADA Pathways (134-137) for synthesis of 6-amino-2,3-dehydro-4-hydroxy-hexanoyl-CoA (51, FIG. 4 or 25, FIG. 3) and its conversion to adipate: 6-amino-2,3-dehydro-4-hydroxy-hexanoyl-CoA is a intermediate in pathways P1, P9-P11. Transamination of 6-amino-2,3-dehydro-4-hydroxy-hexanoyl-CoA 51, by transaminases or amino acid oxidases or dehydrogenases (step 4G4, FIG. 4) gives 2,3-dehydro-4-hydroxy 6-oxo-hexanoyl-CoA 43, that is converted to adipate as described before.

ADA Pathways (139-141) for synthesis of 6-amino-4-hydroxy-hexanoic acid (29, FIG. 3 or 52, FIG. 4) and its conversion to adipate: 6-amino-4-hydroxy-hexanoic acid is an intermediate in pathways P3-P6. Transamination of 6-amino-4-hydroxy-hexanoic acid gives 4-hydroxy-6-oxo-hexanoic acid (step 4G5), which is converted to adipdate as described before.

All substrate product transformations (pathway steps) shown in FIGS. 2-4 are catalyzed by enzymes, which are grouped in the Table below based on the chemical reaction (their Enzyme Commission Numbers) they catalyze (irrespective of the specificity of the substrate). Described below are a number of genes (that encode enzymes) belonging to each such group, which can be specifically used to carry out the transformations on the desired substrate as depicted in FIGS. 2-4 for the synthesis of adipate from pyruvate and C3 aldehydes.

| E.C. | Description | Transformations |
|---|---|---|
| 1.3 | Oxido reductase (alkene to alkane) | 2J, 2C, 2G, 3E1, 3E2, 4E3, 4E4, 3K2, 3K1, 4F4 |
| 1.1.1 | Oxido reductase (alcohol to aldehyde) | 4A1, 4A2, 4A3, 4A4, 4A5 |
| 1.1.1 | Oxido reductase (ketone to alcohol) | 3B1, 3N, 2D, 3C3, 3L2, 3L1, 3F2, 3F1, 3C1, 3C2 |
| 1.2.1. | Oxido reductase (aldehyde to acid) | 4B1, 4B4, 4B5, 4B6, 4B7 |
| 2.8.3 | CoA Transferase | 4F1, 4F2, 4F3, 4F5, 3G1, 2E, 3G2, 3G5 |
| 3.1.2 | CoA Hydrolase | 4F1, 4F2, 4F3, 4F5 |
| 4.1.2 and 4.1.3 | Aldolase | 2A |
| 4.2.1 | Hydro lyase (Dehydratase) | 2B, 2I, 3M, 3H, 2F, 3D3, 3D2, 3D1, 4D3, 4D4 and 4D5 |
| 6.2.1 | CoA Ligase | 4F1, 4F2, 4F3, 4F5, 3G1, 2E, 3G2, 3G5 |
| 2.6.1 | Transaminase | 4G1, 4G2, 4G3, 4G4, 4G5 |
| 1.4.1 | Amino acid dehydrogenase | 4G1, 4G2, 4G3, 4G4, 4G5 |
| 2.1.3 | N-acetylation and N-deacetylation | Generic |

E.C. 4.1.2/3-Aldolases

The aldol addition of pyruvate and C3 aldehydes (3-oxopropionic acid, 3-hydroxypropanal, and 3-amino propanal) (step 2A, FIGS. 2-3) to the corresponding 4-hydroxy-2-keto acids (4-hydroxy-2-oxo-adipic acid, 4,6-dihydroxy-2-oxohexanoic acid and 6-amino-4-hydroxy-2-oxo-hexanoic acid) is catalyzed by class I/II pyruvate dependent aldolases (E.C.4.1.2- and E.C.4.1.3-). Class I pyruvate-aldolases exhibit a conserved lysine residue in the active site, which forms a Schiff base intermediate with the pyruvate compound to generate an enamine nucleophile. In Class II aldolases a divalent metal ion promotes the enolization of the pyruvate substrate via Lewis acid complexation. The nucleophilic enamine or enolate then attacks the carbonyl carbon of the acceptor substrate forming the new C—C bond. The aldol addition reaction is usually reversible with the equilibrium favoring the aldol cleavage reaction, however the equilibrium can be shifted in the synthesis direction by coupling the product with downstream enzymes. It is contemplated that this aldol addition reaction can be catalyzed by pyruvate-aldolases of class I and/or class II. Of interest are pyruvate aldolases involved in the aromatic meta-cleavage pathway that catalyze the aldol-cleavage of 4-hydroxy-2-ketoheptane-1,7-dioate to pyruvate and 4-oxobutyrate, which is structurally similar to the desired substrates. Specifically, aldolases HpaI and BphI[6] have been shown to carry out aldol addition of pyruvate to a range of different C2, C3, C4, and C5 aldehydes including glyceraldehyde/propanal/glycoaldehyde (similar structurally to 3-oxo propanol and 3-oxo propanal) and succinic semialdehyde (similar to 3-oxo propanol). Other promising pyruvate aldolases include DmpG[7], HsaF[8], TTHB42[9] and 2-dehydro-3-deoxy-glucarate aldolases (E.C. 4.1.2.51, KDG aldolases) particularly from *Sulfolobus*[10] that use a range of aldehydes as substrates. BphI is very stereoselective as it allows the pyruvate enolate to only attack the re-face of the aldehyde, thereby forming (4S)-aldol products in the process. In contrast, the larger substrate-binding site of HpaI enables the enzyme to bind aldehydes in alternative conformations, leading to formation of racemic products. Such stereoselectivity or lack of thereof will be important for processing by downstream enzymes in the pathway. Alternatively, protein engineering can be used to alter substrate specificity and/or stereospecificity of aldolases[11]. Other aldolases of interest to carry out this transformation include 4-hydroxy-2-oxo-glutarate aldolase (E.C.4.1.3.16), which uses glyoxylate[12] (similar to malonate semialdehyde), 2-dehydro-3-deoxy-phosphogalactonate aldolases (E.C. 4.1.2.21)[13] and 2-dehydro-3-deoxy-phosphogluconate aldolases (E.C. 4.1.2.14, KDPG aldolases)[14] which uses glyceraldehyde 3-phosphate (similar to malonate semialdehyde), 2-dehydro-3-deoxy-glucarate aldolases (E.C. 4.1.2.20, KDG aldolases) which uses tartronate semialdehyde[15] (similar to malonate semialdehyde), and 4-hydroxy-4-methyl-2-oxo-glutarate aldolase (E.C.4.1.3.17) which uses oxaloacetate[16] (similar to malonate semialdehyde) as a substrate.

hydro-acyl-CoA. Steps 2F (FIG. 2) and 3D1 (FIG. 3) involve the dehydration of 2-hydroxy-acyl-CoA to the corresponding 2,3-dehydro-acyl-CoA. Step 2F includes the dehydration of 2,6-dihydroxy-hexanoyl-CoA to 2,3-dehydro-6-hydroxy-hexanoyl-CoA; 6-amino-2-hydroxy-hexanoyl-CoA to 6-amino-2,3-dehydro-hexanoyl-CoA; and 2-hydroxy-adipyl-CoA to 2,3-dehydro-adipyl-CoA; and Step 3D1 includes the dehydration of 2,6-dihydroxy-4-oxohexanoyl-CoA to 2,3-dehydro-6-hydroxy-4-oxo hexanoyl-CoA; 6-amino-2-hydroxy-4-oxo-hexanoyl-CoA to 6-amino-2,3-dehydro-4-oxo-hexanoyl-CoA; and 2-hydroxy-4-oxoadipyl-CoA to 2,3-dehydro-4oxoadipyl-CoA; when the C3 aldehyde is 3-hydroxypropanal, 3-aminopropanal, and 3-oxo-propionic acid respectively for the adipate pathway. The 2-hydroxyacyl-CoA dehydratases catalyze the reversible dehydration from 2-hydroxyacyl-CoA to (E)-2-enoyl-CoA[17]. In these [4Fe-4S] cluster containing enzymes ketyl radicals are formed by one-electron reduction or oxidation and is recycled after each turnover without further energy input. These enzymes require activation by one-electron transfer from an iron-sulfur protein (ferrodoxin or flavodoxin) driven by the hydrolysis of ATP. The enzyme is very oxygen sensitive and requires an activator protein for activation[17]. Specifically, 2-hydroxyglutaryl-CoA dehydratase (hgdAB) from *Clostridium symbiosum* and activator (hgdC) has been shown to dehydrate 2-hydroxyadipyl-CoA to give 2,3-(E)-dehydroadipyl-CoA (Step 2F)[18]. Given the relatively broad specificity of this dehydratase (hexa-2,4-dienedioyl-CoA, 5-hydroxymuconyl-CoA, and butynedioyl-CoA served as substrates for the

| Gene | Genbank ID | EC | Gene (Name) | Organism |
|---|---|---|---|---|
| BphI | YP_556399.1 (SEQ ID NO: 3) | 4.1.3.39 | 4-hydroxy-2-oxovalerate aldolase | *Burkholderia xenovorans* LB400 |
| HpaI | YP_006127221.1 (SEQ ID NO: 1) | 4.1.2.— | 2,4-dihydroxyhept-2-ene-1,7-dioic acid aldolase | *Escherichia coli* strain W |
| YfaU | YP_001731183.1 (SEQ ID NO: 2) | 4.1.2.— | 2,4-dihydroxyhept-2-ene-1,7-dioic acid aldolase | *Escherichia coli* str. K-12 substr. DH10B |
| Hga | CAA48732.1. | 4.1.3.16 | 4-hydroxy-2-oxoglutarate aldolase | *Escherichia coli* (strain K12) |
|  | AFQ49301.1. | 4.1.2.21 | 2-dehydro-3-deoxy-6-phosphogalactonate aldolase | *Burkholderia cepacia* GG4 |
|  | CAF18463.1. | 4.1.2.14 | 2-dehydro-3-deoxy-phosphogluconate aldolase | *Thermoproteus tenax* |
|  | AAN68126.1. | 4.1.3.17 | 4-carboxy-4-hydroxy-2-oxoadipic acid aldolase | *Pseudomonas putida* (strain KT2440) |
|  | AAK43294.1. | 4.1.2.51 | 2-keto-3-deoxy gluconate aldolase | *Sulfolobus solfataricus* P2 |
| YfaU | YP_490484.1 | 4.1.3.39 | 4-hydroxy-2-oxovalerate aldolase | *E. coli* K12 W3110 |
| DmpG | BAP28478.1 | 4.1.3.39 | 4-hydroxy-2-oxovalerate aldolase | *pseudomonas* CF 600 |
| TTHB246 | BAD72042.1 | 4.1.3.40 | 4-hydroxy-2-oxovalerate aldolase | *Thermus thermophilus* HB8 |
| HsaF | CCP46356.1 | 4.1.3.41 | 4-hydroxy-2-oxovalerate aldolase | *Mycobacterium tuberculosis* H37Rv |
| Saci 0225 | YP_254937.1 | 4.1.2.51 | 2-keto-3-deoxy gluconate aldolase | *Sulfolobus acidocaldarius* DSM 639 |
| SSO3197 | CAA11866.1 | 4.1.2.51 | 2-keto-3-deoxy gluconate aldolase | *Sulfolobus solfataricus* |
| garL | P23522.2 | 4.1.2.20 | 2-dehydro-3-deoxy-glucarate aldolases | *Escherichia coli* K12 |

E.C. 4.2.1-Dehydratase (hydro lyase)

Several transformations in the pathways for synthesis of adipate from C3 aldehydes as described above include a dehydration step, which is catalyzed by dehydratases (also called hydro lyase). These reactions include steps 2B, 2I, 3M, 3H, 2F, 3D3, 3D2, 3D1, 4D1, 4D2, 4D3, 4D4 and 4D5. For each transformation, both stereo centers (R or S) at the hydroxyl group to be dehydrated can be used by the enzyme for carrying out dehydration.

Steps 2F (FIG. 2) and 3D1 (FIG. 3) involve the dehydration of 2-hydroxy-acyl-CoA to the corresponding 2,3-dereverse reaction) we anticipate the enzyme to catalyze the dehydration of other C6 substituted 2-hydroxyhexanoyl-CoA molecules of the adipate pathway. Other relevant 2-hydroxy acyl-CoA dehyratase enzymes that can be used to carry transformation of steps 2F and 3D1 include those from *Clostridium propionicum* (lactyl-CoA dehyratase, E.C. 4.2.1.54), *Acidaminococcus Fermentans* (R-2-hydroxy-glutaryl-CoA dehydratase), *Fusobacterium nucleatum* (R-2-hydroxy glutaryl-CoA dehydratase), *Clostridium sporogenes* (R-phenyllactyl-CoA dehyratase), and *Clostridium difficile* (R-2-hydroxy isocaproyl-CoA)[19].

| Accession Numbers | Name (gene) | Organism |
|---|---|---|
| CAA42196.1. | hgdC | *Acidaminococcus fermentans* |
| CAA32465.1. | hgdA | *Acidaminococcus fermentans* |
| CAA32466.1. | hgdB | *Acidaminococcus fermentans* |
| AAD31676.1. | HgdA | *Clostridium symbiosum* |
| AAD31677.1. | Hgd B | *Clostridium symbiosum* |
| AAD31675.1. | HgdC (activator) | *Clostridium symbiosum* |
| NP-603113.1 | hgdC | *Fusobacterium nucleatum* |
| NP_603114.1 | hgdA | *Fusobacterium nucleatum* |
| NP_603115.1 | hgdB | *Fusobacterium nucleatum* |

Step 3H (conversion of 30 to 16, FIG. 3) includes the dehydration of 4,6-dihydroxy-hexanoyl-CoA to 2,3-dehydro-6-hydroxy-hexanoyl-CoA; 6-amino-4-hydroxy-hexanoyl-CoA to 6-amino-2,3-dehydro-hexanoyl-CoA; and 4-hydroxy-adipyl-CoA to 2,3-dehydro-adipyl-CoA; and Step 3M (conversion of 19 to 20, FIG. 2) includes the dehydration of 2,4,6-trihydroxy-hexanoyl-CoA to 6-hydroxy-2-oxo hexanoyl-CoA; 6-amino-2,4-dihydroxy-hexanoyl-CoA to 6-amino-4-hydroxy-2-oxo hexanoyl-CoA; and 2,4-dihydroxy-adipyl-CoA to 2-oxoadipyl-CoA; when the C3 aldehyde is 3-hydroxypropanal, 3-amino-propanal, and 3-oxo-propionic acid respectively for the adipate pathway. 4-hydroxy-acyl-CoA dehydratase enzyme catalyzes the reversible dehydration of 4-hydroxybutyryl-CoA to crotonyl-CoA (E.C. 4.2.1.120), can be used to catalyze the aforementioned dehydrations. Like 2-hydroxy-acyl-CoA dehydratases, this enzyme also operates through ketyl radical and is oxygen sensitive. Exemplary 4-hydroxy acyl-CoA dehyratase enzymes that can be used to carry transformation of steps 3H and 3M include those from *Clostridium aminobutyricum* (4-hydroxy-butyryl-CoA dehyratase)[20] and *Ignicoccus hospitalis* (4-hydroxy-butyryl-CoA dehyratase) [21]. Such an enzyme has also been identified in *Clostridium Kluyveri*[22], *Metallosphaera*, *Sulfolobus*, *Archaeoglobus*, and *Cenarchaeum* species[4]. Any of these enzymes can also carry out this dehydration.

characterized and can be used to catalyze these dehydrations including radical dehydratases, Iron-Sulphur cluster based dehydratases as well as enolate ion based dehyratases.

Multiple dehyratases from meta-pathway are known and can be used to catalyze the dehydration of 11 (4,6-dihydroxy-2-oxo-hexanoic acid, 6-amino-4-hydroxy-2-oxo-hexanoic acid, 4-hydroxy-2-oxo-adipate, FIG. 2) to corresponding 3,4-dehydro products 12 (Step 2B, FIG. 2). Hydratases from the meta cleavage pathway in many bacteria are known to hydrate 2-hydroxy-alkyl-2,4-dienoate to the corresponding 4-hydroxy-2-keto-alkanoic acid. Dehydration of 4-hydroxy-2-keto-alkanoic acid will lead directly to 2-keto-3-alkenoic acid or alternatively the reverse reaction can lead to the synthesis of 2-hydroxy-alkyl-2,4-dienoate, which will tautomerize to the more stable 2-keto-3-alkenoic acid (FIG. 2, 12). Dehydratase HpcG/HpaH[23][24] has been shown to hydrate 2-hydroxy-hexa-2,4-dienoate to produce 4-hydroxy-2-oxo-hexanoic acid, which is chemically and structurally very similar to the desired dehydration substrate 11 (FIG. 2, differing only in the functionality at C6). Other exemplary meta cleavage pathway dehydratases include MhpD, DmpE, TesE, and BphH [25-27][28] which can also be used to perform this reaction.

| Gene | Genebank ID | Name | Organism |
|---|---|---|---|
| BphH | ABE33952.1 | 2-oxo-hept-3-enedioate hydratase | *Burkholderia xenovorans* LB400 |
| HpcG/HpaH | AAB91474.1. | 2-oxo-hept-4-ene-1,7-dioate hydratase | *E. coli* |
| DmpE | CAA43225.1 | 2-hydroxypent-2,4-dienoate hydratase | *Pseudomonas* sp. CF600 |
| TesE | BAC67694.1. | 2-hydroxyhexa-2,4-dienoate hydratase | *Comamonas testosteroni* |
| MhpD | BAA13055.1 | 2-keto-4-pentenoate hydratase | *E. coli* |

Alternatively, 2-keto-3-deoxy-sugar acid dehydratases belonging to the DHDPS (dihydrodipicolinate synthase)/FAH (fumarylacetoacetate hydrolase) superfamily, can also be used to carry out the dehydration of 11 to 12 (Step 2B, FIG. 2). These dehydratases catalyze the dehydration of 3-deoxy-4-hydroxy-2-oxo-sugar acids, substrates structurally very similar to 11. Exemplary dehydratases include 2-keto-3-deoxy-D-arabinonate dehydratase[29], L-2-Keto-3-deoxyarabonate dehydratase[30], and 2-keto-3-deoxy-L-lyxonate dehydratase[31]. Multiple such dehydratases have been biochemically characterized, and their sequence information is shown in Table below. Since these dehydratases catalyze dehydration of β-hydroxy ketone substrates (through schiff's base formation or Mg 2 stabilized enolate mechanisms), they can also be used to catalyze dehydration

| Genebank Accession Numbers | Name | Organism |
|---|---|---|
| CAB60035.2 | 4-Hydroxybutyryl-CoA dehydratase, abfD | *Clostridium aminobutyricum* |
| WP_011998629.1 | 4-Hydroxybutyryl-CoA dehydratase | *Ignicoccus hospitalis*] |
| ABP95381.1. | 4-Hydroxybutyryl-CoA dehydratase, Msed_1220 | *Metallosphaera sedula* |
| ABP95479.1. | 4-Hydroxybutyryl-CoA dehydratase, Msed_1321 | *Metallosphaera sedula* |

Other steps of the adipate pathways for that involve dehydration include Steps 2B (dehydration of 11 to 12), 21 (dehydration of 19 to 9), 3D2 (dehydration of 21 to 23), 3D1(dehydration of 22 to 24), 4D1 (dehydration of 43 to 45), 4D2 (dehydration of 44 to 46), 4D3 (dehydration of 33 to 34), 4D4 (dehydration of 32 to 37), and 4D5 (dehydration of 54 to 59). Several classes of dehydratases have been step 4D4 (FIG. 4, dehydration of 32 to 37), step 4D5 (dehydration of 54 to 59), step 4D1 (dehydration of 43 to 45), steps 3D2 and 3D1 (FIG. 3, dehydration of 21, 22 to 23, 24 respectively when C3 aldehyde is 3-hydroxypropanal, 3-amino-propanal, and 3-oxo-propionic acid), which involves dehydration of hydroxy group that is in a β-postion to a ketone functionality within the substrate.

| Gene | Genebank ID | Name | Organism |
|---|---|---|---|
| LKDA | AB241136.1 | L-2-keto-3-deoxyarabonate dehydratase | A. brasiliense |
| KdaD | NC_002754.1 | 2-Keto-3-deoxy-D-arabinonate Dehydratase | Sulfolobus solfataricusP2 |
| LKDL | NC_003062.2 | 2-keto-3-deoxy-L-lyxonate dehydratase | Agrobacterium tumefaciens str. C58 |
| LKDL | EAV45210.1 | 2-keto-3-deoxy-L-lyxonate dehydratase | Labrenzia aggregata |
| LKDL | NW_003322889.1 | 2-keto-3-deoxy-L-lyxonate dehydratase | P. aeruginosa PAO1 |

Alternatively, fumarases (E.C. 4.2.1.2) which catalyze the reversible dehydration malate to fumarate, and D-tartarate to enol-oxaloacetate (2- and/or 3-hydroxy acids), can also be used to carry out steps 3D2 and 3D1 (FIG. 3) which involve the dehydration of 2-hydroxy-4-keto acids 21 (2,6-hydroxy-4-keto hexanoate, 6-amino-2-hydroxy-4-keto hexanoate, and 2-hydroxy-4-keto adipate, when C3 aldehyde is 3-hydroxypropanal, 3-amino-propanal, and 3-oxo-propionic acid respectively), and 2-hydroxy-4-keto-acyl-CoA, 22 (2,6-hydroxy-4-keto hexanoyl-CoA, 6-amino-2-hydroxy-4-keto hexanoyl-CoA, and 2-hydroxy-4-keto adipyl-CoA, when C3 aldehyde is 3-hydroxypropanal, 3-amino-propanal, and 3-oxo-propionic acid respectively), which is chemically similar to malate (3-carboxy-2-hydroxy-propanoate). The class I fumarases FumA and FumB contain an oxygen-sensitive catalytic [4Fe-4S] cluster, are found in bacteria, predominantly enterobacteria and bacteriodetes such as Salmonella and Klebsiella. The iron-independent, oxygen-stable FumC belongs to class II and is homologous to eukaryotic fumarases. FumA, FumB, and FumC have been identified and extensively characterized from E. coli [32-34]. Other fumarases also include FumC from Corynebacterium glutamicum[35], fumarase from S. cerevisiaie [36], fumC from Thermus thermophilus [37], fumarase MmcBC of Pelotomaculum thermopropionicum (homologous 33% to fumarase A in Escherichia coli)[38], and fumC from Campylobacter [39]. Fumarases can also catalyze the dehydration steps 4D2 (dehydration of 44 to 46), 4D3 (dehydration of 33 to 34), and 2I (dehydration of 19 to 9), which involve dehydration of 3-hydroxy acids, which is structurally similar to malate/tartarate.

| Gene | Accession No | Name | Organism |
|---|---|---|---|
| fumA | CAA25204.1. | Fumarate dehydratase | Escherichia coli K12 |
| fumB | AAA23827.1. | Fumarate dehydratase | Escherichia coli K12 |
| fumC | CAA27698.1. | Fumarate dehydratase | Escherichia coli K12 |
| fumC | BAB98403.1. | Fumarate dehydratase | Corynebacterium glutamicum |
| fumC | O69294.1 | Fumarate dehydratase | Campylobacter jejuni |
| FumM1 | NP_015061 | Fumarate dehydratase | S. cerevisiaie |
| fumC | P84127 | Fumarate dehydratase | Thermus thermophilus |
| MmcB | YP_001211906 | Fumarate dehydratase | Pelotomaculum thermopropionicum |
| MmcC | YP_001211907 | Fumarate dehydratase | Pelotomaculum thermopropionicum |

Aconitate hydratases (E.C. 4.2.1.3) are widely distributed monomeric enzymes containing a single [4Fe-4S] centre and are known to catalyze the dehydration of 3-hydroxy acids, such as citric acid to aconitic acid as well as isocitrate to aconitic acid and play a crucial role in TCA cycle [40]. Well studied aconitate hydratases include acnA and acnB of E. coli[41] and aconitase of S. cerevisiaie and other similar dehydratases (E.C. 4.2.1.79, 2-methyl citrate dehydratase [43], E.C. 4.2.1.31, maleate hydratase-cis double bond forming[44]).

| Gene | Accession No | Name | Organism |
|---|---|---|---|
| AcnA | CAA42834.1. | Aconitate hydratase 1 | Escherichia coli |
| AcnB | AAC73229.1. | Aconitate hydratese 2 | Escherichia coli |
| AcoI | AAA34389.1. | Aconitase | Saccharomyces cerevisiae |
| AcnC/PrpD | AAB18058.1. | 2-methylcitrate dehydratase | Escherichia coli |
| LeuC | AAB98487.1. | Maleate hydratase | Methanocaldococcus jannaschii |

Several sugar acid dehydratases are known that split off a water molecule from a sugar acid to generate the 2-keto-3-deoxy derivative of the sugar acid and belong to the enolase superfamily (operate by forming divalent cation-stabilized enolate). Several such dehydratases are known and can catalyze dehydration on a range of different sugar acids[45] [46]. Such dehydratases are of interest and can catalyze the dehydration steps described herein. Shown in table below are exemplary sugar acid dehydratases and some enoyl-CoA hydratases, which can be used to carry out the dehydration mentioned herein.

| E.C. No. | Accession No | Name | Organism |
|---|---|---|---|
| 4.2.1.5 | NP_377032.1 | D-Arabinonate dehyratase | *Sulfolobus tokodaii* |
| 4.2.1.6 | EGP22937 | D-Galactonate dehydratase | *Escherichia coli* |
| 4.2.1.7 | BAA18901.1 | Altronate dehydratase | *Escherichia coli* |
| 4.2.1.8 | YP_001461084 | D-mannonate dehydratase | *Escherichia coli* |
| 4.2.1.25 | BAE94269.1 | L-Arabinonate dehyratase | *Azospirillum brasilense* |
| 4.2.1.32 | ACT44736 | L-tartarate dehydratase | *Escherichia coli* |
| 4.2.1.39 | YP_003470410 | gluconate dehydratase | *Staphylococcus lugdunensis* |
| 4.2.1.40 | AAC75829.1. | glucarate dehydratase | *Escherichia coli* |
| 4.2.1.42 | AAA57931.1. | galactarate dehydratase | *Escherichia coli* |
| 4.2.1.68 | 2HXT_A | L-fuconate dehydratase | *Xanthomonas Campestris* |
| 4.2.1.81 | 2DW7_A | D-tartarate dehydratase | *Bradyrhizobium Japonicum* |
| 4.2.1.82 | ADE01444.1. | xylonate dehydratase | *Haloferax volcanii* |
| 4.2.1.90 | 2I5Q_A | L-rhamnonate dehydratase | *Escherichia coli* |
| 4.2.1.146 | BAE77602.1. | L-galactonate dehydratase | *Escherichia coli* |

| Accession No | Name | Organism |
|---|---|---|
| YP_001730392 | enoyl-CoA hydratase | *Escherichia coli* |
| EGI23865 | 3-hydroxy-butyryl-CoA dehydratase | *Escherichia coli* |
| 1DUB_A | Long-chain enoyl-CoA hydratase | *Rattus Norvegicus* |
| YP_003022613 | cyclohexa-1,5-dienecarbonyl-CoA | *Geobacter* sp. M21 |
| ACL95949 | trans-feruloyl-CoA hydratase | *Caulobacter Crescentus* |
| AEE35803 | enoyl-CoA hydratase | *Arabidopsis thaliana* |

E.C. 1.1.1-Oxidoreductase (alcohol to aldehyde)

Several pathway steps 4A1, 4A2, 4A3, 4A4, and 4A5, as depicted in FIG. 4 in the various pathways for synthesis of adipate involve the oxidation of primary alcohol to an aldehyde are catalyzed by alcohol dehydrogenases. Particularly, Step 4A1 is catalyzed by a 4,6-dihydroxy-2,3-dehydrohexanoyl-CoA 6-dehydrogenase (4A1), Step 4A2 is catalyzed by a 4,6-dihydroxyhexanoyl-CoA 6-dehydrogenase (4A2), Step 4A3 is catalyzed by a 6-hydroxyhexanoyl-CoA 6-dehydrogenase (4A3), Step 4A4 is catalyzed by a 6-hydroxyhexanoate 6-dehydrogenase (4A4), 4A5 is catalyzed by a 4,6-dihydroxyhexanoate 6-dehydrogenase (4A5). A 6-hydroxyhexanoate 6-dehydrogenase (4A4) has been identified in the cyclohexanone degradation pathway in *Acinetobacter* NCIB 9871[47], *Rhodococcus* sp. strain Phi2, and *Arthrobacter* sp. strain BP2[48]. The enzyme has been shown to be reversible and can also catalyze the reduction of 6-oxohexanoate. Alternatively, this enzyme can also be used to catalyzed Steps 4A1, 4A2, 4A3 and 4A5 which involve oxidation of substrates chemically and structurally similar to 6-hydroxyhexanoate.

| Genebank No | Name | Organism |
|---|---|---|
| BAC80217.1 | 6-hydroxyhexanoate dehydrogenase | *Acinetobacter* NCIB 9871 |
| AAN37477.1 | 6-hydroxyhexanoate dehydrogenase | *Rhodococcus* sp. strain Phi2 |
| AAN37489.1 | 6-hydroxyhexanoate dehydrogenase | *Arthrobacter* sp. strain BP2 |

Many primary alcohol dehydrogenases are known in literature, and exemplary candidates to catalyze these steps are described below. A number of *E. coli* alcohol-aldehyde dehydrogenases are known including dhE, adhP, eutG, yiaY, yqhD, fucO, and yjgB[49]. Recently, 44 aldehyde reductases have been identified in *E. coli*. These enzymes in the reverse direction can be used to catalyze the desired alcohol oxidations[50]. Butanol dehydrogenases[51] from *C. acetobutylicum* are of interest to catalyze these transformations. A number of *S. cerevisiae* alcohol dehydrogenases have been shown to reversibly oxidize a range of different alcohols including, ADH2-6. ADH6 is a broad specificity enzyme that his been shown to catalyze oxidation of alcohols in a NADP+ dependent manner from C2-C8 lengths and is optimal for C6 lengths[52]. Adh2 from *S. cerevisiae* is also promiscuous enzyme that has been shown to reversibly oxidize diverse range of alcohols[53]. Of particular interest also include ADHI-ADHII from two alkyl alcohol dehydrogenase (ADH) genes[54] from the long-chain alkane-degrading strain *Geobacillus thermodenitrificans* NG80-2. ADH1 and ADH2 can oxidize a broad range of alkyl alcohols up to at least C30. Other promiscuous ADH includes AlrA encodes a medium-chain alcohol dehydrogenase[55]. Also of interest are 4-hydroxy butyrate dehydrogenases (EC 1.1.1.61) that catalyze oxidation of 4-hydroxy butyrate that have been found in *A. thaliana*[56], *E. coli* (yihu)[57], and as well as *C. Kluyveri*[58]. *A. thaliana* enzyme as well as A. terrus enzyme (ATEG in table) can reduce glutarate semialdehyde (WO 2010/068953A2, WO 2010/068953A2).

| Gene | Genebank No | Name | Organism |
|---|---|---|---|
| fucO | NP_417279.1 | Alcohol Dehydrogenase | *Escherichia coli* |
| bdh I | NP_349892.1 | Alcohol Dehydrogenase | *Clostridium acetobutylicum* |
| bdh II | NP_349891.1 | Alcohol Dehydrogenase | *Clostridium acetobutylicum* |
| alrA | BAB12273.1 | Alcohol Dehydrogenase | *Acinetobacter* sp. strain |
| 4hbd | L21902.1 | 4-hydroxy butyrate dehydorgenase | *Clostridium kluyveri* |
| 4hbd | Q94B07 | 4-hydroxy butyrate dehydorgenase | *Arabidopsis thaliana* |
| yihu | AAB03015.1. | 4-hydroxy butyrate dehydorgenase | *Escherichia coli* |
| ADH2 | NP_014032.1 | Alcohol Dehydrogenase | *Saccharomyces cerevisiae* |
| ADH3 | NP_013892.1 | Alcohol Dehydrogenase | *Saccharomyces cerevisiae* |

| Gene | Genebank No | Name | Organism |
|---|---|---|---|
| ADH4 | NP_015019.1 | Alcohol Dehydrogenase | *Saccharomyces cerevisiae* |
| ADH5 | NP_010996.2 | Alcohol Dehydrogenase | *Saccharomyces cerevisiae* |
| ADH6 | ABX39192.1 | Alcohol Dehydrogenase | *Saccharomyces cerevisiae* |
| ATEG | XP_001210625.1 | Alcohol Dehydrogenase | *Aspergillus terreus* |
| ADHI | ABO67118 | Alcohol Dehydrogenase | *Geobacillus thermodenitrificans* NG80-2 |
| ADHII | ABO68223 | Alcohol Dehydrogenase | *Geobacillus thermodenitrificans* NG80-2 |
| YqhD | BAE77068.1 | Alcohol Dehydrogenase | *Escherichia coli* |
| Adhe | CAA47743.1. | Alcohol Dehydrogenase | *Escherichia coli* |

E.C. 1.1.1-Oxidoreductase (keto to alcohol or alcohol to ketone)

Several pathway steps such as steps 2D, 3N, 3B1, 3C3, 3L2, 3L1, 3F2, and 3F1, as depicted in FIGS. 2-3 in the various pathways for synthesis of adipate involve the reduction of keto group to a secondary alcohol. Steps 3C1 and 3C2, involve the oxidation of a secondary alcohol to a keto group. These transformations include step 2D which is the reduction of 2-oxo group of 2-oxoadipate, 6-hydroxy-2-oxohexnoate, and 6-amino-2-oxohexnoate; Step 3N which is the reduction of 2-oxo group of 2-oxoadipyl-CoA, 6-hydroxy-2-oxohexnoyl-CoA, and 6-amino-2-oxohexnoyl-CoA; step 3B1 which is the reduction of 2-oxo group of 4-hydroxy-2-oxoadipate, 4,6-dihydroxy-2-oxohexnoate, and 6-amino-4-hydroxy-2-oxohexnoate; step 3C3 is the reduction of of 2-oxo group of 2,4-dioxoadipate, a 6-hydroxy-2,4-dioxohexanoate, 6-amino-2,4-dioxohexanoate, step 3L2 is the reduction of 4-oxo group of 2,3-dehydro-4-oxoadipate, 6-hydroxy-2,3-dehydro-4-oxohexanoate, 6-amino-2,3-dehydro-4-oxohexanoate, Step 3L1 is the reduction of 4-oxo group of 2,3-dehydro-4-oxoadipyl-CoA, 6-hydroxy-2,3-dehydro-4-oxohexanoyl-CoA, 6-amino-2,3-dehydro-4-oxohexanoyl-CoA, Step 3F2 is the reduction of 4-oxo group of 4-oxoadipate, 6-hydroxy-4-oxohexanoate, 6-amino-4-oxohexanoate, 3F1 is the reduction of 4-oxo group of 4-oxoadipyl-CoA, 6-hydroxy-4-oxohexanoyl-CoA, 6-amino-4-oxohexanoyl-CoA, Step 3C1 is the oxidation of 4-hydroxy group of 2,4-dihydroxyadipyl-CoA, 2,4,6-trihydroxyhexanoyl-CoA, 6-amino-2,4-dihydroxyhexanoyl-CoA, Step 3C2 is the oxidation of 4-hydroxy group of 2,4-dihydroxyadipate, a 2,4,6-trihydroxyhexanoate, 6-amino-2,4-dihydroxyhexanoate.

Typically a quinone (QH2), reduced ferricytochrome, NAD(P)H, FMNH2, FADH2-dependent dehydrogenase can be used to carry out this reduction (or oxidation in reverse direction when applicable). Any enzyme capable towards the reduction of 2-oxoacids or 2-oxoacyl-CoA or 2-oxoesters to their corresponding 2-hydroxy products is suitable to carry out many of these transformations. The ideal enzyme should be able to selectively reduce the C-2 keto group to either a 2(R) or a 2 (S) isomer. Although lactate dehydrogenases are preferred for this reaction, secondary alcohol dehydrogenases can also be used to carry out this transformation. NADH-dependent (R)-2-hydroxyglutarate dehydrogenase (HGDH) from *Acidaminococcus fermentans* has been shown to reversibly catalyze the reduction of 2-oxoadipate to give 2-(R)-hydroxyadipate[59] (Step 2D). Such a enzyme has also been found in human placenta [60] and in *rattus* sp.[61]. Additionally, LdhA from *C. difficile* is a NAD+-dependent (R)-2-hydroxyisocaproate dehydrogenase that has been shown to catalyze the reduction of a range of 2-oxoacds including 2-oxohexanoate, 2-oxopentanoate, and 2-isocaproate in a NADH dependent manner[62]. SerA-encodes a 3-phosphoglycerate (3PG) dehydrogenase in *Escherichia coli*, however the enzyme is also found to reduces 2-oxoglutarate[63]. Replacement of Tyr52 with Valine or Alanine in *Lactobacillus pentosus* D-lactate dehydrogenase induced high activity and preference for large aliphatic 2-ketoacids including 2-ketobutyrate, 2-ketocaproate, 2-ketoisocaproate, 2-ketovalerate, 2-ketoglutarate, and 2-ketoisovalerate[64]. Other 2-oxoacids reductases of interest include panE from *L. lactis* which catalyzes reduction of a variety of 2-ketoacids (2-ketobutyrate, 2-ketocaproate, 2-ketoisocaproate, 2-ketovalerate, and 2-ketobutyrate) and also 2-keto-thioesters such as 2-Ketomethylthiobutyrate (for also reducing 2-oxoacyl-CoAs herein)[65]. Alternatively, mandelate dehydrogenases are also good candidates, as they are known to reduce a broad range of 2-keto acids, including straight-chain aliphatic 2-keto acids, branched-chain 2-keto acids, and 2-keto acids with aromatic side chains. One such enzyme includes D-2-hydroxy 4-methylvalerate dehydrogenase from *Lactobacillus delbrueckii* subsp. *bulgaricus* (tolerates substitutions at C-4)[66]. Other similar alcohol dehydrogenases of interest include lactate dehydrogenase from *E. coli* and *Ralstonia Eutropha*.

| Gene | Genebank ID | Name | Organism |
|---|---|---|---|
| lLDH | AAA22568.1. | L-lactate dehydrogenase | *Geobacillus stearothemrophilus* |
| dLDH | BAA14352.1. | D-lactate dehydrogenase | *Lactobacillus pentosus* |
| hgdH | 1XDW (pdb code) | (R)-2-hydroxyglutarate dehydrogenase | *Clostridium symbiosum* |
| ldhA | CBA60744.1. | (R)-2-hydroxyisocaproate dehydrogenase | *Clostridium Difficle* |
| serA | NP_417388.1 | 3-phospho glycerate dehydrogenase | *E. coli* |
| panE | ADZ63930.1. | D-2-hydroxy acid dehdyrogenase | *Lactococcus lactis* |
| hdhD | AGE40000.1. | D-2-hydroxy acid dehdyrogenase | *Lactobacillus plantarum (bulgaricus)* |
| LdhA | NP_415898.1 | lactate dehydrogenase | *E. coli* |
| ldh | YP_725182.1 | lactate dehydrogenase | *R. Eutropha* |

Keto reductases can also be used to carry out these transformations. Particularly, yeast alcohol dehydrogenases have been shown to be reduce a range of different keto acids and keto esters such 3-ketoesters, 4-ketoacids, 5-ketoacids and esters including ethyl 3-oxobutyrate, ethyl 3-oxohexanoate, 4-oxopentanoic and 5-oxohexanoic acid[67]. 22 oxidreductases of *S. cerevisiae* have been tested and most of them show activity on a range of such ketoesters. Shown in table below are some yeast oxidoreductases[68] and are good candidates to catalyze 4-oxo and 2-oxo reduction steps. As these reactions are reversible in nature these enzymes mentioned herein are also suitable for carrying out oxidation steps of the 4-hydroxy acids in Step 3C1 and step 3C2.

(E.C. 1.2.1.63) from cyclohexanone degradation pathways are known to oxidize 6-oxohexanoate to adipate[47]. Such enzymes have been identified in *Acinetobacter* sp[47]., *Rhodococcus* sp. (strain RHA1), and *Burkholderia rhizoxinica* HKI 454 and their sequences are shown in the table below. Due to the similarity in the length of the substrates and their chemical nature, these enzymes can also be used to

| Gene | Genbank ID | Name | Organism |
|---|---|---|---|
| YDR541C | NC_001136.10 | Carbonyl reductase(NADPH-dependent) | *Saccharomyces cerevisiae* |
| YDR368W | NC_001136.10 | Carbonyl reductase(NADPH-dependent) | *Saccharomyces cerevisiae* |
| YAL060W | NC_001133.9 | R,R)-butanediol dehydrogenase | *Saccharomyces cerevisiae* |
| YOL151W | NC_001147.6 | GRE2 methylglyoxal reductase | *Saccharomyces cerevisiae* |
| YJR096w | AY558257.1 | Aldo-keto reductases | *Saccharomyces cerevisiae* |
| YPL113c | Q02961.1 | 2-hydroxyacid dehydrogenase | *Saccharomyces cerevisiae* |
| YLR070c | Q07993.1 | xylulase reductase | *Saccharomyces cerevisiae* |
| YGL157w | P53111.1 | NADPH-dependent aldehyde reductase ARI1 | *Saccharomyces cerevisiae* |
| YGL039w | AAT92784.1 | Carbonyl reductase(NADPH-dependent) | *Saccharomyces cerevisiae* |

Other relevant alcohol dehydrogenases to catalyze these oxido-reductions steps on the desired substrates include 3-hydroxyl-Acyl-CoA dehydrogenases, 2-hydroxypropyl-COM dehydrogenases, as well short chain and medium chain secondary alcohol dehydrogenases shown in Table below. 3-hydroxyadipyl-CoA dehydrogenase have been shown to be catalyzed by paaC and PhaC [69][70]. Alternatively, acetoacetyl-CoA reductases which give 3-hydroxybutyryl-CoA, of Clostridia are also good candidates[71].

catalyze the other steps. Additional enzymes that serve as good candidates include aldehyde dehydrogenases that oxidize hexanal to hexanoic acid, such as long chain aldehyde dehydrogenases (E.g: *Geobacillus thermoleovorans* B23 AldH which is NAD-dependent enzyme)[54]. Other such biochemically characterized long chain aldehyde dehydrogenases[72,73] of interest are also listed in table below. Additionally, enzymes oxidizing 2,5-dioxovalerate to 2-oxo-

| Genebank ID | EC | Name | Organism |
|---|---|---|---|
| ABC50090.1. | 1.1.1.2 | Secondary-alcohol dehydrogenase | *Thermoanaerobacter ethanolicus* |
| CAA09258 | 1.1.1.1 | Medium and short chain secondary alcohol dehydrogenase | *Sulfolobos solfataricus* |
| AAA34408 | 1.1.1.1 | (R) - secondary alcohol dehydrogenase | *Saccharomyces cerevisiae* |
| CAA99098 | 1.1.1.1 | (S) - secondary alcohol dehydrogenase | *Saccharomyces cerevisiae* |
| Q56840 | 1.1.1.268 | 2-(R)-hydroxypropyl-CoM dehydrogenase | *Xanthobacter Autotrophicus* |
| Q56841 | 1.1.1.269 | 2-(S)-hydroxypropyl-CoM dehydrogenase | *Xanthobacter Autotrophicus* |
| ADX68565 | 1.1.1.211 | 3-hydroxyacyl-CoA dehydrogenase | *Weeksella virosa* |
| AAK18167 | 1.1.1.35 | 3-hydroxyacyl-CoA dehydrogenase | *Pseudomonas putida* |
| YP_004366917 | 1.1.1.78 | 3-hydroxy-2methylbutyrl-CoA-dehydrogenase | *Marinithermus hydrothermalis* |
| ABF82235.1 | 1.1.1.35 | 3-hydroxyacyl-CoA dehydrogenase | *Pseudomonas fluorescens* |
| EDK32512.1 | 1.1.1.35 | 3-hydroxyacyl-CoA dehydrogenase, hdb1 | *Clostridium Kluyveri* |
| EDk34807.1 | 1.1.1.35 | 3-hydroxyacyl-CoA dehydrogenase, hdb2 | *Clostridium Kluyveri* |
| NP_349314.1 | 1.1.1.35 | 3-hydroxyacyl-CoA dehydrogenase, hdb | *Clostridium acetobutyylicum* |
| AAM14586.1 | 1.1.1.35 | 3-hydroxyacyl-CoA dehydrogenase, hdb | *Clostridium beijerinckii* |

E.C. 1.2.1-Oxidoreductase (aldehyde to acid)

Several pathway steps such as steps 4B1, 4B4, 4B5, 4B6, and 4B7, as depicted in FIG. 4, in the various pathways for synthesis of adipate involve the oxidation of aldehyde group to acid. The enzymes for these steps are 4B1 (a 4-hydroxy-2,3-dehydro-6-oxohexanoyl-CoA 6-dehydrogenase), 4B4 (a 4-hydroxy-6-oxohexanoyl-CoA 6-dehydrogenase), 4B5 (a 4,5-dehydro-6-oxohexanoyl-CoA 6-dehydrogenase), 4B6 (a 6-oxohexanoyl-CoA 6-dehydrogenase), and 4B7 (a 6-oxohexanoate 6-dehydrogenase). Aldehyde dehydrogenases glutarate are also of interest, particularly that from Azospirillum brasilense as it also oxidizes a range of aldehydes (C1-C8 linear aldehydes), as well as well substituted aldehydes glutaraldehyde, betaine aldehyde, glycoaldehyde and succinic semialdehyde[74]. Alternatively, succinic semialdehyde dehydrogenase from *R. norvegicus* [75]has been shown to oxidize hexanal a substrate similar to step 4B5 is also of interest.

| EC | Gnebank ID | Name | Organism |
|---|---|---|---|
| 1.2.1.22 | AAB99418.1 | glyceraldehyde-3-phosphate dehydrogenase | *Methanococcus jannaschii* |
| 1.2.1.24 | BAE94276.1 | Succinate-semialdehyde dehydrogenase | *Azospirillum brasilense* |
| 1.2.1.3 | AAG43027.1 | aldehyde dehydrogenase | *Oryza sativa* |
| 1.2.1.5 | BAB96577.1. | aldehyde dehydrogenase | *Flavobacterium frigidimaris* |
| 1.2.7.5 | CAA56170.1 | aldehyde ferredoxin oxidoreductase | *Pyrococcus furiosus* |
| 1.2.1.63 | ABH00320.1. | 6-oxohexanoate dehydrogenase | *Rhodococcus* sp. (strain RHA1) |
| 1.2.7.6 | AAC70892.1. | glyceraldehyde-3-phosphate dehydrogenase | *Pyrococcus furiosus* |
| 1.2.1.63 | YP_004022361 | 6-oxohexanoate dehydrogenase | *Burkholderia rhizoxinica* HKI 454 |

-continued

| EC | Gnebank ID | Name | Organism |
|---|---|---|---|
| 1.2.1.48 | BAB16600.1. | long chain aldehyde dehydrogenase | *Geobacillus thermoleovorans* B23 |
| 1.2.1.48 | ZP_03557706 | long chain aldehyde dehydrogenase | *Geobacillus* sp. Y412MC61 |
| 1.2.1.48 | BAB11888 | long chain aldehyde dehydrogenase | *Acinetobacter* sp. M-1 |
| 1.2.1.48 | BAA75508 | long chain aldehyde dehydrogenase | *Oleomonas sagaranensis* |
| 1.2.1.26 | BAE94276 | glutarate-semialdehyde dehydrogenase, 1 | *Azospirillum brasilense* |
| 1.2.1.26 | AB275768 | glutarate-semialdehyde dehydrogenase, 2 | *Azospirillum brasilense* |
| 1.2.1.26 | AB275769 | glutarate-semialdehyde dehydrogenase, 3 | *Azospirillum brasilense* |
| 1.2.1.24 | AAA67058.1. | Succinate-semialdehyde dehydrogenase | *rattus Norvegicus* |

E.C. 2.8.3-Coenzyme A-Transferases

CoA-transferases catalyze the reversible transfer of a CoA moiety from one molecule to another. Many transformations require a CoA-transferase to interconvert carboxylic acids to their corresponding acyl-CoA derivatives and vice versa, including 4F1 (adipyl-CoA transferase), 4F2 (6-oxo-hexanoyl-CoA transferase), 4F3 (6-hydroxyhexanoyl-CoA transferase), 4F5 (6-aminohexanoyl-CoA transferase), 3G1 (2,4-dihydroxyadipate CoA-transferase, a 2,4,6-trihydroxy-hexanoate CoA-transferase, or a 6-amino-2,4-dihydroxy-hexanoate CoA-transferase), 2E (2-hydroxy-adipate CoA-transferase, 2,6-dihydroxy-hexanoate CoA-transferase or a 6-amino-2-hydroxyhexanoate CoA-transferase), 3G2 (2-hydroxy-4oxoadipate CoA-transferase, a 2,6-dihydroxy-4oxo-hexanoate CoA-transferase, or a 6-amino-2-hydroxy-4oxo-hexanoate CoA-transferase), and 3G5 (4-hydroxyadipate CoA-transferase, a 4,6-dihydroxyhexanoate CoA-transferase, or a 6-amino-4-hydroxyhexanoate CoA-transferase) of FIGS. 2-4. Many CoA transferase enzymes are either known to carry out these transformations ot are suited for this and are described below. Pathway enzymes catalyzing reactions in the esterification direction are termed carboxylate CoA-transferase (E.g. 4-hydroxyadipate CoA-transferase, 3G5), whereas catalysis in the reverse direction are termed as carboxyl-CoA transferase (4F1, Adipyl-CoA transferase). As many different acids or CoA-esters are used as the other reaction partners, it is omitted form the systemic name of the enzyme. It is given that any give metabolically available CoA-ester or acid can be used as the reaction partner by these enzymes to catalyze these steps.

HadA, 2-hydroxyisocaproate CoA transferase, a part of the oxidative branch of leucine fermentation in *C. difficile* has been shown to catalyze the reversible attachment of a CoA molecule to C6 compounds such as 2(R)-hydroxyiso-caproate, isocaproate, and 2(E)-isocaprenoate[62]. Its activity towards C6 compounds that are structurally related to substrates of the desired steps along with the fact that it is located next to LdhA from *C. difficile* (see above), make the enzyme a prime candidate for catalyzing many of these steps. Glutaconate CoA transferase (gctAB) from *Acidaminococcus fermentans* has been shown to transfer Coenzyme A moiety to both R/S isomers of 2-(R/S)-hydroxyglutarate as well as 2-(R)-hydroxyadipate (step 2E) using different CoA donors such as acetyl-CoA, & glutaconyl-CoA. Additionally it has also been shown to use glutaconyl-CoA as the CoA donor to reversibly attach CoA molecule to adipate (step 4F1), propionate, butyrate, 2(R/S)-hydorxyglutarate and glutarate, in addition to glutaconate, acrylate, crotonate and isocrotonate, when acetyl-CoA is the CoA donor[76,77]. Shown in table below are their sequences as well as homologous sequences. Also of particular interest are 3-oxoacid CoA-transferases for catalyzing these steps, especially 3-oxoadipyl-CoA transferases, as it uses a structurally and chemically similar substrate to the desired substrates. Such enzymes encoded by pacI/pacJ in *Pseudomonas putida*[78], *Acinetobacter* baylyi, *Streptomyces coelicolor*, by genes catI/catJ in *Pseudomonas knackmussii*[78] and are also present in *Helicobacter pylori*[79] and *B. subtilis*[80]. Also of interest is CoA-transferase described from *Clostridium aminovalericum* (no gene identified)[81], which is capable of transfering CoA to a range of substrates such as 5-hydroxyvalerate, 5-hydroxy-2-pentenoate and 4-pentenoate that are structurally relevant to the transformations herein. Malate CoA-transferases are also relevant to transformations described herein, particularly to steps 3G1 and 3G2, which lead to C6 substituted 2-hydroxy-4-oxo/hydroxyacyl-CoAs, substrates similar to malyl-CoA. Such an enzyme (genes smtA, smtB accession number NZ_AAAH02000019, 19,200 to 30,600 bps) has been characterized form the 3-hydroxy propionate cycle in the phototrophic bacterium *Chloroflexus aurantiacus*[82]. Other relevant CoA-transferases include aceto-acetyl-CoA transferases of *E. coli*, which has a relatively broad substrate acceptance[83,84].

| Gene | Genebank ID | Name | Organism |
|---|---|---|---|
| gctA | CAA57199.1 | Glutaconate-CoA transferase | *Acidaminococcus fermentans* |
| gctB | CAA57200.1 | Glutaconate-CoA transferase | *Acidaminococcus fermentans* |
| HadA | AY772818 | Glutaconate-CoA transferase | *Clostridium Difficile* |
| gctA | ACJ24333.1 | Glutaconate-CoA transferase | *Clostridium symbiosum* |
| gctB | ACJ24326.1 | Glutaconate-CoA transferase | *Clostridium symbiosum* |
| gctA | NP_603109.1 | Glutaconate-CoA transferase | *Fusobacterium nucleatum* |
| gctB | NP_603110.1 | Glutaconate-CoA transferase | *Fusobacterium nucleatum* |
| pcaI | AAN69545.1 | 3-oxoadipate CoA-transferase | *Pseudomonas putida* |
| pcaJ | NP_746082.1 | 3-oxoadipate CoA-transferase | *Pseudomonas putida* |
| catI | Q8VPF3 | 3-oxoadipate CoA-transferase | *Pseudomonas knackmussii* |
| catJ | Q8VPF2 | 3-oxoadipate CoA-transferase | *Pseudomonas knackmussii* |
| pcaI | AAC37146.1. | 3-oxoadipate CoA-transferase | *Acinetobacter baylyi* |
| pcaJ | AAC37147.1. | 3-oxoadipate CoA-transferase | *Acinetobacter baylyi* |
| smtA/smtB | see text | malyl-CoA-transferase | *Chloroflexus aurantiacus* |
| pcaI | NP_630776.1 | 3-oxoadipate CoA-transferase | *Streptomyces coelicolor* |
| pcaJ | NP_630775.1 | 3-oxoadipate CoA-transferase | *Streptomyces coelicolor* |

| Gene | Genebank ID | Name | Organism |
| --- | --- | --- | --- |
| | YP_627417 | 3-oxoacid CoA-transferase | *Helicobacter pylori* |
| | YP_627418 | 3-oxoacid CoA -transferase | *Helicobacter pylori* |
| scoA | NP_391778 | 3-oxoacid CoA-transferase | *Bacillus subtilis* |
| scoB | NP_391777 | 3-oxoacid CoA-transferase | *Bacillus subtilis* |
| atoA | P76459.1 | acetoacetyl-CoAtransferas | *Escherichia coli* |
| atoD | P76458.1 | acetoacetyl-CoAtransferas | *Escherichia coli* |

E.C. 6.2.1-Coenzyme A-ligases or Synthetases

An alternative to using CoA-transferases is using a CoenzymeA-ligase to catalyze steps 2E, 3G1, 3G2, 3G5, 4F1, 4F2, 4F3, and 4F5. Many acyl-CoA ligases are known to catalyze the reversible hydrolysis of CoA esters using ADP resulting in the concomitant formation of ATP (forming ADP in reverse direction). By generating ATP this subset of ligases do not loose the energy stored in the thiester bond, which is advantageous for production of adipate in microbial host. Succinyl-CoA synthetase (SCS-Tk) from the hyperthermophilic archaea *Thermococcus* kodakaraensishas comprises of two sub units (α/β), and has been shown to encode a acyl-coenzyme A ligase involved in synthesis of diacids such as adipate (Step 2E and step 4F1) and others (lutarate, butyrate, propionate, and oxalate), by preserving the energy present in the thioester bond (due to formation of ATP). ACS-Tk (same sub unit b as SCS-Tk) is another promising candidate to carry out transformations and is also equally flexible in its substrates. Paralogs of these enzymes have been found in other thermophiles such as *P. abyssi* (PAB), *P. furiosus* (PF), and *P. horikoshii* (PH)[85]. Other relevant CoA-ligases include SucCD from *E. coli*[86], CoA-ligases (isozymes) ACDI/II of *Archaeoglobus fulgidus* (active with many linear, branched chain acyl-CoA), and that of *pseudomonas* puitda[88] were found to have activity on many carboxylates (C3-C8 carboxylates) molecules. Another candidate of interest includes 6-carboxy-hexanoyl-CoA ligase (EC 6.2.1.14) form *Pseudomonas mendocina* that works with C8 and C9 dioates to make the corresponding CoA esters[89].

*coli*[91][92]. Ydil, and YbdB both show activity on a diverse range of CoA molecules including hexanoyl-CoA.

| Gene | Genebank ID | Name | Organism |
| --- | --- | --- | --- |
| tesA | NP_415027 | acyl-coa hydrolase | *Escherichia coli* |
| acot12 | NP_570103.1 | acyl-coa hydrolase | *Rattus norvegicus* |
| tesB | NP_414986 | acyl-coa hydrolase | *Escherichia coli* |
| acot8 | AAB71665.1. | acyl-coa hydrolase | *Homo sapiens* |
| ybgC | NP_415264 | acyl-coa hydrolase | *Escherichia coli* |
| paaI | NP_415914 | acyl-coa hydrolase | *Escherichia coli* |
| ybdB | NP_415129 | acyl-coa hydrolase | *Escherichia coli* |
| Ydil | AAC74759.2. | acyl-coa hydrolase | *Escherichia coli* |

E.C. 1.3.1-Alkene reductase

Steps 2J, 2C, 2G, 3E1, 3E2, 4E3, 4E4, 3K2, 3K1, and 4F4, as depicted in FIGS. 2-4, in the various pathways for synthesis of adipate involve the reduction of alkene group to a alkane. Specifically step 2J requires reduction of 4,5-dehydro-2-hydroxy-adipyl-CoA, step 2C requires reduction of 3,4-dehydro-2-oxo-adipate, 6-hydroxy-3,4-dehydro-2-oxohexanoate and 6-amino-3,4-dehydro-2-oxohexanoate, step 2G requires reduction of 2,3-dehydro-adipyl-CoA, 6-hydroxy-2,3-dehydro-hexanoyl-CoA and 6-amino-2,3-dehydro-hexanoyl-CoA 2,3-reductase, step 3E1 requires reduction of 2,3-dehydro-4-oxoadipyl-CoA, 6-hydroxy-2,3-dehydro-4-oxohexanoyl-CoA, and a 6-amino-2,3-dehydro-4-oxohexanoyl-CoA 2,3-reductase, step 3E2 required reduction of 2,3-dehydro-4-oxoadipate, 6-hydroxy-2,3-dehydro-4-oxohexanoate and 6-amino-2,3-dehydro-4-oxohexanoate,

| Gene | Genebank ID | Name | Organism |
| --- | --- | --- | --- |
| TK1880 | BAD86069.1. | succinyl-CoA synthetase-a | *Thermococcus kodakaraensishas* |
| TK0139 | NC_006624.1. | acetyl-CoA synthetase-a | *Thermococcus kodakaraensishas* |
| TK0943 | BAD85132.1. | acetyl-CoA synthetase-b | *Thermococcus kodakaraensishas* |
| sucC | NP_415256.1 | succinyl-CoA synthetase-a | *Escherichia coli* |
| sucD | AAC73823.1 | succinyl-CoA synthetase-b | *Escherichia coli* |
| PF1540 | AAL81664.1. | acetyl-CoA synthetase-a | *Pyrococcus furiosus* |
| PF1787 | AAL81911.1. | acetyl-CoA synthetase-b | *Pyrococcus furiosus* |
| PAB0854 | CCE70736.1. | acetyl-CoA synthetase-a | *Pyrococcus Abyssi* |
| PAB2113 | CAB49275.1 . | acetyl-CoA synthetase-b | *Pyrococcus Abyssi* |
| PH1928 | BAA31055.1. | succinyl-CoA synthetase-a | *Pyrococcus horokoshii* |
| Ph1788 | BAA30907.1 | succinyl-CoA synthetase-b | *Pyrococcus horokoshii* |
| AF1211 | NP_070039.1 | acyl-CoA synthetase | *Archaeoglobus fulgidus* |
| AF1983 | NP_070807.1 | acyl-CoA synthetase | *Archaeoglobus fulgidus* |
| paaF | AAC24333.2 | acyl-CoA synthetase | *Pseudomonas putida* |
| bioW | CAA10043.1 | pimeloyl-CoA ligase | *Pseudomonas mendocina* |

Other enzymes belonging to the following other E.C. 6.2.1-classes can also be used to carry out the desired transformations. E.C. 3.2.1-CoA hydrolases Steps 4F1, 4F2, 4F3 and 4F5 can be catalyzed by CoA hydrolases. CoA hydrolase (4F1) that produces adipate from adipyl-CoA (4F1) has been identified in *Homo sapiens* and biochemically characterized[90]. Other hydrolases of interest include tesA, tesB, Ydil, paaI, ybgC, and YbdB from *E.* step 4E3 requires reduction of 4,5-dehydroadipyl-CoA, step 4E4 requires reduction of 4,5-dehydro-6-oxohexanoyl-CoA, step 3K2 requires reduction of 2,3-dehydro-4-hydroxyadipate, 4,6-dihydroxy-2,3-dehydrohexanoate, and 6-amino-2, 3-dehydro-4-hydroxyhexanoate, step 3K1 requires reduction of 2,3-dehydro-4-hydroxyadipyl-CoA, 4,6-dihydroxy-2,3-dehydrohexanoyl-CoA, and 6-amino-2,3-dehydro-4-hydroxyhexanoyl-CoA and Step 4F4 requires reduction of 4,5-dehydro-6-oxohexanoate. Alkene reductases are well known enzymes in literature and many such enzymes capable of catalyzing each of this step on the desired or similar substrate is described herein.

Enoyl-CoA reductases, that catalyze the reduction of enoyl-CoA to acyl-CoA in absence of or presence of a flavin mediator can be used to catalyze steps 2G, 3E1, and 3K1. Direct reduction of trans2-enoyl-CoA using NADH has been shown to drive flux through a synthetic n-butanol pathway in E. coli by effectively introducing a kinetic trap at the crotonyl-CoA reduction step. Trans-2-enol CoA reductase (TER) from T. denticola has been shown to catalyze this reduction using NADH as the cofactor. TdTER exhibits a 7-fold enhanced activity for trans-2-hexenoyl-CoA[93] as compared to crotonyl-CoA and is a suitable candidate for these transformations. Many of its homologues shown in table below are also relevant. Similarly, TER from *Euglena gracilis* has also been shown to utilize NADH as cofactor, and exhibit activity for reduction of C6 thioesters such as trans-2-hexenoyl-CoA[94]. Many homologues of EgTER have also been reported, which can also be used herein, some of which are shown below. NADPH dependent human peroxisomal TER showed activity towards acyl-CoAs ranging in chain length from 4 to 16 carbon atoms[95] is also a suitable candidate for carrying out these transformations.

ate reductases (enr) of clostridia can be used to catalyze this step[98]. Enoate reductases of OYE family and others, have been shown to be extremely promiscuous towards the substrates they reduce[99]. Of particular interest for carrying out reduction of alkenes conjugated to carbonyl group in Step 2C, 3E2, 3E1, 4F4, and 4E4 is XenA from *Pseudomonas putida*, KYE1 from *Kluyveromyces lactis*, and ER from *Yersinia bercovieri*, that have been shown to reduce a range of linear and cyclic α,β unsaturated ketones and aldehydes [100]. *H. vulgare* alkenal reductase[101], and OYE (*B. subtilis*)[102] are also extremely promiscuous towards the substrates they reduce including trans-2-hexenal (similar to Step 4F4, and 4E4). Other enzymes reducing such "enal" substrates include a tomato OYE capable of reducing hexenal (LeOPR, also reduces α,β-unsaturated aldehydes, ketones, maleimides and nitroalkenes, dicarboxylates and di-methyl esters (e.g., cinnamaldehyde, trans-dodec-2-enal, 2-phenyl-1-nitropropene, ketoi-sophorone, N-ethylmaleimide, a-methylmaleic acid) and 12-oxophytodienoic acid), OYE from *B. subtilis* also reducing 2-hexenal (in addition to α,β-unsaturated aldehydes, ketones, maleimides and nitroalkenes, dicarboxylic acids and dimethyl esters), P1-zeta-crystallin (P1-ZCr) NADPH:quinone oxidoreductase in *Arabidopsis thaliana* (catalyzed the reduc-

| Genebank ID | EC | Name | Organism |
|---|---|---|---|
| ABA80143.1. | 1.3.1.86 | Crotonyl-CoA reductase | *Rhodobacter sphaeroides* |
| AAW66853.1. | 1.3.1.44 | Trans-2-enoyl CoA reductase (NADH) | *Euglena Gracilis* |
| BAA05651.1. | 1.3.1.44 | Trans-2-enoyl-CoA reductase | *Saccharomyces cerevisiae* |
| CAG82338.1. | 1.3.1.44 | Trans-2-enoyl CoA reductase (NADPH) | *Yarrowia lipolytica* |
| CAA88344.1. | 1.3.1.44 | Trans-2-enoyl CoA reductase | *Saccharomyces cerevisiae* |
| ABV64023.1. | 1.3.1.44 | Trans-2-enoyl CoA reductase | *Bacillus pumilus* |
| AE017248 | 1.3.1.44 | Trans-2-enoyl CoA reductase | *Treponema Denticola* |
| ZP01243065 | 1.3.1.44 | Trans-2-enoyl CoA reductase | *Flavobacterium johnsoniae* |
| YP677688; | 1.3.1.44 | Trans-2-enoyl CoA reductase | *Cytophaga hutchinsonii* |
| ZP01118954 | 1.3.1.44 | Trans-2-enoyl CoA reductase | *Polaribacter irgensii* |
| ZP01298067 | 1.3.1.44 | Trans-2-enoyl CoA reductase | *Coxiella burnetii* |
| AF021854 | 1.3.1.45 | Trans-2-enoyl CoA reductase | *Homo Sapiens* |

The reduction of activated double bonds i.e double bonds next to carbonyl or carboxylate group can be catalyzed by many enzymes including enoate reductases of the old yellow enzyme family, alkenal-reductases (EC 1.3.1.74) as well as by quinone-reductases. The OYE enzyme typically uses a flavin (FMNH2) cofactor, which gets oxidized at each turnover and is in turn reduced by NAD(P)H, whereas the alkenal-reductases and quinone-reductases can directly employ NAD(P)H for reduction. Step 3E2 is catalyzed by maleylacetate (2,3-dehydro-4-oxoadipate) reductases, that are well known in literature as they are a part of aromatic degradation pathways. Two such maleylacetate reductases are shown below which have been shown to catalyze Step 3E2[96,97]. Alternatively, 2-enoate reductases can also be used to carry out this step as well as 2J, 3K2, and 4E3 which involve reduction of 2,3-enoate or 4,5-enoate moiety. 2-enotion of 2-alkenals of carbon chain C(3)-C(9) with NADPH including 4-hydroxy hexenal and hexenal), ene-reductases of Synechococcus sp. PCC 7942 and ten different enzymes from cyanobacteria (catalyze reduction of a range of substrates including hexenal) and OYE1-3 from *saccharomyces* (reduce substituted and nonsubstituted α,β-unsaturated aldehydes, ketones, imides, nitroalkenes, carboxylic acids, and esters; cyclic and acyclic enones). [103-108] Many of these enzymes reduce 2-hexenal and tolerate substitution at the C6 position of 2-hexenal (Steps 4E4). Many of these enzymes (sequences shown in table below) described herein are extremely flexible in their substrate specificity and are expected to catalyze other reactions besides their preferred substrates that are also relevant to the steps (such as enoyl-CoA reduction or enoate reduction) described above.

| Genebank Accession No | Name | Organism |
|---|---|---|
| AAX99161.1 | NADPH: 2-alkenal alpha,beta-hydrogenase | *Hordeum vulgare* subsp. |
| NC_000964.3 | Old Yellow Enzyme. YqJM | *Bacillus subtilis* subsp. *subtilis* str. 168 |
| AAA64522 | 2-enoate reductase | *Saccharomyces cerevisiae* |
| BAF44524.1. | maleylacetate reductase | *Rhizobium* sp. MTP-10005 |

| Genebank Accession No | Name | Organism |
| --- | --- | --- |
| FJ821777.2 | maleylacetate reductase | *Pseudomonas* sp 1-7 |
| AAA17755.1. | NADH-dependent enoyl-ACP reductase | *Escherichia coli* (strain K12) |
| Y09960 | 2-enoate reductase | *Clostridium tyrobutyricum* |
| Y16136 | 2-enoate reductase | *Clostridium thermoaceticum* |
| Y16137 | 2-enoate reductase | *Clostridium kluyveri* |
| AAF02538 | 2-enoate reductase | *Pseudomonas putida* |
| P40952 | 2-enoate reductase | *Kluyveromyces lactis* |
| ZP 00823209 | 2-enoate reductase | *Yersinia bercovleri* |
| YP_002370366.1 | ene-reductases | *Cyanothece* sp. PCC 8801 |
| YP_002371879.1 | ene-reductases | *Cyanothece* sp. PCC 8801 |
| ZP_01620253.1 | ene-reductases | *Lyngbya* sp. PCC 8106 |
| YP_001869478.1 | ene-reductases | *Nostoc punctiforme* PCC 73102 |
| NP_485905.1 | ene-reductases | *Nostoc* sp PCC 7120 |
| YP_320425.1 | ene-reductases | *Anabaena variabilis* ATCC 29413 |
| NP_926774.1 | ene-reductases | *Gloeobacter violaceus* PCC 7421 |
| YP_001519129.1 | ene-reductases | *Acaryochloris marina* MBIC11017 |
| YP_001522070. 1 | ene-reductases | *Acaryochloris marina* MBIC11017 |
| YP 399492 | OYE | *Synechococcus* sp. PCC 7942 |
| CAA97878 | OYE | *Saccharomyces cerevisiae* |
| Q02899 | OYE1 | *Saccharomyces carlsbergensis* |
| AJ242551 | OYE. LeOPR | *Lycopersicon esculentum* cv. |
| CAC01710.1. | NADP-dependent alkenal reductase P1 | *Arabidopsis thaliana* |

E.C. 1.4.1-Aminoacid dehydrogenases or E.C. 2.6.1 Transaminases

Transaminases catalyze the reversible transfer of amino group from a amine-donor to aldehyde acceptor. Amination of terminal aldehydes can be catalyzed by PLP (pyridoxal phosphate)-dependent transaminases belonging to E.C. 2.6.1. Transaminases catalyze the transfer of amino group from a range of different donors including amino acids, nucleotides as well as small molecules to the terminal aldehyde group in PLP dependent manner. Steps 3G1-3G5 involve such steps (in the deaminating direction on 6-amino group of the substrates). Of interest to carry out this transformation includes members of 4-aminobutyrate-transaminase (E.C. 2.6.1.9), which can reversibly form 4-aminobutyrate and 2-oxoglutarate from succinic semialdehyde and glutamate, which are similar chemically and structurally to the desired transformations. Also of interest are lysine 6-amino transferases (6-deaminating, E.C. 2.6.1.36) many of these are characterized (sequences in table below), which give 6-oxo-2-aminohexanoate as products, highly structurally similar to the desired substrates of the ADA pathway steps (deaminating direction). Multiple 4-aminobutyrate transaminase have been reported and have broad specificity [109,110][111]. Such class of enzymes have been shown in *E. coli*[112,113], and as well in *Pseudomonas fluorescens, Mus musculus*, and *Sus scrofa*, and use 6-aminohexanoate (Step 4G2) as substrates[114]. Transaminase using terminal amines/aldehydes (E.C. 2.6.1.48 5-amino valerate transaminase; E.C. 2.6.1.43 aminolevulinate transaminase, E.C. 2.6.1.8 beta-alanine transaminase) as substrates or diamines [115][116][117][115][118] as substrates (E.C. 2.6.1.76 diamino butyrate transaminase and 2.6.1.82 putrsescine transaminase[113]) are relevant, some of which have been shown to work on lysine as well as function on 4-aminobutyrate. Enzymes characterized from these members are also listed in Table.

| Gene | Genebank ID | Name | Organism |
| --- | --- | --- | --- |
| gabT | NP_417148.1 | 4-aminobutyrate trasaminase | *Escherichia coli* |
| puuE | NP_415818.1 | 4-aminobutyrate trasaminase | *Escherichia coli* |
| lat | BAB13756.1 | diamine trasnferase | *Flavobacterium letescens* |
| lat | AAA26777.1 | diamine trasnferase | *Streptomyces clavuligenus* |
| dat | P56744.1 | Amintransferase | *Acinetobacter baumanii* |
| ygjG | NP_417544 | diamine trasnferase | *Escherichia coli* |
| spuC | AAG03688 | diamine trasnferase | *Pseudomonas aeruginosa* |
| SkyPYD4 | ABF58893.1 | β-alanine-pyruvate transaminase | *Lachancea kluyveri* |
| SkUGA1 | ABF58894.1 | 4-aminobutyrate trasaminase | *Lachancea kluyveri* |
| UGA1 | NP_011533.1 | 4-aminobutyrate trasaminase | *Saccharomyces cerevisiae* |
| Abat | P50554.3 | GABA | *Rattus norvegicus* |
| Abat | P80147.2 | 4-aminobutyrate trasaminase | *Sus scrofa* |
| abat | NP_766549.2 | 4-aminobutyrate trasarninase | *Mus musculus* |
| gabT | YP_257332.1 | 4-aminobutyrate trasaminase | *Pseudomonas fluorescens* |
| abat | NP_999428.1 | GABA | *Sus scrofa* |

Alternatively, amination can be catalyzed by amino acid dehydrogenases or amine oxidases belonging to E.C. 1.4.-in the presence of cofactors such as reduced ferricytochrome, NAD(P)H, FMNH$_2$, FADH$_2$, H$_2$O$_2$, reduced amicyanin or azurin. Amino acid dehydrogenases and amine oxidases belonging to the E.C. group 1.4.-or homologous enzymes of these sequences can also be used to carry out this step. Alternatively amino acid dehydrogenases that interconvert aminoacids and NADH (electron donor can very) to corresponding 2-oxoacids, ammonia, and NAD can also be used to carry out this reactions. Although any such enzyme can be used, lysine dehydrogenases (6-deaminating to give 2-aminoadipate) are of particular interest in catalyzing these steps. Exemplary enzymes can be found in *Geobacillus stearothermophilus*[119], *Agrobacterium tumefaciens*[120], and *Achromobacter denitrificans*[121].

| Name (Gene) | Genbank ID | Organism |
|---|---|---|
| lysDH | BAB39707 | *Geobacillus stearothermophilus* |
| lysDH | NP_353966 | *Agrobacterium tumefaciens* |
| lysDH | AAZ94428 | *Achromobacter denitrificans* |

E.C.2.1.3-N-acetylation/N-deacetylation:

Although not explitly shown as a step in adipate pathway it is understood that for ADA intermediates from pyruvate and 3-aminopronanal, the C6 amino group can be protected to avoide spontaneous lactamization or unwanted reactions. This results in addition of two additional steps that would involve addition and removal of such a protecting group in any of the pathways using 3-amino propanal as the C3 aldehyde using acetylases and deacetlyases respectively. In addition synthesis of 3-aminopropanal from metabolic precursors may require protection of primary amino group. N-Acetyltransferases transfer an acetyl group to an amine, forming an acetamido moiety. Lysine N-acetyltransferase (EC 2.3.1.32), glutamate N-acetyl transferase (OAT, EC 2.3.1.35 and EC 2.3.1.1), and diamine N-acetyltransferase (EC 2.3.1.57) can be used to carry out the acetylation of primary amine group. Lysine N-acetyltransferase transfers the acetyl moiety from acetyl phosphate to the terminal amino group of L-lysine, beta-L-lysine or L-ornithine can be used to carry this transformation. Lysine N-acetyltransferase has been characterized from *Methanosarcina mazei* (Pfluger et al., Appl Environ. Microbiol. 69:6047-6055 (2003)). Methanogenic archaea are also predicted to encode enzymes with this functionality (Pfluger et al., Appl Environ. Microbiol. 69:6047-6055 (2003)). Diamine N-acteyltransferases use acetyl-CoA as donor to acylate terminal diamines can also be used to carry out this amide formation reaction. Alternatively, glutamate N-acetyl transferase (OAT, EC 2.3.1.35 and EC 2.3.1.1) that catalyzes the acetylation of glutamate using acetyl-CoA or N-acetyl ornithine can also be used to carry out the acetylation reaction as well as the deacetylation reaction.

described herein. ADA pathway steps leading upto the synthesis of these intermediates combined with enzymatic steps that convert these intermediates to 6-aminohexanoate give pathways for synthesis of 6-aminohexanoate (AHA) from pyruvate and C3 aldehydes (3-oxopropionate, 3-hydroxypropanal and 3-aminopropanal). Such pathways for production of 6-aminohexanoate (AHA pathways 1-78) from pyruvate and C3 aldehydes (3-oxopropionate, 3-hydroxypropanal and 3-aminopropanal) are described below along with the enyzmes required to carry out each desired step of all pathways.

Synthesis of 6-amino hexanoate from pyruvate and 3-amino propanal 6-amino hexanoate (AHA) (49, FIG. 4) is an intermediate (product of step 4F5, FIG. 4) in the pathways (ADA86 and ADA89) for the synthesis of adipic acid from pyruvate and 3-amino propanal as described above in Example IV and depicted in FIGS. 2-4. Hence, pathways ADA 84 and 87 can be used to make 6-amino hexanoate. However, removing steps for converting 6-aminohexanoate to adipic acid in these pathways results in a 6-aminohexanoate pathway (pathway AHA 1 and 2, see Table B) from pyruvate and 3-amino propanal, which is selective for its production.

Synthesis of 6-amino hexanoate from pyruvate and 3-oxo propanol 6-oxo-hexanoate (39, FIG. 4) is an intermediate of adipic acid synthesis pathways (ADA 27, 28, 30, 31, 65-75, 80-83, Table A, Example IV) from pyruvate and C3 aldehyde 3-hydroxypropanal. By not including the step 4B7 (FIG. 4) that converts 6-oxo-hexanoate to adipic acid, these pathways are now modified for synthesis of 6-oxo-hexanoate from pyruvate and 3-hydroxypropanal. 6-oxo-hexanoate is converted to 6-amino hexanoate by amination (Step 5J, FIG. 5) resulting in 6-amino hexanoate pathway (AHA 3-21, table B) from pyruvate and 3-hydroxypropanal. Additionally, 6-oxo-hexanoyl-CoA (38, FIG. 4) is a precursor of adipic acid synthesis pathways (ADA 26, 29, 43-53, Table A, and Example IV) from pyruvate and 3-hydroxypropanal. By not including the steps 4B6 and 4F1 (FIG. 4) that convert 6-oxo-hexanoyl-CoA (38, FIG. 4) to adipic acid, these pathways are now modified for synthesis of 6-oxo-hexanoyl-

| Genebank ID | EC | Name | Organism |
|---|---|---|---|
| AAL83905.1. | 2.3.1.57 | diamine N-acetyltransferase 2 | *Homo sapiens* |
| EDZ70156.1. | 2.3.1.1 | Arginine biosynthesis bifunctional protein ArgJ | *Saccharomyces cerevisiae* (strain AWRI1631) |
| AAS90753.1. | 2.3.1.35 | Glutamine N-acetyltransferase | *Corynebacterium crenatum* |
| NP_632959.1 | 2.3.1.32 | Lysine N-acetyltransferase | *Methanosarcina mazei* |

5. Synthesis Of 6-Amino-Hexanoate From Intermediates Of Adipic Acid Synthesis Pathway From Pyruvate And C3 Aldehydes (3-oxopropionate, 3-hydroxypropanal and 3-aminopropanal)

Multiple ADA pathways starting from pyruvate and C3 aldehydes (3-oxopropionate, 3-hydroxypropanal and 3-aminopropanal) have been described in Example IV (FIGS. 2-4), that precede through 6-aminohexanoate, or intermediates such as 6-oxohexanoate, 6-oxo-hexanoyl-CoA, and adipyl-CoA, that are converted to 6-aminohexanoate as CoA from pyruvate and 3-hydroxypropanal. 6-oxo-hexanoyl-CoA is converted to 6-aminohexanoyl-CoA by amination (Step 5I, FIG. 5), that is further converted to 6-amino hexanoate (Step 4F5, FIG. 5) by CoA-transferases, CoA-ligases or CoA hydrolases, to give 6-amino hexanoate synthesis pathways (AHA 22-34) from pyruvate and 3-hydroxypropanal.

Synthesis of 6-amino hexanoate from pyruvate and 3-oxo propionate

Adipyl-CoA an intermediate in the synthesis of adipate from pyruvate and 3-oxo propionate (ADA pathways 1-25, Table A, Example IV). Not including step 4F1 (FIG. 4) in these pathways results in a pathway capable of Adipyl-CoA synthesis. Adipyl-CoA is converted to 6-amino hexanoate in by its conversion to 6-oxo-hexanoate (step 5G, FIG. 5) by a CoA-dependent dehydrogenase followed by its conversion to 6-amino hexanoate (Step 5J) as mentioned above (AHA 35-59, Table B).

Exemplary Enzymes Capable of Catalyzing these Transformations are Described Below:

ADA pathways from pyruvate and C3 aldehydes (3-oxo-propionate, 3-hydroxypropanal and 3-aminopropanal) that precede through intermediates 6-aminohexanoate (from pyruvate and 3-aminopropanal), 6-oxohexanoate (from pyruvate and 3-hydroxypropanal), 6-oxo-hexanoyl-CoA (from pyruvate and 3-hydroxypropanal), and adipyl-CoA (from pyruvate and 3-oxopropionate), have been described in Example IV, along with the enzymes capable of catalyzing each step of these pathways, including steps leading up to the synthesis of these intermediates. Additionally enzymes necessary to convert these intermediates to 6-aminohexanoate are described below.

Step 5G: Conversion of Adipyl-CoA to 6-oxohexanoate by an adipyl-CoA 1-reductase (E.C.1.2.1)

This reaction is carried out CoA-dependent aldehyde dehydrogenase belonging to E.C.1.2.1 Coenzyme-A acylating aldehyde dehydrogenases (ALDH) are predominantly found in bacteria, and they are known to catalyze the reversible conversion of acyl-CoAs to their corresponding aldehydes using NAD(P)H. Additionally, hexanoyl-CoA reductases are relevant candidates to carry out this reaction. *E. coli* ADHE2 has been shown to reduce hexanoyl-CoA to hexanal (onto hexanol). PduP, an enzyme identified from *Salmonella enterica*, is responsible for catalyzing the oxidation of propionaldehyde to propionyl-CoA. PduP from *S. enterica* its homologues *Aeromonas hydrophila, Klebsiella pneumoniae, Lactobacillus brevis, Listeria monocytogenes,* and *Porphyromonas gingivalis* have been shown to be extremely promiscuous in their substrate specificity. They are known to reduce C2-C12 acyl-CoA molecules and are relevant to catalyze Step 5G. Other enzymes of interest include malonyl-CoA reductase, which is an analogues 3-carbon diacid reductase, found in S. todokadii[122], other archaea[3,4], and chloreflexus species[1,2] wherein the enzyme was split into two parts (CoA-ALDH and alcohol dehydrogenase for 3-hydroxypropionat eproduction), succinyl-CoA reductase (analogus C4 diacid) from *Clostridium kluyveri*[123] and sucD of *P. gingivalis*[124], and glutaryl-CoA reductase (analogous C5 diacid). Reduction of 5-hydroxyvaleryl-CoA to 5-hydroxypentanal propionyl-CoA reductase of *Salmonella typhimurium* has also been described (WO 2010/068953A2). ALDH from *Clostridium beijerinckii* strains B 593 is a promising candidate as it has been shown to catalyze the formation of butyraldehyde and acetaldehyde from burtyryl-CoA and acetyl-CoA using primarily NADH (but also work with NADPH). Aldh from *Acinetobacter* sp. HBS-2 has also been shown to carry out reaction in a NADH dependent manner. BphJ is a nonphosphorylating CoA-dependent ALDH from the polychlorinated biphenyl (PCB) pollutant-degrading bacterium *Burkholderia xenovorans* LB400 that catalyzes reversible reduction of Acyl-CoA (C2-C5) in the presence of NADH to the corresponding aldehydes[125]. Homologous dehydrogenases include (DmpG) from *pseudomonas* sp. Strain CF600. Other candidates include fatty acyl-CoA reductases such as that from cyanobacteria that work on longer chain lengths upto C18 acyl-CoA[126].

| Gnebank ID | Name or Gene | Organism |
|---|---|---|
| AAD39015 | PduP | *Salmonella enterica* |
| YP_855873 | PduP | *Aeromonas hydrophila,* |
| YP_001336844 | PduP | *Klebsiella pneumoniae,* |
| YP_795711 | PduP | *Lactobacillus brevis,* |
| NP_464690 | PduP | *Listeria monocytogenes,* |
| YP_001928839 | PduP | *Porphyromonas gingivalis* |
| AF157306 | AldH | *Clostridium beijerinckii* strains B 59 |
| CAA54035.1 | BphJ | *Burkholderia xenovorans* LB400 |
| CAA43226.1 | DmpF | *Pseudomonas* sp. CF600 |
| YP_001190808.1 | Msed_0709 | *Metallosphaera sedula* |
| NP_378167.1 | mcr | *Sulfolobus tokodaii* |
| NP_343563.1 | asd-2 | *Sulfolobus solfataricus* |
| YP_256941.1 | Saci_2370 | *Sulfolobus acidocaldarius* |
| AAA80209 | eutE | *Salmonella typhimurium* |
| NP_416950 | eutE | *Escherichia coli* |
| sucD | P38947.1 | *Clostridium kluyveri* |
| sucD | NP_904963.1 | *Porphyromonas gingivalis* |
| cACRs | YP_001865324 | *N. punctiforme* PCC 73102 |
| cACRs | YP_400611 | *S. elongates* PCC7942 |
| CAQ97226.1. | malonate-semialdehyde dehydrogenase (acetylating) | *Escherichia coli* 08 (strain IAI1) |
| ABS76007.1. | acetaldehyde dehydrogenase (acetylating) | *Bacillus amyloliquefaciens* (strain FZB42) |
| CCE17209.1. | 2-oxoisovalerate dehydrogenase (acylating) | *Arthrospira* sp. PCC 8005 |
| AAU43064.1. | methylmalonate-semialdehyde dehydrogenase (acylating) | *Bacillus licheniformis* (strain DSM 13/ ATCC 14580) |
| EKO43234.1. | hexadecanal dehydrogenase (acylating) | *Acinetobacter baumannii* AC30 |
| CAD21691.1. | phenylglyoxylate dehydrogenase (acylating) | *Azoarcus evansii* |
| AAA92347.1. | succinate-semialdehyde dehydrogenase (acylating) | *Clostridium kluyveri* (strain ATCC 8527/DSM 555/NCIMB 10680) |
| CAJ93826.1. | sulfoacetaldehyde dehydrogenase (acylating) | *Cupriavidus necator* (strain ATCC 17699/H16/DSM 428/Stanier 337) |

Step 5J and 5I: Conversion of 6-oxohexanoyl-CoA to 6-aminohexanoyl-CoA (step 5I) and 6-oxohexanoate to 6-aminohexanoate (step 5J)

Transaminases/amino acid dehydrogenases catalyze the reversible transfer of amino group from a amine-donor to aldehyde acceptor. Deamination of terminal amines 6-aminohexanoyl-CoA (Step 4G1, FIG. 4), and 6-aminohexanoate Step 4G2, FIG. 4), by transaminases/amino acid dehydrogenases to 6-oxohexanoyl-CoA and 6-oxohexanoate respectively has been described in Example IV. Its is understood that same enzyme can be used to carry out the reaction in reverse. The equilibirum products/substrate can be controlled by selecting the right enzyme as well as the reaction conditions.

6. Synthesis Of ε-Caprolactam From Pyruvate And C3 Aldehydes (3-oxopropionate, 3-hydroxypropanal and 3-aminopropanal) Through Precursors 6-aminohexnoate and 6-aminohexanoyl-CoA ε-caprolactam (CPL) is synthesized by spontaneous cyclization of 6-amino-hexanoyl-CoA (Step 5B, FIG. 5) as shown in FIG. 5. 6-amino-hexanoic acid pathways (AHA 1, 2, 22-34, Table B) proceed through 6-amino-hexanoyl-CoA as a intermediate, which can cyclize to give &-caprolactam. Thus pathways, are also pathways for production of ε-caprolactam. Removing step 4F5, which converts 6-aminohexanoyl-CoA to 6-aminohexanoate, from these pathways, will better enable conversion of 6-amino-hexanoyl-CoA to ε-caprolactam (pathways CPL1-13, Table C). ¿-caprolactam is also synthesized by cyclization (Step 5A, FIG. 5) of 6-amino-hexanoic acid by (Ritz, J., H. Fuchs, et al. (2000). Caprolactam. Ullmann's Encyclopedia of $_{SEP}{}^{L}$ Industrial Chemistry, Wiley-VCH Verlag GmbH & Co. KGaA) or by amido hydrolases. Alternatively, 6-amino-hexanoic acid can also be converted to 6-amino-hexanoyl-CoA (Step 5C, FIG. 5) by a 6-amino-hexanoate CoA-trasnferase or 6-aminohexanoate CoA-ligase, which will cyclize spontaneously to give &-caprolactam. Thus combining a amidohydrolase (step5A, FIG. 5) or a 6-amino-hexanoate CoA-transferase or a 6-amino-hexanoate-CoA ligase (Step 5C, FIG. 5), to pathways (AHA 3-21, 35-59) described in Example V that are capable for the synthesis of 6-amino-hexanoic acid from pyruvate and C3 aldehydes (3-Oxo-Propionic Acid, 3-Hydroxy-Propanal & 3-amino-propanal) that do not proceed through 6-amino-hexanoyl-CoA intermediate gives pathways for &-caprolactam production (CPL pathways, Table C) from pyruvate and C3 aldehydes (3-Oxo-Propionic Acid, 3-Hydroxy-Propanal & 3-amino-propanal). An optional N-deacetylation step will be necessary when the primary amino group of 6-aminohexanoate or 6-aminohexanoyl-CoA is protected as an acetamido group to prevent such cyclizations during the synthesis of any interemediates of AHA patwhays from pyruvate and C3 aldehydes. Such N-deacteylating enzymes are described in Example IV.
Exemplary Enzymes Capable of Catalyzing these Transformations are Described Below:

AHA pathways from pyruvate and C3 aldehydes (3-oxopropionate, 3-hydroxypropanal and 3-aminopropanal) have been described in Example V, along with the enzymes capable of catalyzing each step of these pathways, including steps leading to the synthesis of 6-aminohexanoyl-CoA intermediate have been described in Examples IV-V. Additionally enzymes necessary to convert these intermediates to CPL are described below.

Step 5C: Conversion of 6-aminohexanoate to 6-aminohexanoyl-CoA

CoA-transferases and CoA ligases that catalyze the reverse reaction, i.e conversion of 6-aminohexanoyl-CoA to 6-aminohexanoate (Step 4F3, FIG. 4) have been described in Example IV. Since both these enzymes are reversible, they are used to carry out the conversion of 6-aminohexanoate to 6-aminohexanoyl-CoA (step 5C).

Step5A: Cyclization of 6-aminohexanoate to ε-caprolactam (CPL) and Step 5B: Cyclization of 6-aminohexanoyl-CoA 6-amino-hexanoic acid or its thioester version (CoA ester) using amide bond forming enzymes such as peptide synthases (Martin J F., Appl. Microbiol. Biotechnol. 50:1-15 (1998)), beta-lactam synthases ((Tahlan et al., Antimicrob. Agents. Chemother. 48:930-939 (2004), Hamed et al., Nat. Prod. Rep. 30:21-107 (2013)), aminocyclases (belonging to E.C. 3.5.1.14), L-lysine lactamases belonging to E.C. 3.5.2.11, and other enzymes that are known to catalyze the formation of cyclic amides (belonging to E.C. group 3.5.2). Acidic and basic pH also catalyze the spontaneous formation of lactams. 6-aminohexanoyl-CoA is particularly amenable to spontaneous cyclization. Of particular interest is a Lysine lactamase from *Cryptococcus laurentii* and from *Salmonella* strains (no nucleotide or protein sequence available) which has been shown to work in the reverse direction for the production of lysine from L-alpha-amino-epsilon-caprolactam[127]. Such a enzyme can be used to cyclize 6-aminohexanoate. 6-aminohexanoate cyclic dimer-hydrolase has been shown to hydrolyse the 6-aminohexanoate dimer/ trimer and ologomer to 6-aminohexanoate. Several such enzyme are know in literature[128][129][130]. Shown in Table below are exemplary E.C. groups whose protein candidates can be tested to synthesize CPL (Step 5A).

| EC No, | Name | Genebank | Organism |
|---|---|---|---|
| 3.5.2.11 | L-lysine-lactamase | | |
| 3.5.2.6 | β-lactamase | | |
| 3.5.1.14 | aminoacylase | | |
| 3.5.2.12 | 6-aminohexanoate-cyclic-dimer hydrolase | CAA26616.1. | *Flavobacterium* sp. (strain K172) |
| 3.5.2.12 | 6-aminohexanoate-cyclic-dimer hydrolase | AEI79800.1. | *Cupriavidus necator* |
| 3.5.2.12 | 6-aminohexanoate-cyclic-dimer hydrolase | AAA24929.1. | *Pseudomonas* sp. |
| 3.5.2.12 | 6-aminohexanoate-cyclic-dimer hydrolase | AAA25908.1. | *Flavobacterium* sp. (strain K172) |

7. Synthesis Of 6-Hydroxy-Hexanoic Acid From Intermediates Of Adipic Acid Synthesis Pathway From Pyruvate And C3 Aldehydes (3-Oxo-Propionic Acid and 3-Hydroxy-Propanal)

Multiple ADA pathways starting from pyruvate and C3 aldehydes (3-oxopropionate and 3-hydroxypropanal) have been described in Example IV (FIGS. 2-4) and are listed in Table A, that precede through 6-hydroxyhexanoate, or intermediates such as 6-oxohexanoate, 6-oxo-hexanoyl-CoA, and adipyl-CoA, that are converted to 6-hydroxyhexanoate (HHA) as described in this example. ADA pathways leading upto the synthesis of these intermediates combined with enzymatic steps that convert these intermediates to 6-hydroxyhexanoate gives pathways for synthesis of 6-aminohexanoate (HHA) from pyruvate and C3 aldehydes (3-oxopropionate and 3-hydroxypropanal). Such pathways for production of 6-hydroxyhexanoate (HHA pathways listed in Table D) from pyruvate and C3 aldehydes (3-oxopropionate and 3-hydroxypropanal) are described below along with the enyzmes required to carry out each desired step of all pathways.

Synthesis of 6-hydroxyhexanoate from pyruvate and 3-hydroxy propanal 6-hydroxyhexanoate (HHA) (41, FIG. 4) is an intermediate (product of step 4F3, FIG. 4) in the pathways ADA28 and ADA31 for the synthesis of adipic acid from pyruvate and 3-hydroxy propanal as described above in Example IV and depicted in FIGS. 2-4. Hence, pathways ADA28 and ADA31 can be used to synthesize 6-hydroxyhexanoate. However, removing steps for converting 6-hydroxyhexanoate to adipic acid in these pathways results in a 6-hydroxyhexanoate pathway (pathway HHA-1 and -2, Table D) from pyruvate and 3-hydroxypropanal, which is selective for its production.

6-oxo-hexanoate (39, FIG. 4) is an intermediate of adipic acid synthesis pathways (ADA 27, 28, 30, 31, 65-75, 80-83, Table A, Example IV) from pyruvate and 3-hydroxypropanal. By not including the step 4B7 (FIG. 4) that converts 6-oxo-hexanoate to adipic acid, these pathways are now modified for synthesis of 6-oxo-hexanoate from pyruvate and 3-hydroxypropanal, which is converted to 6-hydroxyhexanoate by a 6-oxo-hexanoate 6-reductase (Step 5K, FIG. 5). The corresponding pathways (HHA 3-30) for the synthesis of 6-hydroxyhexanoate from pyruvate and 3-hydroxypropanal through 6-oxohexanoate are listed in the Table D.

Additionally, 6-oxo-hexanoyl-CoA (38, FIG. 4) is a precursor of adipic acid synthesis pathways (ADA 26, 29, 43-53, Table A, and Example IV) from pyruvate and 3-hydroxypropanal. By not including the steps 4B6 and 4F1 (FIG. 4) that convert 6-oxo-hexanoyl-CoA (38, FIG. 4) to adipic acid, these pathways are now modified for synthesis of 6-oxo-hexanoyl-CoA from pyruvate and 3-hydroxypropanal. 6-oxo-hexanoyl-CoA is reduced to 6-hydroxyhexanoyl-CoA by a 6-hydroxyhexanoyl-CoA 6-reductase (Step 5L, FIG. 5), that is further converted to 6-hydroxyhexanoate (Step 4F3, FIG. 5) by a 6-hydroxyhexanoyl-CoA-transferase, a 6-hydroxyhexanoyl-CoA ligase, or a 6-hydroxyhexanoyl-CoA hydrolase, to give 6-hydroxyhexanoate synthesis pathways from pyruvate and 3-hydroxypropanal.

Synthesis of 6-hydroxyhexanoate from pyruvate and 3-oxo propionate

Adipyl-CoA an intermediate in the synthesis of adipate from pyruvate and 3-oxo propionate (ADA pathways 1-23, Example IV). Not including step 4F1 (FIG. 4) in these pathways results in a pathway capable of Adipyl-CoA synthesis. Adipyl-CoA is converted to 6-hydroxyhexanoate by its conversion to 6-oxo-hexanoate (step 5G, FIG. 5) by a Adipyl-CoA 1-reductase followed by its conversion to 6-hydroxyhexanoate as mentioned above (HHA 57-79). Pathways for the synthesis of 6-hydroxyhexanoate from pyruvate and 3-oxo propionate, through adipyl-CoA and 6-oxohexanoate intermediates are listed in Table D
Exemplary Enzymes Capable of Catalyzing these Transformations are Described Below:

ADA pathways starting from pyruvate and C3 aldehydes (3-oxopropionate and 3-hydroxypropanal) have been described in Example IV (FIGS. 2-4), including the enzymes required to carry out each individual step. Enzyme (5G) responsible for catalyzing step 5G is also described in Example V. Additionally enzymes necessary to convert intermediates of these pathways to 6-hydroxyhexanoate as described in this Example are described in detail below.

Step 5L involves the reduction of 6-oxohexanoyl-CoA to 6-hydroxyhexanoyl-CoA. Step 5K involves the reduction of 6-oxohexanoate to 6-hydroxyhexanoate. Reverse reactions of step 5K and step 5L (steps 4A3 and 4A4) respectively, has been described in Example IV along with candidate enzymes that are known or suitable to catalyze these reactions. Alcohol dehydrogenases (particularly 6-hydroxyhexanoate dehydrogenase) has been found to work in the reverse direction and has been shown to catalyze step 5K. Similarly other alcohol dehydrogenase candidates described before in Example IV can also be used to catalyze the oxidation reaction of the alcohol to an aldehyde as needed herein. Certain aldehyde reductases tend to favor reduction of aldehydes and preferred to carry out this reaction.

8. Synthesis Of ε-Caprolactone From Pyruvate And C3 Aldehyde 3-Hydroxy-Propanal through 6-hydroxyhexanoate and 6-hydroxy-hexanoyl-CoA

Synthesis of ε-Caprolactone from pyruvate and 3-hydroxy propanal

ε-Caprolactone is synthesized from any 6-hydroxyhexanoic acid pathway described previously in Example VII from pyruvate and 3-hydroxy propanal. 6-hydroxyhexanoic acid, or its thioester 6-hydroxy-hexanoyl-CoA (intermediate of 6-hydroxyhexanoic acid pathway form pyruvate and 3-hydroxy propanal in Example VII) can undergo spontaneous lactonization to form the corresponding ε-Caprolactone. Acidic and neutral pH favors the formation of lactone. 6-hydroxyhexanoic acid synthesized by pathways HHA3-30, is converted to ε-Caprolactone either directly (step 5P, spontaneous lactonization or by treatment with a lactonizing enzyme, FIG. 5) (pathways CLO 1-30) or after its conversion to 6-hydroxy-hexanoyl-CoA by a 6-hydroxy-hexanoate CoA-transferase (step 5M, FIG. 5), followed by spontaneous lactonization or by treatment with a lactonizing enzyme (step 5Q, FIG. 5) (pathways CLO 31-60). Additionally, 6-hydroxyhexanoate pathways HHA1, HHA2, and HHA33-56, proceed through 6-hydroxy-hexanoyl-CoA intermediate, which is converted to ε-Caprolactone by spontaneous lactonization or by treatment with a lactonizing enzyme (step 5Q respectively, FIG. 5). Due to the ease of cyclization of 6-hydroxy-hexanoyl-CoA (hydroxyl esters) compared to 6-hyhdroxyhexanoate (hydroxyacids) omitting step 4F3 (FIG. 5) in these pathways will increase ε-Caprolactone yield. Enzymatic lactonization (herein the enzyme is referred to as cyclases) of 6-hydroxyhexanoic acid can be carried out by 6-hydroxyhexanoic acid cyclase, and of 6-hydroxy-hexanoyl-CoA by a 6-hydroxy-hexanoyl-CoA cyclase. Exemplary enzymes that are known to carry lactonization reactions (step 5P and 5Q) (herein referred to as cyclases) include lactonases, esterases (E.C.1.1.1), lipases (PCT/US2010/055524) (E.C.3.1.1.3), and peptidases (WO/ 2009/142489). Exemplary candidates (sequence in Table below) carrying out this transformation are caprolactone hydrolases (ChnC) from cyclcohenxanone degrading bacteria[48][47]. Also of interest is lactonase used for the production of Valero Lactones, as well *candida* lipases that are well-known broad substrate esterases. Additionally Step 5M can be catalyzed by CoA-trasnferases or CoA-ligases. 6-hydroxyhexanoyl-CoA-trasnferases and ligases that carry out this reaction is reverse (reversible reaction) are described in Example IV. Lactonases belonging to E.C. class below, are also of interest. Pathways for ε-Caprolactone synthesis from pyruvate and 3-hydroxy propanal through 6-hydroxy-hexanoic acid and/or 6-hydroxyhexanoyl-CoA as described above (CLO 1-69) are listed in Table E.

| Gene | GenBank ID | Organism |
|---|---|---|
| chnC | BAC80218.1 | *Acinetobacter* sp. NCIMB9871 |
| chnC | AAN37478.1 | *Arthrobacter* sp. BP2 |
| chnC | AAN37490.1 | *Rhodococcus* sp. Phi2 |
| calB | P41365.1 | *Candida antarctica* |

| E.C. No: | Name |
|---|---|
| 3.1.1.15 | L-arabinonolactonase |
| 3.1.1.16 | 4-carboxymethyl-4-hydroxyisocrotonolactonase |
| 3.1.1.17 | gluconolactonase |
| 3.1.1.19 | uronolactonase |
| 3.1.1.24 | 3-oxoadipate enol-lactonase |
| 3.1.1.25 | 1,4-lactonase |
| 3.1.1.27 | 4-pyridoxolactonase |
| 3.1.1.30 | D-arabinonolactonase |
| 3.1.1.31 | 6-phosphogluconolactonase |
| 3.1.1.36 | limonin-D-ring-lactonase |
| 3.1.1.37 | steroid-lactonase |
| 3.1.1.38 | triacetate-lactonase |
| 3.1.1.39 | actinomycin lactonase |
| 3.1.1.45 | carboxymethylenebutenolidase |
| 3.1.1.46 | Deoxylimonate A-ring-lactonase |
| 3.1.1.57 | 2-pyrone-4,6-dicarboxylate lactonase |
| 3.1.1.65 | L-rhamnono-1,4-lactonase |
| 3.1.1.68 | xylono-1,4-lactonase |
| 3.1.1.81 | quorum-quenching N-acyl-homoserine lactonase |

9. Synthesis Of 1,6-Hexanediol From Pyruvate And C3 Aldehydes (3-Hydroxy-Propanal and 3-oxopropionate) through 6-hydroxyhexanoate and 6-hydroxy-hexanoyl-CoA Synthesis of 1,6-hexanediol from pyruvate and 3-hydroxy propanal 1,6-hexanediol is synthesized from any 6-hydroxy-hexanoic acid pathway (from pyruvate and C3 aldehydes 3-hydroxy propanal and 3-oxopropionate) described previously in Example VII (HHA1-79). 6-hydroxyhexanoic acid, or its thioester 6-hydroxy-hexanoyl-CoA (intermediate of 6-hydroxyhexanoic acid pathway in Example VII), is converted to 1,6-hexanediol as shown in FIG. 5. 6-hydroxy-hexanoic acid of HHA pathways 3-30 (Example VII, last Step 5K in pathway), is first converted to 6-hydroxyhexanal either directly by a 6-hydroxyhexanoic acid 6-reductase (step 5R, FIG. 5) (pathways HDO 1-28, Table F) or after its conversion to 6-hydroxy-hexanoyl-CoA by a 6-hydroxy-hexanoate CoA-transferase (step 5M, FIG. 5), followed by its reduction by a 6-hydroxy-hexanoyl-CoA 1-reductase (step 50, FIG. 5) (pathways HDO 29-56). 6-hydroxyhexanal is further converted to 1,6-hexanediol by a 6-hydroxyhexa-nal 1-reductase (Step 5S, FIG. 5). Additionally, remaining 6-hydroxyhexanoate pathways (lacking final step 4F3), will give 6-hydroxy-hexanoyl-CoA, which is converted to 1,6-hexanediol (step 50 and 5S, FIG. 5) as mentioned before (pathways HDO 57-69). Pathways for 1,6-hexanediol synthesis from pyruvate and C3 aldehydes (3-hydroxy propanal and 3-oxopropionate) as described above (HDO 1-69) are listed below.

Exemplary Enzymes Capable of Catalyzing these Transformations are Described Below:

HHA pathways starting from pyruvate and C3 aldehydes (3-oxopropionate and 3-hydroxypropanal) have been described in Example VII, including the enzymes required to carry out each individual step have also been described in Example VII and IV. Additionally enzymes necessary to convert intermediates of these pathways to 1,6-hexanediol as described in this Example are described in detail below.

Step 5R: 6-hydroxyhexanoate reduction to 6-hydroxy hexanal.

This energy intensive step is catalyzed by carboxylic acid reductases (CARs) belonging to E.C. 1.2.1 . . . . They typically function by activating the carboxylate as a phosphate ester such as in *Clostridium acetobutylicum* system reducing butyrate to butanol through by phosphorylation, followed by CoAtransfer reaction and then reduction, making this a energy intensive route. CAR from *Nocardia iowensis* catalyzes reduction of a range of acids in a ATP/NADPH dependent fashion[131]. CARs need to be reactivated by a phosphopantetheine transferase (PPTase). Exemplary sequence of such PPTases and CARs is shown below. Other enzymes that are relevant include alpha-aminoadipate reductase (AAR, EC 1.2.1.31), that reduce alpha-aminoadipate to aminoadipate semialdehyde have been also expressed and characterized.

| Genebank ID | Name | Organism |
|---|---|---|
| AAR91681.1. | ATP/NADPH-CAR | *Nocardia iowensis* |
| ABI83656.1 | PPTase | *Nocardia iowensis* |
| P40976.3 | alpha-aminoadipate reductase | *Schizosaccharomyces pombe* |
| Q10474.1 | PPTase | *Schizosaccharomyces pombe* |

Step 50: 6-hydroxyhexanoyl-CoA reduction to 6-hydroxy hexanal.

Such a reaction is carried out by CoA-dependent alcohol dehydrogenases. Many such exemplary enzymes have been described in Example VI. Although many enzymes are described and can be used to carry out this reactions, most relevant enzymes include propionyl-CoA reductase of *Salmonella typhimurium* that carries out a same reaction but on a very similar substrate (5-hydroxyvaleryl-CoA to 5-hydroxypentanal reduction). Any of the other propionyl-CoA reductases that show broad substrate specificity including reducing hexanoyl-CoA to hexanal are also suitable candidates to cayalze Step 50.

Step 5S: Reduction of 6-hydroxy hexanal to 1,6-hexanediol.

Such a reaction can be catalyzed by aldehyde reductases/alcohol dehydrogenases as described in Example IV. Although many of the enzymes mentioned in Example IV can carry out this reaction, relevant enzymes include 4-hdyroxybutyraldehyde reductases that give 1,4-butanediol. Such a enzyme and its encoding gene have been reported in industrial 1,4-BDO producing strain[132]. Alcohol dehydrogenases (4hb) can also be used to carry out this reaction. This enzyme also is suitable candidate to catalyze Step 50. Other aldehyde reductase that work on hexanal are also suitable candidates. These are *E. coli* ADHE, *S. cerevisiae* ADHs especially ADH6[52], and *E. coli* yqhD[49]. Their protein sequences can be found in Example IV.

10. Synthesis Of hexamethylenediamine From Pyruvate And C3 Aldehydes (3-Hydroxy-Propanal, 3-aminopropanal, and 3-oxopropionate) through 6-hydroxyhexanoate, 6-hydroxy-hexanoyl-CoA, and 6-aminopropanol intermediates Hexamethylenediamine (HMDA) can be synthesized from many pathways described previously from pyruvate and C3 aldehydes (3-Oxo-Propionic Acid, 3-Hydroxy-Propanal & 3-amino-Propanal). As shown in FIG. 5, 6-aminohexanoic acid (AHA pathways 1-21, 35-59) is first reduced to 6-amino-hexanal (Step 5V, FIG. 5) by a 6-aminohexanoic acid 1-reductase, which is aminated (Step 5X, FIG. 5) to give HMDA (HMDA by a 6-amino-hexanal transaminase (aminating) or a 6-amino-hexanal dehydrogenase (aminating). Another pathway of HMDA synthesis starts from 6-hydroxyhexanal (FIG. 5) a intermediate of any 1,6-hexanediol pathway of Example IX. 6-hydroxyhexanal is aminated (Step 5T, FIG. 5) by a 6-hydroxyhexanal transaminase (aminating) or a 6-hydroxyhexanal dehydrogenase (aminating) to give 6-aminopropanol, which is oxidized to 6-aminopropanal by a 6-aminopropanol 1-dehydrogenase (Step 5U, FIG. 5) that is converted to HMDA as mentioned above (Step 5X, FIG. 5). Addition of steps 5T, 5U and 5X to any 1,6-hexanediol pathway (HDO 1-69) lacking step 5S (which reduces 6-hdyroxy propanal to HDO), will be result in a HMDA pathway from pyruvate and C3 aldehydes (Table G). Another route involves conversion of 6-aminohexanoyl-CoA to 6-amino hexanal by CoA-dependent aldehyde dehydrogenase (Step 5W). Any CPL pathway (CPL68-119) with 6-aminohexanoyl-CoA as intermediate will give a HMDA pathway upon adding steps 5W and 5X (HMDA115-167). 6-amino-hexanal can undergo cyclic imine formation by reaction between the primary amine and the aldehyde. To prevent this, the amino group can be masked as an amide (acetamido) to avoid this cylicization. Protecting the primary amine of 6-amino-hexanal precursors 6-aminohexanoic acid or 6-amino hexanol in FIG. 5 by using an acetyl or succinyl functional group can prevent such cyclization. The protecting group can be removed after the synthesis of 6-acetamido HMDA is over (Step 5X, FIG. 5). This results in addition of two additional steps that would involve addition and removal of such a protecting group using acetylases and deacetlyases respectively. N-Acetyltransferases transfer an acetyl group to an amine, forming an acetamido moiety. Lysine N-acetyltransferase (EC 2.3.1.32), glutamate N-acetyl transferase (OAT, EC 2.3.1.35 and EC 2.3.1.1), and diamine N-acetyltransferase (EC 2.3.1.57) can be used to carry out the acetylation of primary amine group. Exemplary Enzymes Capable of Catalyzing these Transformations are Described Below:

AHA and HDO pathways starting from pyruvate and C3 aldehydes have been described in above, including the enzymes required to carry out each individual step have also been described in Example IV-IX. Additionally enzymes necessary to convert intermediates of these pathways to HMDA as described in this Example are discussed in detail below.

Step 5T and Step 5X: Step 5T and Step 5X involve amination of 6-hydroxyhexanal and 6-aminohexanal respectively. Such a reaction can be carried out by transaminases and/or amino acid dehydrogenases and candidate enzymes are described in Example IV. Amination of terminal aldehydes can be catalyzed by PLP (pyridoxal phosphate)-dependent transaminases belonging to E.C. 2.6.1. Transaminases catalyze the transfer of amino group from a range of different donors including amino acids, nucleotides as well as small molecules to the terminal aldehyde group in PLP dependent manner. Step 5X and Step 5T, can be catalyzed by dimino trasnferases such as those described before in Example IV. Such a diamine transaminase enzyme that is capable of catalyzing Step 5X has been demonstrated in *E. coli* (Kim. K. H.: Tchen. T. T.: Methods Enzymol. 17B. 812-815 (1971) and purified[133] is listed in Example IV. Other diamine transferases belonging to E.C. 2.6.1.29 are also useful to carry out this reaction including *pseudomonas* enzyme, gaba (gamma-aminobutyrate transaminase), lysine 6-amino transferases, lysine dehydrogenase, and other candidates that are described in Example IV.

Step 5V: Reduction of 6-aminohexanoate to 6-aminohexanal. This step can be carried out by carboxylic acid reductases. Exemplary enzymes to carry this reaction are described in Example IX.

Step 5U: Oxidation of 6-aminohexanol to 6-aminohexanal. Alcohol dehydrogenases belonging E.C.1.1.1. and described in Example IV can be used to carry out this reaction. Specifically, alcohol dehydrogenases oxidize hexanol to hexanal, a substrate structurally similar to 6-aminohexanol, have been described and are suitable to carry out this reaction.

Step 5W: Invovles CoA-dependent reduction of 6-aminohexanoyl-CoA (or 6-acetamidohexanoyl-CoA). Such a reaction is carried out CoA-dependent aldehyde dehydrogenases. Candidates relevant to this reaction include vaious pduP propionyl-CoA dehydrogenases that have a broad substrate specificity, 5-hydroxy-valeryl-CoA reductases as well as hexanoyl-CoA reductases as described in Example IV.

11. Synthesis of 1-hexanol from C3 aldehydes and pyruvate

This example describes pathways for the synthesis of 1-hexanol from pyruvate and propanal and the enzymes that catalyze each of the steps of the pathway Shown in FIG. 6 is a generic cyclical pathway for the synthesis of acyl-CoA from pyruvate and linear aldehydes through 2-hydroxy-acyl-CoA intermediates. The steps depicted correspond to the following transformations: Step 1: aldol addition (catalyzed by aldolase), Step 2: dehydration (catalyzed by dehydratase), Step 3: reduction (catalyzed by ene-reductase), Step 4: reduction (catalyzed by secondary alcohol dehydrogenase), Step 5: thioester formation (catalyzed by 2-hydroxy acid coenzyme A-transferase or ligase), Step 6: dehydration (catalyzed by 2-hydroxy acid dehydratase), Step 7: reduction (catalyzed by 2,3-enoyl reductase), Step 8: optional reduction (catalyzed by reductase). Each elongation cycle (Steps 1-7) results in the extension of the starting linear aldehyde by 3-carbons. Starting with a $C_N$ aldehyde (N=number of cabons) will result in an acyl-CoA that is $C_{N+3x}$ carbons long (N=number of cabons in starting aldehyde and x=number of elongation cycles).

Described herein is a specific example using this set of transformations Shown in FIG. 6 is an exemplary pathway for the synthesis of 1-hexanol using pyruvate and propanal. Described below are the steps involved for the synthesis of 1-hexanol starting from pyruvate and propanal using the proposed pathway and the most likely enzyme candidates that can catalyze each step.

Step 1: The aldol addition of pyruvate to propanal to give 2-oxo-4-hydroxy-hexanoic acid catalyzed by 2-oxo-4-hydroxy-hexanoate aldolase. Many pyruvate-aldolases of class I and/or class II are used for carrying out this reaction.

Exemplary aldolases include those from meta-cleavage pathway BphI, HpaI, YfaU, and DmpG. HpaI and BphI have both been shown to catalyze this step to synthesize 2-oxo-4-hydroxyhexanoate (Wang et al., Biochemistry 49(17): 3774-3782 (2010); Baker et al., Biochemistry 50(17):3559-3569 (2011); Baker et al., J. Am. Chem. Soc. 134(1):507-513 (2012); Rea et al., Biochemistry 47(38):9955-9965 (2018)). The BphI is very stereoselective as it allows the pyruvate enolate to only attack the re-face of the aldehyde, thereby forming (4S)-aldol products in the process. In contrast, the larger substrate-binding site of HpaI enables the enzyme to bind aldehydes in alternative conformations, leading to formation of racemic products. Such stereoselectivity or lack of thereof will be important for processing by downstream enzymes in the pathway.

Step 2: Dehydration of 2-oxo-4-hydroxy-hexanoic acid to 2-oxo-3-hexenoic acid (2-oxohex-3-enoate hydratase). Hydratases from the meta cleavage pathway in many bacteria are known to convert 2-hydroxy-alkyl-2,4-dienoate to the corresponding 4-hydroxy-2-keto-alkanoic acid. Reverse reaction will lead to the synthesis of 2-hydroxy-alkyl-2,4-dienoate which will tautomerize to the more stable 2-keto-3-(E)-alkenoic acid. Other dehydratases of interest include, fumarases, sugar acid dehydratases, 3-dehydro 2-keto acid dehydratases and others. These dehyrdatases have been described in Example IV and many proteins described therein are used to carryout this dehydration.

Step 3: Reduction of 2-oxo-3-hexenoic acid to 2-oxo-hexanoic acid. The reduction of activated double bonds can be catalyzed by enoate reductases of the old yellow enzyme family, alkenal-reductases (EC 1.3.1.74) as well as by quinone-reductases. Many such enzymes have been described in Example IV. Enzymes relevant to this transformation include XenA from *Pseudomonas putida*, KYE1 from *Kluyveromyces lactis*, and ER from *Yersinia bercovieri*, that have been shown to reduce a range of linear and cyclic α,β unsaturated ketones and aldehydes. OYE from yeast are also of interest.

Step 4: Reduction of 2-oxo-hexanoic acid to 2-hydroxy-hexanoic acid (2oxohexanoate-2-reductase): A number of secondary alcohol dehydrogenases that catalyze the reduction ketones to secondary alcohols can serve as starting points to evaluate their activity towards the desired substrate. Typically a quinone (QH2), reduced ferricytochrome, NAD(P)H, FMNH2, FADH2-dependent dehydrogenase can be used to regioselectively reduce 2-ketohexanoate to 2-hydroxyhexanoate. The ideal enzyme should be able to selectively reduce the C-2 keto group to either a 2(R) or a 2 (S) isomer. Although lactate dehydrogenases are preferred for this reaction, secondary alcohol dehydrogenases can also be used to carry out this transformation. LdhA from *C. difficile* is a NAD+-dependent (R)-2-hydroxyisocaproate dehydrogenase that has been shown to catalyze the reduction of 2-ketohexanoate to 2-(R)-hydroxyhexanoate in a NADH dependent manner. Exemplary sequences of these proteins are shown in Example IV.

Step 5: Formation of 2-hydroxyhexanoyl-CoA by 2-hydroxyhexanoate-CoA Transferase or a 2-hydroxyhexanoate-CoA ligase: HadA, 2-hydroxyisocaproate CoA transferase, a part of the oxidative branch of leucine fermentation in *C. difficile* has been shown to catalyze the reversible attachment of a CoA molecule to C6 compounds such as 2(R)-hydroxysocaproate, isocaproate and 2(E)-isocaprenoate. Its activity towards C6 compounds that are structurally related to 2-(R)-hydroxyhexanoate along with the fact that it is located next to LdhA from *C. difficile* (see above), make the enzyme a prime candidate for catalyzing this reaction. Glutaconate CoA transferase (gctAB) from *Acidaminococcus fermentans* has been shown to transfer Coenzyme A moiety to both R/S isomers of 2-(R/S)-hydroxyglutarate as well as 2-(R)-hydroxyadipate using different CoA donors such as acetyl-CoA, & glutaconyl-CoA.

Exemplary Sequences of these Proteins are Shown in Example IV.

Step6: dehydration of 2-hdyroxyhexanoyl-CoA to hexenoyl-CoA by a 2-hydroxyhexanoyl-CoA dehydratase: The 2-hydroxyacyl-CoA dehydratases (E.C. 4.2.1) catalyze the reversible dehydration from 2-hydroxyacyl-CoA to (E)-2-enoyl-CoA. They can be used to catalyze the dehydration of 2-hydroxyhexanoyl-CoA to 2,3-dehydrohexanoyl-CoA. 2-hydroxyacyl-CoA dehydratases apply a very different method of radical generation compared to other radical SAM (S-adenosylmethione) dependent enzymes. In these enzymes ketyl radicals are formed by one-electron reduction or oxidation and is recycled after each turnover without further energy input. These enzymes require activation by one-electron transfer from an iron-sulfur protein (ferrodoxin or flavodoxin) driven by the hydrolysis of ATP. The enzyme is very oxygen sensitive and requires an activator protein for activation. 2-hydroxyglutaryl-CoA dehydratase (hgdC+hgdAB) from *Clostridium symbiosum* has been shown to dehydrate 2-hydroxyadipyl-CoA and 2-hydroxy-5-ketoadipyl-CoA to give 2,3-(E)-dehydroadipyl-CoA and 2,3-(E)-dehydro-5-ketoadipyl-CoA respectively. Given the relatively broad specificity of this dehydratase it should catalyze the dehydration of 2-hydroxyhexanoyl-CoA. Exemplary sequences of these proteins are shown in Example IV.

Step 7: Reduction of hexenoyl-CoA to hexanoyl-CoA by enoyl-reductases (hexenoyl-CoA 2-reductase):

Enoyl-CoA reductases, which belong to the superfamily of oxidoreductases and exist ubiquitously in all organisms, catalyse the reduction of enoyl-CoA to acyl-CoA using NADH or NADPH as a cofactor with usually reversible kinetics. Trans-2-enol CoA reductases (TERs) identified in *Euglena gracilis* and *T. denticola* utilize NADH as cofactor, exhibit moderate activity for reduction of C6 thioesters such as trans-2-hexenoyl-CoA. NADPH dependent human peroxisomal TER showed activity towards acyl-CoAs ranging in chain length from 4 to 16 carbon atoms. Exmplary sequences of these proteins are shown in Example IV.

Step 8: Reduction of hexanoyl-CoA to hexanal (hexanoyl-CoA 1-reductase) and Step 9: Reduction of hexanal to 1-hexanol (hexanol dehydrogenase)

Hexanoyl-CoA can be then reduced twice in NADH-dependent reactions by AdhE2 (Genbank Accession No AAK09379.1) to 1-hexanol. AdhE2 from *C. acetobutylicum* has been shown to catalyze this reaction. Alternatively, separate Coenzyme A dependent reductases and alcohol dehydrogenases can be used to carry out this reaction with greater specificity. The next step of the pathway is the alcohol dehydrogenase catalyzed reduction of hexanal to 1-hexanol. A tomato short-chain dehydrogenase SIscADH1 has been shown to selective reduce hexanal with no activity for propanal. SIscADH1 also favors hexanal reduction to 1-hexanol oxidation by >40-fold. Although, the enzyme favors NADH as a cofactor it also can use NADPH, albeit less efficiently. NADPH-dependent alcohol dehydrogenase ADHI from olive fruit (*olea* europea) has also been shown to selectively reduce hexanal.

12. Synthesis of fatty acids that are 7-25 carbons long starting from pyruvate and linear aldehydes Shown in FIG. 6 is a cyclical pathway for the synthesis of fatty acids. Fatty acid synthesis pathway depicted in FIG. 6 is a cyclical pathway containing 8-steps in each cycle with a 3-carbon extension upon completion of each cycle. Fatty acid synthesis begins with straight-chain aldehyde of a defined length ($C_N$ aldehyde, where N=length of aldehyde carbon chain) with pyruvate as the extension unit. Completion of each extension cycle results in the synthesis of a linear chain aldehyde ($C_{N+3x}$, where N=length of aldehyde carbon chain at the start and x=number of completed elongation cycles). As shown in Table below, controlling the chain length of the starting aldehyde and the number of elongation cycles, a range of different straight-chain aldehydes can be synthesized ranging from 7-25 carbons long. Oxidation of the straight-chain aldehyde will result in the synthesis of the corresponding fatty acid along with the termination of the fatty acid biosynthesis.

Described above and in Example IV are a number of biochemically-characterized candidates that can catalyze each such reaction. In addition many of these enzymes have broad substrate specificity, and are more relevant to catalyze these steps. Generic class of enzymes that can catalyze each such step and the E.C. classes they belong to is described below.

Biochemistry 47(38):9955-9965 (2018)). BphI is very stereoselective as it allows the pyruvate enolate to only attack the re-face of the aldehyde, thereby forming (4S)-aldol products in the process. In contrast, the larger substrate-binding site of HpaI enables the enzyme to bind aldehydes in alternative conformations, leading to formation of racemic products. Such stereoselectivity or lack of thereof will be important for processing by downstream enzymes in the pathway.

Step 2: Dehydration of give 4-hydroxy-2-oxo-carboxylic acid to give 3,4-dehydro-2-oxo-carboxylic acid. As discussed above, dehydratases of the fumarase, enolase and/or crotonase superfamily or mutants obtained by protein engineering can be used to catalyze this reaction. Specifically, both the enantiomers (4S/4R) or either enantiomer can be used by the enzyme for carrying out the dehydration. Other dehydratases belonging to E.C. 4.2.1 can also used to carry out this reaction.

Step 3: Reduction of 3,4-dehydro-2-oxo-carboxylic acid to give 2-oxo-carboxylic acid. As discussed above, the reduction of activated double bonds can be catalyzed by

| Starting Aldehyde | Carbon Length of The Fatty Acid/Fatty Alcohol/Fatty Alkane/Alkene (N − 1) Number of elongation Cycles | | | | | | | |
|---|---|---|---|---|---|---|---|---|
| | 1 | 2 | 3 | 4 | 5 | 6 | 7 | 8 |
| Formaldehyde | C4 | C7 | C10 | C13 | C16 | C19 | C22 | C25 |
| Acetaldehyde | C5 | C8 | C11 | C14 | C17 | C20 | C23 | |
| Glyoxylate | C5-diol | C8-diol | | | | | | |
| Propionaldehyde | C6 | C9 | C12 | C15 | C18 | C21 | C24 | |
| Butyraldehyde | C7 | C10 | C13 | C16 | C19 | C22 | C25 | |
| Pentanal | C8 | C11 | C14 | C17 | C20 | C23 | | |
| Succinic semialdehyde | C7 | C10 | C13 | | | | | |
| Malonatesemialdehydee | C6 | C9 | C12 | | | | | |

Step 1: The aldol addition of pyruvate to linear-chain aldehyde to give 4-hydroxy-2-oxo-carboxylic acid. This reaction can be catalyzed by class I/II pyruvate dependent aldolases. Of particular interest are 2-dehydro-3-deoxy-glucarate aldolases (E.C. 4.1.2.20, KDG aldolases), 2-dehydro-3-deoxy-phosphogluconate aldolases (E.C. 4.1.2.14, KDPG aldolases), 2-dehydro-3-deoxy-phosphogalactonate aldolases (E.C. 4.1.2.21), 4-hydroxy-4-methyl-2-oxo-glutarate aldolase (E.C.4.1.3.17), 4-hydroxy-2-oxo-glutarate aldolase (E.C.4.1.3.16) and 4-hydroxy-2-oxo-valerate aldolases (E.C. 4.1.3.39) that can be used to catalyze the reversible aldol addition of pyruvate to aldehydes. These enzymes can be engineered using modern protein engineering approaches (Protein Engineering Handbook; Lutz S., & Bornscheuer U. T. Wiley-VCH Verlag GmbH & Co. KGaA: 2008; Vol. 1 & 2) to be active towards the desired substrates. Such engineering (using directed evolution, rational mutagenesis, computational design or a combination thereof) may include, achieving the desired substrate specificity for pyruvate and the acceptor aldehyde, controlling the stereoselectivity to synthesize enantiopure or racemic products, stabilizing the enzyme to withstand industrial process conditions like half-life, thermostability, inhibitor/product tolerance and improving enzyme expression and solubility in the desired micro-organism production host of choice.

Of particular interest are HpaI, YfaU and BphI, pyruvate aldolases involved in the aromatic meta-cleavage pathway (Wang et al., Biochemistry 49(17):3774-3782 (2010); Baker et al., Biochemistry 50(17):3559-3569 (2011); Baker et al., J. Am. Chem. Soc. 134(1):507-513 (2012); Rea et al., enoate reductases of the old yellow enzyme family, alkenal-reductases, enoyl-reductases (EC 1.3.1.74) as well as by quinone-reductases.

Step 4: Reduction of 2-oxo-carboxylic acid to 2-hydroxy-carboxylic acid. As discussed above, secondary alcohol dehydrogenases that catalyze the reduction ketones to secondary alcohols can serve as suitable enzymes to carry out this reaction. Typically a quinone ($QH_2$), reduced ferricytochrome, NAD(P)H, $FMNH_2$, $FADH_2$-dependent dehydrogenase can be used to carry out this reduction. Although lactate dehydrogenases are preferred for this reaction, secondary alcohol dehydrogenases can also be used to carry out this transformation. Shown in Step 5: Transfer of Coenzyme-A molecule onto 2-hydroxy-carboxylic acid to yield 2-hydroxy-acyl-CoA. Coenzyme A attachment step can be catalyzed by Acyl-CoA synthases or ligases belonging to the group E.C. 6.2.1-. Enzymes belonging to this group are known to catalyze the formation of CoA esters using a free CoA molecule in an ATP dependent manner. Alternatively, CoA transferases belonging to the group E.C. 2.8.3 can also catalyze the reversible attachment of a CoA molecule to the pathway intermediates using acyl-CoA as CoA donors.

Step 6: Dehydration of 2-hydroxy-acyl-CoA to 2,3-dehydro-acyl-CoA. The 2-hydroxyacyl-CoA dehydratases (E.C. 4.2.1) catalyze the reversible dehydration from 2-hydroxyacyl-CoA to (E)-2-enoyl-CoA (Buckel, et al., Biochim. Biophys. Acta. 1824(11): 1278-1290 (2011)). They can be used to catalyze this dehydration. These enzymes require activation by one-electron transfer from an iron-sulfur protein (ferrodoxin or flavodoxin) driven by hydrolysis of ATP. The enzyme is very oxygen sensitive and requires a activator protein for activation.

Step 7: Reduction of 2,3-dehydro-acyl-CoA to acyl-CoA. As discussed above, the reduction of activated double bonds can be catalyzed by enoate reductases of the old yellow enzyme family, alkenal-reductases, enoyl-reductases (EC 1.3.1.74) as well as by quinone-reductases. Enoyl-CoA reductases that catalyze the reduction of enoyl-CoA to acyl-CoA in absence of a flavin mediator have been shown to drive flux through a synthetic n-butanol pathway in *E. coli* by effectively introducing a kinetic trap at the crotonyl-CoA reduction step [Bond-Watts, B. B., R. J. Bellerose, et al. Nature Chemical Biology 2011, 7(4): 222-227]. Trans-2-enoyl CoA reductase (TERs) from *T. denticola* is a promising candidate to catalyze this reduction as it highly active towards the multiple carbon length trans-2-enoyl-CoA [Bond-Watts, B. B., A. M. Weeks, et al. (2012). Biochemistry 51(34): 6827-6837]. Similarly, TER from *Euglena gracilis* has also been shown to utilize NADH as a cofactor and exhibit moderate activity for reduction of C6 thioesters such as trans-2-hexenoyl-CoA [Dekishima Y, Lan E I, Shen C R, Cho K M, Liao J C. J Am Chem Soc 2011, 133(30): 11399-11401]. NADPH-dependent human peroxisomal TER showed activity towards acyl-CoAs ranging in chain length from 4 to 16 carbon atoms [Gloerich J, Ruiter J P N, Van den Brink D M, Ofman R, Ferdinandusse S, Wanders R J A. Febs Letters 2006, 580(8):2092-2096]. The availability of crystal structures for all the TERs will aid in protein engineering studies for altering substrate specificity of this enzyme if needed.

Step 8: Reduction of Acyl-CoA to an aldehyde. Conversion of acyl-CoA to an aldehyde can be catalyzed by CoA-dependent aldehyde dehydrogenase or oxidoreductase using NAD(P)H. Aldehydes are reactive compounds that are toxic since they can modify cellular biomolecules. Aldolase-dehydrogenase complex allow sequestration of these harmful molecules by the direct channeling of volatile aldehyde products from the dehydrogenase to the aldolase and vice-versa. BphJ is a nonphosphorylating CoA-dependent ALDH from the polychlorinated biphenyl (PCB) pollutant-degrading bacterium *Burkholderia xenovorans* LB400 that catalyzes reversible reduction of Acyl-CoA in the presence of NADH to the corresponding aldehydes [Baker P, Carere J, Seah S Y. Biochemistry 2012, 51(22):4558-4567.]. BphJ forms a stable complex with the aldolase, BphI (see above). Such Pyruvate aldolase-dehydrogenase complexes can be used to carry out step 8 together with step 1.

Step 9: Chain elongation termination. The growing carbon chain can be terminated either at the end of step 8 (by oxidation of the fatty aldehyde, FIG. 7 Step 8E) or at the end of step 7 (by transesterifacation or hydrolysis of the acyl-CoA, FIG. 7 Step 8C) to yield the fatty acid (FIG. 7). The oxidation of straight-chain aldehyde to the corresponding carboxylic acid can be carried out enzymatically by using any aldehyde dehydrogenases or aldehyde oxidoreductase belonging to E.C 1.2.1.3, E.C.1.2.1.4, E.C. 1.2.1.5, E.C.1.2.1.8, E.C 1.2.1.10, E.C. 1.2.1.24, E.C. 1.2.1.36, E.C. 1.2.3.1, E.C. 1.2.7.5, E.C. 1.2.99.3, E.C 1.2.99.6, & E.C 1.2.99.7 (Hempel et al., Protein Science 2(11): 1890-1900 (1993); Sophos et al., Chemico-Biological Interactions 143: 5-22 (2003); McIntire W S, Faseb Journal 8(8):513-521 (1994); Garattini et al., Cellular and Molecular Life Sciences 65(7-8): 1019-1048 (2008)). Typically a quinone, ferricytochrome, NAD(P), FMN, FAD-dependent dehydrogenase will be used Alternatively, CoA transferases belonging to the group E.C. 2.8.3 can also catalyze the reversible removal of a CoA molecule from acyl-CoA using other carboxylic acids as CoA acceptors. Thioesterases belonging to the group E.C. 3.1.2 can be used for catalyzing the hydrolysis of CoA derivatives of pathway intermediates (FIG. 7) to their corresponding free carboxylic acid versions. By selecting or engineering enzymes that show the specificity for the desired chain length of the substrate (similar to thioesterases in native fatty acid biosynthesis), one can engineer synthesis of fatty acids of the desired chain lengths. For example three thioesterases have been shown to be capable of hydrolyzing a range of medium-chain acyl-ACPs [BfTES from Bryantella formatexigens, CpFatB1, and UcFatB2 (Torella JP., et al., PNAS 2013/06/24, 10.1073/pnas. 1307129110]. Alternatively, many mammalian thioesterases are known that have substrate specificity towards a range of different acyl-CoA molecules [Kirkby, B. et al. Progress in Lipid Research, 2010, 49(4) 366-377] can also be used.

13. Synthesis of sebacic acid and dodecanedioc acid

Sebacic acid is a ten carbon long dicarboxylic acid and can be synthesized using the fatty acid biosynthesis pathway described above (shown in FIG. 6/7). When succinic semialdehyde (C4 aldehyde), which can be synthesized from succinyl-CoA a ubiquitous metabolite of TCA cycle using CoA-dependent aldehyde dehydrogenases, is the starting linear chain aldehyde and it undergoes two-consecutive elongation cycles with pyruvate as the donor it will result in the production of sebacic semialdehyde, which can be oxidized to sebacic acid as described above using aldehyde dehydrogenases. Similarly, using 3-oxo-propionic acid as the starting linear chain aldehyde and three consecutive elongation cycles with pyruvate, along with aldehyde dehydrogenase catalyzed oxidation to terminate synthesis will give dodecane dioic acid as the product. The oxidation of straight-chain aldehyde to the corresponding carboxylic acid can be carried out enzymatically by using any aldehyde dehydrogenases or aldehyde oxidoreductase belonging to E.C 1.2.1.3, E.C.1.2.1.4, E.C. 1.2.1.5, E.C.1.2.1.8, E.C 1.2.1.10, E.C. 1.2.1.24, E.C. 1.2.1.36, E.C. 1.2.3.1, E.C. 1.2.7.5, E.C. 1.2.99.3, E.C 1.2.99.6, & E.C 1.2.99.7 (Hempel et al., Protein Science 2(11): 1890-1900 (1993); Sophos et al., Chemico-Biological Interactions 143:5-22 (2003); McIntire W S, Faseb Journal 8(8):513-521 (1994); Garattini et al., Cellular and Molecular Life Sciences 65(7-8): 1019-1048 (2008)). Typically a quinone, ferricytochrome, NAD(P), FMN, FAD-dependent dehydrogenase will be used.

14. Synthesis of fatty alcohols, alkenes and alkanes from fatty acids and fatty aldehydes Synthesis of fatty alcohols from fatty aldehydes and fatty acids Fatty alcohols (C7-C25) can be synthesized from any pathway described previously that is capable for the synthesis of fatty acids (C7-C25) starting from pyruvate and linear chain aldehydes. Chain termination can be carried out by reducing the fatty aldehydes (product of step 8 in FIG. 6) to the fatty alcohol using primary alcohol dehydrogenases (FIG. 7). A number of primary alcohol dehydrogenases that catalyze the oxidation of primary alcohols to aldehydes can serve as starting points to evaluate their activity towards the reduction of desired fatty aldehyde to the corresponding alcohol (Radianingtyas et al., Fems Microbiology Reviews 27(5):593-616 (2003); de Smidt et al., Fems Yeast Research 8(7):967-978; Reid et al., Crit. Rev. Microbiol. 20:13-56 (1994); Vidal R, López-Maury L, Guerrero M G, Florencio F J (2009) J Bacteriol 191(13):4383-4391.). Typically a quinone, ferricytochrome, NAD(P), FMN, FAD-dependent dehydrogenase can be used.

Another way for fatty alcohol synthesis includes reduction of fatty acid, which can be carried out in multiple ways. The reduction can also be carried out chemically using $Pt/H_2$, $LiAlH_4$, Borohydrides or other known methods in literature. Fatty acid can also be reduced to fatty aldehyde by carboxylic acid reductases followed by reduction to fatty alcohol using primary alcohol dehydrogenases described previously. Carboxylic acid reductases belonging to E.C. 1.2.99.6 can be used to carry out the reduction of hexanoic acid to hexanal using reduced viologens as cofactors. Carboxylic acid reductase from *Mycobacterium Marinum* (UniProt accession number B2HN69, CAR) has been shown to catalyze the conversion of fatty acids (C6-C18) using NADPH as cofactor (Akhtar, et al, Proc. Natl. Acad. Sci. USA 2 Jan. 2013: 87-92.) to fatty aldehydes.

Synthesis of terminal alkanes from fatty aldehydes

Alkanes (C6-C24) can be synthesized from any pathway described previously that is capable for the synthesis of fatty aldehydes (intermediates of fatty acid pathway described above and shown in FIG. 7) or acids (C7-C25) starting from pyruvate and linear chain aldehydes. Alkane biosynthesis requires an aldehyde decarbonylase (FIG. 7, Step 7D) to catalyse the decarbonylation of the fatty aldehydes to formic acid and alkanes [Schirmer, A. et al. Microbial biosynthesis of alkanes. Science 329, 559-562 (2010)]. Two such aldehyde decarbonylase genes (Gene Accession Numbers YP_4000610 and ZP_01080370) have been identified and biochemically characterized to carry out this reaction from Synechococcus sp. [Schirmer, A. et al. Microbial biosynthesis of alkanes. Science 329, 559-562 (2010)]. These enzymes or homologous enzymes of these sequences can also be used to carry out this step.

Synthesis of terminal alkenes from fatty acids

Alkenes (C6-C24) can be synthesized from any pathway described previously that is capable for the synthesis of fatty acids (C7-C25) starting from pyruvate and linear chain aldehydes (FIG. 7, Step 7G). At least two pathways exist for the biosynthesis of terminal alkenes. The first uses a cytochrome P450 enzyme (Gene Accession Number HQ709266) that catalyses a decarboxylative oxidation to convert fatty acids to terminal alkenes [Rude, M. A. et al. Appl. Environ. Microbiol. 77, 1718-1727 (2011)]. The second involves a polyketide synthase, and produces terminal alkenes through a sulphonation-assisted decarboxylation [Mendez-Perez, D., Begemann, M. B. & Pfleger, B. F. Appl. Environ. Microbiol. 77, 4264-4267 (2011)] (Gene Accession Number YP_001734428.1). These enzymes or homologous enzymes of these sequences can also be used to carry out this step.

15 Preparation of a Adipic acid Producing Microbial Organism Having a Pathway for Converting Pyruvate and the C3 aldehyde 3-oxopropionate to Adipate

*Escherichia coli* is used as a target organism to engineer the adipate pathway (ADA pathway 8, 2A, 3B1, 3C2, 3D2, 3E2, 3F2, 3G5, 4D3, 4E3, 4F1) shown in FIG. 3-4 that starts from Pyruvate and 3-oxo propionate. To generate *E. coli* capable of making adipate from this pathway, the nucleic acids encoding each individual enzyme of this pathway are cloned and expressed in *E. coli*. In particular, hpaI (YP_006127221.1) 4-hydroxy-2-oxo-adipate aldolase, ldhA (AAA22568.1.) 4-hydroxy-2-oxo-adipate 2-reductase, and ScADH (AAA34408) 2,4-dihydroxyadipate 4-dehydrogenase, are cloned in pETDuet vector under the control of T7 promoter. 2-hydroxy-4oxoadipate 2-dehydratase (CAA27698.1.), 2,3-dehydro-4-oxoadipate 2,3-reductase (BAF44524.1.), 4-oxo-adipate 4-reductase (NC_001136.10), are cloned in pBAD vector under the control of arabinose inducible promoter. Lastly, 4-hydroxyadipate CoA Transferase catI (P38946.1), 4-hydroxyadipyl-CoA dehydratase (NP_377032.1), 4,5-dehydroadipyl-CoA reductase (NC_000964.3), and Adipyl-CoA trasnferase gctAB (CAA57199 and CAA57200) are cloned into pRSF-Duet vector under control of T7 promoter. These vectors are commercially available. The resulting genetically engineered organism is cultured in glucose-containing medium following procedures well known in the art (see, for example, Sambrook et al., supra, 2001). Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS). Microbial strains engineered to have a functional adipate synthesis pathway can be further for increased adipate production by methods well known in the art. For large-scale production of adipate, the above organism is cultured in a fermenter using a medium known in the art to support growth of the organism under anaerobic conditions. Fermentations are performed in either a batch, fed-batch or continuous manner. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia MD), for example, using an Aminex® series of HPLC columns (for example, HPX-87 series) (BioRad, Hercules CA), using a refractive index detector for glucose and alcohols, and a UV detector for organic acids (Lin et al., Biotechnol. Bioeng. 775-779 (2005)).

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

It is to be understood that while the invention has been described in conjunction with the above aspects, that the foregoing description and examples are intended to illustrate and not limit the scope of the invention. Other aspects, advantages and modifications within the scope of the invention will be apparent to those skilled in the art to which the invention pertains.

REFERENCES

[1] M. Hugler, C. Menendez, H. Schagger, G. Fuchs, J. Bacteriol. 184 (2002) 2404.
[2] C. Liu, Q. Wang, M. Xian, Y. Ding, G. Zhao, PLOS ONE 8 (2013) e75554.
[3] B. Alber, M. Olinger, A. Rieder, D. Kockelkorn, B. Jobst, M. Hugler, G. Fuchs, J. Bacteriol. 188 (2006) 8551.
[4] I. A. Berg, D. Kockelkorn, W. Buckel, G. Fuchs, Science 318 (2007) 1782.
[5] E. I. Lan, S. Y. Ro, J. C. Liao, Energy Environ. Sci. 6 (2013) 2672.
[6] W. Wang, P. Baker, S. Y. K. Seah, Biochemistry (Mosc.) 49 (2010) 3774.
[7] J. Powlowski, L. Sahlman, V. Shingler, J. Bacteriol. 175 (1993) 377.
[8] J. Carere, S. E. McKenna, M. S. Kimber, S. Y. K. Seah, Biochemistry (Mosc.) 52 (2013) 3502.
[9] P. Baker, C. Hillis, J. Carere, S. Y. K. Seah, Biochemistry (Mosc.) 51 (2012) 1942.
[10] S. Wolterink-van Loo, A. van Eerde, M. A. J. Siemerink, J. Akerboom, B. W. Dijkstra, J. van der Oost, Biochem. J. 403 (2007) 421.
[11] P. Baker, S. Y. K. Seah, J. Am. Chem. Soc. 134 (2012) 507.
[12] R. V. Patil, E. E. Dekker, J. Bacteriol. 174 (1992) 102.
[13] A. Pauluhn, H. Ahmed, E. Lorentzen, S. Buchinger, D. Schomburg, B. Siebers, E. Pohl, Proteins Struct. Funct. Bioinforma. 72 (2008) 35.
[14] S. W. B. Fullerton, J. S. Griffiths, A. B. Merkel, M. Cheriyan, N. J. Wymer, M. J. Hutchins, C. A. Fierke, E. J. Toone, J. H. Naismith, Bioorg. Med. Chem. 14 (2006) 3002.
[15] T. Izard, N. C. Blackwell, EMBO J. 19 (2000) 3849.
[16] K. Maruyama, M. Miwa, N. Tsujii, T. Nagai, N. Tomita, T. Harada, H. Sobajima, H. Sugisaki, Biosci. Biotechnol. Biochem. 65 (2001) 2701.
[17] W. Buckel, J. Zhang, P. Friedrich, A. Parthasarathy, H. Li, I. Djurdjevic, H. Dobbek, B. M. Martins, Biochim. Biophys. Acta BBA-Proteins Proteomics 1824 (2012) 1278.
[18] A. Parthasarathy, A. J. Pierik, J. Kahnt, O. Zelder, W. Buckel, Biochemistry (Mosc.) 50 (2011) 3540.
[19] J. Kim, D. Darley, W. Buckel, FEBS J. 272 (2005) 550.
[20] B. M. Martins, H. Dobbek, I. Cinkaya, W. Buckel, A. Messerschmidt, Proc. Natl. Acad. Sci. U.S.A 101 (2004) 15645.
[21] H. Huber, M. Gallenberger, U. Jahn, E. Eylert, I. A. Berg, D. Kockelkorn, W. Eisenreich, G. Fuchs, Proc. Natl. Acad. Sci. U.S.A 105 (2008) 7851.
[22] U. Scherf, B. Sohling, G. Gottschalk, D. Linder, W. Buckel, Arch. Microbiol. 161 (1994) 239.
[23] E. A. Burks, W. H. Johnson, C. P. Whitman, J. Am. Chem. Soc. 120 (1998) 7665.
[24] A. Izumi, D. Rea, T. Adachi, S. Unzai, S.-Y. Park, D. I. Roper, J. R. H. Tame, J. Mol. Biol. 370 (2007) 899.
[25] P. Wang, S. Y. K. Seah, FEBS J. 272 (2005) 966.
[26] M. Horinouchi, T. Hayashi, H. Koshino, T. Kurita, T. Kudo, Appl. Environ. Microbiol. 71 (2005) 5275.
[27] V. Shingler, J. Powlowski, U. Marklund, J. Bacteriol. 174 (1992) 711.
[28] J. R. Pollard, T. D. Bugg, Eur. J. Biochem. 251 (1998) 98.
[29] S. J. J. Brouns, T. R. M. Barends, P. Worm, J. Akerboom, A. P. Turnbull, L. Salmon, J. van der Oost, J. Mol. Biol. 379 (2008) 357.
[30] S. Watanabe, N. Shimada, K. Tajima, T. Kodaki, K. Makino, J. Biol. Chem. 281 (2006) 33521.
[31] S. Ghasempur, S. Eswaramoorthy, B. S. Hillerich, R. D. Seidel, S. Swaminathan, S. C. Almo, J. A. Gerlt, Biochemistry (Mosc.) 53 (2014) 3357.
[32] B. M. A. van Vugt-Lussenburg, L. van der Weel, W. R. Hagen, P.-L. Hagedoorn, PLOS ONE 8 (2013) e55549.
[33] J. W. Teipel, G. M. Hass, R. L. Hill, J. Biol. Chem. 243 (1968) 5684.
[34] T. Weaver, M. Lees, L. Banaszak, Protein Sci. 6 (1997) 834.
[35] T. Genda, S. Watabe, H. Ozaki, Biosci. Biotechnol. Biochem. 70 (2006) 1102.
[36] T. Weaver, M. Lees, V. Zaitsev, I. Zaitseva, E. Duke, P. Lindley, S. McSweeny, A. Svensson, J. Keruchenko, I. Keruchenko, K. Gladilin, L. Banaszak, J. Mol. Biol. 280 (1998) 431.
[37] T. Mizobata, T. Fujioka, F. Yamasaki, M. Hidaka, J. Nagai, Y. Kawata, Arch. Biochem. Biophys. 355 (1998) 49.
[38] T. Shimoyama, E. Rajashekhara, D. Ohmori, T. Kosaka, K. Watanabe, FEMS Microbiol. Lett. 270 (2007) 207.
[39] M. A. Smith, G. L. Mendz, M. A. Jorgensen, S. L. Hazell, Int. J. Biochem. Cell Biol. 31 (1999) 961.
[40] M. J. Gruer, P. J. Artymiuk, J. R. Guest, Trends Biochem. Sci. 22 (1997) 3.
[41] M. J. Gruer, J. R. Guest, Microbiol. Read. Engl. 140 (Pt 10) (1994) 2531.
[42] N. Regev-Rudzki, S. Karniely, N. N. Ben-Haim, O. Pines, Mol. Biol. Cell 16 (2005) 4163.
[43] L. Blank, J. Green, J. R. Guest, Microbiol. Read. Engl. 148 (2002) 133.
[44] R. M. Drevland, A. Waheed, D. E. Graham, J. Bacteriol. 189 (2007) 4391.
[45] S. Kim, S. B. Lee, Biochem. J. 387 (2005) 271.
[46] F. A. Motter, J. Kuivanen, H. Keränen, S. Hilditch, M. Penttila, P. Richard, Fungal Genet. Biol. 64 (2014) 67.
[47] N. A. Donoghue, P. W. Trudgill, Eur. J. Biochem. 60 (1975) 1.
[48] P. C. Brzostowicz, D. M. Walters, S. M. Thomas, V. Nagarajan, P. E. Rouvière, Appl. Environ. Microbiol. 69 (2003) 334.
[49] G. M. Rodriguez, S. Atsumi, Microb. Cell Factories 11 (2012) 90.
[50] G. M. Rodriguez, S. Atsumi, Metab. Eng. 25 (2014) 227.
[51] D. J. Petersen, R. W. Welch, F. B. Rudolph, G. N. Bennett, J. Bacteriol. 173 (1991) 1831.
[52] C. Larroy, M. R. Fernández, E. González, X. Parés, J. A. Biosca, Biochem. J. 361 (2002) 163.
[53] S. Atsumi, T. Hanai, J. C. Liao, Nature 451 (2008) 86.
[54] X. Liu, Y. Dong, J. Zhang, A. Zhang, L. Wang, L. Feng, Microbiol. Read. Engl. 155 (2009) 2078.
[55] A. Tani, Y. Sakai, T. Ishige, N. Kato, Appl. Environ. Microbiol. 66 (2000) 5231.

[56] K. E. Breitkreuz, W. L. Allan, O. R. Van Cauwenberghe, C. Jakobs, D. Talibi, B. Andre, B. J. Shelp, J. Biol. Chem. 278 (2003) 41552.
[57] N. Saito, M. Robert, H. Kochi, G. Matsuo, Y. Kakazu, T. Soga, M. Tomita, J. Biol. Chem. 284 (2009) 16442.
[58] R. A. Wolff, W. R. Kenealy, Protein Expr. Purif. 6 (1995) 206.
[59] B. M. Martins, S. Macedo-Ribeiro, J. Bresser, W. Buckel, A. Messerschmidt, FEBS J. 272 (2004) 269.
[60] T. Suda, J. C. Robinson, T. A. Fjellstedt, Arch. Biochem. Biophys. 176 (1976) 610.
[61] T. Suda, J. C. Robinson, T. A. Fjellstedt, Biochem. Biophys. Res. Commun. 77 (1977) 586.
[62] J. Kim, D. Darley, T. Selmer, W. Buckel, Appl. Environ. Microbiol. 72 (2006) 6062.
[63] G. Zhao, M. E. Winkler, J. Bacteriol. 178 (1996) 232.
[64] H. Taguchi, T. Ohta, J. Biol. Chem. 268 (1993) 18030.
[65] E. Chambellon, L. Rijnen, F. Lorquet, C. Gitton, J. E. T. van Hylckama Vlieg, J. A. Wouters, M. Yvon, J. Bacteriol. 191 (2009) 873.
[66] N. Bernard, K. Johnsen, T. Ferain, D. Garmyn, P. Hols, J. J. Holbrook, J. Delcour, Eur. J. Biochem. 224 (1994) 439.
[67] J. HEIDLAS, K.-H. ENGEL, R. TRESSL, Eur. J. Biochem. 172 (1988) 633.
[68] I. A. Kaluzna, T. Matsuda, A. K. Sewell, J. D. Stewart, J. Am. Chem. Soc. 126 (2004) 12827.
[69] Q. Ren, J. B. van Beilen, N. Sierro, M. Zinn, B. Kessler, B. Witholt, Antonie Van Leeuwenhoek 87 (2005) 91.
[70] E. R. Olivera, B. Miñambres, B. García, C. Muñiz, M. A. Moreno, A. Ferrández, E. Díaz, J. L. García, J. M. Luengo, Proc. Natl. Acad. Sci. U.S.A 95 (1998) 6419.
[71] M. Inui, M. Suda, S. Kimura, K. Yasuda, H. Suzuki, H. Toda, S. Yamamoto, S. Okino, N. Suzuki, H. Yukawa, Appl. Microbiol. Biotechnol. 77 (2008) 1305.
[72] T. Kanamori, N. Rashid, M. Morikawa, H. Atomi, T. Imanaka, FEMS Microbiol. Lett. 217 (2002) 255.
[73] T. Kato, A. Miyanaga, S. Kanaya, M. Morikawa, Extrem. Life Extreme Cond. 14 (2010) 33.
[74] S. Watanabe, M. Yamada, I. Ohtsu, K. Makino, J. Biol. Chem. 282 (2007) 6685.
[75] T. C. Murphy, V. Amarnath, K. M. Gibson, M. J. Picklo, J. Neurochem. 86 (2003) 298.
[76] M. Mack, K. Bendrat, O. Zelder, E. Eckel, D. Linder, W. Buckel, Eur. J. Biochem. 226 (1994) 41.
[77] W. BUCKEL, U. DORN, R. SEMMLER, Eur. J. Biochem. 118 (1981) 315.
[78] R. E. Parales, C. S. Harwood, J. Bacteriol. 174 (1992) 4657.
[79] I. E. Corthesy-Theulaz, G. E. Bergonzelli, H. Henry, D. Bachmann, D. F. Schorderet, A. L. Blum, L. N. Ornston, J. Biol. Chem. 272 (1997) 25659.
[80] L. Stols, M. Zhou, W. H. Eschenfeldt, C. S. Millard, J. Abdullah, F. R. Collart, Y. Kim, M. I. Donnelly, Protein Expr. Purif. 53 (2007) 396.
[81] U. Eikmanns, W. Buckel, Biol. Chem. Hoppe. Seyler 371 (1990) 1077.
[82] S. Friedmann, A. Steindorf, B. E. Alber, G. Fuchs, J. Bacteriol. 188 (2006) 2646.
[83] S. Korolev, O. Koroleva, K. Petterson, M. Gu, F. Collart, I. Dementieva, A. Joachimiak, Acta Crystallogr. D Biol. Crystallogr. 58 (2002) 2116.
[84] E. Vanderwinkel, P. Furmanski, H. C. Reeves, S. J. Ajl, Biochem. Biophys. Res. Commun. 33 (1968) 902.
[85] K. Shikata, T. Fukui, H. Atomi, T. Imanaka, J. Biol. Chem. 282 (2007) 26963.
[86] B. J. Yu, B. H. Sung, J. Y. Lee, S. H. Son, M. S. Kim, S. C. Kim, FEMS Microbiol. Lett. 254 (2006) 245.
[87] M. Musfeldt, P. Schönheit, J. Bacteriol. 184 (2002) 636.
[88] M. Fernández-Valverde, A. Reglero, H. Martinez-Blanco, J. M. Luengo, Appl. Environ. Microbiol. 59 (1993) 1149.
[89] A. Binieda, M. Fuhrmann, B. Lehner, C. Rey-Berthod, S. Frutiger-Hughes, G. Hughes, N. M. Shaw, Biochem. J. 340 (Pt 3) (1999) 793.
[90] M. A. K. Westin, M. C. Hunt, S. E. H. Alexson, J. Biol. Chem. 280 (2005) 38125.
[91] J. A. Latham, D. Chen, K. N. Allen, D. Dunaway-Mariano, Biochemistry (Mosc.) 53 (2014) 4775.
[92] E. M. Barnes, Methods Enzymol. 35 (1975) 102.
[93] S. Tucci, W. Martin, FEBS Lett. 581 (2007) 1561.
[94] M. Hoffmeister, M. Piotrowski, U. Nowitzki, W. Martin, J. Biol. Chem. 280 (2005) 4329.
[95] J. Gloerich, J. P. N. Ruiter, D. M. van den Brink, R. Ofman, S. Ferdinandusse, R. J. A. Wanders, FEBS Lett. 580 (2006) 2092.
[96] M. Yoshida, T. Oikawa, H. Obata, K. Abe, H. Mihara, N. Esaki, J. Bacteriol. 189 (2007) 1573.
[97] S. Zhang, W. Sun, L. Xu, X. Zheng, X. Chu, J. Tian, N. Wu, Y. Fan, BMC Microbiol. 12 (2012) 27.
[98] F. Rohdich, A. Wiese, R. Feicht, H. Simon, A. Bacher, J. Biol. Chem. 276 (2001) 5779. H. S. Toogood, J. M. Gardiner, N. S. Scrutton, ChemCatChem 2 (2010) 892.
[99] J. F. Chaparro-Riggers, T. A. Rogers, E. Vazquez-Figueroa, K. M. Polizzi, A.S.
[100] Bommarius, Adv. Synth. Catal. 349 (2007) 1521.
[101] G. Hambraeus, N. Nyberg, J. Agric. Food Chem. 53 (2005) 8714.
[102] T. B. Fitzpatrick, N. Amrhein, P. Macheroux, J. Biol. Chem. 278 (2003) 19891.
[103] K. Durchschein, S. Wallner, P. Macheroux, W. Schwab, T. Winkler, W. Kreis, K. Faber, Eur. J. Org. Chem. 2012 (2012) 4963.
[104] Y. Fu, K. Castiglione, D. Weuster-Botz, Biotechnol. Bioeng. 110 (2013) 1293.
[105] Y. Fu, K. Hoelsch, D. Weuster-Botz, Process Biochem. 47 (2012) 1988.
[106] K. Itoh, K. Yamamoto, M. Adachi, T. Kosaka, Y. Tanaka, Xenobiotica 38 (2008) 249.
[107] H. Moummou, L. B. Tonfack, C. Chervin, M. Benichou, E. Youmbi, C. Ginies, A. Latché, J.-C. Pech, B. van der Rest, J. Plant Physiol. 169 (2012) 1435.
[108] T. Adachi, D. Izumi, D. Rea, S.-Y. Park, J. R. H. Tame, D. I. Roper, Acta Crystallograph. Sect. F Struct. Biol. Cryst. Commun. 62 (2006) 1010.
[109] W. Liu, P. E. Peterson, R. J. Carter, X. Zhou, J. A. Langston, A. J. Fisher, M. D. Toney, Biochemistry (Mosc.) 43 (2004) 10896.
[110] A. Schulz, P. Taggeselle, D. Tripier, K. Bartsch, Appl. Environ. Microbiol. 56 (1990) 1.
[111] F. Ramos, M. el Guezzar, M. Grenson, J. M. Wiame, Eur. J. Biochem. FEBS 149 (1985) 401.
[112] K. Bartsch, A. von Johnn-Marteville, A. Schulz, J. Bacteriol. 172 (1990) 7035.
[113] S. Kurihara, K. Kato, K. Asada, H. Kumagai, H. Suzuki, J. Bacteriol. 192 (2010) 4582.
[114] A. J. Cooper, Methods Enzymol. 113 (1985) 69.

[115] A. B. Andersen, E. B. Hansen, Gene 124 (1993) 105.
[116] N. N. Samsonova, S. V. Smirnov, I. B. Altman, L. R. Ptitsyn, BMC Microbiol. 3 (2003) 2.
[117] K. H. Kim, J. Biol. Chem. 239 (1964) 783.
[118] H. Ikai, S. Yamamoto, J. Bacteriol. 179 (1997) 5118.
[119] M. Heydari, T. Ohshima, N. Nunoura-Kominato, H. Sakuraba, Appl. Environ. Microbiol. 70 (2004) 937.
[120] H. Misono, H. Hashimoto, H. Uehigashi, S. Nagata, S. Nagasaki, J. Biochem. (Tokyo) 105 (1989) 1002.
[121] P. Ruldeekulthamrong, S. Maeda, S. Kato, N. Shinji, S. Sittipraneed, K. Packdibamrung, H. Misono, BMB Rep. 41 (2008) 790.
[122] U. Demmer, E. Warkentin, A. Srivastava, D. Kockelkorn, M. Potter, A. Marx, G. Fuchs, U. Ermler, J. Biol. Chem. 288 (2013) 6363.
[123] B. Sohling, G. Gottschalk, J. Bacteriol. 178 (1996) 871.
[124] N. Takahashi, T. Sato, T. Yamada, J. Bacteriol. 182 (2000) 4704.
[125] P. Baker, J. Carere, S. Y. K. Seah, Biochemistry (Mosc.) 51 (2012) 4558.
[126] F. Lin, D. Das, X. N. Lin, E. N. G. Marsh, FEBS J. 280 (2013) 4773.
[127] B. Laber, N. Amrhein, Anal. Biochem. 181 (1989) 297.
[128] T. Ohki, N. Shibata, Y. Higuchi, Y. Kawashima, M. Takeo, D.-I. Kato, S. Negoro, Protein Sci. Publ. Protein Soc. 18 (2009) 1662.
[129] S. Negoro, T. Ohki, N. Shibata, N. Mizuno, Y. Wakitani, J. Tsurukame, K. Matsumoto, I. Kawamoto, M. Takeo, Y. Higuchi, J. Biol. Chem. 280 (2005) 39644.
[130] S. Negoro, K. Kato, K. Fujiyama, H. Okada, Biodegradation 5 (1994) 185.
[131] P. Venkitasubramanian, L. Daniels, J. P. N. Rosazza, J. Biol. Chem. 282 (2007) 478.
[132] H. Yim, R. Haselbeck, W. Niu, C. Pujol-Baxley, A. Burgard, J. Boldt, J. Khandurina, J. D. Trawick, R. E. Osterhout, R. Stephen, J. Estadilla, S. Teisan, H. B. Schreyer, S. Andrae, T. H. Yang, S. Y. Lee, M. J. Burk, S. Van Dien, Nat. Chem. Biol. 7 (2011) 445.
[133] K. H. Kim, J. Biol. Chem. 239 (1964) 783.

What is claimed is:

1. A method comprising:
contacting

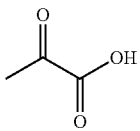

(pyruvic acid) or a salt thereof and

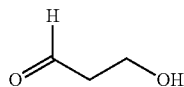

(3-hydroxypropanal) with a polypeptide so that

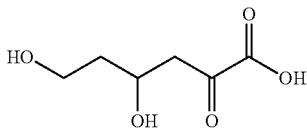 [SMILES: O=C(O)C(=O)CC(O)CCO]

(4,6,-dihydroxy-2-oxohexanoic acid) or a salt thereof is produced, wherein the polypeptide is:
HpaI having the amino acid sequence of SEQ ID NO: 1,
YfaU having the amino acid sequence of SEQ ID NO: 2, or
BphI having the amino acid sequence of SEQ ID NO: 3.

2. The method of claim 1, wherein the polypeptide is in a microbe.

3. The method of claim 2, wherein the microbe is engineered to express the polypeptide.

4. The method of claim 3, wherein the microbe is *E. coli*.

5. The method of claim 2, wherein the contact is performed in a culture comprising the microbe, pyruvic acid or a salt thereof and 3-hydroxy propanal.

6. The method of claim 3, wherein the contact is performed in a culture comprising the microbe, pyruvic acid or a salt thereof and 3-hydroxy propanal.

7. The method of claim 4, wherein the contact is performed in a culture comprising the microbe, pyruvic acid or a salt thereof and 3-hydroxy propanal.

8. The method of claim 2, wherein the polypeptide is HpaI having the amino acid sequence of SEQ ID NO: 1.

9. The method of claim 3, wherein the polypeptide is HpaI having the amino acid sequence of SEQ ID NO: 1.

10. The method of claim 4, wherein the polypeptide is HpaI having the amino acid sequence of SEQ ID NO: 1.

11. The method of claim 5, wherein the polypeptide is HpaI having the amino acid sequence of SEQ ID NO: 1.

12. The method of claim 6, wherein the polypeptide is HpaI having the amino acid sequence of SEQ ID NO: 1.

13. The method of claim 7, wherein the polypeptide is HpaI having the amino acid sequence of SEQ ID NO: 1.

14. The method of claim 2, wherein the polypeptide is YfaU having the amino acid sequence of SEQ ID NO: 2.

15. The method of claim 3, wherein the polypeptide is YfaU having the amino acid sequence of SEQ ID NO: 2.

16. The method of claim 4, wherein the polypeptide is YfaU having the amino acid sequence of SEQ ID NO: 2.

17. The method of claim 5, wherein the polypeptide is YfaU having the amino acid sequence of SEQ ID NO: 2.

18. The method of claim 6, wherein the polypeptide is YfaU having the amino acid sequence of SEQ ID NO: 2.

19. The method of claim 7, wherein the polypeptide is YfaU having the amino acid sequence of SEQ ID NO: 2.

20. The method of claim 2, wherein the polypeptide is BphI having the amino acid sequence of SEQ ID NO: 3.

21. The method of claim 3, wherein the polypeptide is BphI having the amino acid sequence of SEQ ID NO: 3.

22. The method of claim 4, wherein the polypeptide is BphI having the amino acid sequence of SEQ ID NO: 3.

23. The method of claim 5, wherein the polypeptide is BphI having the amino acid sequence of SEQ ID NO: 3.

24. The method of claim 6, wherein the polypeptide is BphI having the amino acid sequence of SEQ ID NO: 3.

25. The method of claim 7, wherein the polypeptide is BphI having the amino acid sequence of SEQ ID NO: 3.

* * * * *